(12) United States Patent
Tao et al.

(10) Patent No.: US 10,344,026 B2
(45) Date of Patent: Jul. 9, 2019

(54) COMPOSITIONS AND METHODS OF TARGETING MUTANT K-RAS

(71) Applicant: NANTBIO, INC., Culver City, CA (US)

(72) Inventors: Chunlin Tao, Newport Coast, CA (US); Laxman Nallan, Rancho Mission Viejo, CA (US); David G. Ho, Monterey Park, CA (US); Qinwei Wang, Alhambra, CA (US); Paul Weingarten, Anaheim, CA (US); Anna B. Juncker-Jensen, San Clemente, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

(21) Appl. No.: 15/874,485

(22) Filed: Jan. 18, 2018

(65) Prior Publication Data

US 2018/0201610 A1 Jul. 19, 2018

Related U.S. Application Data

(60) Provisional application No. 62/447,903, filed on Jan. 18, 2017.

(51) Int. Cl.
*A61P 35/00* (2006.01)
*C07D 417/14* (2006.01)

(52) U.S. Cl.
CPC ............ *C07D 417/14* (2013.01); *A61P 35/00* (2018.01)

(58) Field of Classification Search
CPC ............................... C07D 417/14; A61P 35/00
USPC ................................................. 514/252.04
See application file for complete search history.

(56) References Cited

U.S. PATENT DOCUMENTS

| 2011/0098296 | A1* | 4/2011 | Adjabeng | C07D 413/14 |
| | | | | 514/235.2 |
| 2015/0094307 | A1* | 4/2015 | Schmidt | C07D 319/20 |
| | | | | 514/235.8 |
| 2018/0086752 | A1* | 3/2018 | Rabizadeh | C07D 417/14 |

FOREIGN PATENT DOCUMENTS

| CN | 103784450 A * | 5/2014 | ......... A61K 31/4709 |
| WO | WO/2009/121535 A2 | 10/2009 | |
| WO | WO 2012/161879 A1 | 11/2012 | |
| WO | 2013155223 A1 | 10/2013 | |
| WO | WO 2014/063167 A1 | 4/2014 | |
| WO | WO-2016161361 A1 * | 10/2016 | ........... C07D 417/14 |

OTHER PUBLICATIONS

Healthline "What is Neoplastic Disease" dowloaded from https://www.healthline.com/health/neoplastic-disease on Jun. 21, 2018, 4 pages. (Year: 2018).*
Bos; "ras Oncogenes in Human Cancer: A Review"; Cancer Res 1989, 49, 4682-4689. (Year: 1989).*
Hobbs; "RAS isoforms and mutations in cancer at a glance"; Journal of Cell Science 2016, 129, 1287-1292. (Year: 2016).*
Chemical Abstracts STN Registry Database, record for RN 878115-07-2, first entered into STN database on Mar. 27, 2006, with commercial source information, 2 pages. (Year: 2006).*
Chemical Abstracts STN Registry Database record for RN 1090021-13-8, Entered into STN on Dec. 25, 2008. (Year: 2008).*
Chemical Abstracts STN Registry Database record for RN 1296462-10-6, Entered into STN on May 18, 2011. (Year: 2011).*
Chemical Abstracts STN Registry Database record for RN 949229-29-2, Entered into STN on Oct. 5, 2007. (Year: 2007).*
Chemical Abstracts STN Registry Database record for RN 1386202-88-5, Entered into STN on Aug. 3, 2012. (Year: 2012).*
Chemical Abstracts STN Registry Database, record for RN 1295473-84-5, entered on May 16, 2011. (Year: 2011).*
Chemical Abstracts STN Registry Database, record for RN 1296034-87-1, entered on May 17, 2011. (Year: 2011).*
Grant, Barry J., et al. "Novel Allosteric Sites on Ras for Lead Generation" PLOS One. vol. 6, Issue 10, e25711. 2011. https://doi.org/10.1371/journal.pone.0025711.
European Patent Office, Extended European Search Report, Issued in connection with EP Application No. 16774366.5-1116/Patent No. 3277678. EPO Reference P116924EP00, dated Jul. 12, 2018, pp. 1-9.
Substance Record for SID 145041270, PubChem, Source AKos Consulting & Solutions, External ID AKOS008730007, dated Oct. 18, 2017.
Substance Record for SID 133265758, PubChem, Source AKos Consulting & Solutions, External ID AKOS006983131, dated Jan. 25, 2012.
Substance Record for SID 29748996, PubChem, Source ChemSpider, External ID 16950112, dated Dec. 4, 2007.
Chemical Abstract Compound, STN Express. RN 1090021-13-8, dated Dec. 25, 2008.
Chemical Abstract Compounds, STN Express. RN 1356747-40-4, dated Feb. 14, 2012; and RN 1301208-15-0, dated May 26, 2011.
Chemical Abstract Compounds, STN Express. RN 1374548-73-8, dated May 25, 2012; RN 1317826-78-0, dated Aug. 15, 2011; RN 1316792-31-0 and RN 1316539-20-4, dated Aug. 12, 2011; and RN 1296040-37-3, dated May 17, 2011.
Chemical Abstract Compound, STN Express. RN 1288357-24-3, dated May 1, 2011.
Chemical Abstract Compounds, STN Express. RN 1625469-37-5, dated Sep. 24, 2014; RN 1387153-90-3, dated Aug. 7, 2012; RN 1356638-27-1, dated Feb. 14, 2012; and RN 1320842-60-1, dated Aug. 21, 2011.
Chemical Abstract Compounds, STN Express. RN 1294872-06-2, dated May 15, 2011; and RN 1061592-74-2, dated Oct. 25, 2008.
PCT Notification of Transmittal of the International Search Report and Written Opinion, PCT International Search Report and PCT Written Opinion issued for the corresponding PCT application No. PCT/US16/25697, dated Sep. 6, 2016 (17 pages).

* cited by examiner

*Primary Examiner* — Daniel R Carcanague
(74) *Attorney, Agent, or Firm* — Lucas & Mercanti, LLP

(57) ABSTRACT

Compounds and compositions are presented that inhibit K-Ras, and especially mutant K-Ras. Certain compounds preferentially or even selectively inhibit specific forms of mutant K-Ras, and particularly the G12D mutant form.

15 Claims, 45 Drawing Sheets

Specification includes a Sequence Listing.

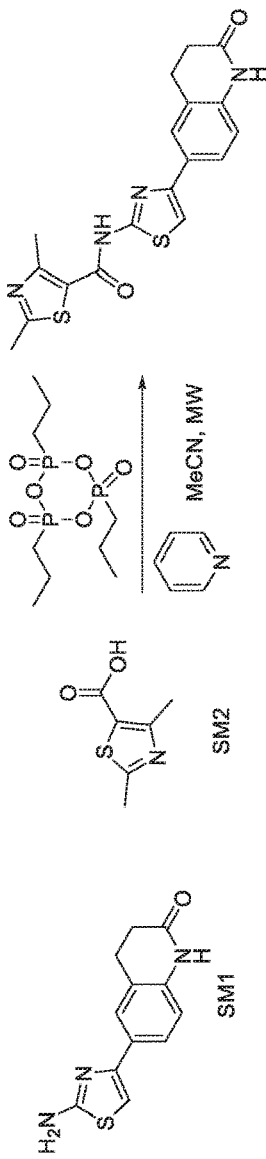

Figure 2

| Test # (Batch) | T | Time | SM1 (eq) | SM2 (eq) | T3P (eq) | Pyridine (eq) | Solvent | Observation | Workup | 1H NMR | LCMS | HPLC | yield |
|---|---|---|---|---|---|---|---|---|---|---|---|---|---|
| Test 2 (SA55_6) | 100 °C | 18h | 1.0 eq | 1.1 eq | 1.2 eq | 4.5 eq | MeCN (2.5 mL) | Solid formation observed | Filtration; wash with cold MeCN (6 mL) | good | good | 98.1% (ML-10.5%) | (71%) |
| Test 3 (SA55_7) | 100 °C | 18h | 1.0 eq | 1.1 eq | 2.3 eq | 4.5 eq | MeCN (2.5 mL) | Solid formation observed | Filtration; wash with cold MeCN (6 mL) | Good | Good | 98.0% (ML-18.6%) | (81%) |
| Test 1 (SA55_4) | 100 °C | 18h | 1.0 eq | 1.1 eq | 3.5 eq | 4.5 eq | MeCN (2.5 mL) | Solid formation observed | Filtration; wash with cold MeCN (6 mL) | | | 98.1% (ML-17.9%) | (77%) |

Figure 3

5 step synthesis to make NANT-4999

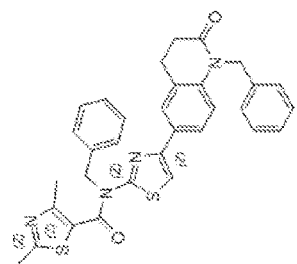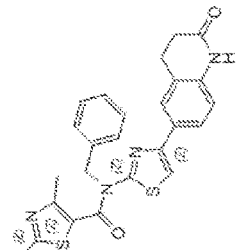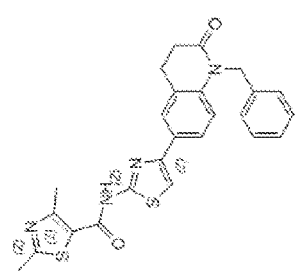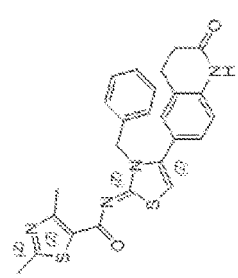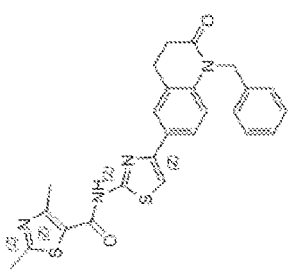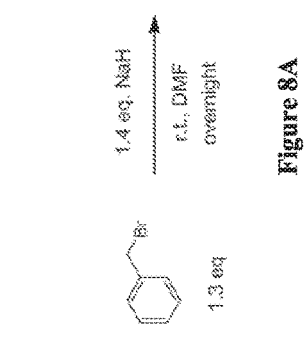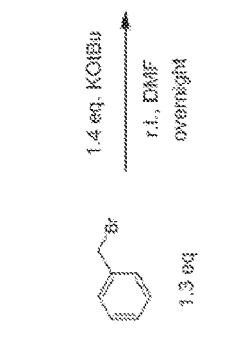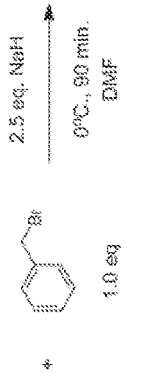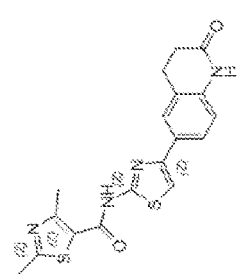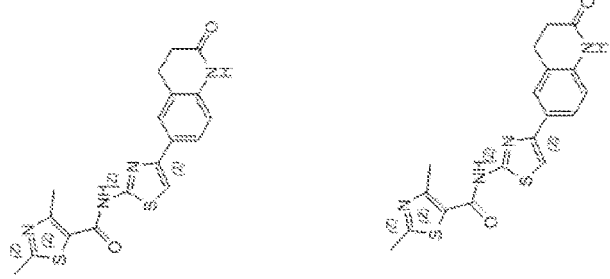
Figure 8A
Figure 8B
Figure 8C

| Assay | Example 152 | Example 1 | Example 4 | Example 9 | Example 22 | Example 23 | Example 21 | Example 17 |
|---|---|---|---|---|---|---|---|---|
| MW | 367.43 | 384.47 | 368.41 | 368.41 | 367.43 | 367.43 | 367.43 | 364.42 |
| pTSA | 94.95 | 82.92 | 92.15 | 92.15 | 86.16 | 86.16 | 86.16 | 82.92 |
| CLogP | 2.45 | 2.57 | 1.94 | 2.28 | 2.09 | 1.75 | 1.75 | 2.26 |
| LogP | 2.52 | 3.96 | 2.59 | 2.59 | 2.89 | 3.04 | 2.83 | 3.16 |
| Wt % inhibition@25µM | | 79-85 | 43-76 | 13 | 87 | | 54/54 | |
| 293H G12D % inhibition@25µM | 8 | | | 0 | 74 | 13 | 72-81 | 19 |
| G-LISA (IC$_{50}$) Wild-type | | 3.8 µM | 25.1 µM | | 12.6µM | | 17.1 µM | |
| G-LISA (IC$_{50}$) G12D | 187 µM | 9.3 µM | 10.9 µM | n/a | 4.6 µM | n/a | 3.8 µM | n/a |
| M.S.(H) T½ (min.) | >60 | >60 | >60 | | | | >60 | |
| M.S.(R) T½ (min.) | >60 | >60 | >60 | | | | >60 | |
| M.S.(M) T½ (min.) | >60 | >60 | >60 | | | | >60 | |
| H. Hepa. Tox. 72 h ATP (CC50 µM) | | 11 µM | 19 µM | | 6 µM | | 12 µM | |

Figure 9

| Assay | Example 1 | Example 20 |
|---|---|---|
| Wt % inhibition@25µM | 79-85 | 0 |
| 293H G12D % inhibition@25µM | 48-49 | |
| 293H G12V % inhibition@25µM | | |
| G-LISA (IC$_{50}$) Wild-type | 3.8 µM | |
| G-LISA (IC$_{50}$) G12D | 9.3 µM | n/a |

Figure 10

| Assay | Example 1 | Example 152 | Example 4 | Example 21 | Example 22 |
|---|---|---|---|---|---|
| Wt % inhibition@25μM | | | | 54/54 | 71 |
| 293H G12D % inhibition@25μM | 79-85 | 8 | 43-76 | 72-81 | 67-74 |
| 293H G12V % inhibition@25μM | 48-49 | 28 | 43 | | |
| G-LISA (IC$_{50}$) Wild-type | 3.8 μM | | 25.1 μM | 17.1 μM | 12.6 μM |
| G-LISA (IC$_{50}$) G12D | 9.3 μM | 187 μM | 10.9 μM | 3.8 μM | 4.6 μM |
| M.S.(H) T½ (min.) | >60 | >60 | >60 | >60 | |
| M.S.(R) T½ (min.) | >60 | >60 | >60 | >60 | |
| M.S.(M) T½ (min.) | >60 | >60 | >60 | >60 | |
| Solubility (pH 7.4, 5% DMSO) | 17.6 μM | 3.39 μM | 26.0 μM | 93.6 | |

Figure 11

| Assay | Example 28 | Example 21 | Example 25 | Example 36 | Example 31 |
|---|---|---|---|---|---|
| Wt % inhibition@25µM | | 54/54 | 74 | 70 | |
| 293H G12D % inhibition@25µM | 0 | 72-81 | 58-74 | 58-69 | 0 |
| G-LISA (IC$_{50}$) Wild-type | | 17.1 µM | 10.7 µM | 18.3 µM | |
| G-LISA (IC$_{50}$) G12D | n/a | 3.8 µM | 6.6 µM | 7.0 µM | n/a |
| 72 hr Cell Viability (CTB) | | | | | |
| Panc1 (G12D) | > 25 µM | 2 µM | 2 µM | 14 µM | > 25 µM |
| Panc10.05 (G12D) | > 25 µM | 0.797 µM | 0.774 µM | 3 µM | > 25 µM |
| H. Hepa. Tox #1 72 hrs ATP (CC50 µM) | | 7 µM | 3 µM | 27 µM | |
| H. Hepa. Tox #2 72 hrs ATP (CC50 µM) | | 12 µM | 8 µM | | |

Figure 12

| Assay | Example 27 | Example 30 | Example 21 | Example 37 | Example 42 | Example 35 | Example 32 | Example 38 | Example 29 |
|---|---|---|---|---|---|---|---|---|---|
| Wt % inhibition@25µM | 16 | 29 | 54/54 | | | | | | |
| 293H G12D % inhibition@25µM | | | 72-81 | 23-39 | 18 | 34-37 | 0-34 | 18 | 0 |
| G-LISA (IC$_{50}$) Wild-type | | | 17.1 µM | | | | | | |
| G-LISA (IC$_{50}$) G12D | n/a | n/a | 3.8 µM | 48 µM | n/a | 28.1 µM | n/a | n/a | n/a |
| 72 hr Cell Viability (CTB) | | | | | | | | | |
| Panc1 (G12D) | > 25 µM | > 25 µM | 2 µM | > 25 µM | > 25 µM | > 25 µM | > 25 µM | > 25 µM | > 25 µM |
| Panc10.05 (G12D) | 16 µM | 23 µM | 0.797 µM | > 25 µM | > 25 µM | > 25 µM | > 25 µM | 7 µM | > 25 µM |

Figure 13

| Assay | Example 40 | Example 41 |
|---|---|---|
| Wt % inhibition@25μM | 44 | 62 |
| 293H G12D % inhibition@25μM | 61-66 | 81-85 |
| G-LISA (IC$_{50}$) Wild-type | 23.3 μM | 7.5 μM |
| G-LISA (IC$_{50}$) G12D | 6.1 μM | 4.3 μM |
| 72 hr Cell Viability (CTB) | | |
| Panc1 (G12D) | 24 μM | 12 μM |
| Panc10.05 (G12D) | >25 μM | 19 μM |
| H. Hepa. Tox.#1 72 hrs ATP (CC50 μM) | 21 μM | 6 μM |

Figure 14

| Assay | Example 9 | Example 24 | Example 26 |
|---|---|---|---|
| Wt % inhibition@25μM | 71 | 82 | 41 |
| 293H G12D % inhibition@25μM | 67-74 | 56-57-77 | 50-68 |
| G-LISA (IC$_{50}$) Wild-type | 12.6 μM | | 25.5 μM |
| G-LISA (IC$_{50}$) G12D | 4.6 μM | 6.5/13.3 μM | 10.6 μM |
| 72 hr Cell Viability (CTB) | | | |
| Panc1 (G12D) | 1.3 μM | 0.243/1.1 μM | 2 μM |
| Panc10.05 (G12D) | 0.734 μM | 0.517/5 μM | 1.1 μM |
| H. Hepa. Tox.#1 72 hrs ATP (CC50 μM) | 3 μM | 10 μM | 12 μM |
| H. Hepa. Tox.#2 72 hrs ATP (CC50 μM) | 6 μM | | 22 μM |

Figure 15

| Assay | Example 5 | Example 59 | Example 64 |
|---|---|---|---|
| Wt % inhibition@25μM |  |  | 34 |
| 293H G12D % inhibition@25μM | 60-67 | 81-84 | 74-82 |
| G-LISA (IC$_{50}$) Wild-type | 14.1 μM | 6.5 μM | 32.3 μM |
| G-LISA (IC$_{50}$) G12D | 10.2 μM | 5.8 μM | 3.0 μM |
| 72 hr Cell Viability (CTB) |  |  |  |
| Panc1 (G12D) | 6 μM | 2 μM | 3-7 μM |
| Panc10.05 (G12D) | 19 μM | 11 μM | 0.9-3 μM |
| M.S.(H) T½ (min.) | >60 | 49.6 | 11 |
| M.S.(R) T½ (min.) | >60 | 4.47 | 36.3 |
| M.S.(M) T½ (min.) | >60 | >60 | 27.2 |
| Solubility (pH 7.4, 5% DMSO) | 10.4 | <1 | 2.2 (30?) |
| Human Hepatocyte Tox #1 72 hrs ATP (CC50 μM) | 4 μM | 6 μM | 4 μM |
| Human Hepatocyte Tox #2 72 hrs ATP (CC50 μM) | 12 μM | 12 μM | 8 μM |

Figure 16

| Assay | Example 70 | Example 64 | Example 72 | Example 91 | Example 92 | Example 85 | Example 101 |
|---|---|---|---|---|---|---|---|
| Wt % inhibition@25μM | 32-38 | 34 | 80 | 72 | 61 | 48 |  |
| 293H G12D % inhibition@25μM | 64-71 | 74-82 | 74-87 | 73-75 | 71 | 68-83 | 44 |
| G-LISA (IC$_{50}$) Wild-type | 44.2 μM | 32.3 μM | 8.0 μM | 11.7 μM | 15.2 μM | 23.4 μM |  |
| G-LISA (IC$_{50}$) G12D | 8.3 μM | 3.0 μM | 8.0 μM | 8.4 μM | 8.5 μM | 7.6 μM |  |
| 72 hr Cell Viability (CTB) |  |  |  |  |  |  |  |
| Panc1 (G12D) | 20 μM | 3-7 μM | 13 μM |  |  | 8 μM |  |
| Panc10.05 (G12D) | 7 μM | 0.9-3 μM | 2 μM |  |  | 6 μM |  |
| Solubility (pH 7.4, 5% DMSO) | 34.7 | 2.2 (~30?) | 36.5 |  |  |  |  |
| H. H. Tox #1 72 hrs ATP (CC50 μM) | 6 μM | 4 μM |  |  |  | 16 μM | >25 μM |
| H. H. Tox #2 72 hrs ATP (CC50 μM) | 25 μM | 8 μM |  |  |  |  |  |

Figure 17

| Assay | Example 105 | Example 112 | Example 70 | Example 113 |
|---|---|---|---|---|
| Wt % inhibition@25μM |  | 84 | 32-38 |  |
| 293H G12D % inhibition@25μM | 76-86 | 78/78 | 64-71 | 82 |
| G-LISA (IC$_{50}$) Wild-type |  | 10.7 μM | 44.2 μM |  |
| G-LISA (IC$_{50}$) G12D | 10.4 μM | 10.0 μM | 8.3 μM | 6.1 μM |

Figure 18

| Assay | Example 70 | Example 76 | Example 77 | Example 78 | Example 74 | Example 73 | Example 93 |
|---|---|---|---|---|---|---|---|
| Wt % inhibition@25μM | 32-38 | 58 | 33 | 19 |  | 49 | 80 |
| 293H G12D % inhibition@25μM | 64-71 | 56-73 |  |  | 42 | 42-60 | 66-71 |
| G-LISA (IC$_{50}$) Wild-type | 44.2 μM | 12.6 μM |  |  |  | 18.8 μM | 10.0 μM |
| G-LISA (IC$_{50}$) G12D | 8.3 μM | 13.9 μM |  |  |  | 19.2 μM | 8.6 μM |

Figure 19

| Assay | Example 70 | Example 89 | Example 95 | Example 96 | Example 97 | Example 98 | Example 99 | Example 100 | Example 103 |
|---|---|---|---|---|---|---|---|---|---|
| Wt % inhibition@25μM | 32-38 | 0 | 60 | 87 | 68 | 0 | 75 | 84 |  |
| 293H G12D % inhibition@25μM | 64-71 | n/a | 74-76 | 63-77 | 65-66 | n/a | 72-75 | 80-84 | 58-63 |
| G-LISA (IC$_{50}$) Wild-type | 44.2 μM | 15.4 μM | 12.1 μM | 12.6 μM |  | 10.2 μM | 9.5 μM |  |
| G-LISA (IC$_{50}$) G12D | 8.3 μM | 5.1 μM | 5.0 μM | 8.1 μM |  | 6.7 μM | 5.1/5.8 μM | 14.9 μM |
| M.S.(H) T½ (min.) | 8.13 | 39.9 | 23.2 | 47.9 |  | <1 | <1 |  |
| M.S.(R) T½ (min.) | 48.4 | 22.4 | 36.7 | 12 |  | <1 | <1 |  |
| M.S.(M) T½ (min.) | 31.9 | 38.8 | 14 | 10.5 |  | <1 | 0.97 |  |
| Solubility (pH 7.4, 5% DMSO) | 34.7 | 13 μM | 12 μM | 12 μM |  |  | 2.15 |  |
| H. H. Tox. 72 h ATP (CC50 μM) | 6, 25 μM |  |  |  |  |  |  | 24 μM |  |

Figure 20

| Assay | Example 1 | Example 12 | Example 4 | Example 7 | Example 8 |
|---|---|---|---|---|---|
| Wt % inhibition@25μM | | 5 | | 74 | 47 |
| 293H G12D % inhibition@25μM | 79-85 | 69 | 43-76 | 79 | 76-81 |
| G-LISA (IC$_{50}$) Wild-type | 3.8 μM | 90 μM | 25.7 μM | 11.6-11.8 μM | 15.5 μM |
| G-LISA (IC$_{50}$) G12D | 9.3 μM | 7-13 μM | 8.2 μM | 4.0-5.5 μM | 5.1-6.6 μM |
| 72 hr Cell Viability (CTB) | | | | | |
| Panc1 (G12D) | 6 μM | 17 μM | 10 μM | 2 μM | 17 μM |
| Panc10.05 (G12D) | 2 μM | 6/14 μM | 2 μM | <780 nM | <780 nM |
| Solubility (pH 7.4, 5% DMSO) | 17.6 μM | 34.2 μM | 26.0 μM | 5.3 | 1.4 |
| Oral Bioav.(%) | 127% | | | 28.08% | 36.61% |
| Bioab.(N to De) | | | | | |
| H. Hepa Tox.#1 72 hrs ATP (CC50 μM) | 11 μM | >25 μM | 19 μM | >25 μM | >25 μM |

Figure 21

| Assay | Example 21 | Example 40 | Example 41 | Example 26 |
|---|---|---|---|---|
| Wt % inhibition@25μM | 54/54 | 44 | 62 | 41 |
| 293H G12D % inhibition@25μM | 72-81 | 61-66 | 81-85 | 50-68 |
| G-LISA (IC$_{50}$) Wild-type | 17.1 μM | 23.3 μM | 7.5 μM | 25.5 μM |
| G-LISA (IC$_{50}$) G12D | 3.8 μM | 6.1 μM | 4.3 μM | 10.6 μM |
| 72 hr Cell Viability (CTB) | | | | |
| Panc1 (G12D) | 2 μM | 24 μM | 12 μM | 2 μM |
| Panc10.05 (G12D) | 0.797 μM | >25 μM | 19 μM | 1.1 μM |
| M.S.(H) T½ (min.) | >60 | | >60 | >60 |
| M.S.(R) T½ (min.) | >60 | | >60 | >60 |
| M.S.(M) T½ (min.) | >60 | | >60 | >60 |
| Solubility (pH 7.4, 5% DMSO) | 93.6 | 21 μM | 6 μM | |
| H. Hepatocyte Tox. 72 hrs ATP (CC50 μM) | 7, 12 μM | | | 12, 22 μM |

Figure 22

| Assay | Example 64 | Example 95 |
|---|---|---|
| MW | 473.55 | 426.49 |
| pTSA | 95.72 | 92.59 |
| CLogP | 2.62 | 2.03 |
| LogP | 3.8 | 2.67 |
| Wt % inhibition@25μM | | |
| 293H G12D % inhibition@25μM | 34 | 60 |
| G-LISA (IC$_{50}$) Wild-type | 74-82 | 74-76 |
| G-LISA (IC$_{50}$) G12D | 32.3 μM | 15.4 μM |
| 72 hr Cell Viability (CTB) | 3.0 μM | 5.1 μM |
| Panc1 (G12D) | 3-7 μM | 7 μM |
| Panc10.05 (G12D) | 0.9-3 μM | 4 μM |
| M.S.(H) T½ (min.) | 11 | 39.9 |
| M.S.(R) T½ (min.) | 36.3 | 22.4 |
| M.S.(M) T½ (min.) | 27.2 | 38.8 |
| Solubility (pH 7.4, 5% DMSO) | 2.2 (30?) | |
| H. Hepa. Tox.#1 72 hrs ATP (CC50 μM) | 4 μM | 13 μM |
| H. Hepa. Tox.#2 72 hrs ATP (CC50 μM) | 8 μM | |

Figure 23

COMPOSITIONS AND METHODS OF TARGETING MUTANT K-RAS

CROSS-REFERENCE TO RELATED APPLICATION

This application claims the benefit of U.S. Provisional Application Ser. No. 62/447,903, filed on Jan. 18, 2017, the disclosure of which is incorporated by reference herein in its entirety.

FIELD OF THE INVENTION

The field of the invention is pharmaceutical compounds, compositions, and methods, and uses thereof in treatment of diseases associated with mutant K-Ras proteins.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and applications referred to herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

K-Ras (or Ki-Ras or Kirsten-Ras or KRAS) is a 21 kD member of the Ras family of GTPase proteins and a necessary component in cell signaling. Activated K-Ras typically activates downstream kinases necessary for the propagation of growth factor and other receptors signals (e.g., c-Raf and PI3-kinase). Unfortunately, genetic alterations in the gene encoding K-Ras are associated with development of neoplasias, and the mechanism of activation is relatively well understood.

Cancer-associated mutant K-Ras is constitutively active, with prolonged stabilization of its GTP-bound (active) state, and is thus able to constitutively activate downstream effectors such as Raf kinase and phosphoinositide-3 kinase (PI3K). Both of these kinases play important roles in pro-liferation/survival/anti-apoptotic signaling pathways. These mutations have been implicated in insensitivity to EGFR-targeted anti-cancer therapies as mutations in K-Ras predispose cancer cells to be significantly less responsive to EGFR targeting therapies (e.g., Panitumumab, Cetuximab, etc.). Interaction with the Ras GTPase activating protein (Ras-GAP) is vital to the timely inactivation of K-Ras, resulting in more efficient hydrolysis of GTP to GDP. The conformational changes in K-Ras structure due to the GTP hydrolysis result in the elimination of K-Ras' affinity for effector proteins, thereby inactivating downstream proliferation and anti-death pathways. Cancer-associated mutations in K-Ras have been shown to interact poorly with RasGAP, therefore remaining in the "on" or constitutively active state.

Approximately 33% of all human tumors express mutant Ras, and these mutations often stabilize Ras in GTP-bound (active) state. Mutations found in K-Ras associate strongly with pancreatic cancer (90%), biliary tract cancer (33%), colorectal cancer (32%), and lung cancer (20%), among others. Approximately 20-25% of all human tumors harbor an activating mutation in gene encoding K-Ras.

Examples of cancer-associated mutations are found at glycine-12 (Gly12), Gly13, and glutamine-61 (Gln61), with Gly12 being the predominant site of mutagenesis (88%). Most notably, while the most common Gly12 mutations are defects in the same position, different mutations have their own different characteristics. For example, expression of G12C is often associated with a reduced response to cisplatin and an increased sensitivity to taxol and pemetrexed, whereas the expression of G12D mutant typically results in resistance to taxol treatment and sensitivity to sorafenib. The G12V mutant shows a strong sensitivity to cisplatin when compared with the wild type variant and is slightly more resistant to pemetrexed. Such diversity in treatment response is compounding difficulties in finding adequate treatment with drugs that are specific to K-Ras, and also highlight that specific mutant forms of K-Ras may require specific drugs for inhibition of the K-Ras activity.

More recently, specific drugs have been proposed to target a particular mutant form of K-Ras. For example, WO2013/155223A1 discloses small molecule inhibitors for G12C mutant forms. While promising, issues with restricted use and potential toxicity may limit compounds presented in the '223 reference. To circumvent mutant specific forms, allosteric inhibitors were proposed (PLOS One October 2011, Volume 6, Issue 10, e25711). However, that report did not distinguish among different mutant forms.

In view of the important role mutant K-Ras plays in various neoplastic disease states, it would be advantageous to be able to identify compounds that bind specifically to the mutant K-Ras protein forms associated with cancer diseases states and/or specific mutant forms, and most preferably to a specific mutant type with little or no binding to the wild type.

Thus, even though various forms of inhibitors for K-Ras are known in the art, there remains a need for compositions and methods that preferentially or even selectively target mutant K-Ras, and especially a single mutant form.

SUMMARY OF THE INVENTION

The inventive subject matter is directed to compounds, compositions, and methods for inhibiting mutant K-Ras, and especially inhibiting G12V and/or G12D mutant K-Ras. Most preferably, the compounds presented herein inhibit G12V and/or CG 12D mutant K-Ras with high selectivity over other mutant forms and high specificity over wild type K-Ras.

In one aspect of the inventive subject matter, a compound having a structure according to Formula I is provided:

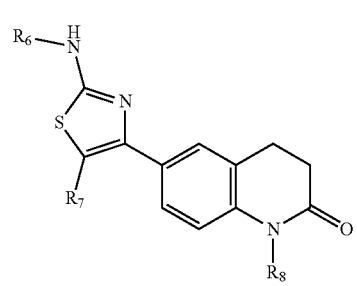

Formula I

In one aspect, $R_6$ has the structure according to either Formula II or Formula III, preferably Formula II.

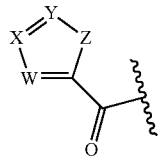

Formula II

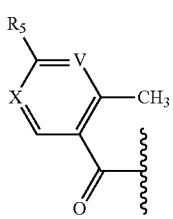

Formula III wherein: V represents $C(R_5)$ or N; W represents $C(R_1)$ or N; X represents $C(R_2)$ or N; Y represents $C(R_3)$ or N; and Z represents O, S, $C(R_{4a})(R_{4b})$ or $N(R_{4a})$; and wherein $R_1$ is selected from the group consisting of H, alkyl, and cycloalkyl; wherein $R_2$ is selected from the group consisting of H, halo, alkyl, substituted alkyl, fluoroalkyl, cycloalkyl, heterocycloalkyl, substituted heterocycloalkyl, aryl, substituted aryl, aralkyl, polycycloalkyl, hetero-polycycloalkyl, polycycloaryl, hetero-polycycloaryl, acyloxy, alkyloxycarbonyl, amino, amido, sulfonamido, pyrazolyl, and substituted pyrazolyl; wherein $R_3$ and $R_7$ are independently H or halo; wherein $R_{4a}$ is independently selected from the group consisting of H, alkyl, substituted alkyl, fluoroalkyl, and aryl; wherein $R_{4b}$ is independently selected from the group consisting of H, alkyl, substituted alkyl, fluoroalkyl, aryl, and alkyloxy; wherein $R_5$ is H or alkyl; and wherein $R_8$ is selected from the group consisting of H, substituted alkyl, aminoalkyl, alkyl amido, cycloalkyl, aralkyl, substituted aralkyl, heteroaralkyl, substituted heteroaralkyl, alkyl cycloalkyl, alkyl heterocycloalkyl, polycycloaryl, alkyloxy, acyloxy, alkyloxycarbonyl, and amino. It should be noted that amido, alkyloxy and amino groups are amine, ether, and amine groups, respectively; and acyloxy and alkyloxycarbonyl are ester groups.

In further preferred aspects, $R_6$ is $R_9$, and has a structure selected from the group consisting of a pyrazolyl, a thiazolyl, an oxazolyl, and a thiophenyl group. Most preferably, but not necessarily, $R_9$ has the structure according to one of Formulae IV through XIV, with $R_1$-$R_{4a}$ and $R_1$-$R_{4b}$ as described above.

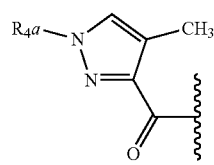

Formula IV

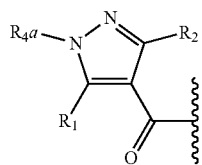

Formula V

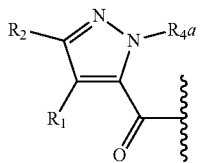

Formula VI

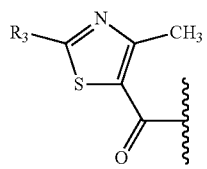

Formula VII

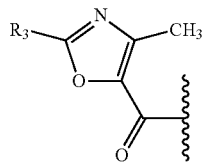

Formula VIII

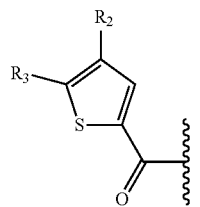

Formula IX

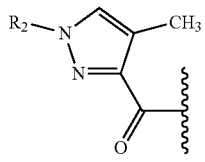

Formula X

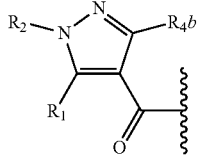

Formula XI

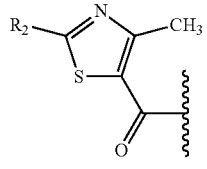

Formula XII

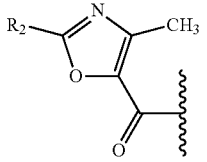

Formula XIII

-continued

Formula XIV

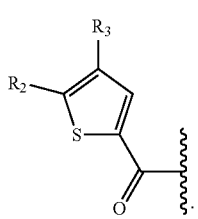

In such embodiments, it is generally preferred that $R_8$ of Formula I be H, optionally substituted benzyl, heterobenzyl, aminoalkyl, alkyl amido, alkyloxy, acyloxy, alkyloxycarbonyl. In especially preferred embodiments, $R_8$ has a structure selected from the group consisting of

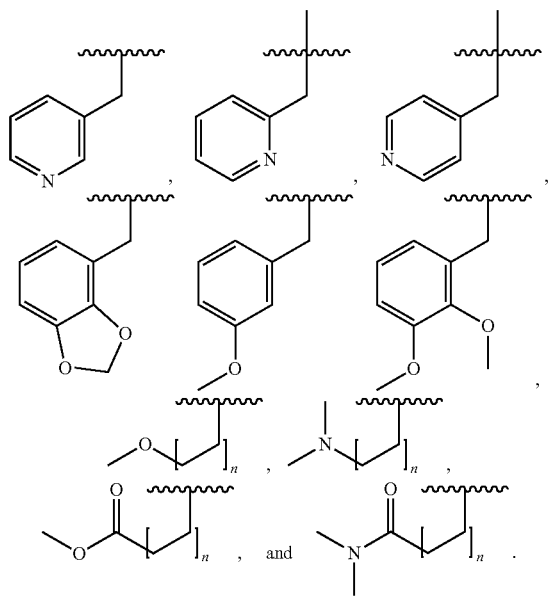

wherein n=1-3.

It is generally preferred that for compounds with Formula V or Formula XI structures, $R_{4a}$ is preferably H, $CF_3$, $CHF_2$, $CH_2F$, or $CH_3$, and $R_{4b}$ is preferably H, $CF_3$, $CHF_2$, $CH_2F$, $CH_3$, or alkyloxy. More preferably, $R_{4a}$ in Formula V and $R_{4b}$ in Formula XI is methyl when $R_2$ is methyl. Further, $R_2$ may be alkyl, aryl, or aralkyl when $R_{4a}$ in Formula V or $R_{4b}$ in Formula XI is methyl.

In some embodiments of Formula VI and Formula XI, only one of $R_2$ and $R_{4a}$ in Formula VI or $R_{4b}$ in Formula XI is H when $R_1$ is cycloalkyl. Also, in Formula VI or Formula XI, $R_2$ can also be alkyl when $R_{4a}$ in Formula VI or $R_{4b}$ in Formula XI is methyl.

Also for compounds having structures according to Formula VI and Formula XI, it is preferred that $R_1$ and $R_2$ form an aromatic ring, such as a five or six carbocyclic or heterocyclic ring that is optionally substituted with $R_8$ as described above. In some embodiments, it is more preferred that $R_{4a}$ in Formula VI or $R_{4b}$ in Formula XI is methyl when $R_2$ is alkyl.

For compounds having Formula VII and Formula XII structures, it is generally preferred that $R_3$ in Formula VII and $R_2$ in Formula XII is alkyl. As to Formula VIII and Formula XIII based compounds, $R_3$ in Formula VII and $R_2$ in Formula XII is preferably alkyl or cycloalkyl.

In another aspect of the inventive subject matter, the inventors contemplate a pharmaceutical composition comprising a pharmaceutically acceptable carrier and one or more compounds as presented above. Most preferably, the compound(s) is/are present at a concentration effective to inhibit K-Ras in a mammal when administered to the mammal at a dosage effective to inhibit K-Ras in the mammal. Moreover, it is generally preferred that the K-Ras is a mutant K-Ras. For example, especially contemplated composition include those in which the compound preferentially inhibits mutant K-Ras G12D relative to mutant K-Ras G12V and mutant K-Ras G12C. The nucleic acid sequence of wild type K-Ras is provided in SEQ ID NO: 1 The nucleic acid sequence of mutant K-Ras G12C is provided in SEQ ID NO: 2. The nucleic acid sequence of mutant K-Ras G12D is provided in SEQ ID NO: 3, The nucleic acid sequence of wild type K-Ras G12V is provided in SEQ ID NO: 4.

Consequently, the inventors also contemplate the use of a compound as presented above to inhibit K-Ras signaling, and in most preferred uses, the compound has a structure according to Formula II, Formula III, or Formula IV. Thus, it is also contemplated that K-Ras signaling is mediated by a mutant K-Ras. For example, the mutant K-Ras is K-Ras G21D, and the compound preferentially inhibits mutant K-Ras G12D relative to mutant K-Ras G12V and mutant K-Ras G12C.

Viewed from another perspective, the inventors therefore also contemplate the use of a compound as presented herein in the manufacture of a medicament to treat a neoplastic disease, and especially where the neoplastic disease is associated with a mutant K-Ras (e.g., K-Ras G12D). For example, the compounds in such medicament may have a structure according to Formula II, Formula III, or Formula IV. The neoplastic disease to be treated can be present in any animal, and in particular in a mammal. The mammal is preferably a human, but is should be appreciated that the animal to be treated can also include any other animal for which treatment is desired, including animals typically encountered in a veterinary practice, e.g., canines, felines, equines, porcines, ovines, and other domestic or exotic animals for which treatment of a neoplastic disease is desired.

Alternatively, the inventors also contemplate a method of inhibiting mutant K-Ras. Such methods will typically include a step of contacting (in vitro or in vivo) the mutant K-ras with contemplated compounds at a concentration effective to inhibit the mutant K-Ras (e.g., where the mutant K-Ras is K-Ras G12D). For example, especially preferred compounds preferentially inhibit mutant K-Ras G12D relative to mutant K-Ras G12V and mutant K-Ras G12C. Suitable concentrations will be effective to reduce downstream signaling with respect to at least one of MEK signaling and ERK signaling.

In yet a further aspect of the inventive subject matter, the inventors also contemplate a method of treating a neoplastic disease (e.g., colon cancer, pancreatic cancer, and non-small cell lung cancer) in a mammal in need thereof, wherein such methods comprise a step of administering to the mammal contemplated compounds under a protocol effective to inhibit K-Ras in the mammal. For example, suitable compound will have a structure according to Formula II, Formula III, or Formula IV, and/or it is contemplated that the step of administering will comprise oral administration or injection. In certain aspects, the neoplastic disease comprises a tumor or cancer cells expressing one or more mutant K-Ras genes with a mutation at glycine-12 (Gly12), (Gly13, and/or glutamine-61 (Gln61).

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 2 depicts a protocol for optimized synthesis of selected compounds of the inventive subject matter.

FIG. 3 depicts results for various protocol conditions for optimized synthesis of selected compounds of the inventive subject matter.

FIGS. 8A-8C depict exemplary protocols to synthesize selected compounds of the inventive subject matter.

FIGS. 9-23 depict experimental data comparing various assay results for selected compounds of the inventive subject matter.

DETAILED DESCRIPTION

Figure 1:
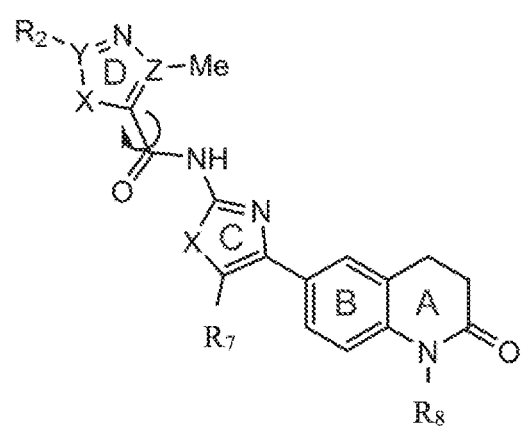
FIG. 1 depicts a general chemical structure for exemplary compounds of the inventive subject matter.

The inventors have now discovered that certain compounds can be prepared that will preferentially or even selectively inhibit mutant K-Ras. Such compounds were found to have a scaffold as schematically illustrated in Formula I

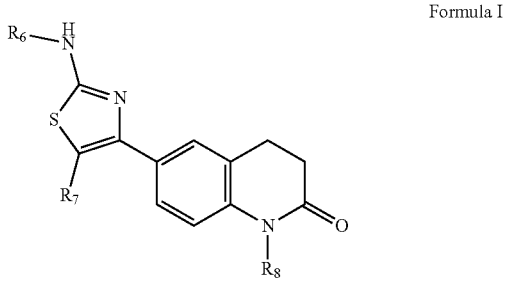

Formula I where $R_7$ is H or a halogen, $R_8$ is H, substituted alkyl, aminoalkyl, alkyl amide, cycloalkyl, aralkyl, substituted aralkyl, heteroaralkyl, substituted heteroaralkyl, alkyl cycloalkane, alkyl heterocycloalkane, polycycloaryl, ether, ester, or an amine, and $R_6$ is typically an optionally substituted 5- or 6-membered heteroaromatic ring, and most typically an optionally substituted pyrazole, thiazole, thiophene, or oxazole.

In order to appreciate the present invention, the following terms are defined. Unless otherwise indicated, the terms listed below will be used and are intended to be defined as stated, unless otherwise indicated. Definitions for other terms can occur throughout the specification. It is intended that all singular terms also encompass the plural, active tense and past tense forms of a term, unless otherwise indicated.

The phrase "consisting essentially of" as used herein means that the composition or method may include additional ingredients and/or steps, but only if the additional ingredients and/or steps do not materially alter the basic and novel characteristics of the claimed composition or method, i.e., the additional ingredient and/or step(s) would serve no purpose material to the claimed composition or method.

The term "substituted" as used herein refers to a replacement of a hydrogen atom on a carbon or nitrogen atom with a functional or non-functional atom or group. Particularly contemplated groups include —$NH_2$, —OH, SH, —NCC(O)OR, aryl, alkyl, alkenyl, alkynyl $NH_3^+$, and halo (e.g., —F, —Cl, and Br), as well as all chemically reasonable combinations thereof. The R group may be an alkyl or aryl group. In this specification, an alkyl group has a minimum of one carbon atom, and a maximum of six carbon atoms, preferably four carbon atoms. Some preferred alkyl groups include methyl, ethyl, propyl, isopropyl, butyl, and isobutyl. For a chain in any such alkyl group or part of an alkyl group, no more than half of the carbon atoms in the chain may be substituted by O, S, NH, or $N(CH_3)$. A fluoroalkyl groups is an alkyl group wherein at least one hydrogen atom and up to all of the hydrogen atoms have been replaced by a fluorine atom.

An aryl group comprises a five or six member ring, and optionally 1-3 heteroatoms selected from the group consisting of N, O, and S. Some suitable aryl groups include pyrazolyl, oxazolyl, thiazolyl, imidazolyl, triazolyl, furanyl, thiophenyl, phenyl, pyridinyl, etc. The aryl group may optionally be substituted as described above.

While not limiting to the inventive subject matter, the inventors discovered that the heterocyclic ring systems for $R_6$ are preferably five-membered heteroaryl systems that may or may not be substituted with one or more substituents. Therefore, and among other suitable heteroaryl systems, especially preferred $R_6$ structures comprise a thiazole ring, an oxazole ring, an imidazole ring, a trizole ring, a furan ring, and a thoiphene ring. In still further preferred aspects, and particularly where $R_6$ is an oxazole, pyrazole, or thiazole, it is preferred that one or two hydrogen atoms in $R_6$ in the oxazole, pyrazole, or thiazole are substituted by an optionally substituted $C_1$-$C_6$ alkyl moiety, which may be cyclic. Especially preferred substituents include, halogen, alkyl, substituted alkyl, fluoroalkyl, cycloalkyl, heterocycloalkyl, substituted heterocycloalkyl, aryl, substituted aryl, aralkyl, heteroaralkyl, substituted heteroaralkyl, alkyl cycloalkane, alkyl heterocycloalkanyl, polycycloalkyl, hetero-polycycloalkyl, polycycloaryl, hetero-polycycloaryl, ester, ether, amine, amide, aminoalkyl, alkyl amido, sulfonamido, pyrazolyl, and substituted pyrazolyl for each of the substituents as depicted in the exemplary list of $R_9$ moieties (Formulae IV through IX) having one or more substituents (here identified as $R_1$ through $R_{4a}$ and $R_{4b}$, and described above.

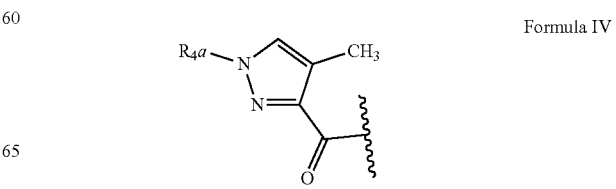

Formula IV

-continued

Formula V

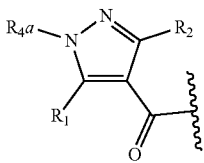

Formula VI

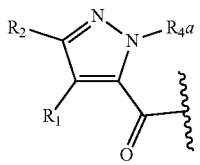

Formula VII

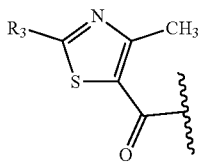

Formula VIII

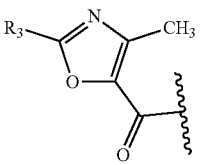

Formula IX

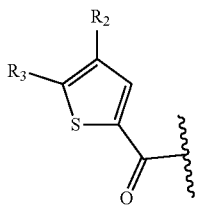

Formula X

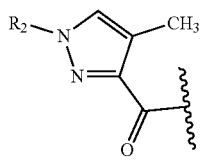

Formula XI

Formula XII

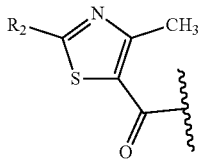

Formula XIII

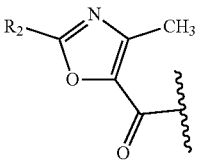

Formula XIV

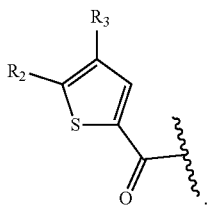

With respect to $R_8$, it is contemplated that such group will preferably include an aryl, heteroaryl, heterocyclic, or substituted alkyl moiety that may be aromatic, or include an aromatic portion. The $R_8$ group can therefore comprise a phenyl ring that may be fused with one or more other aromatic, saturated, or unsaturated ring systems, which may or may not include a heteroatom. For example, suitable $R_8$ groups include those listed below.

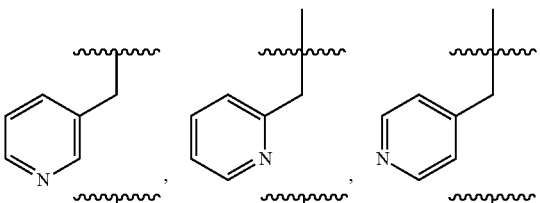

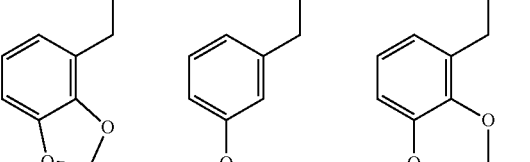

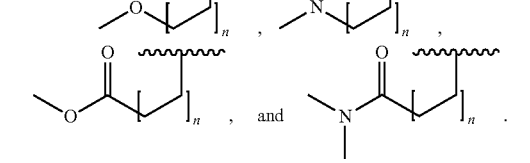

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As further clarification of the scope of the compounds of the present invention described above, cycloalkyl refers to a group that comprises a saturated or unsaturated, non-aromatic, carbocyclic or heterocyclic 3-7 member ring. Some examples of cycloalkyl groups include cyclopropyl, aziridinyl, oxiranyl, thiiranyl, azetidinyl, oxetanyl, thiolanyl, cyclohexyl, cyclopentenyl, azepinyl, and cyclopentyl. Aralkyl and aryl refer to a group that comprises a substituted or unsubstituted, five or six member carbocyclic aromatic ring, e.g., phenyl. Heteroaralkyl or heteroaryl refers to an aryl group that comprises a five member ring and 1-3 heteroatoms or that comprises a six member ring and 1-3 nitrogen atoms. Some examples of heteroaralkyl and heteroaryl groups include pyridinyl, pyrrolidinyl, imidazolinyl, oxazolidinyl, thiazolidinyl, thiazolyl, dioxalyl, triazolyl, piperadinyl, tetrahydropyranyl, dihydropyranyl, pyranyl, thianyl, piperazinyl, morpholinyl, pyranyl, triazolyl, imidazolyl, thiopyranyl, furanyl, etc. Polycycloalkyl refers to a group that comprises two or three fused, saturated or unsaturated, five or six member, substituted or unsubstituted, aromatic or non-aromatic rings that are carbocyclic or that contain one to three heteroatoms in one or more rings if they are five member rings and 1-3 nitrogen atoms if they are six member rings. Some examples of polycycloalkyl groups include naphthyl, quinolinyl, and isoquinolinyl, and benzimidazole. A heteroatom may be a N, S, or O atom.

Certain compounds contemplated herein may comprise one or more asymmetric centers, and therefore exist in different enantiomeric forms. It should be recognized that all enantiomeric forms of contemplated compounds are specifically contemplated herein. Similarly, where contemplated compounds exhibit optical activity and/or have stereoisomers, all isomeric forms are contemplated herein. Furthermore, where double bonds distinguish a Z-form from an E-form (or cis- from trans-), both isomers are contemplated.

Still further, it should be recognized that the compounds according to the inventive subject matter may also be isotopically-labeled. Examples of suitable isotopes include $^2$H, $^3$H, $^{13}$C, $^{14}$C, $^{15}$N, $^{18}$O, $^{17}$O, $^{18}$F, or $^{36}$Cl. Certain isotopically-labeled compounds of the inventive subject matter, for example those into which $^{14}$C or $^3$H is incorporated, may be useful in drug and/or substrate tissue distribution assays. On the other hand, substitution with non-radioactive isotopes (e.g., $^2$H or $^{13}$C) can afford certain therapeutic advantages resulting from greater metabolic stability, for example increased in vivo half-life or reduced dosage requirements and, hence, may be preferred in some circumstances.

Contemplated compounds may be prepared as pharmaceutically acceptable salt(s), which especially include salts of acidic or basic groups which may be present in the contemplated compounds. For example, contemplated compounds that are basic in nature may form a wide variety of salts with various inorganic and organic acids. Suitable acids will provide pharmacologically acceptable anions, including chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate [1,1'-methylene-bis-(2-hydroxy-3-naphthoate)] anions. Similarly, compounds that are acidic in nature may form base salts with various pharmacologically acceptable cations, and especially suitable cations include alkali metal or alkaline earth metal ions (e.g., sodium and potassium cations).

It is still further especially contemplated that compounds according to the inventive subject matter may also be prepared as prodrugs, and all known manners and types of prodrugs are considered suitable for use herein, so long as such prodrug will increase the concentration of the drug (or metabolite of the prodrug) at a target organ or target cell. For example, where the compounds have a free amino, amido, hydroxy, thio, or carboxylic group, it is contemplated that such groups can be employed to covalently and releasably bind a moiety that converts the drug into a prodrug. Therefore, prodrugs particularly include those in which contemplated compounds forms an ester, amide, or disulfide bond with another cleavable moiety. Such moieties may assist in organ or cell-specific delivery of the drug. For instance, a carboxyl group can be derivatized to form an amide or alkyl ester, which may include an ether, amine-, and/or carboxylic acid group. Free hydroxy groups may be derivatized using hemisuccinates, phosphate esters, dimethylaminoacetates, and phosphoryloxymethyloxycarbonyls, as outlined in D. Fleisher, R. Bong, B. H. Stewart, Advanced Drug Delivery 40 Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethylethers, wherein the acyl group may be an alkyl ester (optionally substituted), or where the acyl group is an amino acid ester are also contemplated (Prodrugs of this type are described in R. P. Robinson et al., J. Medicinal Chemistry (1996) 39:p. 10).

Still further, it should also be recognized that contemplated compounds may be metabolized in a cell or extracellular compartment, and that such metabolites may exhibit the same or different pharmacological effect. For example, contemplated compounds may be phosphorylated and thus be more active than the parent compound. On the other hand, reduction or glycosylation may affect bioavailability of contemplated compounds. Consequently, contemplated compounds will not only include those as described above, but also include metabolites thereof.

Viewed from another perspective, it should thus be appreciated that contemplated compounds and compositions may be used for all conditions and/or disorders that are associated with a dysregulation and/or dysfunction of K-Ras, and especially with a mutant form of K-Ras (particularly G12D and/or G12V). For example, contemplated conditions and disorders include various cancers, and especially pancreatic cancer, colon cancer, and non-small cell lung cancer.

Viewed from yet another perspective, the present inventive subject matter is directed to various compounds that modulate (e.g., inhibit or reduce) K-Ras dependent signaling in a cell, and/or that directly or indirectly affect (mutant) K-Ras, GTP binding, and effector protein interaction to so interfere with signal transduction. Exemplary compounds will therefore not only include the compounds as discussed above, but also various derivatives that impart one or another advantageous property.

Based on the inventors' discovery of biological activity of contemplated compounds, it is generally contemplated that the compounds according to the inventive subject matter may be formulated for treatment of various diseases associated with dysregulation and/or dysfunction of K-Ras or mutant K-Ras. Therefore, and among other contemplated uses, the inventors especially contemplate that pharmaceutical compositions comprising contemplated compounds may be effective for the treatment or prevention of K-Ras signaling dependent cancers, and especially colon cancer, pancreatic cancer, and non-small cell lung cancer, wherein contemplated pharmaceutical compositions comprise a therapeutically effective amount of contemplated compounds (or pharmaceutically acceptable salt, hydrate, or prodrug thereof), and a pharmaceutically acceptable carrier. Therefore, it should be recognized that contemplated compounds are suitable for use to inhibit K-Ras signaling, and/or for the manufacture of a medicament to treat a neoplastic disease that is associated with a mutation in K-Ras, especially where the K-Ras has a G12D or G12V mutation. Therefore, the inventors also contemplate a method of inhibiting mutant K-Ras, comprising a step of contacting the mutant K-Ras with a method of inhibiting K-Ras or mutant K-Ras using contemplated compounds at a concentration effective to inhibit the (mutant) K-Ras. As used herein, the term "inhibit" or "inhibition" in conjunction with K-Ras activity means a reduction in activation of downstream signaling components (e.g., MEK, Erk, etc.) as compared to activity of the same (mutant) K-Ras without exposure to the inhibitory compound under otherwise identical conditions.

It is therefore particularly preferred that contemplated compounds are included in a composition that is formulated with one or more non-toxic and pharmaceutically acceptable carriers. Preferred pharmaceutical compositions are formulated for oral administration in solid or liquid form, or for parenteral injection. Thus, it should be recognized that the pharmaceutical compositions according to the inventive subject matter may be administered to humans and other animals using various routes, including oral, rectal, parenteral, intraperitoneal, vaginal, or topical administration.

For example, suitable pharmaceutical compositions for injection preferably comprise pharmaceutically acceptable sterile aqueous or nonaqueous solutions, dispersions, emulsions, or suspensions, as well as sterile powders for reconstitution into sterile injectable solutions or dispersions prior to use. Examples of suitable aqueous and nonaqueous carriers, diluents, solvents, or vehicles include water, ethanol, polyols (e.g., glycerol, propylene glycol, polyethylene glycol, etc.), and suitable mixtures thereof, oils, and injectable organic esters (e.g., ethyl oleate). Contemplated compositions may also contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.). Where appropriate, osmotically active agents may be included (e.g., sugars, sodium chloride, etc.).

Alternatively, contemplated compositions may be formulated into solid dosage forms for oral administration, and may therefore be capsules, tablets, pills, powders, and granules. In preferred solid dosage forms, contemplated compound are mixed with at least one of a pharmaceutically acceptable excipient or carrier (e.g., sodium citrate or dicalcium phosphate), a filler or extender (e.g., starch, lactose, sucrose, glucose, mannitol, or silicic acid), a binder (e.g., carboxymethylcellulose, alginates, gelatin, polyvinylpyrrolidone, sucrose, etc.), a humectant (e.g., glycerol), a disintegrating agent (e.g., agar-agar, calcium carbonate, potato or tapioca starch, alginic acid, certain silicates, or sodium carbonate), a solution retarding agent (e.g., paraffin), an absorption accelerator (e.g., quaternary ammonium compound), a wetting agents (e.g., cetyl alcohol and glycerol monostearate), and absorbents (e.g., kaolin, or bentonite clay), and a lubricant (e.g., talc, calcium stearate, magnesium stearate, solid polyethylene glycols, sodium lauryl sulfate).

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Contemplated compositions may further be formulated to release the active ingredient(s) only, or preferentially, in a certain part of the intestinal tract, optionally, in a delayed manner. Examples of embedding compositions which can be used include polymeric substances and waxes. Contemplated compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, liquid dosage forms may contain inert diluents commonly used in the art (e.g., water, or other solvent, solubilizing agents), emulsifiers (e.g., ethyl alcohol, isopropyl alcohol, ethyl carbonate, ethyl acetate, benzyl alcohol, benzyl benzoate, propylene glycol, 1,3-butylene glycol, dimethyl formamide), oils (and in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound. Compounds according to the inventive subject matter can also be administered in form of liposomes, which may be unilamellar, oligolamellar, or polylamellar. Contemplated compositions in liposome form may further contain stabilizers, preservatives, excipients, etc. Preferred lipids for liposome formation include phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Actual dosage levels of contemplated compounds in pharmaceutical compositions according to the inventive subject matter may be varied so as to obtain an amount of contemplated compound(s) that is effective to achieve the desired therapeutic response for a particular patient, composition, and mode of administration. Thus, the selected dosage level will depend upon various factors, including the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Generally, dosage levels of about 0.01 mg/kg to about 0.1 mg/kg, or about 0.1 mg/kg to about 1 mg/kg, or about 1 mg/kg to about 10 mg/kg, or about 10 mg/kg to about 50 mg/kg of body weight per day. Thus, single dosage units for administration will typically be between 0.1 mg and 1 mg, between 1 mg and 50 mg, between 50 mg and 250 mg, between 250 mg-1,000 mg, between 1,000 mg and 5,000 or even higher when administered orally to a mammalian patient. If desired, it should be appreciated that the effective daily dose may be divided into multiple doses for purposes of administration, e.g., two to four separate doses per day.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary. In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

It should still further be appreciated that contemplated pharmaceutical compositions may also include additional pharmaceutically active compounds, and especially contemplated additional pharmaceutically active compounds include anti-metabolic and/or antineoplastic agents and/or immunologically active agents, which may act upon cell division, apoptosis, T-cell recognition, NK-cell activity, memory cell formation, checkpoint inhibition, and/or immune stimulation. Of course, it should be recognized that additional pharmaceutically active compounds may be included in the same pharmaceutical composition, or may be administered separately, and a person of ordinary skill in the art will readily determine schedule and route of suitable co-administration of the additional pharmaceutically active compounds.

EXAMPLES

FIG. 1 depicts a core structure for preferred compounds of the inventive subject matter comprising ring structures A, B, C, and D, groups $R_1$, $R_2$, and $R_3$, and radicals X, Y, and Z. Experimental data indicates the N of ring structure D and the ketone component of ring structure A provide key binding sites for preferred compounds K-Ras inhibitory activity. Data presented below and accompanying FIGS. 2A-G indicate the $R_3$ group of ring structure A provides a further key binding site to increase preferred compound's K-Ras inhibition potency or selectivity of K-Ras mutants over wild types. Data further indicates the methyl (or similarly sized) substituent of radical Z may be necessary to orient the D ring for increased potency and selectivity. Further, data shows $R_2$ can be selectively modified to increase potency and selectivity of preferred compounds.

FIGS. 24-54 depict examples of preferred compounds having structures according to Formula I.

Example Intermediates

The following examples are intended to provide a non-limiting general protocol for the preparation of various intermediates that can be subsequently used to prepare compounds according to the inventive subject matter. Based on the below exemplary protocols, the person of ordinary skill in the art will be readily able to produce similar compounds starting with similar educts. Likewise, the examples provided for biological activities exemplarily set out systems and methods for ascertaining inhibitory activity and preference/selectivity.

Intermediate 1

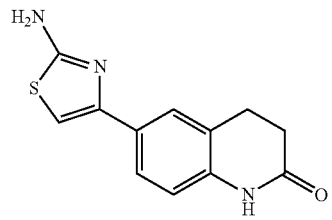 [SMILES: Nc1nc(-c2ccc3c(c2)CCC(=O)N3)cs1]

To a 500 mL round-bottomed flask equipped with condenser and argon inlet were added aluminum chloride (7.93 g, 59.45 mmol), carbon disulfide (40 mL), and chloroacetyl chloride (2.30 g, 20.38 mmol) under ice-bath. The mixture was stirred for 15 mins. To the stirring mixture was added 3,4-dihydro-2(H)-quinolinone (2.50 g, 16.99 mmol) in portions over 5 mins. The mixture was stirred for 10 minutes prior to reflux for 2.5 hours. The reaction mixture was cooled and the solvent was decanted off. Then ice and cold water (50 mL) was slowly added while stirred thoroughly. The beige precipitate filtered, washed with water (3×50 mL) followed by tetrahydrofuran (2×100 mL) and hexanes (1×200 mL). The solid was dried under vacuum to give 6-(2-chloroacetyl)-3,4-dihydroquinolin-2(1H)-one (3.44 g, 90%) as a beige solid. $^1$H NMR (400 MHz, DMSO-d): δ 10.47 (bs, 1H), 7.83 (s, 1H), 7.80 (dd, 1H, J=8.8, 1.6 Hz), 6.94 (d, 1H, J=8.0 Hz), 5.08 (s, 2H), 2.95 (m, 2H), 2.49 (partial masked under d-DMSO, m, 2H). MS (ESI): Calcd. for $C_{11}H_{10}ClNO_2$: 223, found 224 (M+1)$^+$.

6-(Chloroacetyl)-3,4-dihydroquinolin-2(1H)-one (1.00 g, 4.47 mmol) and thiourea (0.36 g, 4.69 mmol) were suspended in anhydrous ethanol (10 ml) in a sealed tube under argon atmosphere. The sealed tube was microwaved at 120° C. for 30 min. The mixture was diluted with tetrahydrofuran (200 mL) and neutralized with 1N aq. NaOH solution and then extracted with ethyl acetate (2×200 mL). The combined organic layers were dried over anhydrous $Na_2SO_4$ and concentrated in vacuo. The residue was purified by precipitating in dichloromethane and filtration to give 6-(2-aminothiazol-4-yl)-3,4-dihydroquinolin-2(1H)-one (0.920 g, 73%) as a light brown solid. $^1$H NMR (400 MHz, DMSO-d): δ 10.27 (s, 1H), 8.71 (br s, 2H), 7.61 (s, 1H), 7.55 (dd, 1H, J=8.8, 2.0 Hz), 7.05 (s, 1H), 6.91 (d, 1H, J=8.4 Hz), 2.91 (t, 2H, J=7.6 Hz), 2.48 (partial masked under d-DMSO, m, 2H). MS (ESI): Calcd. for $C_{12}H_{11}N_3OS$: 245, found 246 (M+1)$^+$.

Intermediate 2

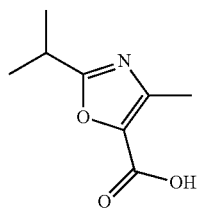

To a suspension of 2-chloroethyl acetoacetate (10.0 g, 60.76 mmol) and isobutyramide (5.30 g, 60.76 mmol) was heated at 120° C. for overnight. The mixture was cooled to room temperature, ethyl acetate (100 mL) was added and the insoluble matters were filtered off. Water was added to the filtrate, the organic layer was separated and the aqueous layer was extracted with ethyl acetate. The combined organic layers were washed with saturated brine, dried over anhydrous sodium sulfate and then concentrated. The residue was purified by silica gel column chromatography (hexane/ethyl acetate, 3:1) to give ethyl 2-isopropyl-4-methyloxazole-5-carboxylate 3 g, 25%). ¹H NMR (400 MHz, DMSO-d): δ, 3.29 (m, 2H), 3.09 (m, 1H), 2.35 (s, 3H), 1.28 (s, 3H), 1.26 (s, 3H).

A solution of ethyl 2-isopropyl-4-methyloxazole-5-carboxylate (1.67 g, 8.47 mmol) in MeOH (80 mL) was added LiOH.H₂O (0.71 g, 16.93 mmol) and 20 mL of water. The resulting solution was stirred at room temperature for 18 h and the pH was adjusted to 3 with 6N HCl. This mixture was further extracted with ethyl acetate (3×50 mL). The combined organic layers were washed with saturated brine, dried over anhydrous sodium sulfate and then concentrated to give 2-isopropyl-4-methyloxazole-5-carboxylic acid 0.78 g, 55%). ¹H NMR (400 MHz, DMSO-d): δ, 3.01 (m, 1H), 2.33 (s, 3H), 1.27 (s, 3H), 1.25 (s, 3H).

Intermediate 3

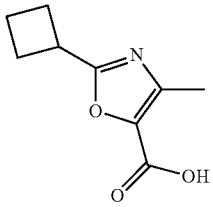

A solution of cyclobutanecarboxylic acid (1.00 g, 9.99 mmol), 2-chloroethyl acetoacetate (1.64 g, 9.99 mmol) and TEA (3.03 g, 29.96 mmol) in DMF (20 mL) was stirred at room temperature for 18 h. Added water (50 mL) and extracted with EtOAc (3×50 mL) and the combined organic layers were washed with water (3×50 mL) and brine (2×50 mL). After separation, organic layers were dried over sodium sulfate and then concentrated to give 1-ethoxy-1,3-dioxobutan-2-yl cyclobutanecarboxylate and used in the next step without further purification.

A solution of 1-ethoxy-1,3-dioxobutan-2-yl cyclobutanecarboxylate (1.00 g, 4.38 mmol) and ammonium trifluoroacetate (6.03 g, 46.0 mmol) was stirred at 150° C. for 5 min. The resulting mixture was cooled to room temperature, then 50 mL of water was added and the organic layer was separated and the aqueous layer was extracted with ethyl acetate (3×50 mL). The combined organic layers were washed with saturated brine, dried over anhydrous sodium sulfate and then concentrated. The residue was purified by silica gel column chromatography (hexane/ethyl acetate, 3:1) to give ethyl 2-cyclobutyl-4-methyloxazole-5-carboxylate 0.63 g, 69%). ¹H NMR (400 MHz, DMSO-d): δ, 4.31 (m, 2H), 3.66 (m, 1H), 1.98-2.36 (9H), 1.30 (3H, J=7.2 Hz)

A solution of ethyl 2-cyclobutyl-4-methyloxazole-5-carboxylate (0.3 g, 1.43 mmol) in MeOH (32 mL) was added LiOH.H₂O (0.18 g, 4.30 mmol) and 8 mL of water. The resulting solution was stirred at room temperature for 18 h and the pH was adjusted to 3 with 6N HCl. This mixture was further extracted with ethyl acetate (3×50 mL). The combined organic layers were washed with saturated brine, dried over anhydrous sodium sulfate and then concentrated to give 2-cyclobutyl-4-methyloxazole-5-carboxylic acid 0.160 g, 55%). ¹H NMR (400 MHz, DMSO-d): δ, 4.31 (m, 2H), 3.66 (m, 1H), 1.98-2.36 (9H), 1.30 (3H, J=7.2 Hz)

Intermediate 4

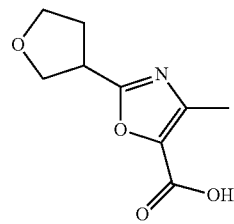

To a solution of tetrahydro-3-furancarboxylic acid (20.00 g, 172 mmol) in MeOH (350 mL) was added sulfuric acid (27.54 mL, 517 mmol). The reaction was heated to reflux for 18 h. The reaction was then cooled to rt and concentrated. The residue was partitioned between water (500 mL) and DCM (200 mL). The phases were separated and the aqueous fraction was extracted with DCM (200 mL). The combined organic fractions were washed with saturated aqueous NaHCO₃ (200 mL) and brine (200 mL), dried over Na₂SO₄, filtered, and concentrated to afford methyl tetrahydro-3-furancarboxylate (15.0 g, 67% yield) as a pale yellow oil. ¹H NMR (400 MHz, DMSO-d) δ ppm 3.85 (t, J=8.4 Hz, 1H), 3.77-3.66 (m, 3H), 3.62 (s, 3H), 3.07-3.22 (m, 1H), 1.97-2.12 (m, 2H).

To a solution of methyl tetrahydrofuran-3-carboxylate (15 g) in ammonia (7 N solution in MeOH, 110 mL) was heated to 80° C. for 72 h. The reaction mixture was then concentrated and dried under high vacuum to afford tetrahydrofuran-3-carboxamide (15 g, quantitative yield) as an off-white solid. ¹H NMR (400 MHz, DMSO-d) δ ppm 7.38 (brs, 1H), 6.87 (brs, 1H), 3.84 (t, J=8.0 Hz, 1H), 3.72-3.62 (m, 3H), 2.92 (m, 1H), 1.98 (m, 2H).

To a suspension of 2-chloroethyl acetoacetate (5.50 g, 33.42 mmol) and tetrahydrofuran-3-carboxamide (2.07 g, 35.09 mmol) was heated at 120° C. for overnight. The mixture was cooled to room temperature, ethyl acetate (100 mL) was added and the insoluble matters were filtered off. Water was added to the filtrate, the organic layer was separated and the aqueous layer was extracted with ethyl acetate. The combined organic layers were washed with saturated brine, dried over anhydrous sodium sulfate and then concentrated. The residue was purified by silica gel column chromatography (dichloromethane/methanol, 95:5) to give ethyl 4-methyl-2-(tetrahydrofaran-3-yl)oxazole-5-carboxylate 1.80 g, 24%). ¹H NMR (400 MHz, DMSO-d): δ, 4.34-4.26 (m, 3H), 3.84 (m, 6H), 2.35-2.10 (m, 6H), 1.30 (m, 3H).

A solution of ethyl 4-methyl-2-(tetrahydrofuran-3-yl)oxazole-5-carboxylate (1.80 g, 7.99 mmol) in MeOH (40 mL) was added LiOH.H₂O (0.71 g, 16.93 mmol) and 10 mL of water. The resulting solution was stirred at room temperature for 18 h and the pH was adjusted to 3 with 6N HCl. This mixture was further extracted with ethyl acetate (3×50 mL). The combined organic layers were washed with saturated brine, dried over anhydrous sodium sulfate and then concentrated to give 4-methyl-2-(tetrahydrofuran-3-yl)oxazole-5-carboxylic acid (0.45 g, 28%). ¹H NMR (400 MHz, DMSO-d): δ 12.85 (br s, 1H), 3.85 (m, 5H).

Intermediate 5

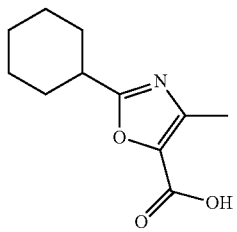

To a suspension of 2-chloroethyl acetoacetate (4.00 g, 24.30 mmol) and cyclohexanecarboxamide (3.09 g, 24.30 mmol) was heated at 120° C. for 18 h. The mixture was cooled to room temperature, ethyl acetate (100 mL) was added and the resulting precipitates were filtered off and washed with hexanes. This compound was used in the next step without further purification.

A solution of ethyl 2-cyclohexyl-4-methyloxazole-5-carboxylate (3.00 g, 12.64 mmol) in THF (45 mL) was added LiOH.H$_2$O (0.71 g, 16.93 mmol) and 10 mL of water. The resulting solution was stirred at room temperature for 18 h and the pH was adjusted to 3 with 6N HCl. This mixture was further extracted with ethyl acetate (3×50 mL). The combined organic layers were washed with saturated brine, dried over anhydrous sodium sulfate and then concentrated to give 4-methyl-2-(tetrahydrofuran-3-yl)oxazole-5-carboxylic acid. After the vacuum dry, the crude solid was used directly in the next step without further purification. MS (ESI): Calcd. for C$_{11}$H$_{15}$NO$_3$: 209, found 210 (M+1)$^+$.

Intermediate 6

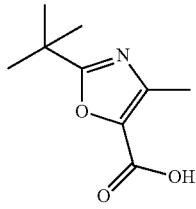

A solution of pivalic acid (1.00 g, 9.79 mmol), 2-chloroethyl acetoacetate (1.64 g, 9.79 mmol) and TEA (2.97 g, 29.37 mmol) in DMF (20 mL) was stirred at room temperature for 18 h. Added water (50 mL) and extracted with EtOAc (3×50 mL) and the combined organic layers were washed with water (3×50 mL) and brine (2×50 mL). After separation, organic layers were dried over sodium sulfate and then concentrated to give ethyl 3-oxo-2-(pivaloyloxy) butanoate and used in the next step without further purification.

A solution of 3-oxo-2-(pivaloyloxy)butanoate (1.00 g, 4.62 mmol) and ammonium trifluoroacetate (6.06 g, 46.25 mmol) was stirred at 150° C. for 5 min. The resulting mixture was cooled to room temperature, then 50 mL of water was added and the organic layer was separated and the aqueous layer was extracted with ethyl acetate (3×50 mL). The combined organic layers were washed with saturated brine, dried over anhydrous sodium sulfate and then concentrated. The residue was purified by silica gel column chromatography (hexane/ethyl acetate, 3:1) to give ethyl 2-(tert-butyl)-4-methyloxazole-5-carboxylate and used in the next step without further purification.

A solution of ethyl 2-(tert-butyl)-4-methyloxazole-5-carboxylate (1.00 g, 4.73 mmol) in MeOH (16 mL) was added LiOH.H$_2$O (0.596 g, 14.20 mmol) and 4 mL of water. The resulting solution was stirred at room temperature for 18 h and the pH was adjusted to 3 with 6N HCl. This mixture was further extracted with ethyl acetate (3×50 mL). The combined organic layers were washed with saturated brine, dried over anhydrous sodium sulfate and then concentrated to give 2-(tert-butyl)-4-methyloxazole-5-carboxylic acid, 0.465 g, 53%). $^1$H NMR (400 MHz, DMSO-d): δ, 13.11 (br s, 1H), 2.33 (s, 3H), 1.32 (s, 9H); MS (ESI): Calcd. for C9H13NO3: 183, found 184 (M+1)$^+$.

Intermediate 7

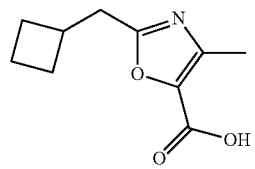

A solution of 2-cyclobutylacetic acid (2.00 g, 17.52 mmol), 2-chloroethyl acetoacetate (2.88 g, 17.52 mmol) and TEA (1.77 g, 17.52 mmol) in DMF (20 mL) was stirred at room temperature for 18 h. Added water (50 mL) and extracted with EtOAc (3×50 mL) and the combined organic layers were washed with water (3×50 mL) and brine (2×50 mL). After separation, organic layers were dried over sodium sulfate and then concentrated to give ethyl 2-(2-cyclobutylacetoxy)-3-oxobutanoate and used in the next step without further purification.

A solution of ethyl 2-(2-cyclobutylacetoxy)-3-oxobutanoate (1.00 g, 4.13 mmol) and ammonium trifluoroacetate (5.41 g, 41.0 mmol) was stirred at 150° C. for 15 min. The resulting mixture was cooled to room temperature, then 50 mL of water was added and the organic layer was separated and the aqueous layer was extracted with ethyl acetate (3×50 mL). The combined organic layers were washed with saturated brine, dried over anhydrous sodium sulfate and then concentrated. The residue was purified by silica gel column chromatography (hexane/ethyl acetate, 3:1) to give ethyl 2-cyclobutyl-4-methyloxazole-5-carboxylate 0.63 g, 69%) and which was used in the next step without further characterization.

A solution of ethyl 2-cyclobutyl-4-methyloxazole-5-carboxylate (0.63 g, 2.82 mmol) in MeOH (16 mL) was added LiOH.H$_2$O (0.563 g, 13.44 mmol) and 4 mL of water. The resulting solution was stirred at room temperature for 18 h and the pH was adjusted to 3 with 6N HCl. This mixture was further extracted with ethyl acetate (3×50 mL). The combined organic layers were washed with saturated brine, dried over anhydrous sodium sulfate and then concentrated to give 2-(cyclobutylmethyl)-4-methyloxazole-5-carboxylic acid 0.22 g, 35%). $^1$H NMR (400 MHz, DMSO-d): δ, 13.30 (br s, 1H), 2.85 (m 2H), 2.68 (m, 1H), 2.31 (s, 3H), 2.05 (m, 2H), 1.82 (m, 4H). MS (ESI): Calcd. for C$_{10}$H$_{13}$NO$_3$: 195, found 196 (M+1)$^+$.

Intermediate 8

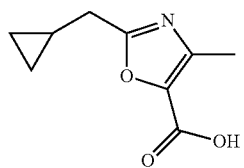

A solution of 2-cyclopropylacetic acid (1.00 g, 9.99 mmol), 2-chloroethyl acetoacetate (1.64 g, 9.99 mmol) and TEA (3.03 g, 29.96 mmol) in DMF (20 mL) was stirred at room temperature for 18 h. Added water (50 mL) and extracted with EtOAc (3×50 mL) and the combined organic layers were washed with water (3×50 mL) and brine (2×50 mL). After separation, organic layers were dried over sodium sulfate and then concentrated to give ethyl 2-(2-cyclopropylacetoxy)-3-oxobutanoate and used in the next step without further purification.

A solution of ethyl ethyl 2-(2-cyclopropylacetoxy)-3-oxobutanoate (1.00 g, 4.38 mmol) and ammonium trifluoroacetate (5.74 g, 44.0 mmol) was stirred at 150° C. for 15 min. The resulting mixture was cooled to room temperature, then 50 mL of water was added and the organic layer was separated and the aqueous layer was extracted with ethyl acetate (3×50 mL). The combined organic layers were washed with saturated brine, dried over anhydrous sodium sulfate and then concentrated. The residue was purified by silica gel column chromatography (hexane/ethyl acetate, 3:1) to give ethyl 2-(cyclopropylmethyl)-4-methyloxazole-5-carboxylate 0.108 g) and which was used in the next step without further characterization.

A solution of ethyl 2-(cyclopropylmethyl)-4-methyloxazole-5-carboxylate (1.00 g, 4.78 mmol) in MeOH (16 mL) was added LiOH.H$_2$O (0.60 g, 14.34 mmol) and 4 mL of water. The resulting solution was stirred at room temperature for 18 h and the pH was adjusted to 3 with 6N HCl. This mixture was further extracted with ethyl acetate (3×50 mL). The combined organic layers were washed with saturated brine, dried over anhydrous sodium sulfate and then concentrated to give 2-(cyclobutylmethyl)-4-methyloxazole-5-carboxylic acid 0.108 g). $^1$H NMR (400 MHz, DMSO-d): δ, 13.30 (br s, 1H), 2.68 (m, 2H), 2.33 (s, 3H), 1.08 (m, 1H), 0.50 (m, 2H), 0.22 (m, 2H); MS (ESI): Calcd. for C$_9$H$_{11}$NO$_3$: 181, found 182 (M+1)$^+$.

Intermediate 9

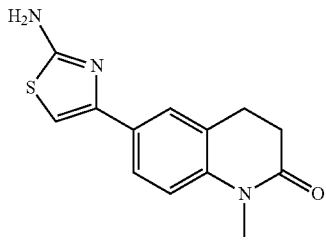 [SMILES: CN1C(=O)CCc2cc(-c3csc(N)n3)ccc21]

6-(2-Chloroacetyl)-1-methyl-1,2,3,4-tetrahydroquinoinolin-2-one (0.50 g, 2.10 mmol) and thiourea (0.17 g, 2.21 mmol) suspended in anhydrous ethanol (4 ml) in a sealed tube under argon atmosphere. The sealed tube was microwaved at 120° C. for 35 min. The mixture was diluted with tetrahydrofuran (100 mL), neutralized with triethylamine (2 mL), and extracted with ethyl acetate (2×200 mL) followed by washing with saturated sodium bicarbonate (2×100 mL). The combined organic layers were dried over anhydrous Na$_2$SO$_4$ and concentrated in vacuo. The residue was purified by precipitating in dichloromethane and filtration to give 6-(2-aminothiazol-4-yl)-1-methyl-3,4-dihydroquinolin-2(1H)-one (0.50 g, 92%) as a vanilla, solid. $^1$H NMR (400 MHz, DMSO-d): δ 7.67 (dd, 1H, J=8.4, 2.0 Hz), 7.64 (d, 1H, J=1.6 Hz), 7.06 (d, 1H, J=8.4 Hz), 7.02 (s, 2H), 6.91 (s, 1H), 3.26 (s, 3H), 2.88 (t, 2H, J=6.4 Hz), 2.55 (t, 2H, J=6.8 Hz). MS (ESI): Calcd. for C$_{13}$H$_{13}$N$_3$OS: 259, found 260 (M+1)$^+$.

Intermediate 10

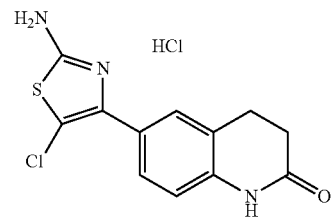 [SMILES: Nc1nc(-c2ccc3c(c2)CCC(=O)N3)c(Cl)s1 ; Cl]

6-(2,2-dichloroacetyl)-3,4-dihydroquinolin-2(1H)-one (1.00 g, 3.87 mmol) and thiourea (0.310 g, 4.07 mmol) suspended in anhydrous acetonitrile (12 ml) in a sealed under argon atmosphere. The sealed tube was heated at 45° C. for 4 days. The yellow precipitate was collected by filtration and washed with cold ethanol. The solid was dried in vacuo to give 6-(2-amino-5-chlorothiazol-4-yl)-3,4-dihydroquinolin-2(1H)-one hydrochloride (0.90 g, 74%) as a yellow solid. $^1$H NMR (400 MHz, DMSO-d): δ 10.22 (s, 1H), 7.61 (s, 1H), 6.89 (d, 1H, J=8.4 Hz), 6.30 (bs, 2H), 2.91 (m, 2H), 2.47 (partial masked under d-DMSO, m, 2H). MS (ESI): Calcd. for C$_{12}$H$_{11}$Cl$_2$N$_3$OS: 316, found 280 (M+1−HCl)$^+$.

Example Compounds

Example 1

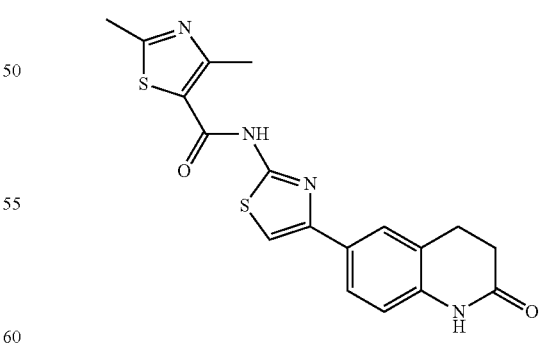

To a suspension of 6-(2-aminothiazol-4-yl)-3,4-dihydroquinoiolin-2(1H)-one (0.050 g, 0.203 mmol) and 2,4-dimethylthiazole-5-carboxylic acid (0.035 g, 0.224 mmol), and pyridine (0.06 mL, 0.713 mmol) in acetonitrile (2 mL) in a sealed tube was added propylphosphonic anhydride solution (50 wt % in ethyl acetate, 0.29 mL, 0.489 mmol). The sealed tube was heated to 48.5° (C for 4 days and the precipitation formed. After cooling, the solid was collected by filtration and washed with cold dichloromethane to give 2,4-dimethyl-N-(4-(2-oxo-1,2,3,4-tetrahydroquinolin-6-yl)thiazol-2-yl)thiazole-5-carboxamide (0.045 g, 58%) as a beige solid. $^1$H NMR (400 MHz, DMSO-d): δ 12.58 (bs, 1H), 10.18 (s, 1H), 7.74 (s, 1H), 7.69 (dd, 1H, J=8.4, 1.6 Hz), 7.45 (bs, 1H), 6.88 (d, 1H, J=8.4 Hz), 2.93 (m, 2H), 2.66 (s, 3H), 2.61 (s, 3H), 2.48 (partial masked under d-DMSO, m, 2H). MS (ESI): Calcd. for $C_{18}H_{16}N_4O_2S_2$: 384, found 385 (M+1)$^+$.

Example 2

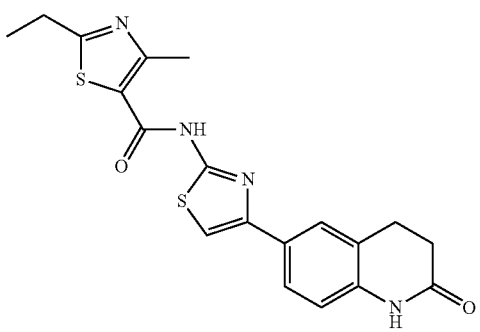

To a suspension of 6-(2-aminothiazol-4-yl)-3,4-dihydroquinolin-2(1H)-one (0.100 g, 0.408 mmol) and 2-ethyl-4-methyl-1,3-thiazole-5-carboxylic acid (0.077 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days and the precipitation formed. After cooling, the precipitate was collected by filtration and washed with cold 1:1 acetonitrile/water to give 2-ethyl-4-methyl-N-(4-(2-oxo-1,2,3,4-tetrahydroquinolin-6-yl)thiazol-2-yl)thiazole-5-carboxamide (0.094 g, 58%) as a beige solid. $^1$H NMR (400 MHz, DMSO-d): δ 12.56 (bs, 1H), 10.19 (s, 1H), 7.74 (s, 1H), 7.69 (dd, 1H, J=8.4, 1.6 Hz), 7.51 (bs, 1H), 6.89 (d, 1H, J=8.4 Hz), 2.99 (q, 2H, J=7.6 Hz), 2.93 (m, 2H), 2.62 (s, 3H), 2.49 (partial masked under d-DMSO, m, 2H), 1.32 (t, 3H, J=7.6 Hz), MS (ESI): Calcd. for $C_{19}H_{18}N_4O_2S_2$: 398, found 399 (M+1)$^+$.

Example 3

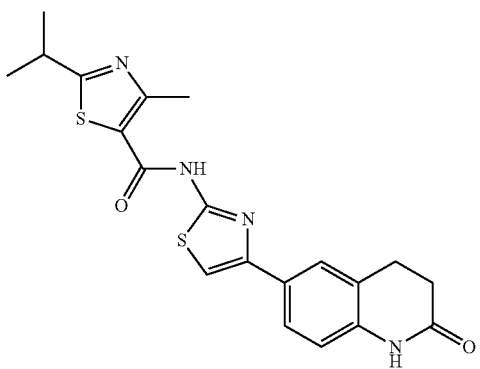 [SMILES: Cc1nc(C(C)C)sc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one hydrochloride (0.100 g, 0.408 mmol) and 4-methyl-2-(propan-2-yl)-1,3-thiazole-5-carboxylic acid (0.083 g, 0.448 mmol), and pyridine (0.15 m L, 1.831 mmol) in acetonitrile (4 mL) in a sealed tube was added propylphosphonic anhydride solution (50 wt % in ethyl acetate, 0.85 mL, 1.431 mmol). The sealed tube was heated to 50° C. for 5 days and the precipitation formed. After cooling, the precipitate was collected by filtration and washed with cold 1:1 acetonitrile/water to give 2-isopropyl-4-methyl-N-(4-(2-oxo-1,2,3,4-tetrahydroquinolin-6-yl)thiazol-2-yl)thiazole-5-carboxamide (0.104 g, 62%) as a beige solid. $^1$H NMR (400 MHz, DMSO-d): δ 12.56 (bs, 1H), 10.19 (s, 1H), 7.74 (s, 1H), 7.69 (dd, 1H, J=8.4, 1.6 Hz), 7.51 (s, 1H), 6.89 (d, 1H, J=8.4 Hz), 3.29 (m, 1H), 2.93 (m, 2H), 2.62 (s, 3H), 2.49 (partial masked under d-DMSO, m, 2H), 1.36 (s, 3H), 1.34 (s, 3H). MS (ESI): Calcd. for $C_{20}H_{20}N_4O_2S_2$: 412, found 413 (M+1)$^+$.

Example 4

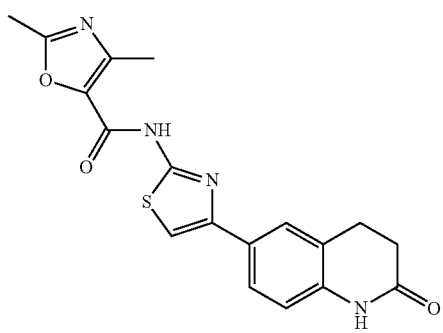 [SMILES: Cc1nc(C)c(C(=O)Nc2nc(-c3ccc4c(c3)CCC(=O)N4)cs2)o1]

To a suspension of 6-(2-aminothiazol-4-yl)-3,4-dihydroquinolin-2(1H)-one (0.100 g, 0.408 mmol) and dimethyl-1,3-oxazole-5-carboxylic acid (0.063 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 6 days. After cooling, the mixture was quenched with water (3 mL) and the precitate was collected by filtration washing with cold 1:1 acetonitrile/water mixture. The residue was purified by precipitating in dichloromethane and filtration to give 2,4-dimethyl-N-(4-(2-oxo-1,2,3,4-tetrahydroquinolin-6-yl)thiazol-2-yl)oxazole-5-carboxamide (0.12 g, 83%) as a beige solid. $^1$H NMR (400 MHz, DMSO-d): δ 12.38 (bs, 1H), 10.19 (s, 1H), 7.75 (s, 1H), 7.70 (dd, 1H, J=8.4, 2.0 Hz), 7.52 (s, 1H), 6.89 (d, 1H, J=8.4 Hz), 2.93 (t, 2H, J=7.2 Hz), 2.48 (partial masked under d-DMSO, m, 5H), 2.40 (s, 3H). MS (ESI): Calcd. for $C_{18}H_{16}N_4O_3S$: 368, found 369 (M+1)$^+$.

Example 5

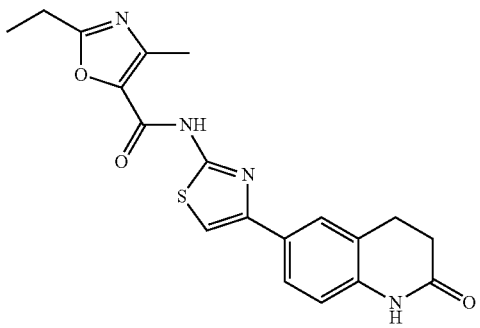 [SMILES: CCc1nc(C)c(C(=O)Nc2nc(-c3ccc4c(c3)CCC(=O)N4)cs2)o1]

To a suspension of 6-(2-aminothiazol-4-yl)-3,4-dihydroquinolin-2(1H)-one (0.300 g, 1.221 mmol) and 2-ethyl-4-methyl-1,3-oxazole-5-carboxylic acid (0.209 g, 1.352 mmol), and pyridine (0.45 mL, 5.501 mmol) in acetonitrile (12 mL) in a sealed tube was added propylphosphonic anhydride solution (50 wt % in ethyl acetate, 2.55 mL, 4.281 mmol). The sealed tube was heated to 50° C. for 6 days and the precipitation formed. After cooling, the precipitate was collected by filtration and washed with cold 1:1 acetonitrile/water to give 2-ethyl-4-methyl-N-(4-(2-oxo-1,2,3,4-tetrahydroquinolin-6-yl)thiazol-2-yl)oxazole-5-carboxamide (0.381 g, 81%) as a beige solid. $^1$H NMR (400 MHz, DMSO-d): δ 12.57 (bs, 1H), 10.19 (s, 1H), 7.75 (s, 1H), 7.71 (dd, 1H, J=8.0, 1.6 Hz), 7.52 (s, 1H), 6.89 (d, 1H, J=8.4 Hz), 2.93 (m, 2H), 2.81 (q, 2H, J=7.2 Hz), 2.49 (partial masked under d-DMSO, m, 2H), 2.42 (s, 3H), 1.32 (t, 3H, J=7.6 Hz). MS (ESI): Calcd. for $C_{19}H_{18}N_4O_3S$: 382, found 383 $(M+1)^+$.

Example 6

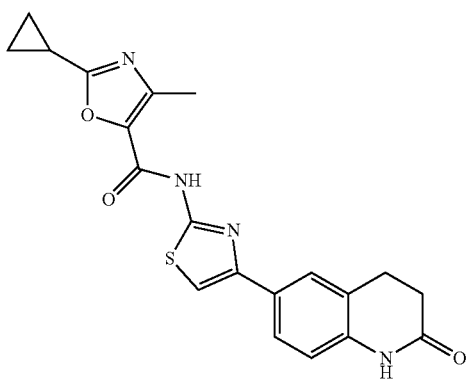 [SMILES: Cc1nc(C2CC2)oc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one hydrochloride (0.100 g, 0.408 mmol) and 2-cyclopropyl-4-methyl-1,3-oxazole-5-carboxylic acid (0.072 g, 0.428 mmol), and pyridine (0.15 mL, 1.831 mmol) in acetonitrile (4 mL) in a sealed was added propylphosphonic anhydride solution (50 wt % in ethyl acetate, 0.85 mL, 1.431 mmol). The sealed tube was heated to 50° C. for 5 days and the precipitation formed. After cooling, the precipitate was collected by filtration and washed with cold 1:1 acetonitrile/water to give 2-cyclopropyl-4-methyl-N-(4-(2-oxo-1,2,3,4-tetrahydroquinolin-6-yl)thiazol-2-yl)oxazole-5-carboxamide (0.143 g, 89%) as a beige solid. $^1$H NMR (400 MHz, DMSO-d): δ 12.52 (bs, 1H), 10.19 (s, 1H), 7.75 (s, 1H), 7.71 (dd, 1H, J=8.4, 1.6 Hz), 7.52 (s, 1H), 6.89 (d, 1H, J=8.4 Hz), 2.93 (m, 2H), 2.49 (partial masked under d-DMSO, in, 2H), 2.39 (s, 3H), 2.14 (m, 1H), 1.25 (m, 2H), 1.12 (m, 2H). MS (ESI): Calcd. for $C_{20}H_{18}N_4O_3S$: 394, found 395 $(M+1)^+$.

Example 7

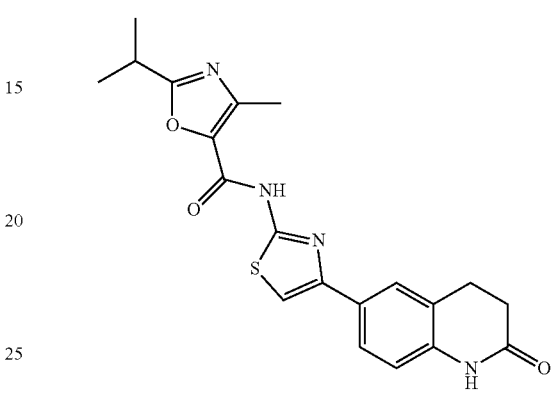

To a suspension of 6-(2-amino-5-chlorothiazol-4-yl)-3,4-dihydroquinolin-2(1H)-one (0.136 g, 0.59 mmol) and 2-isopropyl-4-methyloxazole-5-carboxylic acid (0.11 g, 0.65 mmol), and pyridine (0.21 mL, 2.67 mmol) in acetonitrile (4 mL) in a sealed tube was added propylphosphonic anhydride solution (50 wt % in ethyl acetate, 0.91 mL, 2.08 mmol). The sealed tube was heated to 50° C. for 5 days and the precipitation formed. After cooling, the precipitate was collected by filtration and washed with cold 1:1 acetonitrile/water to give 2-isopropyl-4-methyl-N-(4-(2-oxo-1,2,3,4-tetrahydroquinolin-6-yl)thiazol-2-yl)oxazole-5-carboxamide (0.061 g, 26%). $^1$H NMR (400 MHz, DMSO-d): δ 12.63 (bs, 1H), 10.19 (s, 1H), 7.76 (s, 1H), 7.70 (dd, 1H, J=8.4, 2.0 Hz), 7.52 (s, 1H), 6.89 (d, 1H, J=8.0 Hz), 3.13 (m, 1H), 2.93 (t, 2H, J=7.2 Hz), 2.48 (partial masked under d-DMSO, nm, 2H), 2.42 (s, 3H), 1.36 (s, 3H), 1.34 (s, 3H. MS (ESI): Calcd. for $C_{20}H_{20}N_4O_3S$: 396, found 397 $(M+1)^+$.

Example 8

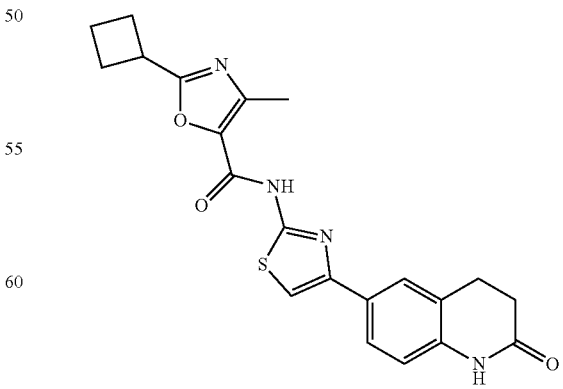

To a suspension of 6-(2-amino-5-chlorothiazol-4-yl)-3,4-dihydroquinolin-2(1H)-one (0.100 g, 0.406 mmol) and 2-cyclobutyl-4-methyloxazole-5-carboxylic acid (0.077 g, 0.428 mmol), and pyridine (0.15 mL, 1.831 mmol) in acetonitrile (4 mL) in a sealed tube was added propylphosphonic anhydride solution (50 wt % in ethyl acetate, 0.85 mL, 1.83 mmol). The sealed tube was heated to 50° C. for 5 days and the precipitation formed. After cooling, the precipitate was collected by filtration and washed with cold 1:1 acetonitrile/water to give 2-cyclobutyl-4-methyl-N-(4-(2-oxo-1,2,3,4-tetrahydroquinolin-6-yl)thiazol-2-yl)oxazole-5-carboxamide (0.044 g, 25%) as a beige solid. $^1$H NMR (400 MHz, DMSO-d): δ 12.67 (bs, 1H), 10.19 (s, 1H), 7.76 (s, 1H), 7.70 (dd, 1H, J=8.4, 2.0 Hz), 7.53 (s, 1H), 6.91 (d, 1H, J=8.0 Hz), δ, 3.70 (m, 1H), 2.95 (t, 2H, J=7.2 Hz), 2.48 (partial masked under d-DMSO, m, 2H), 1.98-2.36 (8H); MS (ESI): Calcd. for $C_{21}H_{20}N_4O_3S$: 408, found 409 (M+1)$^+$.

Example 9

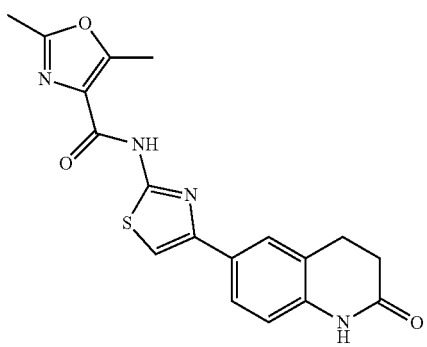 [SMILES: Cc1nc(C(=O)Nc2nc(-c3ccc4c(c3)CCC(=O)N4)cs2)c(C)o1]

To a suspension of 6-(2-amino-5-chlorothiazol-4-yl)-3,4-dihydroquinolin-2(1H)-one (0.100 g, 0.44 mmol) and 2,5-dimethyl-1,3-oxazole-4-carboxylic acid (0.068 g, 0.48 mmol), and pyridine (0.16 mL, 1.96 mmol) in acetonitrile (4 mL) in a sealed tube was added propylphosphonic anhydride solution (50 wt % in ethyl acetate, 0.91 mL, 1.53 mmol). The sealed tube was heated to 50° C. for 5 days and the precipitation formed. After cooling, the precipitate was collected by filtration and washed with cold 1:1 acetonitrile/water to give 2,5-dimethyl-N-(4-(2-oxo-1,2,3,4-tetrahydroquinolin-6-yl)thiazol-2-yl)oxazole-4-carboxamide (0.039 g, 23%). $^1$H NMR (400 MHz, DMSO-d): δ 11.49 (bs, 1H), 10.19 (s, 1H), 7.75 (m, 1H), 7.70 (dd, 1H, J=8.4, 2.0 Hz), 7.52 (s, 1H), 6.89 (d, 1H, J=8.0 Hz), 3.13 (m, 1H), 2.93 (t, 2H, J=7.2 Hz), 2.61 (s, 3H), 2.48 (partial masked under d-DMSO, m, 2H), 2.47 (s, 3H); MS (ESI): Calcd. for $C_{18}H_{16}N_4O_3S$: 368, found 369 (M+1)$^+$.

Example 10

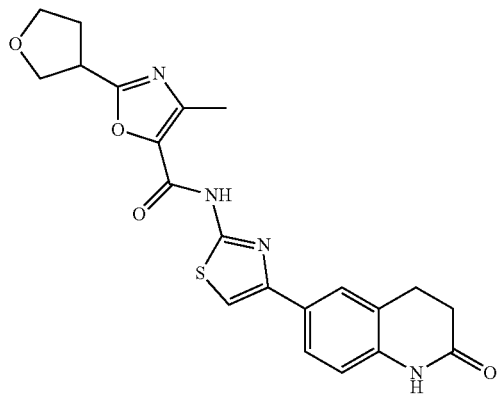 [SMILES: Cc1nc(C2CCOC2)oc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.406 mmol) and 4-methyl-2-(tetrahydrofuran-3-yl)oxazole-5-carboxylic acid (0.095 g, 0.48 mmol), and pyridine (0.15 mL, 1.831 mmol) in acetonitrile (4 mL) in a sealed tube was added propylphosphonic anhydride solution (50 wt % in ethyl acetate, 0.80 mL, 0.78 mmol). The sealed tube was heated to 100° C. for over night and the precipitation formed. After cooling, the precipitate was collected by filtration and washed with cold 1:1 acetonitrile/water to give 4-methyl-N-(4-(2-oxo-1,2,3,4-tetrahydroquinolin-6-yl)thiazol-2-yl)-2-(tetrahydrofuran-3-yl)oxazole-5-carboxamide (0.065 g, 35%) as a beige solid. $^1$H NMR (400 MHz, DMSO-d): δ 12.67 (bs, 1H), 10.19 (s, 1H), 7.75 (s, 1H), 7.69 (dd, 1H, J=8.4, 2.0 Hz), 6.91 (d, 1H, J=8.0 Hz), 4.05 (m, 2H), 3.92-3.64 (m, 5H), 2.95 (t, 2H, J=7.2 Hz), 2.48 (partial masked under d-DMSO, m, 2H), 2.42 (s, 3H); MS (ESI): Calcd. for $C_{21}H_{20}N_4O_4S$: 424, found 425 (M+1)$^+$.

Example 11

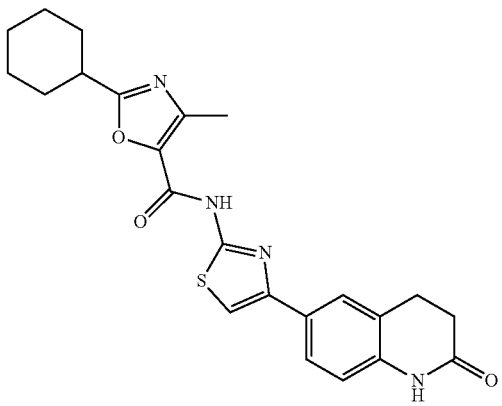 [SMILES: Cc1nc(C2CCCCC2)oc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 2-cyclohexyl-4-methyloxazole-5-carboxylic acid (0.094 g, 0.45 mmol), and pyridine (0.15 mL, 1.83 mmol) in acetonitrile (5 mL) in a sealed tube was added propylphosphonic anhydride solution (50 wt % in ethyl acetate, 0.61 mL, 1.02 mmol). The sealed tube was heated to 100° C. for over night and the precipitation formed. After cooling, the precipitate was collected by filtration and washed with cold 1:1 acetonitrile/water to give 2-cyclohexyl-4-methyl-N-(4-(2-oxo-1,2,3,4-tetrahydroquinolin-6-yl)thiazol-2-yl)oxazole-5-carboxamide (0.100 g, 56%). $^1$H NMR (400 MHz, DMSO-d): δ 12.67 (bs, 1H), 10.19 (s, 1H), 7.76 (s, 1H), 7.69 (dd, 1H, J=8.4, 2.0 Hz), 6.91 (d, 1H, J=8.0 Hz), 2.85 (m, 3H, 2.41 (s, 3H), 2.06 (m, 2H), 1.71 (m, 4H), 1.25 (m, 4H). MS (ESI): Calcd. for $C_{23}H_{24}N_4O_3S$: 436, found 437 (M+1)$^+$.

Example 12

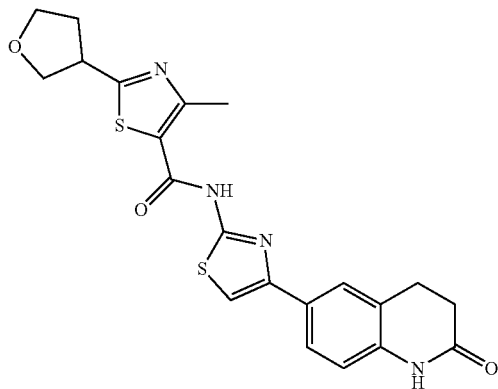 [SMILES: Cc1nc(C2CCOC2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 4-methyl-2-(oxolan-3-yl)-1,3-thiazole-5-carboxylic acid (0.096 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days and the precipitation formed. After cooling, the precipitate was collected by filtration and washed with cold 1:1 acetonitrile/water to give 4-methyl-N-(4-(2-oxo-1,2,3,4-tetrahydroquinolin-6-yl)thiazol-2-yl)-2-(tetrahydrofran-3-yl)thiazole-5-carboxamide (0.114 g, 63%) as a light brown solid. $^1$H NMR (400 MHz, DMSO-d): δ 12.60 (bs, 1H), 10.19 (s, 1H), 7.74 (s, 1H), 7.69 (dd, 1H, J=8.4, 1.6 Hz), 7.51 (bs, 1H), 6.89 (d, 1H, J=8.4 Hz), 4.06 (dd, 1H, J=8.0, 7.2 Hz), 3.92 (m, 1H), 3.86 (m, 1H), 3.81 (m, 1H), 2.93 (m, 2H), 2.63 (s, 3H), 2.49 (partial masked under d-DMSO, m, 2H), 2.40 (m, 1H), 2.12 (m, 1H). MS (ESI): Calcd. for $C_{21}H_{20}N_4O_2S_2$: 440, found 441 (M+1)$^+$.

Example 13

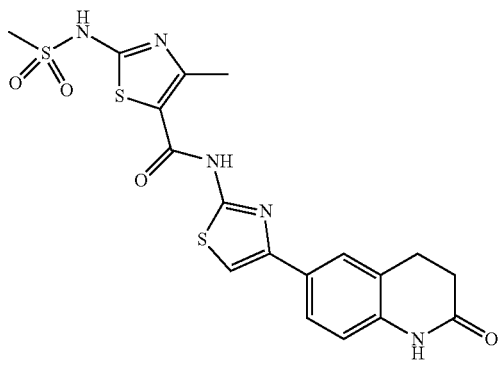 [SMILES: Cc1nc(NS(C)(=O)=O)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 2-methanesulfonylamino-4-thiazole-5-carboxylic acid (0.106 g, 0.448 mmol), and pyridine (0.15 mL, 1.831 mmol) in acetonitrile (4 mL) in a sealed tube was added propylphosphonic anhydride solution (50 wt % in ethyl acetate, 0.85 mL, 1.431 mmol). The sealed tube was heated to 50° C. for 6 days and the precipitation formed. After cooling, the precipitate was collected by filtration and washed with cold 1:1 acetonitrile/water to give 4-methyl-2-(methylsulfonamido)-N-(4-(2-oxo-1,2,3,4-tetrahydroquinolin-6-yl)thiazol-2-yl)thiazole-5-carboxamide (0.122 g, 65%) as a beige solid. $^1$H NMR (400 MHz, DMSO-d): δ 12.91 (bs, 1H), 12.48 (bs, 1H), 10.21 (s, 1H), 7.72 (bs, 1H), 7.67 (d, 1H, J=7.6 Hz), 7.43 (bs, 1H), 6.89 (d, 1H, J=8.8 Hz), 2.97 (s, 3H), 2.93 (m, 2H), 2.49 (partial masked under d-DMSO, m, 5H). MS (ESI): Calcd. for $C_{18}H_{17}N_5O_4S_3$: 463, found 464 (M+1)$^+$.

Example 14

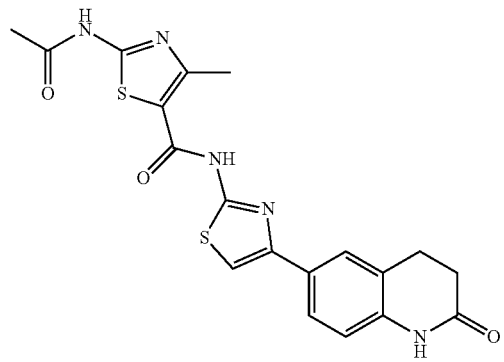 [SMILES: CC(=O)Nc1nc(C)c(C(=O)Nc2nc(-c3ccc4c(c3)CCC(=O)N4)cs2)s1]

To a suspension of 6-(2-amino-5-chlorothiazol-4-yl)-3,4-dihydroquinolin-2(1H)-one (0.110 g, 0.45 mmol) and 2-acetamido-4-methylthiazole-5-carboxylic acid (0.099 g, 0.49 mmol), and pyridine (0.16 mL, 2.02 mmol) in acetonitrile (4 mL) in a sealed tube was added propylphosphonic anhydride solution (50 wt % in ethyl acetate, 0.91 mL, 1.571 mmol). The sealed tube was heated to 50° C. for 5 days and the precipitate formed. After cooling, the precipitate was collected by filtration and washed with cold 1:1 acetonitrile/water to give 2-acetamido-4-methyl-N-(4-(2-oxo-1,2,3,4-tetrahydroquinolin-6-yl)thiazol-2-yl)thiazole-5-carboxamide (0.009 g, 5%) as a beige solid. $^1$H NMR (400 MHz, DMSO-d): δ 12.41 (bs, 1H), 10.19 (s, 1H), 7.74 (s, 1H), 7.69 (m, 1H), 6.90 (m, 1H), 3.17 (m, 1H), 2.94 (m, 3H), 2.58 (s, 3H), 2.18 (s, 3H).

Example 15

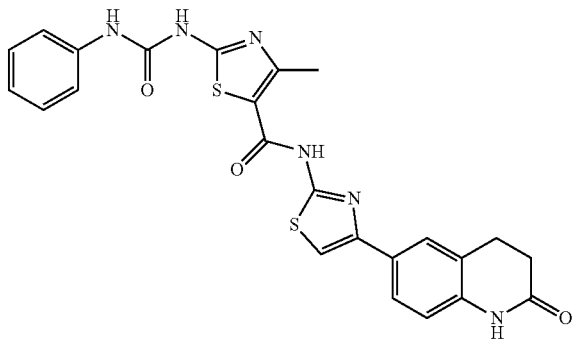 [SMILES: Cc1nc(NC(=O)Nc2ccccc2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 2-[(anilinocarbonyl)amino]-4-methyl-1,3-thiazole-5-carboxylic acid (0.124 g, 0.448 mmol), and pyridine (0.15 mL, 1.831 mmol) in acetonitrile (4 mL) in a sealed tube was added propylphosphonic anhydride solution (50 wt % in ethyl acetate, 0.85 mL, 1.431 mmol). The sealed tube was heated to 50° C. for 7 days and the precipitation formed. After cooling, the precipitate was collected by filtration and washed with cold 1:1 acetonitrile/water. The crude solid was dried loaded onto silica and purified by flash chromatography over silica gel using 95:5 dichloromethane/methanol to give (0.009 g, 4%) as a white solid. $^1$H NMR (400 MHz, DMSO-d): δ 12.36 (bs, 1H), 10.88 (bs, 1H), 10.18 (s, 1H), 9.07 (s, 1H), 7.43 (bs, 1H), 6.89 (dd, 1H, J=8.4, 1.6 Hz), 7.50 (d, 2H, J=8.0 Hz), 7.46 (bs, 1H), 7.34 (m, 2H), 7.06 (m, 1H), 6.89 (d, 1H, J=8.0 Hz), 2.93 (m, 2H), 2.49 (partial masked under d-DMSO, m, 5H). MS (ESI): Calcd. for $C_{24}H_{20}N_6O_3S_2$: 504, found 505 $(M+1)^+$.

Example 16

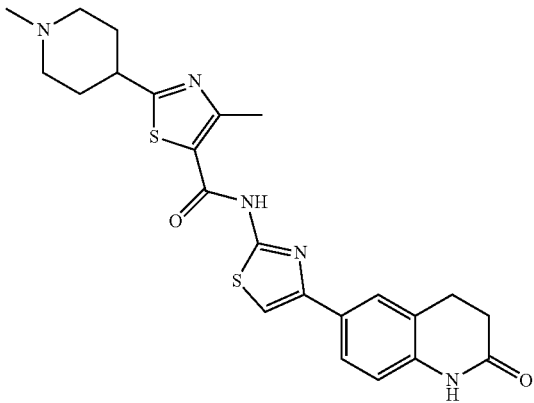 [SMILES: Cc1nc(C2CCN(C)CC2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 4-methyl-2-(1-methylpiperidin-4-yl)thiazole-5-carboxylic acid dihydrochloride (0.141 g, 0.448 mmol), and pyridine (0.15 mL, 1.831 mmol) in acetonitrile (4 mL) in a sealed tube was added propylphosphonic anhydride solution (50 wt % in ethyl acetate, 0.85 mL, 1.431 mmol). The sealed tube was heated to 50° C. for 7 days. The reaction mixture was quenched with sat. NaHCO$_3$ and extracted with 8:2 dichloromethane/isopropanol mixture (3×20 mL). The combined organic layers were washed once with sat. NaHCO$_3$, dried over anhydrous Na$_2$SO$_4$ and concentrated in vacuo. The residue was purified by precipitation in minimum amount of dichloromethane to give 4-methyl-2-(1-methylpiperidin-4-yl)-N-(4-(2-oxo-1,2,3,4-tetrahydroquinolin-6-yl)thiazol-2-yl)thiazole-5-carboxamide (0.146 g, 77%) as an orange solid. $^1$H NMR (400 MHz, DMSO-d): δ 12.31 (bs, 1H), 10.18 (s, 1H), 7.73 (bs, 1H), 7.69 (dd, 1H, J=8.4, 1.6 Hz), 7.46 (s, 1H), 6.89 (d, 1H, J=8.4 Hz), 2.94 (m, 1H), 2.92 (m, 4H), 2.62 (s, 3H), 2.49 (partial masked under d-DMSO, m, 2H), 2.26 (s, 3H), 2.13 (m, 2H), 2.03 (m, 2H), 1.72 (m, 2H). MS (ESI): Calcd. for $C_{23}H_{25}N_5O_2S_2$: 467, found 468 $(M+1)^+$.

Example 17

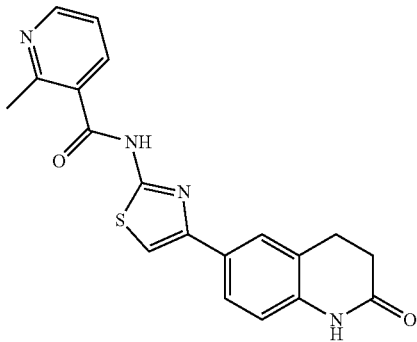 [SMILES: Cc1ncccc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.436 mmol) and 2-methylnicotinic acid (0.066 g, 0.48 mmol), and pyridine (0.16 mL, 1.96 mmol) in acetonitrile (4 mL) in a sealed tube was added propylphosphonic anhydride solution (50 wt % in ethyl acetate, 0.91 mL, 1.53 mmol). The sealed tube was heated to 50° C. for 5 days and clear solution was observed. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 2-methyl-N-(4-(2-oxo-1,2,3,4-tetrahydroquinolin-6-yl)thiazol-2-yl)nicotinamide (0.023 g, 14%). $^1$H NMR (400 MHz, DMSO-d): δ 12.80 (bs, 1H), 10.19 (s, 1H), 8.59 (dd, 1H, J=1.6, 2.0 Hz), 7.76 (m, 1H), 7.71 (m, 1H), 7.69 (m, 1H), 7.56 (s, 1H), 7.36 (m, 1H), 6.91 (d, 1H, J=8.0 Hz), 2.95 (t, 2H, J=7.2 Hz), 2.59 (s, 3H), 2.48 (partial masked under d-DMSO, m, 2H); MS (ESI): Calcd. for $C_{19}H_{16}N_4O_2S$: 364, found 365 $(M+1)^+$.

Example 18

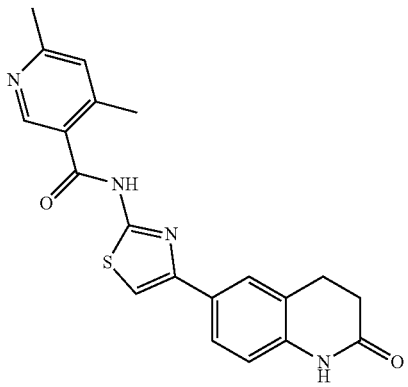 [SMILES: Cc1cc(C)c(C(=O)Nc2nc(-c3ccc4c(c3)CCC(=O)N4)cs2)cn1]

To a suspension of 6-(2-amino-5-chlorothiazol-4-yl)-3,4-dihydroquinolin-2(1H)-one (0.100 g, 0.408 mmol) and 2,4-dimethylpyrimidine-5-carboxylic acid (0.068 g, 0.448 mmol), and pyridine (0.15 mL, 1.831 mmol) in acetonitrile (4 mL) in a sealed tube was added propylphosphonic anhydride solution (50 wt % in ethyl acetate, 0.56 mL, 0.094 mmol). The sealed tube was heated to 100° C. for 16 h and the precipitation formed. After cooling, the precipitate was collected by filtration and washed with cold 1:1 acetonitrile/water to give 2,4-dimethyl-N-(4-(2-oxo-1,2,3,4-tetrahydroquinoinolin-6-yl)thiazol-2-yl)pyrimidine-5-carboxamide (0.117 g, 83%). $^1$H NMR (400 MHz, DMSO-d): δ 12.78 (bs, 1H), 10.18 (s, 1H), 8.63 (s, 1H), 7.74 (m, 1H), 7.69 (m, 1H), 7.54 (s, 1H), 7.24 (s, 1H), 6.91 (d, 1H, J=8.0 Hz), 2.94 (t, 2H, J=7.2 Hz), 2.65 (s, 3H), 2.48 (partial masked under d-DMSO, m, 5H), 2.42 (s, 3H); MS (ESI): Calcd. for $C_{20}H_{18}N_4O_2S$: 378, found 379 (M+1)$^+$.

Example 19

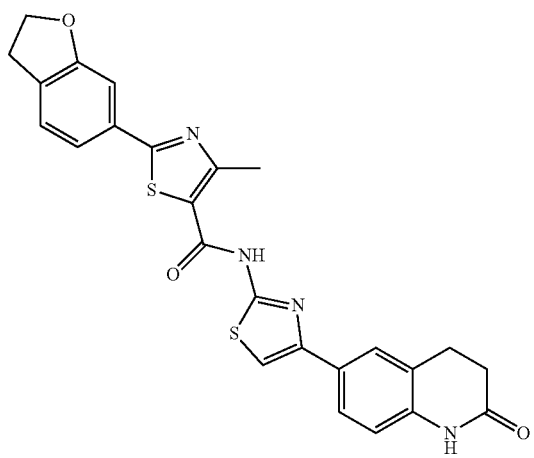 [SMILES: Cc1nc(-c2ccc3c(c2)OCC3)sc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.436 mmol) and 2-(2,3-dihydrobenzofuran-6-yl)-4-methylthiazole-5-carboxylic acid (0.092 g, 0.43 mmol), and pyridine (0.16 mL, 1.96 mmol) in acetonitrile (4 mL) in a sealed tube was added propylphosphonic anhydride solution (50 wt % in ethyl acetate, 0.91 mL, 1.53 mmol). The sealed tube was heated to 100° C. for overnight and precipitate was observed. After cooling, the precipitate was collected by filtration and washed with cold 1:1 acetonitrile/water to give 2-(2,3-dihydrobenzofuran-6-yl)-4-methyl-N-(4-(2-oxo-1,2,3,4-tetrahydroquinolin-6-yl)thiazol-2-yl)thiazole-5-carboxamide (0.145 g, 81%), $^1$H NMR (400 MHz, DMSO-d): δ 12.63 (bs, 1H), 10.20 (s, 1H), 7.86 (m, 1H), 7.76-7.69 (m, 2H), 7.51 (s, 1H), 6.91-6.89 (m, 2H), 4.65 (m, 2H), 3.25 (m, 2H), 2.94 (t, 2H, J=7.2 Hz), 2.68 (m, 2H) 2.48 (partial masked under d-DMSO, m, 5H), MS (ESI): Calcd. for $C_{25}H_{20}N_4O_2S$: 488, found 489 (M+1)$^+$.

Example 20

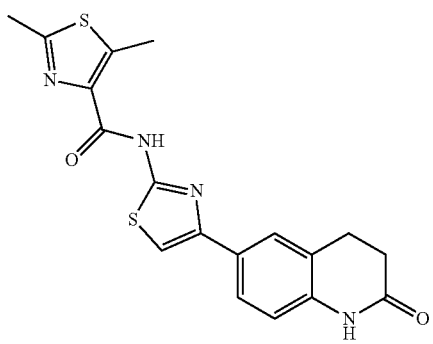 [SMILES: Cc1nc(C(=O)Nc2nc(-c3ccc4c(c3)CCC(=O)N4)cs2)c(C)s1]

To a suspension of 6-(2-amino-5-chlorothiazol-4-yl)-3,4-dihydroquinolin-2(1H)-one (0.100 g, 0.41 mmol) and 2,5-dimethylthiazole-4-carboxylic acid (0.071 g, 0.45 mmol), and pyridine (0.15 mL, 1.83 mmol) in acetonitrile (2.5 mL) in a sealed tube was added propylphosphonic anhydride solution (50 wt % in ethyl acetate, 0.61 m L, 1.02 mmol). The sealed tube was heated to 100° C. for 16 h and the precipitation formed. After cooling, the precipitate was collected by filtration and washed with cold 1:1 acetonitrile/water to give 2,5-dimethyl-N-(4-(2-oxo-1,2,3,4-tetrahydroquinolin-6-yl)thiazol-2-yl)thiazole-4-carboxamide (0.120 g, 77%). $^1$H NMR (400 MHz, DMSO-d): δ 11.32 (bs, 1H), 10.17 (s, 1H), 7.74 (m, 1H), 7.69 (dd, 1H, J=8.4, 2.0 Hz), 7.54 (s, 1H), 6.90 (d, 1H, J=8.4 Hz), 2.95 (t, 2H, J=7.2 Hz), 2.76 (s, 3H), 2.68 (s, 3H) 2.48 (partial masked under d-DMSO, m, 2H), MS (ESI): Calcd, for C18H16N4O2S2: 384, found 385 (M+1)$^+$.

Example 21

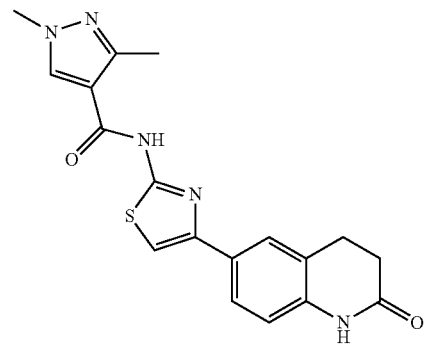 [SMILES: Cc1nn(C)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one hydrochloride (1.501 g, 0.611 mmol) and 1,3-dimethyl-1H-pyrazole-4-carboxylic acid (0.943 g, 0.67 mmol), and pyridine (2.23 mL, 27.52 mmol) in acetonitrile (60 mL) in a sealed tube was added propylphosphonic anhydride solution (50 wt % in ethyl acetate, 9.10 mL, 15.29 mmol). The sealed tube was heated to 100° C. for 24 hours and precipitation was observed. After cooling, the precipitates were collected by filtration washed with 1:1 cold acetonitrile/water to give a beige solid product. The resulting filtrate was partitioned between EtOAc (50 mL) and 50 mL of water. Several extraction with EtOAc (4×25 mL) were made. The combined organic layers were washed with saturated brine, dried over anhydrous sodium sulfate and then concentrated in vacou. The residue was dried loaded onto silica and purified by silica gel column chromatography using 95:5 dichloromethane/methanol to give combined 1,3-dimethyl-N-(4-(2-oxo-1,2,3,4-tetrahydroquinolin-6-yl)thiazol-2-yl)-1H-pyrazole-4-carboxamide (1.04 g, 46%). $^1$H NMR (400 MHz, DMSO-d): δ 12.16 (bs, 1H), 10.18 (s, 1H), 8.55 (s, 1H), 7.73 (bs, 1H), 7.68 (dd, 1H, J=8.0, 2.0 Hz), 7.44 (s, 1H), 6.89 (d, 1H, J=8.0 Hz), δ, 3.82 (s, 3H), 2.93 (m, 2H) 2.48 (partial masked under d-DMSO, m, 2H), 2.39 (s, 3H). MS (ESI): Calcd. for $C_{18}H_{17}N_5O_2S$: 367, found 368 $(M+1)^+$.

Example 22

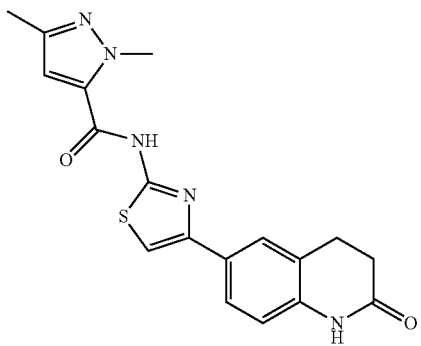 [SMILES: Cc1cc(C(=O)Nc2nc(-c3ccc4c(c3)CCC(=O)N4)cs2)n(C)n1]

To a suspension of 6-(2-amino-5-chlorothiazol-4-yl)-3,4-dihydroquinolin-2(1H)-one (0.100 g, 0.44 mmol) and 1,3-dimethyl-1H-pyrazole-5-carboxylic acid (0.067 g, 0.48 mmol), and pyridine (0.16 mL, 1.96 mmol) in acetonitrile (4 mL) in a sealed tube was added propylphosphonic anhydride solution (50 wt % in ethyl acetate, 0.91 mL, 1.53 mmol). The sealed tube was heated to 50° C. for 5 days and clear solution was observed. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 1,3-dimethyl-N-(4-(2-oxo-1,2,3,4-tetrahydroquinolin-6-yl)thiazol-2-yl)-1H-pyrazole-5-carboxamide (0.035 g, 22%). $^1$H NMR (400 MHz, DMSO-d): δ 12.65 (bs, 1H), 10.18 (s, 1H), 7.76 (m, 1H), 7.69 (dd, 1H, J=8.4, 2.0 Hz), 7.54 (s, 1H), 7.15 (s, 3H), 6.91 (d, 1H, J=8.0 Hz), 4.06 (s, 3H), 2.93 (t, 2H, J=7.2 Hz), 2.48 (partial masked under d-DMSO, in, 2H), 2.20 (s, 3H). MS (ESI): Calcd. for $C_{18}H_{17}N_5O_2S$: 367, found 368 $(M+1)^+$.

Example 23

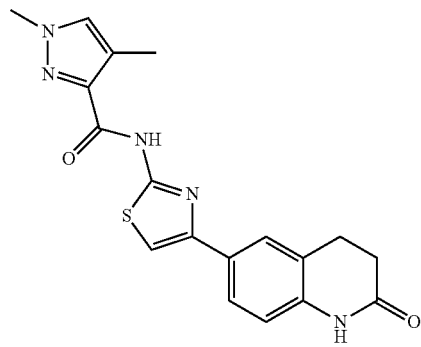 [SMILES: Cc1cn(C)nc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.408 mmol) and 1,4-dimethyl-1H-pyrazole-3-carboxylic acid (0.067 g, 0.48 mmol), and pyridine (0.16 mL, 1.96 mmol) in acetonitrile (4 mL) in a sealed tube was added propylphosphonic anhydride solution (50 wt % in ethyl acetate, 0.91 mL, 1.53 mmol). The sealed tube was heated to 50° C. for 5 days and the precipitation formed. After cooling, the precipitate was collected by filtration and washed with cold 1:1 acetonitrile/water to give 1,4-dimethyl-N-(4-(2-oxo-1,2,3,4-tetrahydroquinolin-6-yl)thiazol-2-yl)-1H-pyrazole-3-carboxamide (0.019 g, 12%). $^1$H NMR (400 MHz, DMSO-d): δ 11.41 (bs, 1H), 10.17 (s, 1H), 7.75 (m, 1H), 7.69 (m, 2H), 7.49 (m, 1H), 6.91 (d, 1H, J=8.0 Hz), 3.91 (s, 3H), 2.94 (t, 2H, J=7.2 Hz), 2.48 (partial masked under d-DMSO, in, 2H), 2.26 (s, 3H). MS (ESI): Calcd. for $C_{18}H_{17}N_5O_2S$: 367, found 368 $(M+1)^+$.

Example 24

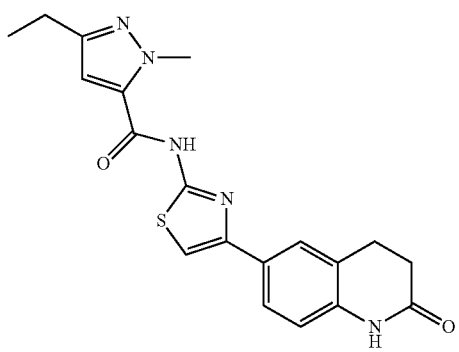 [SMILES: CCc1cc(C(=O)Nc2nc(-c3ccc4c(c3)CCC(=O)N4)cs2)n(C)n1]

To a suspension of 6-(2-amino-5-chlorothiazol-4-yl)-3,4-dihydroquinolin-2(1H)-one (0.100 g, 0.44 mmol) and 3-ethyl-1-methyl-1H-pyrazole-5-carboxylic acid (0.074 g, 0.48 mmol), and pyridine (0.16 mL, 1.96 mmol) in acetonitrile (4 mL) in a sealed tube was added propylphosphonic anhydride solution (50 wt % in ethyl acetate, 0.91 mL, 1.53 mmol). The sealed tube was heated to 50° C. for 5 days and the precipitation formed. After cooling, the precipitate was collected by filtration and washed with cold 1:1 acetonitrile/water to give 3-ethyl-1-methyl-N-(4-(2-oxo-1,2,3,4-tetrahydroquinolin-6-yl)thiazol-2-yl)-1H-pyrazole-5-carboxamide (0.044 g, 26%). $^1$H NMR (400 MHz, DMSO-d): δ 12.64 (bs, 1H), 10.19 (s, 1H), 7.76 (m, 1H), 7.69 (dd, 1H, J=8.4, 2.0 Hz), 7.54 (s, 1H), 7.22 (s, 3H), 6.91 (d, 1H, J=8.0 Hz), 4.07 (s, 3H), 2.93 (t, 2H, J=7.2 Hz), 2.59 (m, 2H), 1.19 (t, 3H, J=7.6 Hz). MS (ESI): Calcd. for $C_{19}H_{19}N_5O_2S$: 381, found 382 (M+1)$^+$.

Example 25

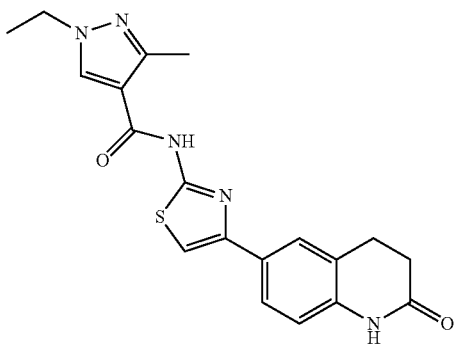 [SMILES: CCn1cc(C(=O)Nc2nc(-c3ccc4c(c3)CCC(=O)N4)cs2)c(C)n1]

To a suspension of 6-(2-amino-5-chlorothiazol-4-yl)-3,4-dihydroquinolin-2(1H)-one (0.300 g, 1.221 mmol) and 1-ethyl-3-methyl-1H-pyrazole-4-carboxylic acid (0.21 g, 1.35 mmol), and DIPEA (0.98 mL, 5.501 mmol) in acetonitrile (12 mL) in a, sealed tube was added propylphosphonic anhydride solution (50 wt % in ethyl acetate, 1.82 mL, 3.06 mmol). The sealed tube was heated to 100° C. for 24 h. After cooling, the mixture was quenched with water (2 mL) and the precitate was collected by filtration washing with cold 1:1 acetonitrile/water mixture. The residue was purified by precipitating in dichloromethane and filtration to give 1-ethyl-3-methyl-N-(4-(2-oxo-1,2,3,4-tetrahydroquinolin-6-yl)thiazol-2-yl)-1H-pyrazole-4-carboxamide (0.41 g, 88%). $^1$H NMR (400 MHz, DMSO-d): δ 12.13 (bs, 1H), 10.18 (s, 1H), 8.63 (s, 1H), 7.73 (m, 1H), 7.69 (dd, 1H, J=8.4, 2.0 Hz), 7.44 (s, 1H), 6.89 (d, 1H, J=8.0 Hz), 4.10 (q, 2H, J=6.8 Hz), 2.93 (m, 2H), 2.48 (partial masked under d-DMSO, m, 2H), 2.40 (s, 3H)), 1.40 (t, 3H, J=6.8 Hz). MS (ESI): Calcd. for $C_{19}H_{19}N_5O_2S$: 381, found 382 (M+1)$^+$.

Example 26

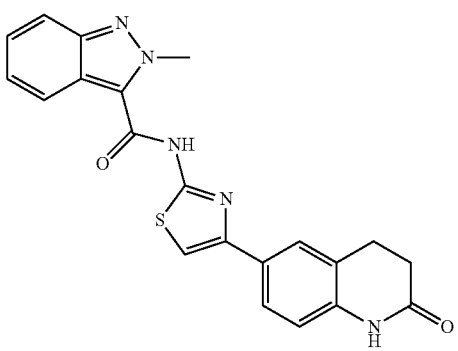 [SMILES: Cn1nc2ccccc2c1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.44 mmol) and 2-methyl-2H-indazole-3-carboxylic acid (0.081 g, 0.46 mmol), and pyridine (0.16 mL, 1.96 mmol) in acetonitrile (4 mL) in a sealed tube was added propylphosphonic anhydride solution (50 wt % in ethyl acetate, 0.56 mL, 0.094 mmol). The sealed tube was heated to 100° C. for overnight and precipitate was observed. After cooling, the precipitate was collected by filtration and washed with cold 1:1 acetonitrile/water to give 2-methyl-N-(4-(2-oxo-1,2,3,4-tetrahydroquinolin-6-yl)thiazol-2-yl)-2H-indazole-3-carboxamide (0.130 g, 74%). $^1$H NMR (400 MHz, DMSO-d): δ 12.93 (bs, 1H), 10.21 (s, 1H), 7.95 (brs, 1H), 7.78-7.72 (m, 3H), 7.57 (s, 1H), 7.39-7.35 (m, 1H), 7.31-7.27 (m, 1H), 6.91 (d, 1H, J=8.0 Hz), 4.41 (s, 3H), 2.94 (t, 2H, J=7.2 Hz), 2.48 (partial masked under d-DMSO), m, 5H), MS (ESI): Calcd. for $C_{21}H_{17}N_5O_2S$: 403, found 404 (M+1)$^+$.

Example 27

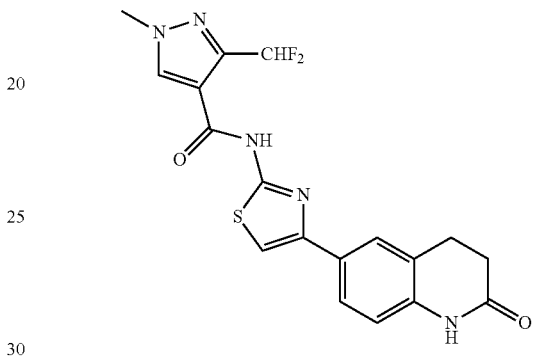

To a suspension of 6-(2-amino-5-chlorothiazol-4-yl)-3,4-dihydroquinolin-2(1H)-one (0.100 g, 0.41 mmol) and 3-(difluoromethyl)-1-methyl-1H-pyrazole-4-carboxylic acid (0.079 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 100° C. for over night and the precipitation formed. After cooling, the precipitate was collected by filtration and washed with cold 1:1 acetonitrile/water to give 3-(difluoromethyl)-1-methyl-N-(4-(2-oxo-1,2,3,4-tetrahydroquinolin-6-yl)thiazol-2-yl)-1H-pyrazole-4-carboxamide (0.104 g, 63%). $^1$H NMR (400 MHz, DMSO-d): δ 12.57 (bs, 1H), 10.19 (s, 1H), 8.71 (s, 1H), 7.74 (m, 1H), 7.69 (dd, 1H, J=8.4, 2.0 Hz), 7.50 (s, 1H), 7.36 (t, $J_{HF}$=54 Hz, 1H), 6.90 (d, 1H, J=8.0 Hz), δ, 3.98 (s, 3H), 2.93 (t, 2H, J=7.2 Hz), 2.48 (partial masked under d-DMSO, m, 2H); MS (ESI): Calcd. for $C_{18}H_{15}F_2N_5O_2S$: 403, found 404 (M+1)$^+$.

Example 28

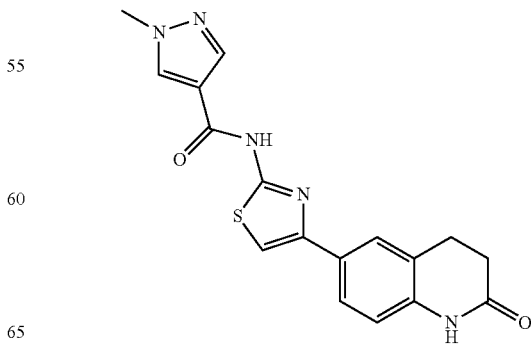

To a suspension of 6-(2-amino-5-chlorothiazol-4-yl)-3,4-dihydroquinolin-2(1H)-one (0.100 g, 0.41 mmol) and 1-methyl-1H-pyrazole-4-carboxylic acid (0.056 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 100° C. for over night and the precipitation formed. After cooling, the precipitate was collected by filtration and washed with cold 1:1 acetonitrile/water to give 1-methyl-N-(4-(2-oxo-1,2,3,4-tetrahydroquinolin-6-yl)thiazol-2-yl)-1H-pyrazole-4-carboxamide (0.090 g, 63%). $^1$H NMR (400 MHz, DMSO-d): δ 12.34 (bs, 1H), 10.19 (s, 1H), 8.47 (s, 1H), 8.19 (s, 1H), 7.74 (m, 1H), 7.69 (dd, 1H, J=8.4, 2.0 Hz), 7.46 (s, 1H), 6.90 (d, 1H, J=8.0 Hz), δ, 3.91 (s, 3H), 2.93 (t, 2H, J=7.2 Hz), 2.48 (partial masked under d-DMSO, m, 2H); MS (ESI): Calcd. for $C_{17}H_{15}N_5O_2S$: 353, found 354 (M+1)$^+$.

Example 29

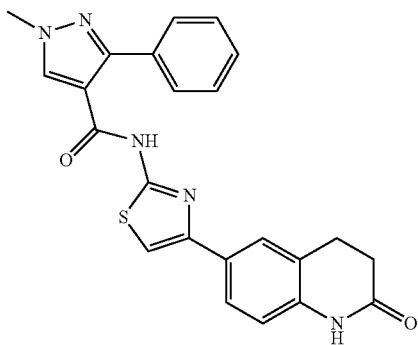 [SMILES: Cn1cc(C(=O)Nc2nc(-c3ccc4c(c3)CCC(=O)N4)cs2)c(-c2ccccc2)n1]

To a suspension of 6-(2-amino-5-chlorothiazol-4-yl)-3,4-dihydroquinolin-2(1H)-one (0.100 g, 0.41 mmol) and 1-methyl-3-phenyl-1H-pyrazole-4-carboxylic acid (0.091 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 100° C. for over night and the precipitation formed. After cooling, the precipitate was collected by filtration and washed with cold 1:1 acetonitrile/water to give 1-methyl-N-(4-(2-oxo-1,2,3,4-tetrahydroquinolin-6-yl)thiazol-2-yl)-3-phenyl-1H-pyrazole-4-carboxamide (0.077 g, 44%). $^1$H NMR (400 MHz, DMSO-d): δ 12.32 (bs, 1H), 10.18 (s, 1H), 8.57 (s, 1H), 7.73 (m, 1H), 7.69 (m, 3H), 7.45 (s, 1H), 7.39 (m, 3H), 6.90 (d, 1H, J=8.0 Hz), 3.95 (s, 3H), 2.92 (t, 2H, J=7.2 Hz), 2.48 (partial masked under d-DMSO, m, 2H); MS (ESI): Calcd. for $C_{23}H_{19}N_5O_2S$: 429, found 430 (M+1)$^+$.

Example 30

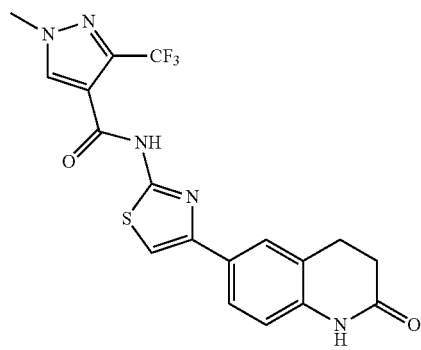 [SMILES: Cn1cc(C(=O)Nc2nc(-c3ccc4c(c3)CCC(=O)N4)cs2)c(C(F)(F)F)n1]

To a suspension of 6-(2-amino-5-chlorothiazol-4-yl)-3,4-dihydroquinolin-2(1H)-one (0.100 g, 0.41 mmol) and 1-methyl-3-(trifluoromethyl)-1H-pyrazole-4-carboxylic acid (0.087 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 100° C. for over night and the precipitation formed. After cooling, the precipitate was collected by filtration and washed with cold 1:1 acetonitrile/water to give 1-methyl-N-(4-(2-oxo-1,2,3,4-tetrahydroquinolin-6-yl)thiazol-2-yl)-3-(trifluoromethyl)-1H-pyrazole-4-carboxamide (0.120 g, 70%). $^1$H NMR (400 MHz, DMSO-d): δ 12.61 (bs, 1H), 10.19 (s, 1H), 8.76 (s, 1H), 7.74 (m, 1H), 7.69 (dd, 1H, J=8.4, 2.0 Hz), 7.50 (s, 1H), 6.90 (d, 1H, J=8.0 Hz), 4.00 (s, 3H), 2.92 (t, 2H, J=7.2 Hz), 2.48 (partial masked under d-DMSO, m, 2H); MS (ESI): Calcd. For $C_{18}H_{14}F_3N_5O_2S$: 421, found 422 (M+1)$^+$.

Example 31

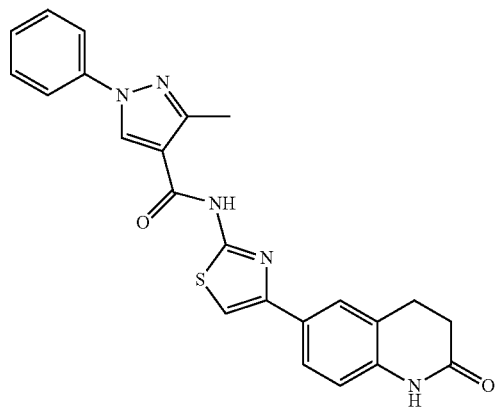 [SMILES: Cc1nn(-c2ccccc2)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.10 g, 0.41 mmol) and 3-methyl-1-phenyl-1H-pyrazole-4-carboxylic acid (0.091 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 100° C. for over night and the precipitation formed. After cooling, the precipitate was collected by filtration and washed with cold 1:1 acetonitrile/water to give 3-methyl-N-(4-(2-oxo-1,2,3,4-tetrahydroquinolin-6-yl)thiazol-2-yl)-1-phenyl-1H-pyrazole-4-carboxamide (0.125 g, 71%). $^1$H NMR (400 MHz, DMSO-d): δ 12.28 (bs, 1H), 10.20 (s, 1H), 9.36 (s, 1H), 7.74 (m, 5H), 7.57 (m, 2H), 7.48 (s, 1H), 7.39 (m, 1H), 6.90 (d, 1H, J=8.0 Hz), 2.92 (t, 2H, J=7.2 Hz), 2.52 (s, 3H) 2.48 (partial masked under d-DMSO, in, 2H); MS (ESI): Calcd. for $C_{23}H_{19}N_5O_2S$: 429, found 430 (M+1)$^+$.

Example 32

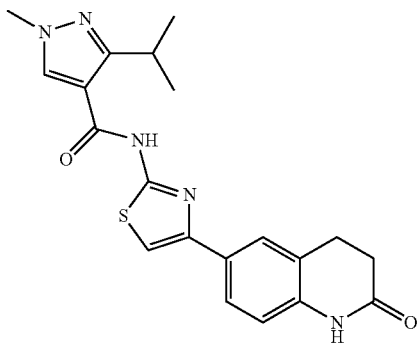 [SMILES: CC(C)c1nn(C)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 3-isopropyl-1-methyl-1H-pyrazole-4-carboxylic acid (0.075 g, 0.45 mmol), and pyridine (0.15 mL, 1.83 mmol in acetonitrile (3 mL) in a sealed tube was added propylphosphonic anhydride solution (50 wt % in ethyl acetate, 0.60 mL, 1.02 mmol). The sealed tube was heated to 70° C. for 48 h. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 3-isopropyl-1-methyl-N-(4-(2-oxo-1,2,3,4-tetrahydroquinolin-6-yl)thiazol-2-yl)-1H-pyrazole-4-carboxamide (0.020 g, 12%). $^1$H NMR (400 MHz, DMSO-d): δ 12.15 (bs, 1H), 10.18 (s, 1H), 8.54 (s, 1H), 7.74 (m, 1H), 7.69 (dd, 1H, J=8.4, 2.0 Hz), 7.44 (s, 1H), 6.90 (d, 1H, J=8.0 Hz), 3.84 (s, 3H), 3.59 (m, 1H), 2.93 (t, 2H, J=7.2 Hz), 2.48 (partial masked under d-DMSO, m, 2H), 1.23 (s, 6H); MS (ESI): Calcd. For $C_{20}H_{21}N_5O_2S$: 395, found 396 (M+1)$^+$.

Example 33

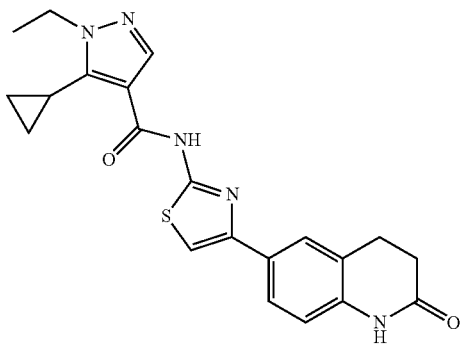 [SMILES: CCn1ncc(C(=O)Nc2nc(-c3ccc4c(c3)CCC(=O)N4)cs2)c1C1CC1]

To a suspension of 6-(2-amino-5-chlorothiazol-4-yl)-3,4-dihydroquinolin-2(1H)-one (0.100 g, 0.41 mmol) and 5-cyclopropyl-1-ethyl-1H-pyrazole-4-carboxylic acid (0.081 g, 0.45 mmol), and pyridine (0.15 mL, 1.83 mmol in acetonitrile (3 mL) in a sealed tube was added propylphosphonic anhydride solution (50 wt % in ethyl acetate, 0.60 mL, 1.02 mmol). The sealed tube was heated to 70° C. for 48 h. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 5-cyclopropyl-1-ethyl-N-(4-(2-oxo-1,2,3,4-tetrahydroquinolin-6-yl)thiazol-2-yl)-1H-pyrazole-4-carboxamide (0.022 g, 13%). $^1$H NMR (400 MHz, DMSO-d): δ 12.15 (bs, 1H), 10.18 (s, 1H), 8.60 (s, 1H), 7.74 (m, 1H), 7.69 (dd, 1H, J=8.4, 2.0 Hz), 7.45 (s, 1H), 6.90 (d, 1H, J=8.0 Hz), 4.07 (m, 2H), 2.93 (t, 2H, J=7.2 Hz), 2.67 (m, 1H), 2.50 (partial masked under d-DMSO, m, 2H), 1.39 (m, 3H), 0.92 (m, 2H), 0.81 (m, 2H); MS (ESI): Calcd. for $C_{21}H_{21}N_5O_2S$: 407, found 408 (M+1)$^+$.

Example 34

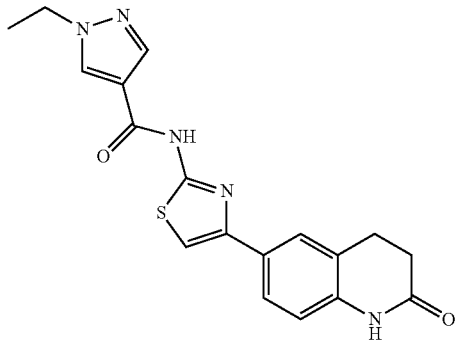 [SMILES: CCn1cc(C(=O)Nc2nc(-c3ccc4c(c3)CCC(=O)N4)cs2)cn1]

To a suspension of 6-(2-amino-5-chlorothiazol-4-yl)-3,4-dihydroquinolin-2(1H)-one (0.100 g, 0.41 mmol) and 1-ethyl-1H-pyrazole-4-carboxylic acid (0.063 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 70° C. for 48 h and the precipitation formed. After cooling, the precipitate was collected by filtration and washed with cold 1:1 acetonitrile/water to give 1-ethyl-N-(4-(2-oxo-1,2,3,4-tetrahydroquinolin-6-yl)thiazol-2-yl)-1H-pyrazole-4-carboxamide (0.055 g, 37%). $^1$H NMR (400 MHz, DMSO-d): δ 12.37 (bs, 1H), 10.19 (s, 1H), 8.54 (s, 1H), 8.20 (s, 1H), 7.74 (m, 1H), 7.69 (dd, 1H, J=8.4, 2.0 Hz), 7.45 (s, 1H), 6.90 (d, 1H, J=8.0 Hz), 4.21 (m, 2H), 2.92 (t, 2H, J=7.2 Hz), 2.48 (partial masked under d-DMSO, m, 2H), 1.42 (s, 3H); MS (ESI): Calcd. for $C_{18}H_{17}N_5O_2S$: 367, found 368 (M+1)$^+$.

Example 35

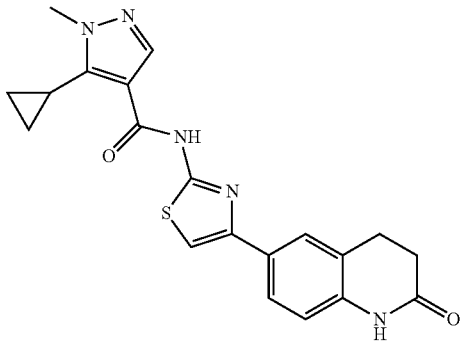 [SMILES: Cn1ncc(C(=O)Nc2nc(-c3ccc4c(c3)CCC(=O)N4)cs2)c1C1CC1]

To a suspension of 6-(2-amino-5-chlorothiazol-4-yl)-3,4-dihydroquinolin-2(1H)-one (0.100 g, 0.41 mmol) and 5-cyclopropyl-1-methyl-1H-pyrazole-4-carboxylic acid (0.074 g, 0.45 mmol), and pyridine (0.15 mL, 1.83 mmol in acetonitrile (3 mL) in a sealed tube was added propylphosphonic anhydride solution (50 wt % in ethyl acetate, 0.60 mL, 1.02 mmol). The sealed tube was heated to 70° C. for 48 h. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 5-cyclopropyl-1-methyl-N-(4-(2-oxo-1,2,3,4-tetrahydroquinolin-6-yl)thiazol-2-yl)-1H-pyrazole-4-carboxamide (0.024 g, 15%). $^1$H NMR (400 MHz, DMSO-d): δ 12.15 (bs, 1H), 10.18 (s, 1H), 8.50 (s, 1H), 7.74 (m, 1H), 7.69 (dd, 1H, J=8.4, 2.0 Hz), 7.45 (s, 1H), 6.90 (d, 1H, J=8.0 Hz), 3.78 (s, 3H), 2.93 (t, 2H, J=7.2 Hz), 2.68 (m, 1H), 2.50 (partial masked under d-DMSO, m, 2H), 0.92 (m, 2H), 0.81 (m, 2H); MS (ESI): Calcd. for $C_{20}H_{19}N_5O_2S$: 393, found 394 (M+1)$^+$.

Example 36

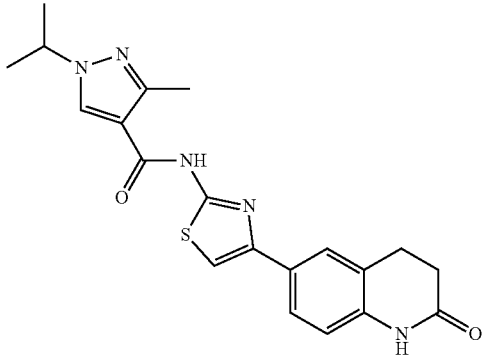 [SMILES: Cc1nn(C(C)C)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 1-isopropyl-3-methyl-1H-pyrazole-4-carboxylic acid (0.075 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 70° C. for 48 h and the precipitation formed. After cooling, the precipitate was collected by filtration and washed with cold 1:1 acetonitrile/water to give 1-isopropyl-3-methyl-N-(4-(2-oxo-1,2,3,4-tetrahydroquinolin-6-yl)thiazol-2-yl)-1N-pyrazole-4-carboxamide (0.019 g, 12%). $^1$H NMR (400 MHz, DMSO-d): δ 12.13 (bs, 1H), 10.18 (s, 1H), 8.46 (s, 1H), 7.74 (m, 1H), 7.69 (dd, 1H, J=8.4, 2.0 Hz), 7.44 (s, 1H), 6.90 (d, 1H, J=8.0 Hz), 3.81 (m, 1H), 2.93 (t, 2H, J=7.2 Hz), 2.48 (partial masked under d-DMSO, m, 2H), 1.37 (s, 9H); MS (ESI): Calcd. for $C_{20}H_{21}N_5O_2S$: 395, found 396 (M+1)$^+$.

Example 37

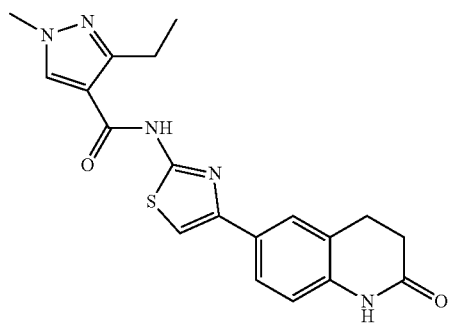 [SMILES: CCc1nn(C)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 3-ethyl-1-methyl-1H-pyrazole-4-carboxylic acid (0.069 g, 0.45 mmol), and pyridine (0.15 mL, 1.83 mmol in acetonitrile (3 mL) in a sealed tube was added propylphosphonic anhydride solution (50 wt % in ethyl acetate, 0.60 mL, 1.02 mmol). The sealed tube was heated to 70° C. for 48 h. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 3-ethyl-1-methyl-N-(4-(2-oxo-1,2,3,4-tetrahydroquinolin-6-yl)thiazol-2-yl)-1H-pyrazole-4-carboxamide (0.035 g, 23%). $^1$H NMR (400 MHz, DMSO-d): δ 12.16 (bs, 1H), 10.18 (s, 1H), 8.55 (s, 1H), 7.74 (m, 1H), 7.69 (dd, 1H, J=8.4, 2.0 Hz), 7.44 (s, 1H), 6.90 (d, 1H, J=8.0 Hz), 4.09 (m, 2H), 3.83 (s, 3H), 3.17 (d, 2H, J=13 Hz), 2.86 (m, 4H), 1.20 (s, 3H); MS (ESI): Calcd. for $C_{19}H_{19}N_5O_2S$: 382, found 383 (M+1)$^+$.

Example 38

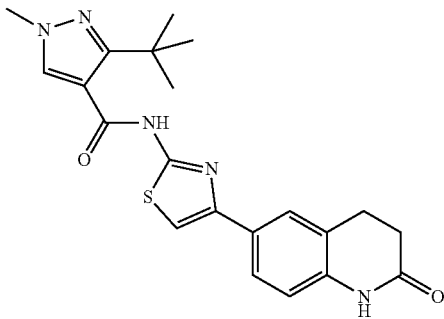 [SMILES: Cn1cc(C(=O)Nc2nc(-c3ccc4c(c3)CCC(=O)N4)cs2)c(C(C)(C)C)n1]

To a suspension of 6-(2-amino-5-chlorothiazol-4-yl)-3,4-dihydroquinolin-2(1H)-one (0.100 g, 0.41 mmol) and 3-(tert-butyl)-1-methyl-1H-pyrazole-4-carboxylic acid (0.082 g, 0.45 mmol), and pyridine (0.15 mL, 1.83 mmol in acetonitrile (5 mL) in a sealed tube was added propylphosphonic anhydride solution (50 wt % in ethyl acetate, 0.60 mL, 1.02 mmol). The sealed tube was heated to 70° C. for 48 h and the precipitation formed. After cooling, the precipitate was collected by filtration and washed with cold 1:1 acetonitrile/water to give 3-(tert-butyl)-1-methyl-N-(4-(2-oxo-1,2,3,4-tetrahydroquinolin-6-yl)thiazol-2-yl)-1H-pyrazole-4-carboxamide (0.021 g, 13%). $^1$H NMR (400 MHz, DMSO-d): δ 12.09 (bs, 1H), 10.18 (s, 1H), 8.71 (s, 1H), 7.74 (m, 1H), 7.69 (dd, 1H, J=8.4, 2.0 Hz), 7.43 (s, 1H), 6.90 (d, 1H, J=8.0 Hz), 4.45 (m, 1H), 2.92 (t, 2H, J=7.2 Hz), 2.48 (partial masked under d-DMSO, m, 2H), 2.40 (s, 3H); MS (ESI): Calcd. for $C_{21}H_{23}N_5O_2S$: 409, found 410 (M+1)$^+$.

Example 39

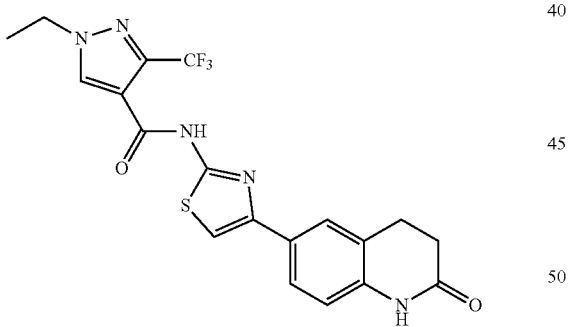

To a suspension of 6-(2-amino-5-chlorothiazol-4-yl)-3,4-dihydroquinolin-2(1H)-one (0.100 g, 0.41 mmol) and 1-ethyl-3-(trifluoromethyl)-1H-pyrazole-4-carboxylic acid (0.093 g, 0.45 mmol), and pyridine (0.15 m L, 1.83 mmol in acetonitrile (5 mL) in a sealed tube was added propylphosphonic anhydride solution (50 wt % in ethyl acetate, 0.60 mL, 1.02 mmol). The sealed tube was heated to 100° C. for over night and the precipitation formed. After cooling, the precipitate was collected by filtration and washed with cold 1:1 acetonitrile/water to give 1-ethyl-N-(4-(2-oxo-1,2,3,4-tetrahydroquinolin-6-yl)thiazol-2-yl)-3-(trifluoromethyl)-1H-pyrazole-4-carboxamide (0.076 g, 43%). $^1$H NMR (400 MHz, DMSO-d): δ 12.59 (bs, 1H), 10.19 (s, 1H), 8.84 (s, 1H), 7.74 (m, 1H), 7.69 (dd, 1H, J=8.4, 2.0 Hz), 7.50 (s, 1H), 6.90 (d, 1H, J=8.0 Hz), 4.29 (q, J=7.2 Hz, 2H), 2.92 (t, 2H, J=7.2 Hz), 2.48 (partial masked under d-DMSO, m, 2H), 1.48 (t, J=7.2 Hz, 3H). MS (ESI): Calcd. For $C_{19}H_{16}F_3N_5O_2S$: 435, found 436 (M+1)$^+$.

Example 40

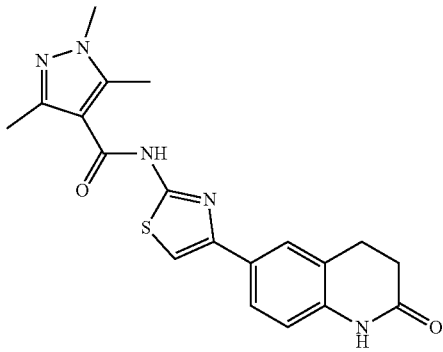 [SMILES: Cc1nn(C)c(C)c1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.05 g, 0.20 mmol) and 1,3,5-trimethyl-1H-pyrazole-4-carboxylic acid (0.035 g, 0.22 mmol), and DIPEA (0.08 mL, 0.51 mmol in acetonitrile (5 mL) in a sealed tube was added propylphosphonic anhydride solution (50 wt % in ethyl acetate, 0.30 mL, 0.51 mmol). The sealed tube was heated to 70° C. for 72 h. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 1,3,5-trimethyl-N-(4-(2-oxo-1,2,3,4-tetrahydroquinolin-6-yl)thiazol-2-yl)-1H-pyrazole-4-carboxamide (0.018 g, 23%). $^1$H NMR (400 MHz, DMSO-d): δ 11.77 (bs, 1H), 10.17 (s, 1H), 7.74 (m, 1H), 7.69 (dd, 1H, J=8.4, 2.0 Hz), 7.46 (s, 1H), 6.90 (d, 1H, J=8.0 Hz), δ, 3.69 (s, 3H), 2.93 (t, 2H, J=7.2 Hz), 2.50 (partial masked under d-DMSO, m, 2H), 2.40 (s, 3H), 2.30 (s, 3H); MS (ESI): Calcd. For $C_{19}H_{19}N_5O_2S$: 381, found 382 (M+1)$^+$.

Example 41

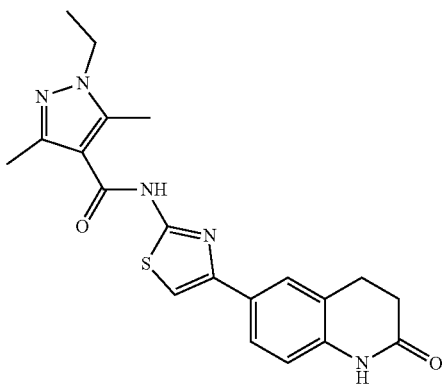 [SMILES: CCn1nc(C)c(C(=O)Nc2nc(-c3ccc4c(c3)CCC(=O)N4)cs2)c1C]

To a suspension of 6-(2-amino-5-chlorothiazol-4-yl)-3,4-dihydroquinolin-2(1H)-one (0.20 g, 0.81 mmol) and 1-ethyl-3,5-dimethyl-1H-pyrazole-4-carboxylic acid (0.15 g, 0.89 mmol), and pyridine (0.3 mL, 3.67 mmol) in acetonitrile (3 mL) in a sealed tube was added propylphosphonic anhydride solution (50 wt % in ethyl acetate, 0.30 mL, 0.51 mmol). The sealed tube was heated to 70° C. for 72 h and the precipitation formed. After cooling, the precipitate was collected by filtration and washed with cold 1:1 acetonitrile/water to give 1-ethyl-3,5-dimethyl-N-(4-(2-oxo-1,2,3,4-tetrahydroquinolin-6-yl)thiazol-2-yl)-1H-pyrazole-4-carboxamide (0.072 g, 22%). $^1$H NMR (400 MHz, DMSO-d): δ 11.75 (bs, 1H), 10.17 (s, 1H), 7.74 (m, 1H), 7.69 (dd, 1H, J=8.4, 2.0 Hz), 7.46 (s, 1H), 6.90 (d, 1H, J=8.0 Hz), δ, 4.05 (m, 2H), 2.93 (t, 2H, J=7.2 Hz), 2.50 (partial masked under d-DMSO, m, 2H), 2.40 (s, 3H), 2.30 (s, 3H), 1.31 (s, 3H); MS (ESI): Calcd. For $C_{20}H_{21}N_5O_2S$: 395, found 396 (M+1)$^+$ HPLC purity: 89%.

Example 42

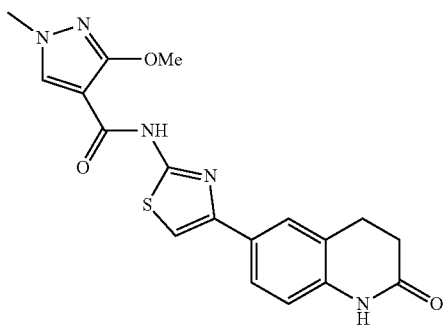 [SMILES: COc1nn(C)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 3-methoxy-1-methyl-1H-pyrazole-4-carboxylic acid (0.070 g, 0.45 mmol), and pyridine (0.15 mL, 1.83 mmol in acetonitrile (2.5 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 3-methoxy-1-methyl-N-(4-(2-oxo-1,2,3,4-tetrahydroquinolin-6-yl)thiazol-2-yl)-1H-pyrazole-4-carboxamide (0.106 g, 68%). $^1$H NMR (400 MHz, DMSO-d): δ 11.75 (bs, 1H), 10.17 (s, 1H), 7.74 (m, 1H), 7.69 (dd, 1H, J=8.4, 2.0 Hz), 7.46 (s, 1H), 6.90 (d, 1H, J=8.0 Hz), 4.03 (q, 2H, J=7.2 Hz), 2.93 (m, 2H), 2.50 (partial masked under d-DMSO, m, 2H), 2.42 (s, 3H), 2.31 (s, 3H), 1.29 (t, 3H, J=7.2 Hz); MS (ESI): Calcd. for $C_{20}H_{21}N_5O_2S$: 395, found 396 (M+1)$^+$.

Example 43

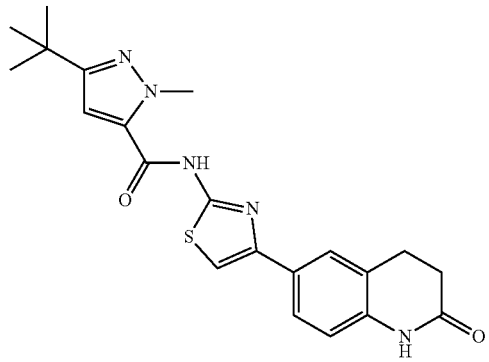 [SMILES: Cn1nc(C(C)(C)C)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.200 g, 0.82 mmol) and 3-(tert-butyl)-1-methyl-1H-pyrazole-5-carboxylic acid (0.164 g, 0.96 mmol), and pyridine (0.32 mL, 4 mmol) in acetonitrile (5 mL) in a sealed tube was added propylphosphonic anhydride solution (50 wt % in ethyl acetate, 0.13 mL, 2.04 mmol). The sealed tube was heated to 100° C. for 16 h and the precipitation formed. After cooling, the precipitate was collected by filtration and washed with cold 1:1 acetonitrile/water to give 3-(tert-butyl)-1-methyl-N-(4-(2-oxo-1,2,3,4-tetrahydroquinolin-6-yl)thiazol-2-yl)-1H-pyrazole-5-carboxamide (0.216 g, 65%). $^1$H NMR (400 MHz, DMSO-d): δ 12.60 (bs, 1H), 10.19 (s, 1H), 7.75 (m, 1H), 7.71 (dd, 1H, J=8.4, 2.0 Hz), 7.53 (s, 1H), 7.33 (s, 1H), 6.91 (d, 1H, J=8.0 Hz), 4.09 (s, 3H), 2.94 (t, 2H, J=7.2 Hz), 2.48 (partial masked under d-DMSO, m, 2H), 1.27 (s, 9H). MS (ESI): Calcd. for $C_{21}H_{23}N_5O_2S$: 409, found 410 (M+1)$^+$.

Example 44

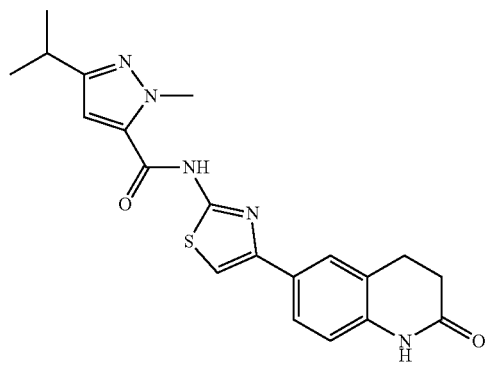 [SMILES: CC(C)c1cc(C(=O)Nc2nc(-c3ccc4c(c3)CCC(=O)N4)cs2)n(C)n1]

To a suspension of 6-(2-amino-5-chlorothiazol-4-yl)-3,4-dihydroquinolin-2(1H)-one (0.100 g, 0.41 mmol) and 3-isopropyl-1-methyl-1H-pyrazole-5-carboxylic acid (0.075 g, 0.45 mmol), and pyridine (0.16 mL, 1.96 mmol) in acetonitrile (2.5 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 3-isopropyl-1-methyl-N-(4-(2-oxo-1,2,3,4-tetrahydroquinolin-6-yl)thiazol-2-yl)-1H-pyrazole-5-carboxamide (0.139 g, 86%). $^1$H NMR (400 MHz, DMSO-d): δ 12.60 (bs, 1H), 10.19 (s, 1H), 7.75 (m, 1H), 7.71 (dd, 1H, J=8.4, 2.0 Hz), 7.53 (s, 1H), 7.27 (s, 1H), 6.91 (d, 1H, J=8.0 Hz), 4.07 (s, 3H), 2.93 (t, 2H, J=7.2 Hz), 2.48 (partial masked under d-DMSO, m, 2H), 1.23 (s, 6H). MS (ESI): Calcd. for $C_{20}H_{21}N_5O_2S$: 395, found 396 $(M+1)^+$.

Example 45

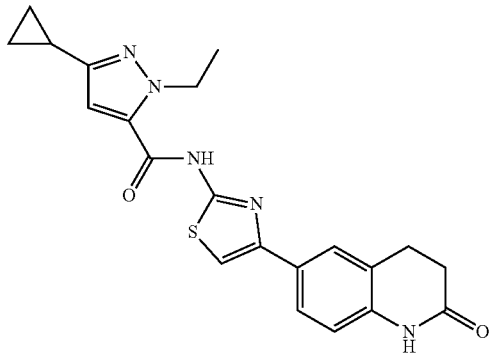 [SMILES: CCn1nc(C2CC2)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 3-cyclopropyl-1-ethyl-1H-pyrazole-5-carboxylic acid (0.081 g, 0.45 mmol), and pyridine (0.16 mL, 1.96 mmol) in acetonitrile (2.5 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 3-cyclopropyl-1-ethyl-N-(4-(2-oxo-1,2,3,4-tetrahydroquinolin-6-yl)thiazol-2-yl)-1H-pyrazole-5-carboxamide (0.127 g, 76%). $^1$H NMR (400 MHz, DMSO-d): δ 12.20 (bs, 1H), 10.19 (s, 1H), 7.75 (m, 1H), 7.71 (dd, 1H, J=8.4, 2.0 Hz), 7.53 (s, 1H), 7.07 (s, 1H), 6.91 (d, 1H, J=8.0 Hz), 4.49 (m, 2H), 2.93 (t, 2H, J=7.2 Hz), 2.48 (partial masked under d-DMSO, m, 2H), 1.91 (m, 1H), 0.93 (m, 2H), 0.65 (m, 2H); MS (ESI): Calcd. for $C_{21}H_{21}N_5O_2S$: 407, found 408 $(M+1)^+$.

Example 46

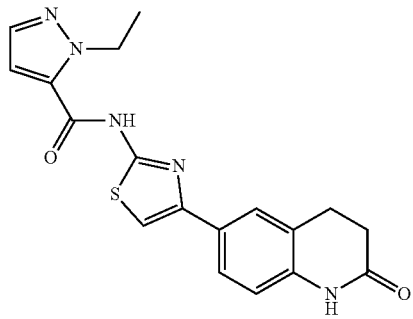 [SMILES: CCn1nccc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 1-ethyl-1H-pyrazole-5-carboxylic acid (0.063 g, 0.45 mmol), and pyridine (0.16 mL, 1.96 mmol) in acetonitrile (2.5 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 1-ethyl-N-(4-(2-oxo-1,2,3,4-tetrahydroquinolin-6-yl)thiazol-2-yl)-1H-pyrazole-5-carboxamide (0.114 g, 76%). $^1$H NMR (400 MHz, DMSO-d): δ 12.74 (bs, 1H), 10.20 (s, 1H), 7.75 (m, 1H), 7.71 (dd, 1H, J=8.4, 2.0 Hz), 7.60 (m, 2H), 7.55 (s, 1H), 7.39 (m, 1H), 6.91 (d, 1H, J=8.0 Hz), 4.58 (m, 2H), 2.93 (t, 2H, J=7.2 Hz), 2.48 (partial masked under d-DMSO, m, 2H), 1.38 (m, 3H); MS (ESI): Calcd. for $C_{18}H_{17}N_5O_2S$: 367, found 368 $(M+1)^+$.

Example 47

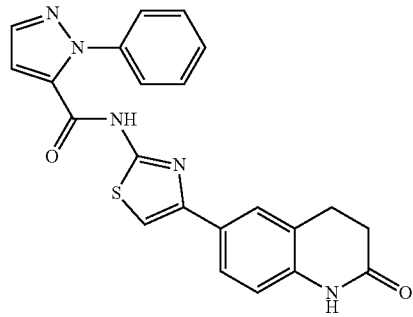 [SMILES: O=C1CCc2cc(-c3csc(NC(=O)c4ccnn4-c4ccccc4)n3)ccc2N1]

To a suspension of 6-(2-amino-5-chlorothiazol-4-yl)-3,4-dihydroquinolin-2(1H)-one (0.100 g, 0.4 mmol) and 1-phenyl-1H-pyrazole-5-carboxylic acid (0.091 g, 0.45 mmol), and pyridine (0.16 mL, 1.96 mmol) in acetonitrile (2.5 mL) in a sealed tube was added propylphosphonic anhydride solution (50 wt % in ethyl acetate, 0.61 mL, 1.02 mmol). The sealed tube was heated and the resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give N-(4-(2-oxo-1,2,3,4-tetrahydroquinolin-6-yl)thiazol-2-yl)-1-phenyl-1H-pyrazole-5-carboxamide (0.012 g, 7%). $^1$H NMR (400 MHz, DMSO-d): δ 12.94 (bs, 1H), 10.19 (s, 1H), 7.75 (m, 1H), 7.70 (dd, 1H, J=8.4, 2.0 Hz), 7.51 (s, 1H), 7.48 (m, 6H), 7.16 (m, 1H), 6.91 (d, 1H, J=8.0 Hz), 2.93 (t, 2H, J=7.2 Hz), 2.48 (partial masked under d-DMSO, in, 2H), 2.30 (s, 3H); MS (ESI): Calcd. for $C_{23}H_{19}N_5O_2S$: 429, found 430 $(M+1)^+$.

Example 48

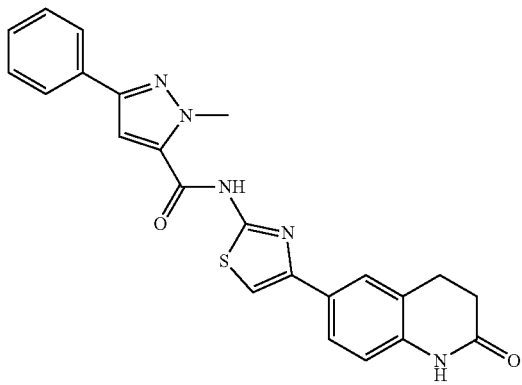 [SMILES: Cn1nc(-c2ccccc2)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 1-methyl-3-phenyl-1H-pyrazole-5-carboxylic acid (0.091 g, 0.45 mmol), and pyridine (0.16 mL, 1.96 mmol) in acetonitrile (2.5 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 1-methyl-N-(4-(2-oxo-1,2,3,4-tetrahydroquinolin-6-yl)thiazol-2-yl)-3-phenyl-1H-pyrazole-5-carboxamide (0.151 g, 86%). $^1$H NMR (400 MHz, DMSO-d): δ 12.94 (bs, 1H), 10.20 (s, 1H), 7.60 (m, 5H), 7.56 (s, 1H), 7.47 (m, 2H), 7.37 (m, 1H), 6.91 (d, 1H, J=8.0 Hz), 4.20 (s, 3H), 2.93 (t, 2H, J=7.2 Hz), 2.48 (partial masked under d-DMSO, m, 2H); MS (ESI): Calcd. for $C_{23}H_{19}N_5O_2S$: 429, found 430 (M+1)$^+$.

Example 49

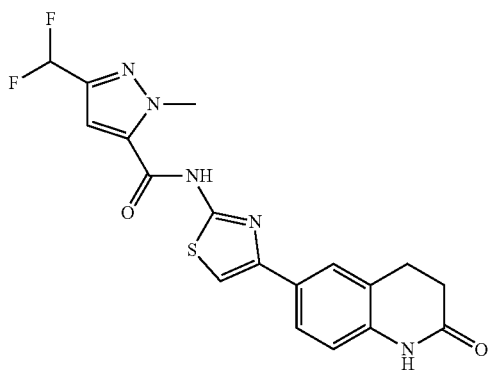 [SMILES: Cn1nc(C(F)F)cc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 3-(difluoromethyl)-1-methyl-1H-pyrazole-5-carboxylic acid (0.079 g, 0.45 mmol), and pyridine (0.16 mL, 1.96 mmol) in acetonitrile (2.5 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 3-(difluoromethyl)-1-methyl-N-(4-(2-oxo-1,2,3,4-tetrahydroquinolin-6-yl)thiazol-2-yl)-1H-pyrazole-5-carboxamide (0.140 g, 85%). $^1$H NMR (400 MHz, DMSO-d): δ 12.94 (bs, 1H), 10.20 (s, 1H), 7.74 (m, 1H), 7.71 (dd, 1H, J=8.4, 2.0 Hz), 7.63 (s, 1H), 7.57 (s, 1H), 7.09 (t, 1H, J=56 Hz) 6.91 (d, 1H, J=8.0 Hz), 4.19 (s, 3H), 2.93 (t, 2H, J=7.2 Hz), 2.48 (partial masked under d-DMSO, m, 2H); MS (ESI): Calcd. for $C_{18}H_{15}F_2N_5O_2S$: 403, found 404 (M+1)$^+$.

Example 50

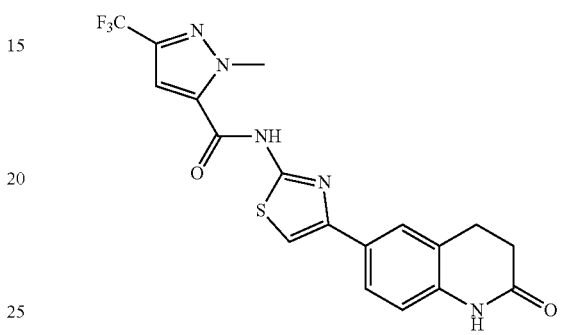

To a suspension of 6-(2-amino-5-chlorothiazol-4-yl)-3,4-dihydroquinolin-2(1H)-one (0.100 g, 0.41 mmol) and 1-methyl-3-(trifluoromethyl)-1H-pyrazole-5-carboxylic acid (0.087 g, 0.45 mmol), and pyridine (0.16 m L, 1.96 mmol) in acetonitrile (2.5 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, 1-methyl-N-(4-(2-oxo-1,2,3,4-tetrahydroquinolin-6-yl)thiazol-2-yl)-3-(trifluoromethyl)-1H-pyrazole-5-carboxamide (0.160 g, 93%). $^1$H NMR (400 MHz, DMSO-d): δ 12.97 (bs, 1H), 10.20 (s, 1H), 7.74 (m, 1H), 7.71 (m, 1H), 7.59 (s, 1H), 6.91 (d, 1H, J=8.0 Hz), 4.23 (s, 3H), 2.93 (t, 2H, J=7.2 Hz), 2.48 (partial masked under d-DMSO, m, 2H); MS (ESI): Calcd. for $C_{18}H_{14}F_3N_5O_2S$: 421, found 422 (M+1)$^+$.

Example 51

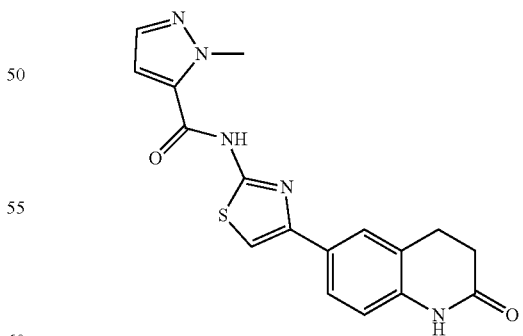

To a suspension of 6-(2-amino-5-chlorothiazol-4-yl)-3,4-dihydroquinolin-2(1H)-one (0.100 g, 0.41 mmol) and 1-methyl-1H-pyrazole-5-carboxylic acid (0.057 g, 0.45 mmol), and DIPEA (0.96 mL, 5.50 mmol) in acetonitrile (7.5 mL) in a sealed tube was added propylphosphonic anhydride solution (50 wt % in ethyl acetate, 1.82 mL, 3.06 mmol). The sealed tube was heated to 100° C. for 16 h and the precipitation formed. After cooling, the precipitate was collected by filtration and washed with cold 1:1 acetonitrile/water to give 1-methyl-N-(4-(2-oxo-1,2,3,4-tetrahydroquinolin-6-yl)thiazol-2-yl)-1H-pyrazole-5-carboxamide (0.120 g, 83%). $^1$H NMR (400 MHz, DMSO-d): δ 12.74 (bs, 1H), 10.20 (s, 1H), 7.75 (m, 1H), 7.71 (dd, 1H, J=8.4, 2.0 Hz), 7.60 (m, 2H), 7.55 (s, 1H), 7.39 (m, 1H), 6.91 (d, 1H, J=8.0 Hz), 4.15 (s, 3H), 2.93 (t, 2H, J=7.2 Hz), 2.48 (partial masked under d-DMSO, m, 2H); MS (ESI): Calcd. for $C_{18}H_{17}N_5O_2S$: 367, found 368 (M+1)$^+$.

Example 52

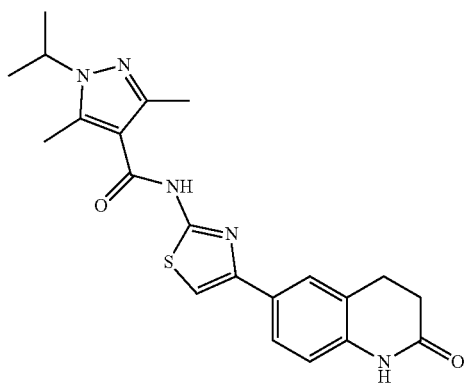 [SMILES: Cc1nn(C(C)C)c(C)c1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.300 g, 1.22 mmol) and 1-isopropyl-3,5-dimethyl-1H-pyrazole-4-carboxylic acid (0.245 g, 1.35 mmol), and DIPEA (0.96 mL, 5.50 mmol) in acetonitrile (7.5 mL) in a sealed tube was added propylphosphonic anhydride solution (50 wt % in ethyl acetate, 1.82 mL, 3.06 mmol). The sealed tube was heated to 100° C. for 16 h. After cooling, The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was triturated with dichloromethane (5 ml) and the precipitate was collected by filtration and washed with cold 1:1 acetonitrile/water to give 1-isopropyl-3,5-dimethyl-N-(4-(2-oxo-1,2,3,4-tetrahydroquinolin-6-yl)thiazol-2-yl)-1H-pyrazole-4-carboxamide (0.230 g, 46%). $^1$H NMR (400 MHz, DMSO-d): δ 11.74 (bs, 1H), 10.17 (s, 1H), 7.74 (m, 1H), 7.69 (dd, 1H, J=8.4, 2.0 Hz), 7.46 (s, 1H), 6.90 (d, 1H, J=8.0 Hz), δ, 4.50 (m, 2H), 2.93 (t, 2H, J=7.2 Hz), 2.50 (partial masked under d-DMSO, m, 2H), 2.42 (s, 3H), 2.32 (s, 3H), 1.35 (s, 6H); MS (ESI): Calcd. For $C_{21}H_{22}N_5O_2S$: 409 found 410 (M+1)$^+$.

Example 53

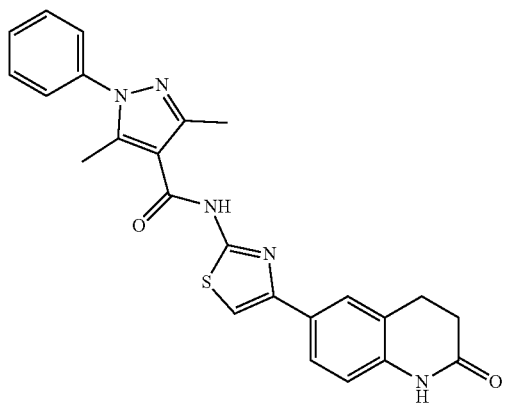 [SMILES: Cc1nn(-c2ccccc2)c(C)c1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol), 3,5-dimethyl-1-phenyl-1H-pyrazole-4-carboxylic acid (0.097 g, 0.45 mmol), DIPEA (0.32 mL, 1.83 mmol) in acetonitrile (3 mL) in a sealed tube was added propylphosphonic anhydride solution (50 wt % in ethyl acetate, 0.61 mL, 1.02 mmol). The sealed tube was heated to 100° C. for 16 h. After cooling, The resulting mixture was cooled to room temperature, and partitioned between dichloromethane (20 mL) and 20 mL of water. The organic layer was separated and the aqueous layer was extracted with dichloromethane (3×30 mL). The combined organic layers were washed with saturated brine, dried over anhydrous sodium sulfate and then concentrated. The residue was triturated with dichloromethane (5 ml) and the precipitate was collected by filtration and washed with cold 1:1 acetonitrile/water to give 3,5-dimethyl-N-(4-(2-oxo-1,2,3,4-tetrahydroquinolin-6-yl)thiazol-2-yl)-1-phenyl-1H-pyrazole-4-carboxamide (0.115 g, 64%). $^1$H NMR (400 MHz, DMSO-d): δ 12.00 (bs, 1H), 10.18 (s, 1H), 7.74 (m, 1H), 7.69 (dd, 1H, J=8.4, 2.0 Hz), 7.50 (m, 6H), 6.90 (d, 1H, J=8.0 Hz), 2.93 (t, 2H, J=7.2 Hz), 2.50 (partial masked under d-DMSO, nm, 2H), 2.46 (s, 3H), 2.40 (s, 3H); MS (ESI): Calcd. For $C_{24}H_{21}N_5O_2S$: 443 found 444 (M+1)$^+$.

Example 54

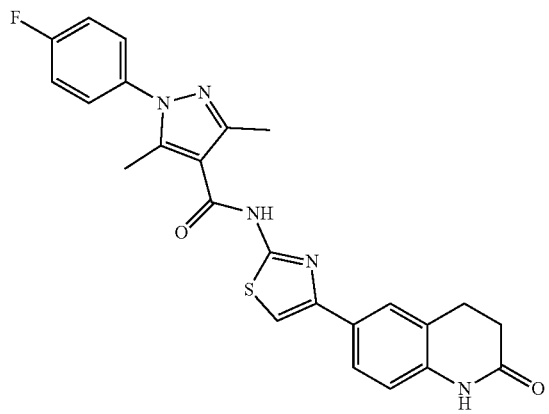 [SMILES: Cc1nn(-c2ccc(F)cc2)c(C)c1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol), 1-(4-fluorophenyl)-3,5-dimethyl-1H-pyrazole-4-carboxylic acid (0.105 g, 0.45 mmol), DIPEA (0.32 mL, 1.83 mmol) in acetonitrile (3 mL) in a sealed tube was added propylphosphonic anhydride solution (50 wt % in ethyl acetate, 0.61 mL, 1.02 mmol). The sealed tube was heated to 100° C. for 16 h. After cooling, The resulting mixture was cooled to room temperature, and partitioned between dichloromethane (20 mL) and 20 mL of water. The organic layer was separated and the aqueous layer was extracted with dichloromethane (3×30 mL). The combined organic layers were washed with saturated brine, dried over anhydrous sodium sulfate and then concentrated. The residue was triturated with dichloromethane (5 ml) and the precipitate was collected by filtration and washed with cold 1:1 acetonitrile/water to give 1-(4-fluorophenyl)-3,5-dimethyl-N-(4-(2-oxo-1,2,3,4-tetrahydroquinolin-6-yl)thiazol-2-yl)-1-pyrazole-4-carboxamide (0.110 g, 58%). $^1$H NMR (400 MHz, DMSO-d): δ 12.00 (bs, 1H), 10.18 (s, 1H), 7.74 (m, 1H), 7.69 (dd, 1H, J=8.4, 2.0 Hz), 7.57 (m, 2H), 7.50 (s, 1H), 7.41 (m, 2H), 6.90 (d, 1H, J=8.0 Hz), 2.93 (t, 2H, J=7.2 Hz), 2.50 (partial masked under d-DMSO, nm, 2H), 2.44 (s, 3H), 2.40 (s, 3H); MS (ESI): Calcd. For $C_{24}H_{20}FN_5O_2S$: 461 found 462 (M+1)+.

Example 55

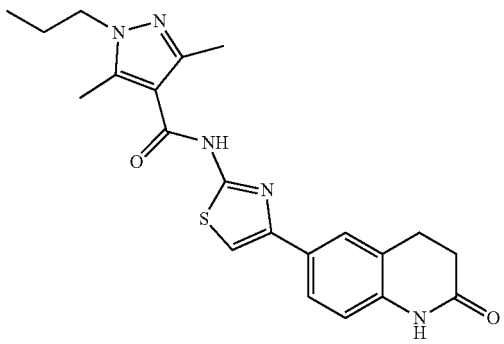 [SMILES: CCCn1nc(C)c(C(=O)Nc2nc(-c3ccc4c(c3)CCC(=O)N4)cs2)c1C]

To a suspension of 6-(2-amino-5-chlorothiazol-4-yl)-3,4-dihydroquinolin-2(1H)-one (0.100 g, 0.41 mmol), 3,5-dimethyl-1-propyl-1H-pyrazole-4-carboxylic acid (0.082 g, 0.45 mmol), DIPEA (0.32 mL, 1.83 mmol) in acetonitrile (3 mL) in a sealed tube was added propylphosphonic anhydride solution (50 wt % in ethyl acetate, 0.61 mL, 1.02 mmol). The sealed tube was heated to 100° C. for 16 h. After cooling, The resulting mixture was cooled to room temperature, and partitioned between dichloromethane (20 mL) and 20 mL of water. The organic layer was separated and the aqueous layer was extracted with dichloromethane (3×30 mL). The combined organic layers were washed with saturated brine, dried over anhydrous sodium sulfate and then concentrated. The residue was triturated with dichloromethane (5 ml) and the precipitate was collected by filtration and washed with cold 1:1 acetonitrile/water to give 3,5-dimethyl-N-(4-(2-oxo-1,2,3,4-tetrahydroquinolin-6-yl)thiazol-2-yl)-1-propyl-1H-pyrazole-4-carboxamide (0.119 g, 71%). $^1$H NMR (400 MHz, DMSO-d): δ 11.76 (bs, 1H), 10.17 (s, 1H), 7.74 (m, 1H), 7.69 (dd, 1H, J=8.4, 2.0 Hz), 7.46 (s, 1H), 6.90 (d, 1H, J=8.0 Hz), 3.97 (m, 2H), 2.93 (t, 2H, J=7.2 Hz), 2.50 (partial masked under d-DMSO, in, 2H), 2.42 (s, 3H), 2.31 (s, 3H), 1.76 (m, 2H), 0.88 (m, 3H); MS (ESI): Calcd. For $C_{21}H_{23}N_5O_2S$: 409, found 410 (M+1)$^+$.

Example 56

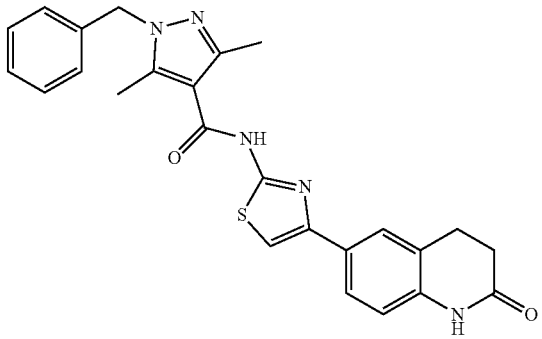 [SMILES: Cc1nn(Cc2ccccc2)c(C)c1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol), 1-benzyl-3,5-dimethyl-1H-pyrazole-4-carboxylic acid (0.103 g, 0.45 mmol), DIPEA (0.32 mL, 1.83 mmol) in acetonitrile (3 mL) in a sealed tube was added propylphosphonic anhydride solution (50 wt % in ethyl acetate, 0.61 mL, 1.02 mmol). The sealed tube was heated to 100° C. for 16 h. After cooling, The resulting mixture was cooled to room temperature, and partitioned between dichloromethane (20 mL) and 20 mL of water. The organic layer was separated and the aqueous layer was extracted with dichloromethane (3×30 mL). The combined organic layers were washed with saturated brine, dried over anhydrous sodium sulfate and then concentrated. The residue was triturated with dichloromethane (5 ml) and the precipitate was collected by filtration and washed with cold 1:1 acetonitrile/water to give 1-benzyl-3,5-dimethyl-N-(4-(2-oxo-1,2,3,4-tetrahydroquinolin-6-yl)thiazol-2-yl)-1H-pyrazole-4-carboxamide (0.057 g, 33%). $^1$H NMR (400 MHz, DMSO-d): δ 11.86 (bs, 1H), 10.17 (s, 1H), 7.74 (m, 1H), 7.69 (dd, 1H, J=8.4, 2.0 Hz), 7.46 (s, 1H), 7.36 (m, 2H), 7.30 (m, 2H), 7.19 (m, 2H), 6.90 (d, 1H, J=8.0 Hz), 5.30 (m, 2H), 2.93 (t, 2H, J=7.2 Hz), 2.50 (partial masked under d-DMSO, nm, 2H), 2.40 (s, 3H), 2.32 (s, 3H), MS (ESI): Calcd. For $C_{25}H_{23}N_5O_2S$: 457, found 458 (M+1)$^+$.

Preferably, to a suspension of 6-(2-amino-5-chlorothiazol-4-yl)-3,4-dihydroquinolin-2(1H)-one (0.135 g, 0.550 mmol) and 1-benzyl-3,5-dimethyl-1H-pyrazole-4-carboxylic acid (0.139 g, 0.605 mmol), and DIPEA (0.43 mL, 2.481 mmol) in acetonitrile (13 mL) in a sealed tube was added propylphosphonic anhydride solution (50 wt % in ethyl acetate, 0.82 mL, 1.382 mmol). The sealed tube was heated to 100° C. for 24 h. After cooling, the mixture was quenched with water (3 mL) and the precitate was collected by filtration washing with cold 1:1 acetonitrile/water mixture. The residue was purified by precipitating in dichloromethane and filtration to give 1-benzyl-3,5-dimethyl-N-(4-(2-oxo-1,2,3,4-tetrahydroquinolin-6-yl)thiazol-2-yl)-1H-pyrazole-4-carboxamide (0.174 g, 69%). $^1$H NMR (400 MHz, DMSO-d): δ 11.86 (bs, 1H), 10.17 (s, 1H), 7.74 (m, 1H), 7.69 (dd, 1H, J=8.4, 2.0 Hz), 7.46 (s, 1H), 7.36 (m, 2H), 7.30 (m, 2H), 7.19 (m, 2H), 6.90 (d, 1H, J=8.0 Hz), 5.30 (s, 2H), 2.92 (m, 2H), 2.48 (partial masked under d-DMSO, m, 2H), 2.41 (s, 3H), 2.32 (s, 3H), MS (ESI): Calcd. For $C_{25}H_{23}N_5O_2S$: 457, found 458 (M+1)$^+$.

Example 57

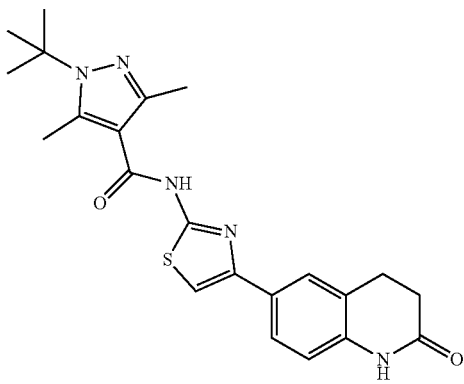 [SMILES: Cc1nn(C(C)(C)C)c(C)c1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol), 1-(tert-butyl)-3-methyl-1H-pyrazole-4-carboxylic acid (0.088 g, 0.45 mmol), DIPEA (0.32 mL, 1.83 mmol) in acetonitrile (3 mL) in a sealed tube was added propylphosphonic anhydride solution (50 wt % in ethyl acetate, 0.61 mL, 1.02 mmol). The sealed tube was heated to 100° C. for 16 h. After cooling, The resulting mixture was cooled to room temperature, and partitioned between dichloromethane (20 mL) and 20 mL of water. The organic layer was separated and the aqueous layer was extracted with dichloromethane (3×30 mL). The combined organic layers were washed with saturated brine, dried over anhydrous sodium sulfate and then concentrated. The residue was purified by silica gel column chromatography by 0-5% methanol-dichloromethane to give 1-(tert-butyl)-3,5-dimethyl-N-(4-(2-oxo-1,2,3,4-tetrahydroquinolin-6-yl) thiazol-2-yl)-1H-pyrazole-4-carboxamide (0.110 g, 63%). 1H NMR (400 MHz, DMSO-d): δ 11.84 (bs, 1H), 10.17 (s, 1H), 7.74 (m, 1H), 7.69 (dd, 1H, J=8.4, 2.0 Hz), 7.46 (s, 1H), 6.90 (d, 1H, J=8.0 Hz), 2.93 (t, 2H, J=7.2 Hz), 2.56 (s, 3H), 2.50 (partial masked under d-DMSO, in, 2H), 2.30 (s, 3H), 1.58 (s, 9H); MS (ESI): Calcd. For $C_{22}H_{25}N_5O_2S$: 423, found 424 $(M+1)^+$.

Example 58

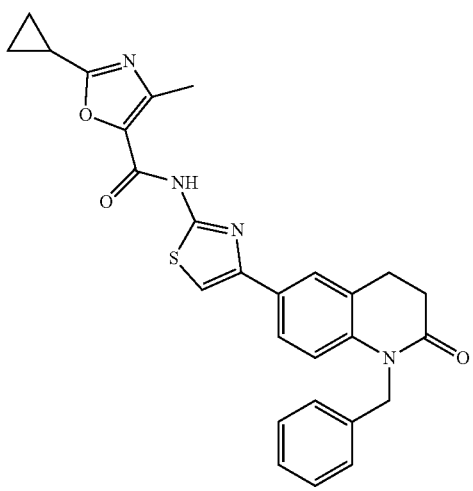 [SMILES: Cc1nc(C2CC2)oc1C(=O)Nc1nc(-c2ccc3c(c2)CCC(=O)N3Cc2ccccc2)cs1]

To a solution of 2-cyclopropyl-4-methyl-N-(4-(2-oxo-1,2,3,4-tetrahydroquinolin-6-yl)thiazol-2-yl)oxazole-5-carboxamide (0.050 g, 0.127 mmol) in anhydrous dimethylformamide (3 mL) in a flamed dried flask under argon atmosphere at 0° C. was added sodium hydride (60% in mineral oil, 0.013 g, 0.317 mmol) was added in one portion. The reaction was stirred for 10 min at 0° C. then benzylbromide (0.023 g, 0.133 mmol) was added via syringe. The mixture was then stirred for 90 min at 0° C. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-benzyl-2-oxo-1,2,3,4-tetrahydroquinolin-6-yl)thiazol-2-yl)-2-cyclopropyl-4-methyloxazole-5-carboxamide (0.036 g, 58%) as an off white solid. $^1$H NMR (400 MHz, DMSO-d): δ 12.52 (bs, 1H), 7.81 (d, 1H, J=2.0 Hz), 7.66 (dd, 1H, J=8.4, 2.0 Hz), 7.55 (bs, 1H), 7.32 (m, 2H), 7.24 (m, 3H), 6.98 (d, 1H, J=8.4 Hz), 5.18 (s, 2H), 3.01 (m, 2H), 2.75 (m, 2H), 2.38 (s, 3H), 2.14 (m, 1H), 1.24 (m, 2H), 1.11 (m, 2H), MS (ESI): Calcd. for $C_{27}H_{24}N_4O_3S$: 484, found 485 $(M+1)^+$.

Example 59

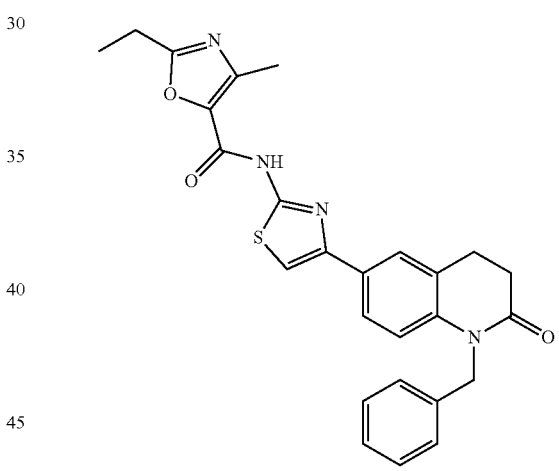

To a solution of 2-ethyl-4-methyl-N-(4-(2-oxo-1,2,3,4-tetrahydroquinolin-6-yl)thiazol-2-yl)oxazole-5-carboxamide (0.05 g, 0.13 mmol) in anhydrous dimethylformamide (3 mL) in a flamed dried flask under argon atmosphere at 0° C. was added sodium hydride (60% in mineral oil, 0.013 g, 0.33 mmol) was added in one portion. The reaction was stirred for 10 min at 0° C. then benzylbromide (0.022 g, 0.131 mmol) was added via syringe. The mixture was then stirred for 90 min at 0° C. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-benzyl-2-oxo-1,2,3,4-tetrahydroquinolin-6-yl)thiazol-2-yl)-2-ethyl-4-methyloxazole-5-carboxamide (0.062 g, 98%) as an off white solid. $^1$H NMR (400 MHz, DMSO-d): δ 12.57 (s, 1H), 7.81 (d, 1H, J=2.0 Hz), 7.67 (dd, 1H, J=8.4, 2.0 Hz), 7.56 (bs, 1H), 7.32 (m, 2H), 7.24 (m, 3H), 6.98 (d, 1H, J=8.4 Hz), 5.18 (s, 2H), 3.01 (m, 2H), 2.81 (q, 2H, J=7.2 Hz), 2.75 (m, 2H), 2.41 (s, 3H), 1.35 (t, 3H, J=7.2 Hz). MS (ESI): Calcd. for $C_{26}H_{24}N_4O_3S$: 472, found 473 (M+1)$^+$.

Example 60

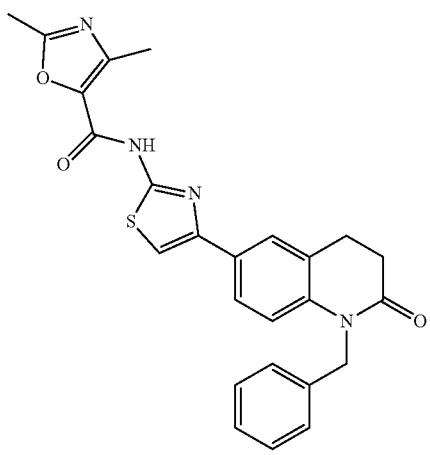 [SMILES: Cc1nc(C)c(C(=O)Nc2nc(-c3ccc4c(c3)CCC(=O)N4Cc3ccccc3)cs2)o1]

To a solution of 2,4-dimethyl-N-(4-(2-oxo-1,2,3,4-tetrahydroquinolin-6-yl)thiazol-2-yl)oxazole-5-carboxamide (0.05 g, 0.135 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then benzylbromide (0.023 g, 0.136 mmol) was added via syringe. The mixture was then stirred for 90 min at 0° C. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-benzyl-2-oxo-1,2,3,4-tetrahydroquinolin-6-yl)thiazol-2-yl)-2,4-dimethyloxazole-5-carboxamide (0.059 g, 95%) as an off white solid. $^1$H NMR (400 MHz, DMSO-d): δ 12.51 (s, 1H), 7.80 (d, 1H, J=2.0 Hz), 7.67 (dd, 1H, J=8.4, 2.0 Hz), 7.56 (bs, 1H), 7.32 (m, 2H), 7.24 (m, 3H), 6.98 (d, 1H, J=8.4 Hz), 5.18 (s, 2H), 3.01 (m, 2H), 2.48 (s, 3H), 2.40 (s, 3H). MS (ESI): Calcd. for $C_{26}H_{24}N_4O_3S$: 472, found 473 (M+1)$^+$.

Example 61

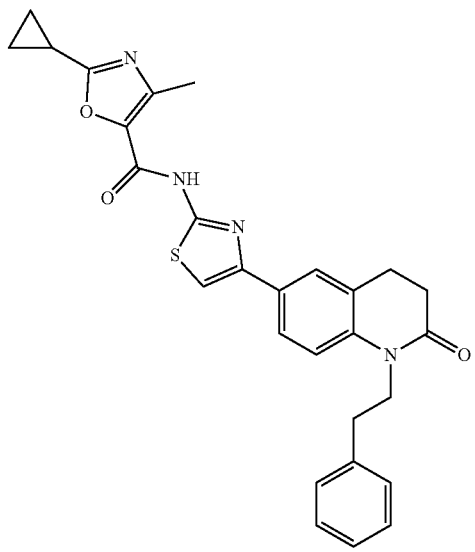 [SMILES: Cc1nc(C2CC2)oc1C(=O)Nc1nc(-c2ccc3c(c2)CCC(=O)N3CCc2ccccc2)cs1]

To a solution of 2-cyclopropyl-4-methyl-N-(4-(2-oxo-1,2,3,4-tetrahydroquinolin-6-yl)thiazol-2-yl)oxazole-5-carboxamide (0.050 g, 0.127 mmol) in anhydrous dimethylformamide (3 mL) in a flamed dried flask under argon atmosphere at 0° C. was added sodium hydride (60% in mineral oil, 0.013 g, 0.317 mmol) was added in one portion. The reaction was stirred for 10 min at 0° C. then (2-bromoethyl)benzene (0.024 g, 0.127 mmol) was added via syringe. The mixture was then stirred for 23 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-cyclopropyl-4-methyl-N-(4-(2-oxo-1-phenethyl-1,2,3,4-tetrahydroquinolin-6-yl)thiazol-2-yl)oxazole-5-carboxamide (0.042 g, 66%) as light yellow solid. $^1$H NMR (400 MHz, DMSO-d): δ 12.57 (bs, 1H), 7.95 (s, 1H), 7.82 (dd, 1H, J=8.4, 2.0 Hz), 7.80 (d, 1H, J=8.8, 2.4 Hz), 7.58 (bs, 1H), 7.32-7.18 (m, 6H), 4.13 (m, 2H), 2.84 (m, 2H), 2.55 (m, 2H), 2.39 (s, 3H), 2.15 (m, 1H), 1.24 (m, 2H), 1.13 (m, 2H). MS (ESI): Calcd. for $C_{28}H_{26}N_4O_3S$: 498, found 499 (M+1)$^+$.

Example 62

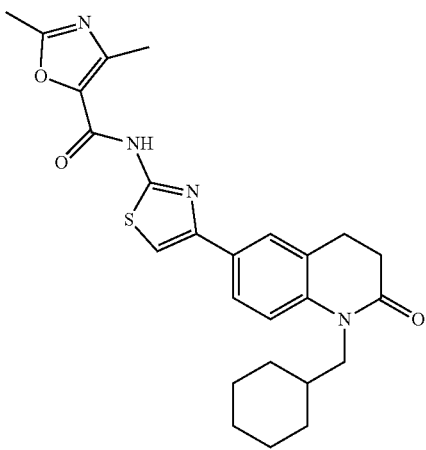 [SMILES: Cc1nc(C)c(C(=O)Nc2nc(-c3ccc4c(c3)CCC(=O)N4CC3CCCCC3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.135 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then (bromomethyl)cyclohexane (0.024 g, 0.136 mmol) was added via syringe. The mixture was then stirred for 23 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(cyclohexylmethyl)-2-oxo-1,2,3,4-tetrahydroquinolin-6-yl)thiazol-2-yl)-2,4-dimethyloxazole-5-carboxamide (0.049 g, 78%) as a white solid. $^1$H NMR (400 MHz, DMSO-d): δ 12.53 (s, 1H), 7.80 (m, 2H), 7.60 (s, 1H), 7.21 (d, 1H, J=8.4 Hz), 3.84 (d, 2H, J=6.8 Hz), 2.90 (m, 2H), 2.59 (m, 2H), 2.49 (s, 3H), 2.41 (s, 3H), 1.61 (m, 5H), 1.23 (m, 1H), 1.11 (m, 3H), 0.97 (m, 2H). MS (ESI): Calcd. for $C_{26}H_{24}N_4O_3S$: 464, found 465 (M+1)$^+$.

Example 63

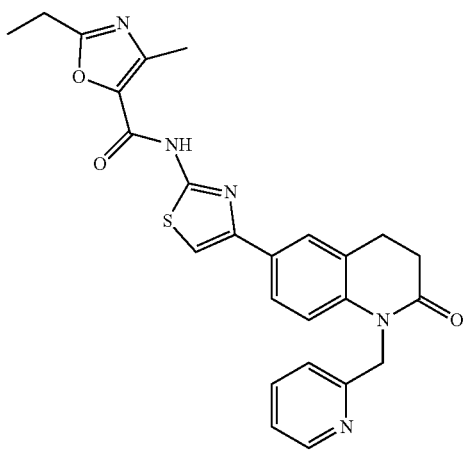 [SMILES: CCc1nc(C)c(C(=O)Nc2nc(-c3ccc4c(c3)CCC(=O)N4Cc3ccccn3)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.130 mmol) in anhydrous dimethylformamide (3 mL) in a flamed dried flask under argon atmosphere at 0° C. was added sodium hydride (60% in mineral oil, 0.018 g, 0.458 mmol) was added in one portion. The reaction was stirred for 10 min at 0° C. then 2-(bromomethyl)pyridine hydrobromide (0.022 g, 0.131 mmol) was added via syringe. The mixture was then stirred for 2 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-ethyl-4-methyl-N-(4-(2-oxo-1-(pyridin-2-ylmethyl)-1,2,3,4-tetrahydroquinolin-6-yl)thiazol-2-yl)oxazole-5-carboxamide (0.057 g, 92%) as a white solid. $^1$H NMR (400 MHz, DMSO-d): δ 12.58 (s, 1H), 8.53 (m, 1H), 7.81 (d, 1H, J=2.0 Hz), 7.73 (ddd, 1H, J=8.0, 2.0, 2.0 Hz), 7.68 (dd, 1H, J=8.4, 2.0 Hz), 7.56 (s, 1H), 7.26 (m, 1H), 7.21 (d, 1H, J=8.0 Hz), 6.95 (d, 1H, J=8.8 Hz), 5.21 (s, 2H), 3.02 (m, 2H), 2.81 (q, 2H, J=7.2 Hz), 2.73 (m, 2H), 2.41 (s, 3H), 1.35 (t, 3H, J=7.2 Hz). MS (ESI): Calcd. for $C_{25}H_{23}N_5O_3S$: 473, found 474 (M+1)$^+$.

Example 64

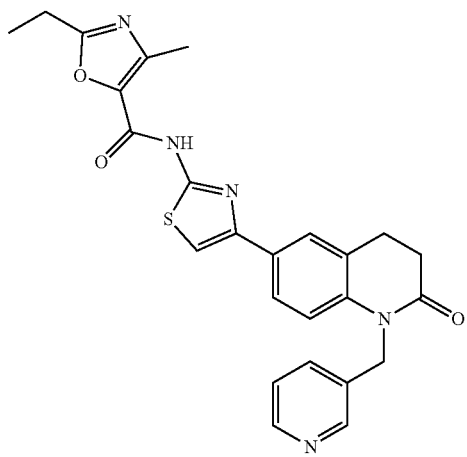 [SMILES: CCc1nc(C)c(C(=O)Nc2nc(-c3ccc4c(c3)CCC(=O)N4Cc3cccnc3)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.130 mmol) in anhydrous dimethylformamide (3 mL) in a flamed dried flask under argon atmosphere at 0° C. was added sodium hydride (60% in mineral oil, 0.018 g, 0.458 mmol) was added in one portion. The reaction was stirred for 10 min at 0° C. then 3-(bromomethyl)pyridine hydrobromide (0.022 g, 0.131 mmol) was added via, syringe. The mixture was then stirred for 2 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-ethyl-4-methyl-N-(4-(2-oxo- 1-(pyridin-3-ylmethyl)-1,2,3,4-tetrahydroquinolin-6-yl)thiazol-2-yl)oxazole-5-carboxamide (0.037 g, 60%) as a white solid. $^1$H NMR (400 MHz, DMSO-d): δ 12.58 (s, 1H), 8.53 (d, 1H, J=1.6 Hz), 8.44 (dd, 1H, J=4.4, 1.6 Hz), 7.81 (d, 1H, J=2.0 Hz), 7.69 (dd, 1H, J=8.4, 2.0 Hz), 7.62 (m, 1H), 7.56 (s, 1H), 7.26 (m, 1H), 7.33 (ddd, 1H, J=8.4, 4.8, 0.8 Hz), 7.03 (d, 1H, J=8.8 Hz), 5.22 (s, 2H), 3.02 (m, 2H), 2.81 (q, 2H, J=7.2 Hz), 2.75 (m, 2H), 2.41 (s, 3H), 1.32 (t, 3H, J=7.2 Hz). MS (ESI): Calcd. for $C_{25}H_{23}N_5O_3S$: 473, found 474 $(M+1)^+$.

Example 65

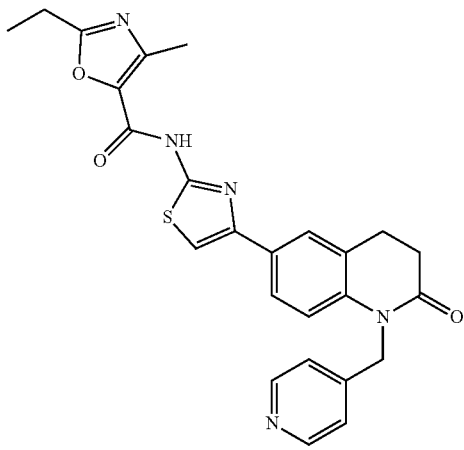 [SMILES: CCc1nc(C)c(C(=O)Nc2nc(-c3ccc4c(c3)CCC(=O)N4Cc3ccncc3)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.130 mmol) in anhydrous dimethylformamide (3 mL) in a flamed dried flask under argon atmosphere at 0° C. was added sodium hydride (60% in mineral oil, 0.018 g, 0.458 mmol) was added in one portion. The reaction was stirred for 10 min at 0° C. then 4-(bromomethyl)pyridine hydrobromide (0.022 g, 0.131 mmol) was added via syringe. The mixture was then stirred for 2 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-ethyl-4-methyl-N-(4-(2-oxo-1-(pyridin-4-ylmethyl)-1,2,3,4-tetrahydroquinolin-6-yl)thiazol-2-yl)oxazole-5-carboxamide (0.037 g, 60%) as a white solid. $^1$H NMR (400 MHz, DMSO-d): δ 12.59 (s, 1H), 8.49 (dd, 1H, J=4.0, 1.6 Hz), 7.83 (d, 1H, J=2.0 Hz), 7.68 (dd, 1H, J=8.4, 2.0 Hz), 7.58 (s, 1H), 7.24 (dd, 1H, J=4.4, 1.6 Hz), 6.89 (d, 1H, J=8.8 Hz), 5.20 (s, 2H), 3.04 (m, 2H), 2.81 (q, 2H, J=7.2 Hz), 2.77 (m, 2H), 2.41 (s, 3H), 1.32 (t, 3H, J=7.2 Hz). MS (ESI): Calcd. for $C_{25}H_{23}N_5O_3S$: 473, found 474 $(M+1)^+$.

Example 66

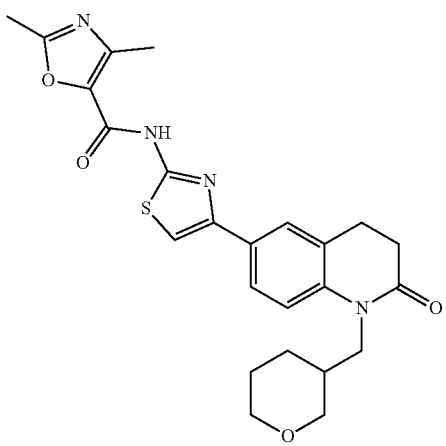 [SMILES: Cc1nc(C)c(C(=O)Nc2nc(-c3ccc4c(c3)CCC(=O)N4CC3CCCOC3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 3-(bromomethyl)tetrahydro-2H-pyran (0.024 g, 0.136 mmol) was added via syringe. The mixture was then stirred for 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2,4-dimethyl-N-(4-(2-oxo-1-((tetrahydro-2H-pyran-3-yl)methyl)-1,2,3,4-tetrahydroquinolin-6-yl)thiazol-2-yl)oxazole-5-carboxamide (0.062 g, 97%) as a white solid. $^1$H NMR (400 MHz, DMSO-d): δ 12.53 (s, 1H), 7.80 (m, 2H), 7.61 (s, 1H), 7.24 (d, 1H, J=8.4 Hz), 3.87 (d, 2H, J=7.2 Hz), 3.68 (m, 2H), 3.32 (m, 1H), 3.17 (dd, 1H, J=11.6, 9.6 Hz), 2.92 (m, 2H), 2.59 (m, 2H), 2.41 (s, 3H), 1.87 (m, 1H), 1.72 (m, 1H), 1.58 (m, 1H). MS (ESI): Calcd. for $C_{24}H_{26}N_4O_4S$: 466, found 467 $(M+1)^+$.

Example 67

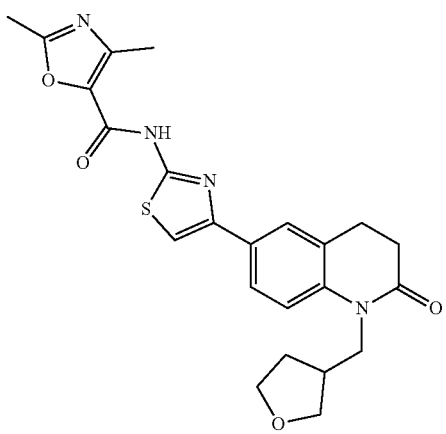 [SMILES: Cc1nc(C)c(C(=O)Nc2nc(-c3ccc4c(c3)CCC(=O)N4CC3CCOC3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then (3-bromomethyl)tetrahydrofuran (0.023 g, 0.136 mmol) was added via syringe. The mixture was then stirred for 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2,4-dimethyl-N-(4-(2-oxo-1-((tetrahydrofuran-3-yl)methyl)-1,2,3,4-tetrahydroquinolin-6-yl)thiazol-2-yl)oxazole-5-carboxamide (0.053 g, 87%) as a white solid. $^1$H NMR (400 MHz, DMSO-d): δ 12.53 (s, 1H), 7.81 (m, 2H), 7.61 (s, 1H), 7.28 (d, 1H, J=8.4 Hz), 4.00 (m, 2H), 3.77 (ddd, 1H, J=8.4, 6.0, 5.6 Hz), 3.61 (m, 2H), 3.45 (dd, 1H, J=8.4, 5.2 Hz), 2.91 (m, 2H), 2.59 (m, 2H), 2.53 (m, 1H), 2.41 (s, 3H), 1.87 (m, 1H), 1.59 (m, 1H). MS (ESI): Calcd. for $C_{23}H_{24}N_4O_4S$: 452, found 453 (M+1)$^+$.

Example 68

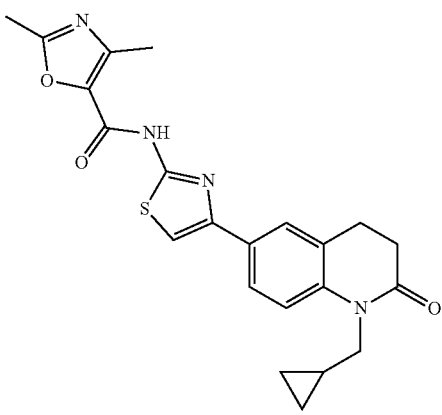 [SMILES: Cc1nc(C)c(C(=O)Nc2nc(-c3ccc4c(c3)CCC(=O)N4CC3CC3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.34 mmol) was added in one portion. The reaction was stirred for 10 min at 0° C. then (bromomethyl)cyclopropane (0.018 g, 0.14 mmol) was added via syringe. The mixture was then stirred for 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(cyclopropylmethyl)-2-oxo-1,2,3,4-tetrahydroquinolin-6-yl)thiazol-2-yl)-2,4-dimethyloxazole-5-carboxamide (0.029 g, 51%) as an off-white solid. $^1$H NMR (400 MHz, DMSO-d): δ 12.53 (s, 1H), 7.81 (m, 2H), 7.60 (s, 1H), 7.30 (d, 1H, J=8.4 Hz), 3.85 (d, 2H, J=6.8 Hz), 2.92 (m, 2H), 2.59 (m, 2H), 2.41 (s, 3H), 1.11 (m, 1H), 0.54 (m, 2H), 0.35 (m, 2H). MS (ESI): Calcd. for $C_{22}H_{22}N_4O_3S$: 422, found 423 (M+1)$^+$.

Example 69

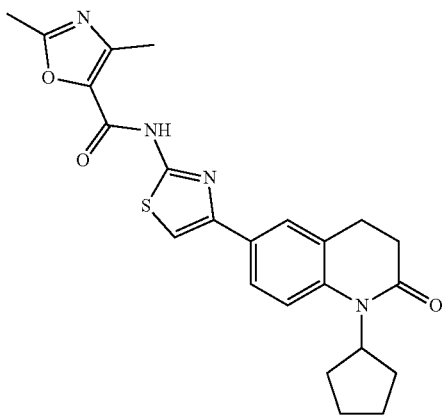 [SMILES: Cc1nc(C)c(C(=O)Nc2nc(-c3ccc4c(c3)CCC(=O)N4C3CCCC3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then cyclopentyl bromide (0.021 g, 0.136 mmol) was added via syringe. The mixture was then stirred for 24 hours at room temperature. The following day, another 14 mg of NaH and 20 mg of cyclopentyl bromide added and kept in the hood for 3 months. The reaction gave a significant ⅓ conversion by LCMS. The reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-cyclopentyl-2-oxo-1,2,3,4-tetrahydroquinolin-6-yl)thiazol-2-yl)-2,4-dimethyloxazole-5-carboxamide (0.017 g, 29%) as beige solid. $^1$H NMR (400 MHz, DMSO-d): δ 12.53 (s, 1H), 7.80 (m, 2H), 7.60 (s, 1), 7.23 (d, 1H, J=8.8 Hz), 4.62 (quintet, 1H, J=8.0 Hz), 2.84 (m, 2H), 2.50 (masked under d-DMSO, m, 5H), 2.41 (s, 3H), 2.09 (m, 2H), 1.91 (m, 4H), 1.58 (m, 2H). MS (ESI): Calcd. for $C_{23}H_{24}N_4O_3S$: 436, found 437 (M+1)$^+$.

Example 70

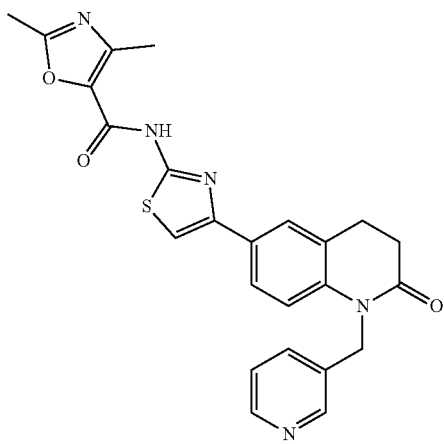 [SMILES: Cc1nc(C)c(C(=O)Nc2nc(-c3ccc4c(c3)CCC(=O)N4Cc3cccnc3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.019 g, 0.475 mmol) was added in one portion. The reaction was stirred for 10 min at 0° C. then 3-(bromomethyl)pyridine hydrobromide (0.034 g, 0.136 mmol) was added as a solid in one portion. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2,4-dimethyl-N-(4-(2-oxo-1-(pyridin-3-ylmethyl)-1,2,3,4-tetrahydroquinolin-6-yl)thiazol-2-yl)oxazole-5-carboxamide (0.027 g, 43%) as light yellow solid. $^1$H NMR (400 MHz, DMSO-d): δ 12.53 (s, 1H), 8.53 (d, 1H, J=1.6 Hz), 8.44 (dd, 1H, J=4.4, 1.6 Hz), 7.61 (m, 1H), 7.55 (s, 1H), 7.33 (ddd, 1H, J=4.4, 4.4, 0.8 Hz), 7.03 (d, 1H, J=8.4 Hz), 3.02 (m, 2H), 2.75 (m, 2H), 2.48 (s, 3H), 2.40 (s, 3H). MS (ESI): Calcd. for $C_{24}H_{21}N_5O_3S$: 459, found 460 (M+1)$^+$.

Example 71

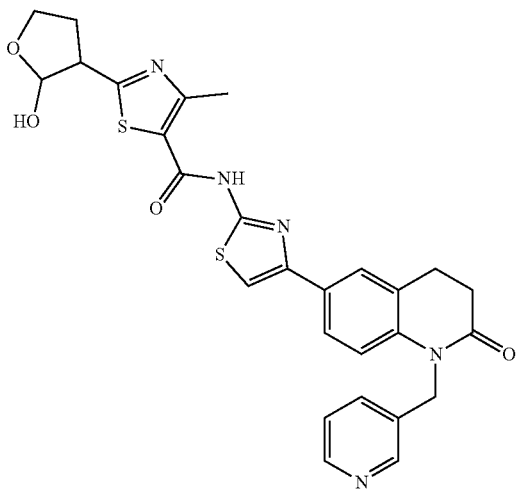 [SMILES: Cc1nc(C2CCOC2O)sc1C(=O)Nc1nc(-c2ccc3c(c2)CCC(=O)N3Cc2cccnc2)cs1]

To a solution of 4-methyl-N-(4-(2-oxo-1,2,3,4-tetrahydroquinolin-6-yl)thiazol-2-yl)-2-(tetrahydrofuran-3-yl)thiazole-5-carboxamide (0.050 g, 0.114 mmol) in anhydrous dimethylformamide (3 mL) in argon atmosphere at 0° C. was added sodium hydride (60% in mineral oil, 0.016 g, 0.397 mmol) was added in one portion. The reaction was stirred for 10 min at 0° C. then 3-(bromomethyl)pyridine hydrobromide (0.029 g, 0.114 mmol) was added as a solid in one portion was explosed to air atmosphere. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-(2-hydroxytetrahydrofuran-3-yl)-4-methyl-N-(4-(2-oxo-1-(pyridin-3-ylmethyl)-1,2,3,4-tetrahydroquinolin-6-yl)thiazol-2-yl)thiazole-5-carboxamide (0.040 g, 65%) as light yellow solid. $^1$H NMR (400 MHz, DMSO-d): δ 12.64 (s, 1H), 8.53 (d, 1H, J=1.6 Hz), 8.44 (dd, 1H, J=4.4, 1.2 Hz), 7.80 (d, 1H, J=1.6 Hz), 7.67 (dd, 1H, J=8.8, 2.0 Hz), 7.62 (m, 1H), 7.55 (s, 1H), 7.33 (ddd, 1H, J=4.4, 4.4, 0.8 Hz), 7.03 (d, 1H, J=8.4 Hz), 6.30 (s, 1H), 4.01 (dd, 2H, J=9.2, 5.2 Hz), 3.89 (dd, 2H, J=9.2, 9.2 Hz), 3.02 (m, 2H), 2.75 (m, 2H), 2.62 (s, 3H), 2.46 (m, 1H), 2.19 (m, 1H). MS (ESI): Calcd. for $C_{27}H_{25}N_5O_4S_2$: 547, found 548 (M+1)$^+$.

Example 72

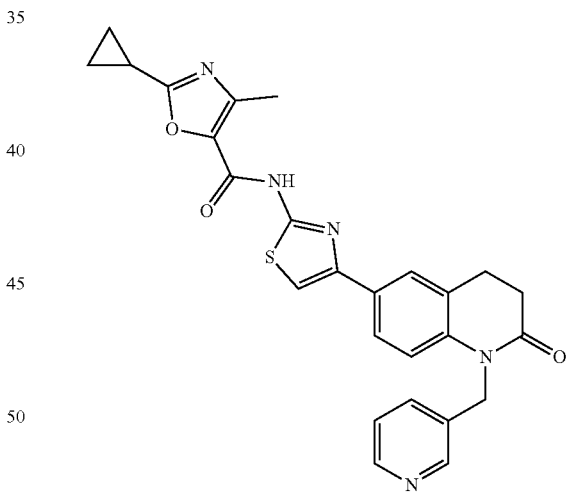

To a solution of 2-cyclopropyl-4-methyl-N-(4-(2-oxo-1,2,3,4-tetrahydroquinolin-6-yl)thiazol-2-yl)oxazole-5-carboxamide (0.050 g, 0.127 mmol) in anhydrous dimethylformamide (3 mL) in a flamed dried flask under argon atmosphere at 0° C. was added sodium hydride (60% in mineral oil, 0.018 g, 0.444 mmol) was added in one portion. The reaction was stirred for 10 min at 0° C. then 3-(bromomethyl)pyridine hydrobromide (0.032 g, 0.127 mmol) was added as a solid in one portion. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-cyclopropyl-4-methyl-N-(4-(2-oxo-1-(pyridin-3-ylmethyl)-1,2,3,4-tetrahydroquinolin-6-yl)thiazol-2-yl)oxazole-5-carboxamide (0.040 g, 65%) as white solid. $^1$H NMR (400 MHz, DMSO-d): δ 12.52 (s, 1H), 8.53 (d, 1H, J=1.6 Hz), 8.44 (dd, 1H, J=4.4, 1.6 Hz), 7.82 (d, 1H, J=1.6 Hz), 7.69 (dd, 1H, J=8.8, 2.4 Hz), 7.62 (m, 1H), 7.56 (s, 1H), 7.33 (ddd, 1H, J=4.4, 4.4, 0.8 Hz), 7.02 (d, 1H, J=8.4 Hz), 3.01 (m, 2H), 2.75 (m, 2H), 2.38 (s, 3H), 2.14 (m, 1H), 1.23 (m, 2H), 1.11 (m, 1H). MS (ESI): Calcd. for $C_{26}H_{23}N_5O_3S$: 485, found 486 (M+1)$^+$.

Example 73

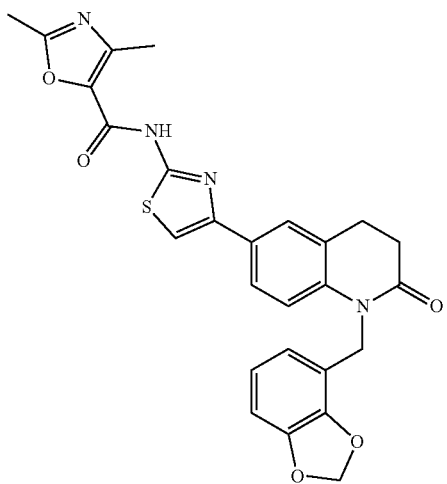 [SMILES: Cc1nc(C)c(C(=O)Nc2nc(-c3ccc4c(c3)CCC(=O)N4Cc3cccc4c3OCO4)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 4-(bromomethyl)benzo[d][1,3]diozole (0.031 g, 0.142 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(benzo[d][1,3]dioxol-4-ylmethyl)-2-oxo-1,2,3,4-tetrahydroquinolin-6-yl)thiazol-2-yl)-2,4-dimethyloxazole-5-carboxamide (0.063 g, 92%) as light yellow solid. $^1$H NMR (400 MHz, DMSO-d): δ 12.52 (s, 1H), 7.80 (d, 1H, J=1.6 Hz), 7.70 (dd, 1H, J=8.4, 2.0 Hz), 7.56 (bs, 1H), 6.97 (d, 1H, J=8.4 Hz), 6.80 (dd, 1H, J=8.0, 1.6 Hz), 6.75 (m, 1H), 6.59 (dd, 1H, J=8.0, 1.6 Hz), 6.05 (s, 2H), 5.10 (s, 2H), 2.99 (m, 2H), 2.71 (m, 2H), 2.48 (s, 3H), 2.40 (s, 3H). MS (ESI): Calcd. for $C_{26}H_{22}N_4O_5S$: 502, found 503 (M+1)$^+$.

Example 74

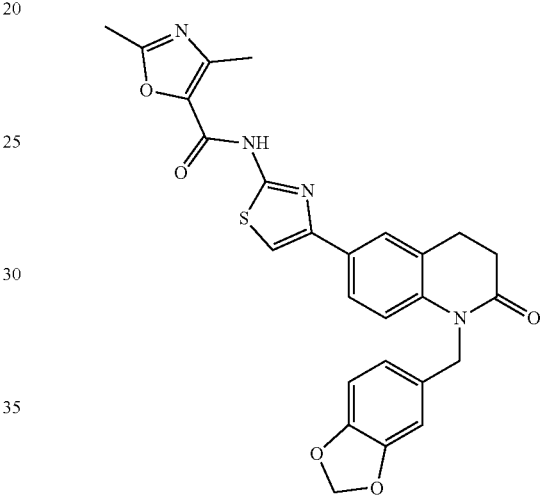

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 5-(bromomethyl)benzo[d][1,3]dioxole (0.031 g, 0.142 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(benzo[d][1,3]dioxol-5-ylmethyl)-2-oxo-1,2,3,4-tetrahydroquinolin-6-yl)thiazol-2-yl)-2,4-dimethyloxazole-5-carboxamide (0.051 g, 74%) as an off-white solid. $^1$H NMR (400 MHz, DMSO-d): δ 12.51 (s, 1H), 7.79 (d, 1H, J=2.0 Hz), 7.68 (dd, 1H, J=8.8, 2.0 Hz), 7.56 (bs, 1H), 7.02 (d, 1H, J=8.4 Hz), 6.83 (d, 1H, J=8.0 Hz), 6.81 (d, 1H, J=1.6 Hz), 6.73 (dd, 1H, J=8.0, 1.6 Hz), 5.97 (s, 2H), 5.08 (s, 2H), 2.99 (m, 2H), 2.73 (m, 2H), 2.48 (s, 3H), 2.40 (s, 3H). MS (ESI): Calcd. for $C_{26}H_{22}N_4O_5S$: 502, found 503 (M+1)$^+$.

Example 75

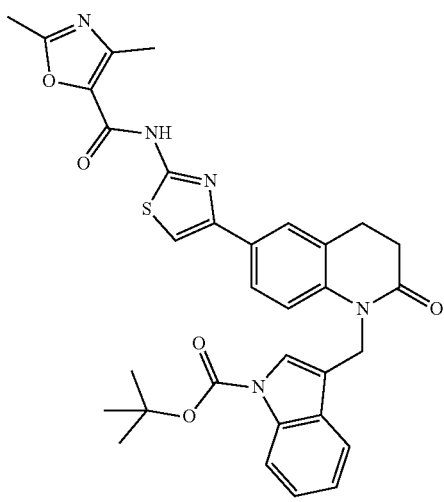 [SMILES: Cc1nc(C)c(C(=O)Nc2nc(-c3ccc4c(c3)CCC(=O)N4Cc3cn(C(=O)OC(C)(C)C)c4ccccc34)cs2)o1]

To a solution of 2,4-dimethyl-N-(4-(2-oxo-1,2,3,4-tetrahydroquinolino-6-yl)thiazol-2-yl)oxazole-5-carboxamide (0.100 g, 0.271 mmol) in anhydrous dimethylformamide (6 mL) in a flamed dried flask under argon atmosphere at 0° C. was added sodium hydride (60% in mineral oil, 0.014 g, 0.339 mmol) was added in one portion. The reaction was stirred for 15 min at 0° C. then 5-(bromomethyl)benzo[d][1,3]diozole (0.031 g, 0.142 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give tert-butyl 7-((6-(2-(2,4-dimethyloxazole-5-carboxamido)thiazol-4-yl)-2-oxo-3,4-dihydroquinolin-1 (2H)-yl)methyl)-1H-indole-1-carboxylate (0.122 g, 90%) as yellow solid. $^1$H NMR (400 MHz, DMSO-d): δ 12.41 (s, 1H), 7.98 (m, 1H), 7.76 (d, 1H, J=2.0 Hz), 7.72 (dd, 1H, J=8.8, 2.4 Hz), 7.68 (dd, 1H, J=8.0, 0.8 Hz), 7.61 (s, 1H), 7.53 (s, 1H), 7.33 (m 2H), 7.28 (m, 1H), 5.33 (bs, 2H), 2.88 (m, 4H), 2.74 (m, 4H0, 2.47 (s, 3H), 2.40 (s, 3H), 1.60 (s, 9H), MS (ESI): Calcd. for $C_{27}H_{23}N_5O_3S$: 597, found 598 (M+1)$^+$.

Example 76

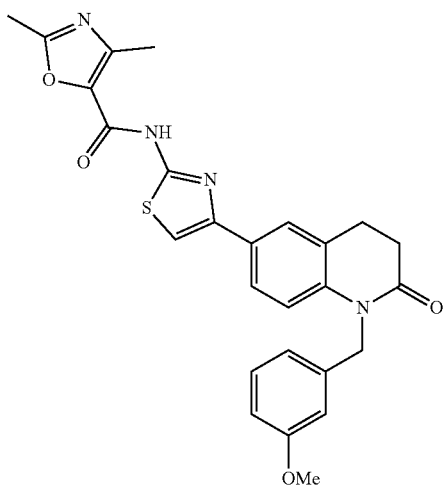 [SMILES: COc1cccc(CN2C(=O)CCc3cc(-c4csc(NC(=O)c5oc(C)nc5C)n4)ccc32)c1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 3-methoxylbenzyl bromide (0.029 g, 0.143 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(3-methoxybenzyl)-2-oxo-1,2,3,4-tetrahydroquinolin-6-yl)thiazol-2-yl)-2,4-dimethyloxazole-5-carboxamide (0.066 g, 99%) as an off-white solid. $^1$H NMR (400 MHz, DMSO-d): δ 12.51 (s, 1H), 7.80 (d, 1H, J=8.4, 2.0 Hz), 7.56 (s, 1H), 7.22 (ddd, 1H, J=7.6, 7.6, 1.2 Hz), 6.98 (d, 1H, J=8.4 Hz), 6.79 (m, 3H), 5.14 (bs, 2H), 3.71 (s, 3H), 3.00 (m, 2H), 2.74 (m, 2H), 2.48 (s, 3H), 2.40 (s, 3H0. MS (ESI): Calcd. for $C_{26}H_{24}N_4O_4S$: 488, found 489 (M+1)$^+$.

Example 77

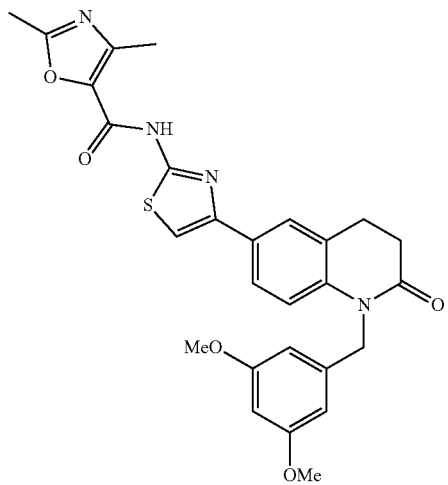 [SMILES: COc1cc(CN2C(=O)CCc3cc(-c4csc(NC(=O)c5oc(C)nc5C)n4)ccc32)cc(OC)c1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 3,5-dimethoxylbenzyl bromide (0.033 g, 0.143 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(3,5-dimethoxybenzyl)-2-oxo-1,2,3,4-tetrahydroquinolin-6-yl)thiazol-2-yl)-2,4-dimethyloxazole-5-carboxamide (0.064 g, 91%) as light yellow solid. $^1$H NMR (400 MHz, DMSO-d): δ 12.51 (s, 1H), 7.80 (d, 1H, J=2.0 Hz), 7.68 (dd, 1H, J=8.8, 2.0 Hz), 7.57 (s, 1H), 6.99 (d, 1H, J=8.8 Hz), 6.37 (m, 3H), 5.09 (bs, 2H), 3.69 (6H, s), 3.00 (m, 2H0, 2.73 (m, 2H), 2.48 (s, 3H), 2.40 (s, 3H). MS (ESI): Calcd. for $C_{27}H_{26}N_4O_5S$: 518, found 519 (M+1)$^+$.

Example 78

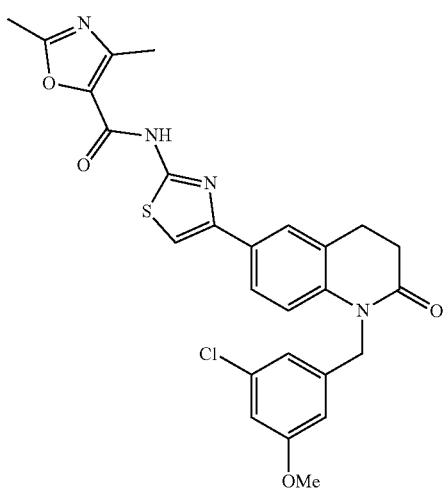 [SMILES: COc1cc(Cl)cc(CN2C(=O)CCc3cc(-c4csc(NC(=O)c5oc(C)nc5C)n4)ccc32)c1]

To a solution of 2,4-dimethyl-2-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 1-(bromomethyl)-3-chloro-5-methoxybenzene (0.034 g, 0.143 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(4-(1-(3-chloro-5-methoxybenzyl)-2-oxo-1,2,3,4-tetrahydroquinolin-6-yl)thiazol-2-yl)-2,4-dimethyloxazole-5-carboxamide (0.068 g, 96%) as beige solid. $^1$H NMR (400 MHz, DMSO-d): δ 12.52 (s, 1H), 7.81 (d, 1H, J=2.0 Hz), 7.70 (dd, 1H, J=8.4, 1.6 Hz), 7.58 (s, 1H), 6.98 (d, 1H, J=8.4 Hz), 6.90 (m, 1H), 6.86 (m, 1H), 6.78 (m, 1H), 5.13 (bs, 2H), 3.74 (s, 3H), 3.01 (m, 2H), 2.75 (m, 2H), 2.48 (s, 3H), 2.40 (s, 3H). MS (ESI): Calcd. for $C_{26}H_{23}ClN_4O_4S$: 523, found 524 (M+1)$^+$.

Example 79

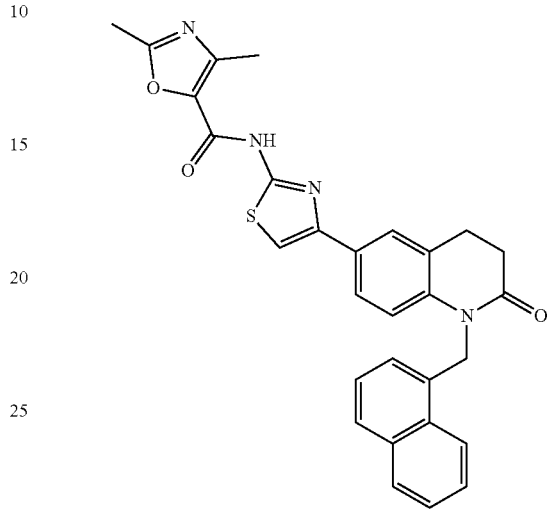

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 1-(bromomethyl)napthalene (0.033 g, 0.149 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2,4-dimethyl-N-(4-(1-(naphthalen-1-ylmethyl)-2-oxo-1,2,3,4-tetrahydroquinolin-6-yl)thiazol-2-yl)oxazole-5-carboxamide (0.068 g, 98%) as light yellow solid. $^1$H NMR (400 MHz, DMSO-d): δ 12.52 (s, 1H), 8.21 (d, 1H, J=8.0 Hz), 7.99 (dd, 1H, J=6.8, 1.6 Hz), 7.85 (d, 1H, J=2.4 Hz), 7.83 (d, 1H, J=8.4 Hz), 7.62 (m, 3H), 7.55 (bs, 1H), 7.39 (dd, 1H, J=8.4, 7.2 Hz), 7.09 (d, 1H, J=7.2 Hz), 6.84 (d, 1H, J=8.4 Hz), 5.61 (bs, 2H), 3.08 (m, 2H), 2.83 (m, 2H), 2.47 (s, 3H), 2.39 (s, 3H). MS (ESI): Calcd. for $C_{29}H_{24}N_4O_3S$: 508, found 509 (M+1)$^+$.

Example 80

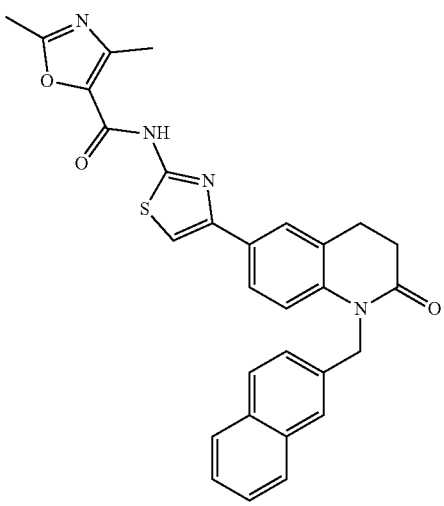 [SMILES: Cc1nc(C)c(C(=O)Nc2nc(-c3ccc4c(c3)CCC(=O)N4Cc3ccc4ccccc4c3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 2-(bromomethyl)napthalene (0.033 g, 0.149 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2,4-dimethyl-N-(4-(1-(naphthalen-2-ylmethyl)-2-oxo-1,2,3,4-tetrahydroquinolin-6-yl)thiazol-2-yl)oxazole-5-carboxamide (0.068 g, 98%) as light yellow solid, $^1$H NMR (400 MHz, DMSO-d): δ 12.50 (s, 1H), 7.91-7.83 (m, 3H), 7.81 (d, 1H, J=2.0 Hz), 7.72 (bs, 1H), 7.54 (bs, 1H), 7.47 (m, 1H), 7.43 (dd, 1H, J=8.0, 1.6 Hz), 7.03 (d, 1H, J=8.4 Hz), 5.34 (bs, 2H), 3.06 (m, 2H), 2.81 (m, 2H), 2.47 (s, 3H), 2.39 (s, 3H). MS (ESI): Calcd. for $C_{29}H_{24}N_4O_3S$: 508, found 509 (M+1)$^+$.

Example 81

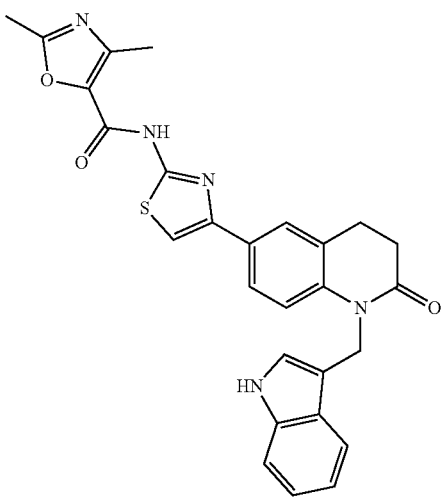 [SMILES: Cc1nc(C)c(C(=O)Nc2nc(-c3ccc4c(c3)CCC(=O)N4Cc3c[nH]c4ccccc34)cs2)o1]

tert-butyl 7-((6-(2-(2,4-dimethyloxazole-5-carboxamido)thiazol-4-yl)-2-oxo-3,4-dihydroquinolin-1 (2H)-yl)methyl)-1H-indole-1-carboxylate (0.110 g, 0.184 mmol) was suspended 6 mL of 4M hydrogen chloride solution in dioxane in sealed flask. The mixture was stirred for 6 hours at room temperature. The reaction mixture was concentrated in vacuo. The HCl salt was dissolved in minimum amount of methanol and quenched with sat. sodium bicarbonate. The mixture was extracted with 8:2 dichloromethane/isopropanol (6×10 mL). The combined organic layers were washed once with sat. NaHCO$_3$, dried over anhydrous Na$_2$SO$_4$ and concentrated in vacuo. to give N-(4-(1-((1H-indol-7-yl)methyl)-2-oxo-1,2,3,4-tetrahydroquinolin-6-yl)thiazol-2-yl)-2,4-dimethyloxazole-5-carboxamide (0.069 g, 83%) as beige solid, $^1$H NMR (400 MHz, DMSO-d): δ 12.49 (s, 1H), 10.92 (s, 1H), 7.73 (d, 1H, J=1.6 Hz), 7.69 (dd, 1H, J=8.4, 2.0 Hz), 7.61 (d, 1H, J=8.0 Hz), 7.54 (bs, 1H), 7.33 (d, 1H, J=8.4 Hz), 7.30 (m, 1H), 7.06 (ddd, 1H, J=6.8, 6.8, 1.2 Hz), 6.99 (ddd, 1H, J=6.8, 6.8, 0.8 Hz), 5.32 (bs, 2H), 2.86 (m, 2H0, 2.70 (m, 2H), 2.48 (s, 3H), 2.40 (s, 3H). MS (ESI): Calcd. for $C_{27}H_{23}N_5O_3S_2$: 497, found 498 (M+1)$^+$.

Example 82

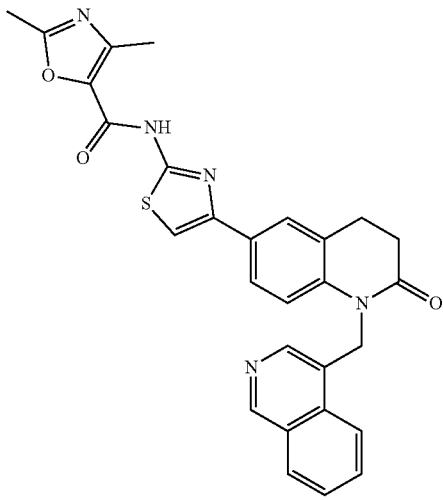

To a solution of 2,4-dimethyl-2-(4-(2-oxo-1,2,3,4-tetrahydroquinolin-1-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 4-(bromomethyl)isoquinoline hydrobromide (0.045 g, 0.149 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(isoquinolin-4-ylmethyl)-2-oxo-1,2,3,4-tetrahydroquinolin-6-yl)thiazol-2-yl)-2,4-dimethyloxazole-5-carboxamide (0.059 g, 85%) as an off-white solid. $^1$H NMR (400 MHz, DMSO-d): δ 12.53 (s, 1H), 9.23 (s, 1H), 8.23 (d, 1H, J=8.8 Hz), 8.18

(d, 1H, J=8.0 Hz), 8.14 (s, 1H), 7.91 (ddd, 1H, J=8.8, 7.2, 1.2 Hz), 7.84 (d, 1H, J=2.0 Hz), 7.77 (m, 1H), 7.66 (dd, 1H, J=8.4, 2.0 Hz), 7.56 (s, 1H), 6.99 (d, 1H, J=8.8 Hz), 5.63 (s, 2H), 3.04 (m, 2H), 2.83 (m, 2H), 2.47 (s, 3H), 2.39 (s, 3H). MS (ESI): Calcd. for $C_{28}H_{23}N_5O_3S$: 509, found 510 $(M+1)^+$.

Example 83

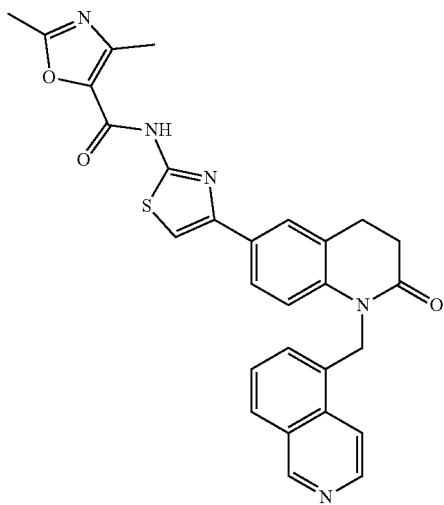 [SMILES: Cc1nc(C)c(C(=O)Nc2nc(-c3ccc4c(c3)CCC(=O)N4Cc3cccc4cnccc34)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 5-(bromomethyl)isoquinoline hydrobromide (0.045 g, 0.149 mmol) was added as a solid in one portion. The mixture was stirred for 90 minutes, then 1 hour at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(isoquinolin-5-ylmethyl)-2-oxo-1,2,3,4-tetrahydroquinolin-6-yl)thiazol-2-yl)-2,4-dimethyloxazole-5-carboxamide (0.043 g, 62%) as white solid. $^1$H NMR (400 MHz, DMSO-d): δ 12.53 (s, 1H), 9.37 (s, 1H), 8.62 (d, 1H, J=5.6 Hz), 8.10 (d, 1H, J=6.4 Hz), 8.03 (d, 1H, J=8.0 Hz), 7.85 (d, 1H, J=2.0 Hz), 7.63 (dd, 1H, J=8.8, 2.4 Hz), 7.57 (m, 2H), 7.36 (d, 1H, J=7.6 Hz), 6.87 (d, 1H, J=8.4 Hz), 5.61 (s, 2H), 3.08 (m, 2H), 2.83 (m, 2H), 2.47 (s, 3H), 2.39 (s, 3H). MS (ESI): Calcd. for $C_{28}H_{23}N_5O_3S$: 509, found 510 $(M+1)^+$.

Example 84

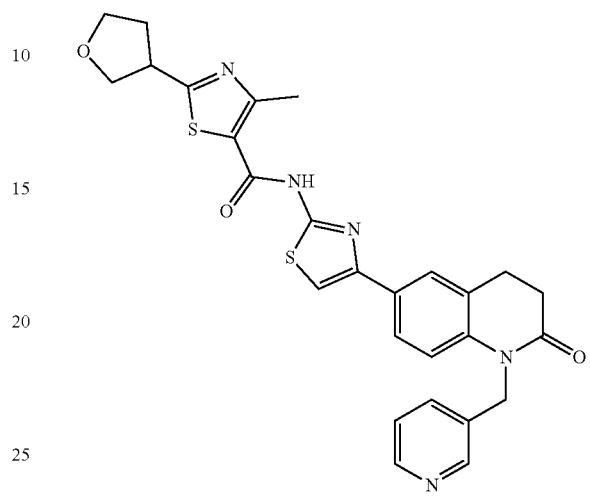

To a solution of 4-methyl-N-(4-(2-oxo-1,2,3,4-tetrahydroquinolin-6-yl)thiazol-2-yl)-2-(tetrahydrofuran-3-yl)thiazole-5-carboxamide (0.050 g, 0.114 mmol) in anhydrous dimethylformamide (3 mL) in argon atmosphere at 0° C. was added sodium hydride (60% in mineral oil, 0.016 g, 0.397 mmol) was added in one portion. The reaction was stirred for 10 min at 0° C. then 3-(bromomethyl)pyridine hydrobromide (0.032 g, 0.114 mmol) was added as a solid in one portion. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 4-methyl-N-(4-(2-oxo-1-(pyridin-3-ylmethyl)-1,2,3,4-tetrahydroquinolin-6-yl)thiazol-2-yl)-2-(tetrahydrofuran-3-yl)thiazole-5-carboxamide (0.036 g, 61%) as an off-white solid. $^1$H NMR (400 MHz, DMSO-d): δ 12.65 (s, 1H), 8.52 (d, 1H, J=1.6 Hz), 8.44 (dd, 1H, J=4.4, 1.6 Hz), 7.80 (d, 1H, J=1.6 Hz), 7.68 (dd, 1H, J=8.4, 2.0 Hz), 7.62 (dt, 1H, J=7.6, 1.6 Hz), 7.56 (bs, 1H), 7.32 (ddd, 1H, J=8.0, 4.8, 0.8 Hz), 7.03 (d, 1H, J=8.4 Hz), 5.22 (bs, 2H), 4.05 (dd, 1H, J=8.0, 6.8 Hz), 3.91 (m, 1H), 3.85 (m, 1H), 3.81 (m, 2H), 3.01 (m, 2H), 2.75 (m, 2H), 2.62 (s, 3H), 2.39 (m, 1H), 2.13 (m, 1H). MS (ESI): Calcd. for $C_{27}H_{25}N_5O_3S_2$: 531, found 532 $(M+1)^+$.

Example 85

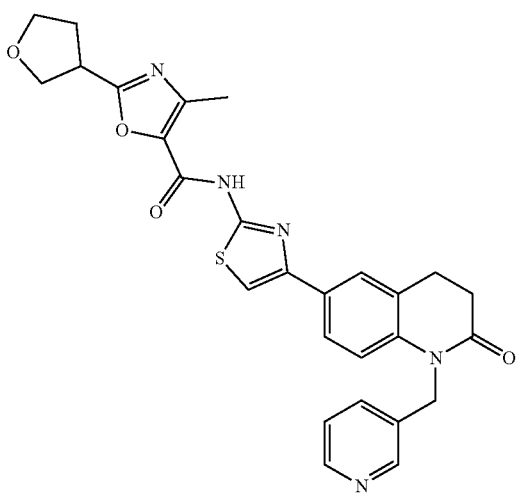 [SMILES: Cc1nc(C2CCOC2)oc1C(=O)Nc1nc(-c2ccc3c(c2)CCC(=O)N3Cc2cccnc2)cs1]

To a solution of 4-methyl-N-(4-(2-oxo-1,2,3,4-tetrahydroquinolin-6-yl)thiazol-2-yl)-2-(tetrahydrofran-3-yl)oxazole-5-carboxamide (0.047 g, 0.111 mmol) in anhydrous dimethylformamide (3 mL) in argon atmosphere at 0° C. was added sodium hydride (60% in mineral oil, 0.016 g, 0.387 mmol) was added in one portion. The reaction was stirred for 10 min at 0° C. then 3-(bromomethyl)pyridine hydrobromide (0.031 g, 0.122 mmol) was added as a solid in one portion. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 4-methyl-N-(4-(2-oxo-1-(pyridin-3-ylmethyl)-1,2,3,4-tetrahydroquinolin-6-yl)thiazol-2-yl)-2-(tetrahydrofuran-3-yl)oxazole-5-carboxamide (0.024 g, 42%) as an off-white solid. $^1$H NMR (400 MHz, DMSO-d): δ 12.68 (s, 1H), 8.53 (d, 1H, J=2.0 Hz), 8.44 (dd, 1H, J=4.4, 1.6 Hz), 7.82 (d, 1H, J=2.0 Hz), 7.70 (dd, 1H, J=8.4, 2.0 Hz), 7.62 (dt, 1H, J=7.6, 1.6 Hz), 7.58 (bs, 1H), 7.31 (ddd, 1H, J=8.0, 4.8, 0.8 Hz), 7.03 (d, 1H, J=8.8 Hz), 5.22 (bs, 2H), 4.02 (m, 2H), 3.87 (m, 1H), 3.81 (m, 1H), 3.66 (m, 1H), 3.02 (m, 2H), 2.75 (m, 2H), 2.39 (s, 3H), 2.36 (m, 1H), 2.29 (m, 1H). MS (ESI): Calcd. for $C_{27}H_{25}N_5O_4S$: 515, found 516 (M+1)$^+$.

Example 86

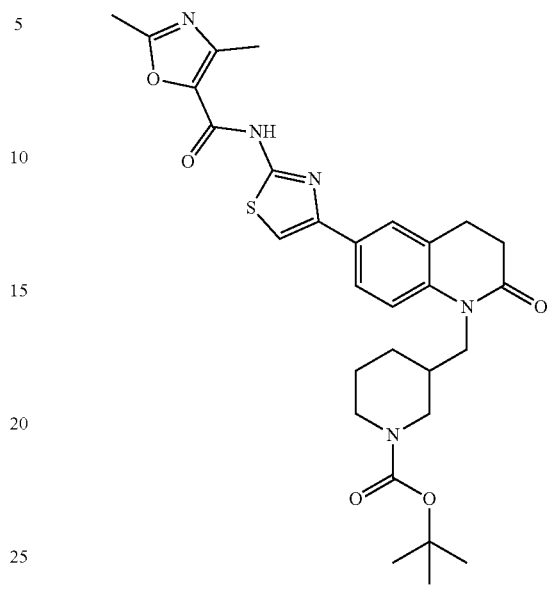

To a solution of 2,4-dimethyl-N-(4-(2-oxo-1,2,3,4-tetrahydroquinolin-6-yl)thiazol-2-yl)oxazole-5-carboxamide (0.150 g, 0.407 mmol) in anhydrous dimethylformamide (6 mL) in a flamed dried flask under argon atmosphere at 0° C. was added sodium hydride (60% in mineral oil, 0.057 g, 1.431 mmol) was added in one portion. The reaction was stirred for 10 min at 0° C. then tert-butyl-3-(bromomethyl)piperidine-1-carboxylate (0.125 g, 0.448 mmol) was added as a solid in one portion. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give tert-butyl 3-((6-(2-(2,4-dimethyloxazole-5-carboxamido)thiazol-4-yl)-2-oxo-3,4-dihydroquinolin-1(2H)-yl)methyl)piperidine-1-carboxylate (0.162 g, 70%) as a white solid. $^1$H NMR (400 MHz, DMSO-d): δ 12.49 (bs, 1H), 7.80 (m, 2H), 7.57 (s, 1H), 7.24 (d, 1H, J=8.8 Hz), 3.96 (m, 1H), 3.81 (m, 1H), 3.72 (m, 2H), 3.24 (m, 1H), 2.90 (m, 2H), 2.75 (m, 1H), 2.60 (m, 2H), 2.48 (s, 3H), 2.41 (s, 3H), 1.74 (m, 2H), 1.61 (m, 1H), 1.29 (bs, 9H), 1.23 (m, 2H). MS (ESI): Calcd. for $C_{29}H_{35}N_5O_5S$: 565, found 588, 466 (M+Na, M-tert-butyl)$^+$.

Example 87

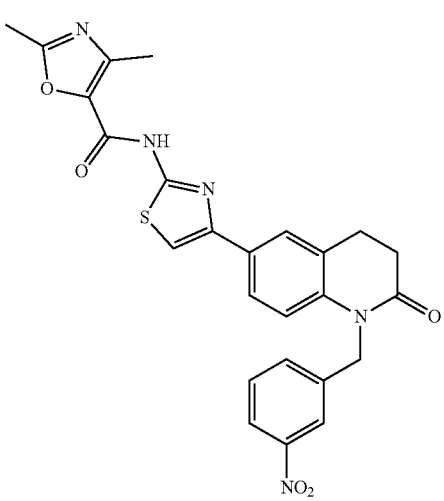 [SMILES: Cc1nc(C)c(C(=O)Nc2nc(-c3ccc4c(c3)CCC(=O)N4Cc3cccc([N+](=O)[O-])c3)cs2)o1]

To a solution of 2,4-dimethyl-2-(4-(2-oxo-1,2,3,4-tetrahydroquinolin-6-yl)thiazol-2-yl)oxazole-5-carboxamide (0.150 g, 0.407 mmol) in anhydrous dimethylformamide (6 mL) in a flamed dried flask under argon atmosphere at 0° C. was added sodium hydride (60% in mineral oil, 0.041 g, 1.021 mmol) was added in one portion. The reaction was stirred for 10 min at 0° C. then 3-nitrobenzyl bromide (0.097 g, 0.448 mmol) was added as a solid in one portion. The mixture was stirred for 90 minutes, then 2 hour at room temperature. After consumption of starting material, the reaction mixture was quenched with saturated ammonium chloride (25 mL) and extracted with ethyl acetate (2×50 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2,4-dimethyl-N-(4-(1-(3-nitrobenzyl)-2-oxo-1,2,3,4-tetrahydroquinolin-6-yl)thiazol-2-yl)oxazole-5-carboxamide (0.193 g, 94%) a yellow solid. $^1$H NMR (400 MHz, DMSO-d): δ 12.49 (bs, 1H), 8.16 (m, 1H), 8.10 (ddd, 1H, J=8.0, 2.4, 1.2 Hz), 7.82 (d, 1H, J=2.4 Hz), 7.69 (d, 1H, J=2.0 Hz), 7.67 (d, 1H, J=2.0 Hz), 7.62 (m, 1H), 7.55 (s, 1H), 7.03 (d, 1H, J=8.4 Hz), 5.32 (s, 2H), 3.03 (m, 2H), 2.77 (m, 2H), 2.47 (s, 3H), 2.40 (s, 3H). MS (ESI): Calcd. for $C_{25}H_{21}N_5O_5S$: 503, found 504 (M+1)$^+$.

Example 88

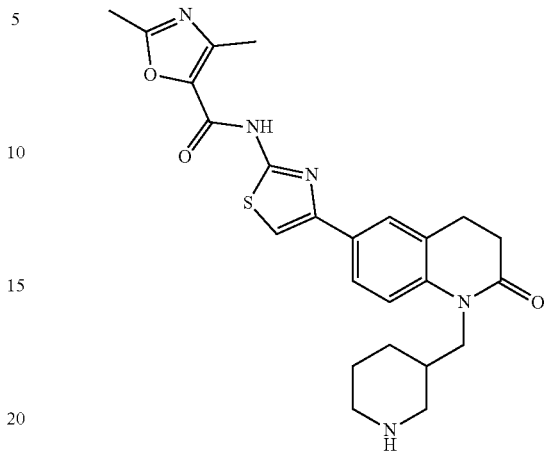

tert-Butyl 3-((6-(2-(2,4-dimethyloxazole-5-carboxamido)thiazol-4-yl)-2-oxo-3,4-dihydroquinolin-1(2H)-yl)methyl)piperidine-1-carboxylate (0.100 g, 0.177 mmol) was suspended 6 mL of 4M hydrogen chloride solution in dioxane in sealed flask. The mixture was stirred for 20 hours at room temperature. The reaction mixture was concentrated in vacuo. The HCl salt was dissolved in minimum amount of methanol and quenched with sat. sodium bicarbonate. The mixture was extracted with 8:2 dichloromethane/isopropanol (6×10 mL). The combined organic layers were washed once with sat. NaHCO$_3$, dried over anhydrous Na$_2$SO$_4$ and concentrated in vacuo. to give 2,4-dimethyl-N-(4-(4-(2-oxo-1-(piperidin-3-ylmethyl)-1,2,3,4-tetrahydroquinolin-6)thiazol-2-yl)thiazol-2-yl)oxazole-5-carboxamide (0.082 g, 100%) as beige solid. $^1$H NMR (400 MHz, DMSO-d): δ 8.75 (bs, 1H), 7.78 (m, 2H), 7.40 (s, 1H), 7.22 (d, 1H, J=9.2 Hz), 3.95 (m, 1H), 3.83 (m, 1H), 3.68 (m, 1H), 3.47 (m, 1H), 3.03 (m, 2H), 2.90 (m, 2H), 2.65 (m, 1H), 2.59 (m, 2H), 2.45 (s, 3H), 2.41 (s, 3H), 1.94 (m, 1H), 1.71 (m, 2H), 1.41 (m, 1H), 1.19 (m, 1H). MS (ESI): Calcd. for $C_{24}H_{27}N_5O_3S$: 465, found 466 (M+1)$^+$.

Example 89

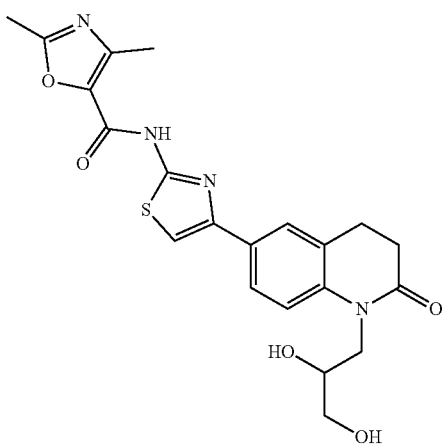 [SMILES: Cc1nc(C)c(C(=O)Nc2nc(-c3ccc4c(c3)CCC(=O)N4CC(O)CO)cs2)o1]

To a solution of 2,4-dimethyl-N-(4-(2-oxo-1,2,3,4-tetrahydroquinolin-6-yl)thiazol-2-yl)oxazole-5-carboxamide (0.040 g, 0.109 mmol) in anhydrous dimethylformamide (3 mL) in a flamed dried flask under argon atmosphere at 0° C. was added sodium hydride (60% in mineral oil, 0.011 g, 0.271 mmol) was added in one portion. The reaction was stirred for 10 min at 0° C. then epibromohydrin (0.016 g, 0.119 mmol) was added via syringe. The mixture was stirred for 90 minutes, then 23 hours at room temperature. After consumption of starting material, the reaction mixture was quenched with saturated saturated sodium bicarbonate (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give N-(4-(1-(2,3-dihydroxypropyl)-2-oxo-1,2,3,4-tetrahydroquinolin-6-yl)thiazol-2-yl)-2,4-dimethyloxazole-5-carboxamide (0.43 g, 89%) as a, white solid. $^1$H NMR (400 MHz, DMSO-d): δ 12.53 (s, 1H), 7.78 (m, 2H), 7.60 (s, 1H), 7.33 (d, 1H, J=8.8 Hz), 4.83 (d, 1H, J=5.2 Hz), 4.62 (t, 1H, J=5.6 Hz), 4.00 (dd, 1H, J=14.0, 4.8 Hz), 3.82 (m, 1H), 3.76 (m, 1H), 3.37 (t, 2H, J=5.6 Hz), 2.92 (m, 2H), 2.58 (m, 2H), 2.49 (s, 3H), 2.41 (s, 3H). MS (ESI): Calcd. for $C_{21}H_{22}N_4O_5S$: 442, found 443 (M+1)$^+$.

Example 90

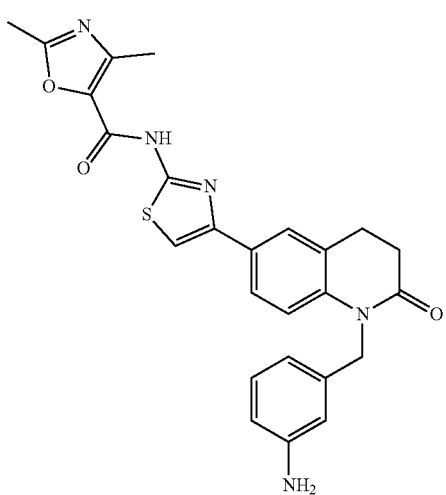 [SMILES: Cc1nc(C)c(C(=O)Nc2nc(-c3ccc4c(c3)CCC(=O)N4Cc3cccc(N)c3)cs2)o1]

To a solution of 2,4-dimethyl-N-(4-(1-(3-nitrobenzyl)-2-oxo-1,2,3,4-tetrahydroquinolin-6-yl)thiazol-2-yl)oxazole-5-carboxamide (0.150 g, 0.407 mmol) in anhydrous dichloromethane/methanol mixture (4 mL/3 mL) in a flamed dried flask under argon atmosphere was added Pd/carbon (10% activate, 0.021 g, 19.86 mmol) was added in one portion. The reaction mixture was bubbled with hydrogen for 15 min and kept under hydrogen balloon atmosphere stirring overnight (20 h). After consumption of starting material, the reaction mixture was filtered through a small pad of celite washing thoroughly with 8:2 dichloromethane/isopropanol mixtures. The concentrated residue was purified by flash chromatography over silica gel using 95:5 dichloromethane/methanol to give N-(4-(1-(3-aminobenzyl)-2-oxo-1,2,3,4-tetrahydroquinolin-6-yl)thiazol-2-yl)-2,4-dimethyloxazole-5-carboxamide (0.076 g, 81%) an off-white solid. $^1$H NMR (400 MHz, DMSO-d): δ 12.52 (bs, 1H), 7.80 (s, 1H), 7.67 (dd, 1H, J=8.4, 1.6 Hz), 7.55 (s, 1H), 6.94 (m, 2H), 6.39 (m, 3H), 5.01 (bs 4H), 3.00 (m, 2H), 2.72 (m, 2H), 2.48 (s, 3H), 2.40 (s, 3H). MS (ESI): Calcd. for $C_{25}H_{23}N_5O_3S$: 473, found 474 (M+1)$^+$.

Example 91

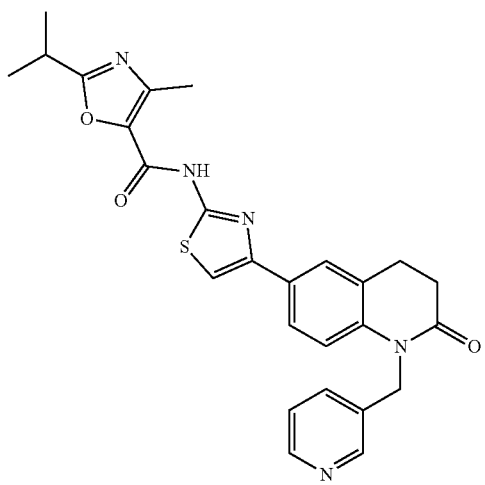 [SMILES: Cc1nc(C(C)C)oc1C(=O)Nc1nc(-c2ccc3c(c2)CCC(=O)N3Cc2cccnc2)cs1]

To a solution of 2-isopropyl-4-methyl-N-(4-(2-oxo-1,2,3,4-tetrahydroquinolin-6-yl)thiazol-2-yl)oxazole-5-carboxamide (0.050 g, 0.126 mmol) in anhydrous dimethylformamide (3 mL) in argon atmosphere at 0° C. was added sodium hydride (60% in mineral oil, 0.013 g, 0.316 mmol) was added in one portion. The reaction was stirred for 10 min at 0° C. then 3-(bromomethyl)pyridine hydrobromide (0.035 g, 0.139 mmol) was added as a solid in one portion. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-isopropyl-4-methyl-N-(4-((2-oxo-1-(pyridin-3-ylmethyl)-1,2,3,4-tetrahydroquinolin-6-yl)thiazol-2-yl)oxazole-5-carboxamide (0.020 g, 33%) as an white solid. $^1$H NMR (400 MHz, DMSO-d): δ 12.64 (s, 1H), 8.53 (d, 1H, J=2.0 Hz), 8.44 (dd, 1H, J=4.4, 1.6 Hz), 7.82 (d, 1H, J=2.0 Hz), 7.69 (dd, 1H, J=6.8, 2.0 Hz), 7.62 (dt, 1H, J=7.6, 2.0 Hz), 7.56 (bs, 1H), 7.33 (ddd, 1H, J=5.6, 4.4, 0.8 Hz), 7.03 (d, 1H, J=8.4 Hz), 5.22 (s, 2H), 3.10 (quintet, 1H, J=7.2 Hz), 3.01 (m, 2H), 2.75 (m, 2H), 2.41 (s, 3H), 1.35 (s, 3H), 1.34 (s, 3H). MS (ESI): Calcd. for $C_{26}H_{25}N_5O_3S_1$: 487, found 488 (M+1)$^+$.

Example 92

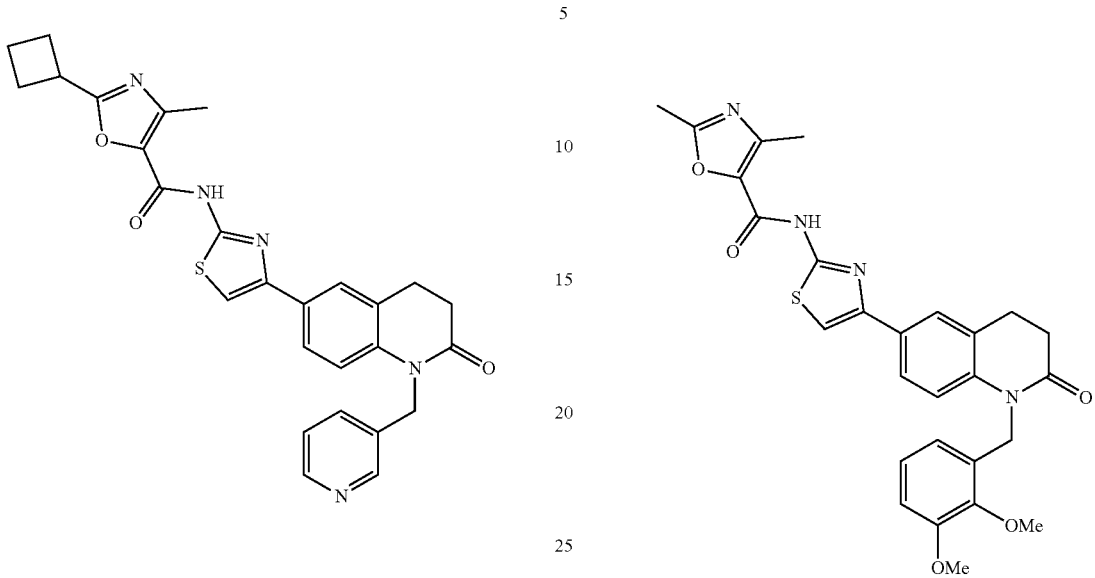

To a solution of 2-cyclobutyl-4-methyl-N-(4-(2-oxo-1,2,3,4-tetrahydroquinolin-6-yl)thiazol-2-yl)oxazole-5-carboxamide (0.050 g, 0.123 mmol) in anhydrous dimethylformamide (3 mL) in argon atmosphere at 00° C. was added sodium hydride (60% in mineral oil, 0.012 g, 0.306 mmol) was added in one portion. The reaction was stirred for 10 min at 0° C. then 3-(bromomethyl)pyridine hydrobromide (0.034 g, 0.135 mmol) was added in one portion as a solid. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 2-cyclobutyl-4-methyl-N-(4-(2-oxo-1-(pyridin-3-ylmethyl)-1,2,3,4-tetrahydroquinolin-6-yl)thiazol-2-yl)oxazole-5-carboxamide (0.016 g, 26%) as an white solid. $^1$H NMR (400 MHz, DMSO-d): δ 12.66 (s, 1H), 8.53 (d, 1H, J=2.0 Hz), 8.44 (dd, 1H, J=4.4, 1.6 Hz), 7.83 (d, 1H, J=2.0 Hz), 7.70 (dd, 1H, J=8.0, 2.0 Hz), 7.62 (dt, 1H, J=7.6, 2.4 Hz), 7.58 (s, 1H), 7.33 (ddd, 1H, J=7.6, 4.4, 0.8 Hz), 7.03 (d, 1H, J=8.8 Hz), 5.22 (s, 2H), 3.67 (d-quintet, 1H, J=8.8, 0.8 Hz), 3.02 (m, 2H), 2.76 (m, 2H), 2.44 (m, 2H), 2.41 (s, 3H), 2.32 (m, 2H), 2.05 (m, 1H), 1.95 (m, 1H). MS (ESI): Calcd. for $C_{27}H_{25}N_5O_3S_2$: 499, found 500 (M+1)$^+$.

Example 93

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.343 mmol) was added in one portion. The reaction was stirred for 10 min at 0° C. then 2,3-dimethoxyl benzyl chloride (0.028 g, 0.149 mmol) was added in one portion as a solid. The mixture was stirred for 90 minutes, then 2 hour at room temperature. After consumption of starting material, the reaction mixture was quenched with saturated ammonium chloride (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-(2,3-dimethoxybenzyl)-2-oxo-1,2,3,4-tetrahydroquinolin-6-yl)thiazol-2-yl)-2,4-dimethyloxazole-5-carboxamide (0.044 g, 63%) a white solid. $^1$H NMR (400 MHz, DMSO-d): δ 12.51 (bs, 1H), 7.81 (d, 1H, J=2.0 Hz), 7.68 (dd, 1H, J=8.8, 2.0 Hz), 7.56 (s, 1H), 6.94 (m, 2H), 6.87 (d, 1H, J=8.8 Hz), 6.51 (m, 1H), 5.13 (s, 2H), 3.84 (s, 3H), 3.81 (s, 3H), 3.01 (m, 2H), 2.73 (m, 2H), 2.48 (s, 3H), 2.40 (s, 3H). MS (ESI): Calcd. for $C_{27}H_{26}N_4O_5S$: 518, found 519 (M+1)$^+$.

Example 94

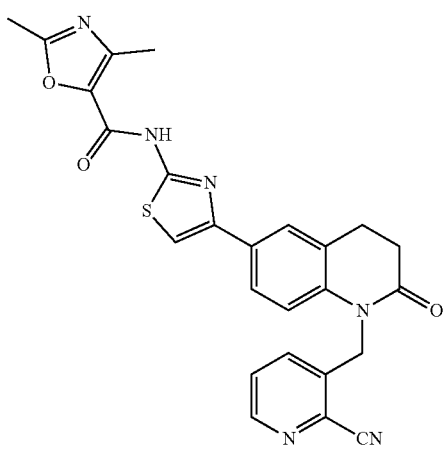 [SMILES: Cc1nc(C)c(C(=O)Nc2nc(-c3ccc4c(c3)CCC(=O)N4Cc3cccnc3C#N)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 3-(bromomethyl)picolinonitrile (0.029 g, 0.149 mmol) was added in one portion as a solid. The mixture was stirred for 90 minutes, then 2 hour at room temperature. After consumption of starting material, the reaction mixture was quenched with saturated ammonium chloride (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-((2-cyanopyridin-3-yl)methyl)-2-oxo-1,2,3,4-tetrahydroquinolin-6-yl)thiazol-2-yl)-2,4-dimethyloxazole-5-carboxamide (0.056 g, 85%) a yellow solid. $^1$H NMR (400 MHz, DMSO-d): δ 12.52 (bs, 1H), 8.65 (dd, 1H, J=4.4, 1.6 Hz), 7.85 (d, 1H, J=2.0 Hz), 7.71 (dd, 2H, J=8.0, 1.6 Hz), 7.65 (dd, 1H, J=7.6, 4.0 Hz), 7.61 (bs, 1H), 6.99 (dd, 1H, J=8.8 Hz), 5.35 (s, 2H), 3.05 (m, 2H), 2.76 (m, 2H), 2.48 (s, 3H), 2.40 (s, 3H). MS (ESI): Calcd. for $C_{25}H_{20}N_6O_3S$: 484, found 485 (M+1)$^+$.

Example 95

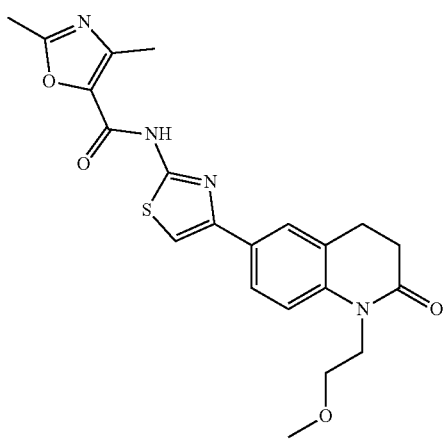 [SMILES: COCCN1C(=O)CCc2cc(-c3csc(NC(=O)c4oc(C)nc4C)n3)ccc21]

To a solution of 2,4-dimethyl-N-(4-(2-oxo 1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 2-bromoethyl methyl ether (0.021 g, 0.149 mmol) was added via syringe. The mixture was stirred for 90 minutes, then 20 hours at room temperature. After consumption of starting material, the reaction mixture was quenched with saturated ammonium chloride (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-(2-methoxyethyl)-2-oxo-1,2,3,4-tetrahydroquinolin-6-yl)thiazol-2-yl)-2,4-dimethyloxazole-5-carboxamide (0.050 g, 87%) a, white solid. $^1$H NMR (400 MHz, DMSO-d): δ 12.53 (bs, 1H), 7.79 (m, 2H), 7.60 (s, 1H), 7.27 (d, 1H, J=8.4 Hz), 4.08 (t, 2H, J=6.0 Hz), 3.52 (t, 2H, J=6.0 Hz), 3.32 (s, 3H), 2.90 (m, 2H), 2.59 (m, 2H), 2.49 (s, 3H), 2.41 (s, 3H). MS (ESI): Calcd. for $C_{21}H_{22}N_4O_4S$: 426, found 427 (M+1)$^+$.

Example 96

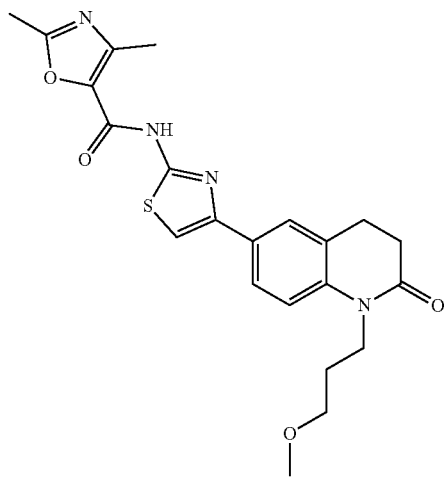 [SMILES: COCCCN1C(=O)CCc2cc(-c3csc(NC(=O)c4oc(C)nc4C)n3)ccc21]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 1-bromo-3-methoxypropane (0.023 g, 0.149 mmol) was added via syringe. The mixture was stirred for 90 minutes, then 20 hours at room temperature. After consumption of starting material, the reaction mixture was quenched with saturated ammonium chloride (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-(3-methoxypropyl)-2-oxo-1,2,3,4-tetrahydroquinolin-6-yl)thiazol-2-yl)-2,4-dimethyloxazole-5-carboxamide (0.050 g, 85%) a white solid. $^1$H NMR (400 MHz, DMSO-d): δ 12.53 (bs, 1H), 7.80 (m, 2H), 7.60 (s, 1H), 7.27 (d, 1H, J=8.4 Hz), 3.95 (t, 2H, J=6.4 Hz), 3.37 (t, 2H, J=6.4 Hz), 3.23 (s, 3H), 2.91 (m, 2H), 2.57 (m, 2H), 2.49 (s, 3H), 2.41 (s, 3H), 1.79 (pentet, 2H, J=6.4 Hz). MS (ESI): Calcd. for $C_{22}H_{24}N_4O_4S$: 440, found 441 (M+1)$^+$.

Example 97

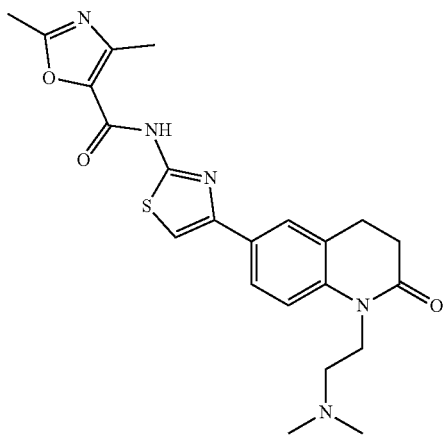 [SMILES: Cc1nc(C)c(C(=O)Nc2nc(-c3ccc4c(c3)CCC(=O)N4CCN(C)C)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 2-bromo-N,N-dimethylethylamine hydrobromide (0.035 g, 0.149 mmol) was added as a solid. The mixture was stirred for 90 minutes, then 20 hours at room temperature. After consumption of starting material, the reaction mixture was quenched with water (5 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-(2-(dimethylamino) ethyl)-2-oxo-1,2,3,4-tetrahydroquinolin-6-yl)thiazol-2-yl)-2,4-dimethyloxazole-5-carboxamide (0.051 g, 86%) an off-white solid. $^1$H NMR (400 MHz, DMSO-d): δ 12.46 (bs, 1H), 7.80 (m, 2H), 7.59 (s, 1H), 7.19 (d, 1H, J=8.4 Hz), 4.01 (t, 2H, J=7.2 Hz), 2.89 (m, 2H), 2.57 (m, 2H), 2.50 (masked under d-DMSO, 3H), 2.43 (t, 2H, J=6.8 Hz), 2.41 (s, 3H), 2.21 (s, 6H). MS (ESI): Calcd. for $C_{22}H_{25}N_5O_3S$: 439, found 440 (M+1)$^+$.

Example 98

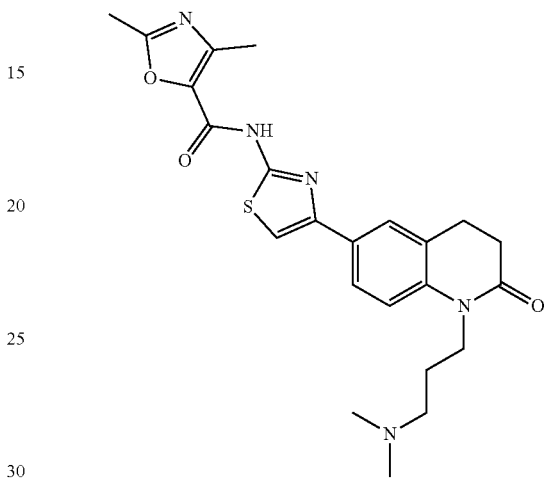

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 3-bromo-N,N-dimethylpropan-1-amine hydrobromide (0.037 g, 0.149 mmol) was added as a solid. The mixture was stirred for 90 minutes, then 20 hours at room temperature. After consumption of starting material, the reaction mixture was quenched with saturated ammonium chloride (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-(3-(dimethylamino) propyl)-2-oxo-1,2,3,4-tetrahydroquinolin-6-yl)thiazol-2-yl)-2,4-dimethyloxazole-5-carboxamide (0.045 g, 74%) a white solid. $^1$H NMR (400 MHz, DMSO-d): δ 12.19 (bs, 1H), 7.80 (m, 2H), 7.51 (s, 1H), 7.22 (d, 1H, J=8.8 Hz), 3.92 (t, 2H, J=7.6 Hz), 2.91 (m, 2H), 2.57 (m, 2H), 2.49 (s, 3H), 2.49 (s, 3H), 2.36 (t, 2H, J=7.6 Hz), 2.19 (s, 6H), 1.70 (pentet, 2H, J=7.6 Hz). MS (ESI): Calcd. for $C_{23}H_{27}N_5O_3S$: 453, found 454 (M+1)$^+$.

Example 99

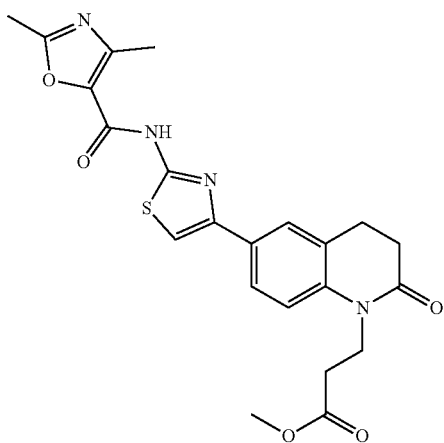 [SMILES: COC(=O)CCN1C(=O)CCc2cc(-c3csc(NC(=O)c4oc(C)nc4C)n3)ccc21]

To a solution of 2,4-dimethyl-N-(4-(2-oxo-1,2,3,4-tetra-hydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 3-bromopropionate (0.025 g, 0.149 mmol) was added via syringe. The mixture was stirred for 90 minutes, then 20 hours at room temperature. After consumption of starting material, the reaction mixture was quenched with sat. ammonium chloride (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give methyl 3-(6-(2-(2,4-dimethyl-oxazole-5-carboxamido)thiazol-4-yl)-2-oxo-3,4-dihydro-quinoiolin-1 (2H)-yl)propanoate (0.048 g, 78%) a white solid. $^1$H NMR (400 MHz, DMSO-d): δ 12.53 (bs, 1H), 7.80 (m, 2H), 7.61 (s, 1H), 7.21 (d, 1H, J=8.8 Hz), 4.16 (m, 2H), 3.58 (s, 3H), 2.90 (m, 2H), 2.59 (m, 4H), 2.49 (s, 3H), 2.41 (s, 3H). MS (ESI): Calcd. for $C_{22}H_{22}N_4O_5S$: 454, found 455 $(M+1)^+$.

Example 100

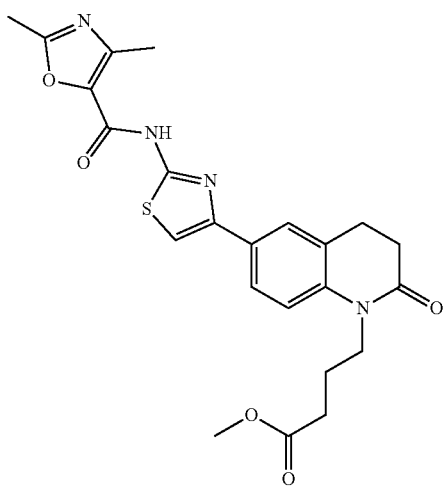 [SMILES: COC(=O)CCCN1C(=O)CCc2cc(-c3csc(NC(=O)c4oc(C)nc4C)n3)ccc21]

To a solution of 2,4-dimethyl-N-(4-(2-oxo-1,2,3,4-tetra-hydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 4-bromobutanoate (0.027 g, 0.149 mmol) was added via syringe. The mixture was stirred for 90 minutes, then 20 hours at room temperature. After consumption of starting material, the reaction mixture was quenched with sat. ammonium chloride (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give methyl 4-(6-(2-(2,4-dimethyl-oxazole-5-carboxamido)thiazol-4-yl)-2-oxo-3,4-dihydro-quinolin-1 (2H)-yl)butanoate (0.021 g, 34%) a white solid. $^1$H NMR (400 MHz, DMSO-d): δ 12.52 (bs, 1H), 7.80 (m, 2H), 7.61 (s, 1H), 7.26 (d, 1H, J=8.4 Hz), 3.93 (t, 2H, J=7.2 Hz), 3.58 (s, 3H), 2.91 (m, 2H), 2.58 (m, 2H), 2.49 (s, 3H), 2.41 (s, 3H), 2.39 (t, 2H, J=7.6 Hz), 1.81 (pentet, 2H, J=7.2 Hz). MS (ESI): Calcd. for $C_{23}H_{24}N_4O_5S$: 468, found 469 $(M+1)^+$.

Example 101

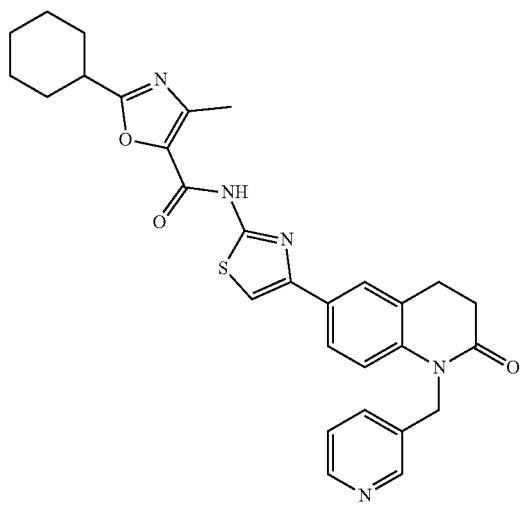 [SMILES: Cc1nc(C2CCCCC2)oc1C(=O)Nc1nc(-c2ccc3c(c2)CCC(=O)N3Cc2cccnc2)cs1]

To a solution of 2-cyclohexyl-4-methyl-N-(4-(2-oxo-1,2,3,4-tetrahydroquinolin-6-yl)thiazol-2-yl)oxazole-5-carboxamide (0,050 g, 0.115 mmol) in anhydrous dimethylformamide (3 mL) in a flamed dried flask under argon atmosphere at 0° C. was added sodium hydride (60% in mineral oil, 0.016 g, 0.401 mmol) was added in one portion. The reaction was stirred for 10 min at 0° C. then 3-(bromomethyl)pyridine hydrobromide (0.032 g, 0.115 mmol) was added in one portion as a solid. The mixture was stirred for 90 minutes, then 20 hours at room temperature. After consumption of starting material, the reaction mixture was quenched with water (1 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give methyl 2-cyclohexyl-4-methyl-N-(4-(2-oxo-1-(pyridin-3-ylmethyl)-1,2,3,4-tetrahydroquinolin-6-yl)thiazole-2-yl)oxazole-5-carboxamide (0.041 g, 68%) a white solid. $^1$H NMR (400 MHz, DMSO-d): δ 12.63 (bs, 1H), 8.53 (d, 1H, J=1.6 Hz), 8.44 (dd, 1H, J=4.4, 1.6 Hz), 7.82 (d, 1H, J=1.6 Hz), 7.70 (dd, 1H, J=8.4, 1.6 Hz), 7.62 (dt, 1H, J=7.6, 1.6 Hz), 7.58 (s, 1H), 7.33 (dd, 1H, J=7.6, 4.4 Hz), 7.03 (d, 1H, J=8.4 Hz), 5.22 (s, 2H), 3.02 (m, 2H), 2.81 (tt, 1H, J=10.8, 4.0 Hz), 2.75 (m, 2H), 2.41 (s, 3H), 2.06 (m, 2H), 1.74 (m, 2H), 1.62 (m, 2H), 1.36 (m, 2H), 1.25 (m, 2H). MS (ESI): Calcd. for $C_{29}H_{29}N_5O_3S$: 527, found 528 (M+1)$^+$.

Example 102

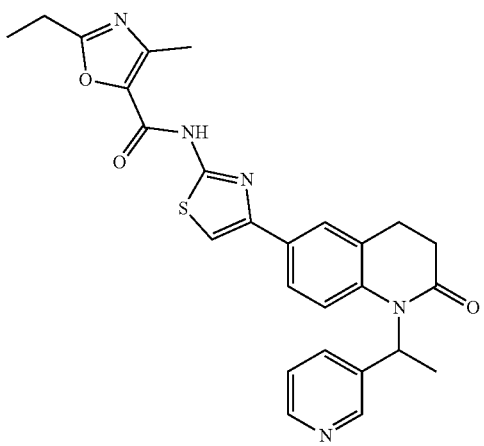 [SMILES: CCc1nc(C)c(C(=O)Nc2nc(-c3ccc4c(c3)CCC(=O)N4C(C)c3cccnc3)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.458 mmol) was added in one portion. The reaction was stirred for 10 min at 0° C. then 3-(chloroethyl)pyridine hydrochloride (0.026 g, 0.144 mmol) was added in one portion as a solid and stirred for 90 mins. The mixtures were then slowly equilibrate to room temperature and stirred overnight (15 hours). After consumption of starting material, the reaction mixture was quenched with water (2 mL) and saturated sodium bicarbonate (2 mL). The mixtures were extracted with ethyl acetate (2×25 mL), washed with brine (2×25 mL), and dried over anhydrous sodium sulfate. The concentrated residue was purified by flash chromatography over silica gel using 95:5 dichloromethane/methanol to give 2-ethyl-4-methyl-N-(4-(2-oxo-1-(1-(pyridin-3-yl)ethyl)-1,2,3,4-tetrahydroquinolin-6-yl)thiazol-2-yl)oxazole-5-carboxamide (0.021 g, 32%) as a white solid. $^1$H NMR (400 MHz, DMSO-d): δ 12.58 (s, 1H), 8.53 (d, 1H, J=2.0 Hz), 8.45 (d, 1H, J=4.0 Hz), 7.82 (d, 1H, J=2.0 Hz), 7.69 (m, 1H), 7.60 (dd, 1H, J=8.0, 1.6 Hz), 7.56 (s, 1H), 7.36 (dd, 1H, J=8.4, 4.8 Hz), 6.79 (d, 1H, J=8.8 Hz), 6.12 (m, 1H), 2.96 (m, 2H), 2.81 (q, 2H, J=7.6 Hz), 2.65 (m, 2H), 2.41 (s, 3H), 1.80 (d, 3H, J=7.2 Hz), 1.32 (t, 3H, J=7.6 Hz). MS (ESI): Calcd. for $C_{26}H_{25}N_5O_3S$: 487, found 488 (M+1)$^+$.

Example 103

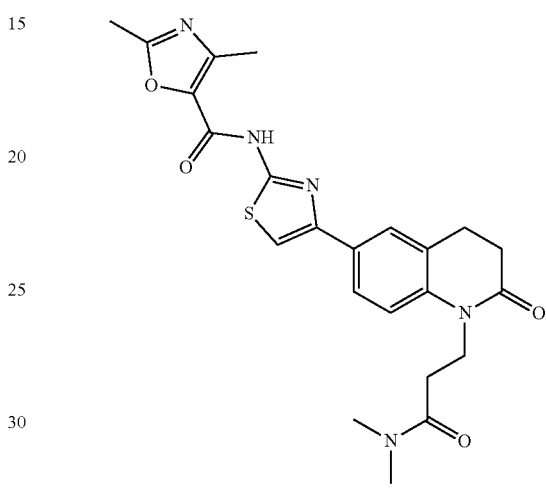

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 3-bromo-N,N-dimethylpropionamide (0.014 g, 0.149 mmol) was added via syringe. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give N-(4-(1-(3-(dimethylamino)-3-oxopropyl)-2-oxo-1,2,3,4-tetrahydroquinolin-6-yl)thiazol-2-yl)-2,4-dimethyloxazole-5-carboxamide (0.027 g, 43%) a white solid. $^1$H NMR (400 MHz, DMSO-d): δ 12.54 (s, 1H), 7.80 (m, 2H), 7.61 (s, 1H), 7.18 (d, 1H, J=8.4 Hz), 4.08 (m, 2H), 2.93 (s, 3H), 2.91 (m, 2H), 2.83 (s, 3H), 2.59 (m, 4H), 2.49 (s, 3H), 2.41 (s, 3H). MS (ESI): Calcd. for $C_{23}H_{25}N_5O_4S$: 467, found 468 (M+1)$^+$.

Example 104

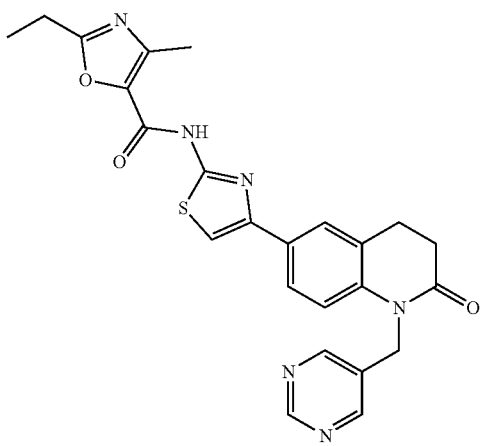 [SMILES: CCc1nc(C)c(C(=O)Nc2nc(-c3ccc4c(c3)CCC(=O)N4Cc3cncnc3)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.459 mmol) was added in one portion. The reaction was stirred for 10 min at 0° C. then 5-(chloromethyl)pyrimidine hydrochloride (0.024 g, 0.144 mmol) was added in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 2-ethyl-4-methyl-N-(4-(2-oxo-1-(pyrimidin-5-ylmethyl)-1,2,3,4-tetrahydroquinolin-6-yl)thiazol-2-yl)oxazole-5-carboxamide (0.051 g, 82%) a white solid. $^1$H NMR (400 MHz, DMSO-d): δ 12.57 (s, 1H), 9.08 (s, 1H), 8.72 (s, 2H), 7.83 (d, 2H, J=2.0 Hz), 7.71 (dd, 1H, J=8.4, 2.4 Hz), 7.60 (s, 1H), 7.08 (d, 1H, J=8.8 Hz), 5.24 (s, 2H), 3.03 (m, 2H), 2.81 (q, 2H, J=7.6 Hz), 2.75 (m, 2H), 2.41 (s, 3H), 1.32 (t, 2H, J=7.6 Hz). MS (ESI): Calcd. for $C_{24}H_{22}N_6O_3S$: 474, found 475 (M+1)$^+$.

Example 105

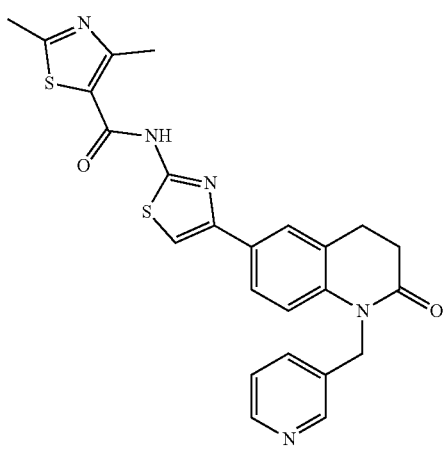

To a solution of 2,4-dimethyl-N-(4-(2-oxo-1,2,3,4-tetrahydroquinolin-6-yl)thiazol-2-yl)thiazole-5-carboxamide (0.050 g, 0.130 mmol) in anhydrous dimethylformamide (3 mL) in a flamed dried flask under argon atmosphere at 0° C. was added sodium hydride (60% in mineral oil, 0.018 g, 0.455 mmol) was added in one portion. The reaction was stirred for 10 min at 0° C. then 3-(bromomethyl)pyridine hydrobromide (0.036 g, 0.143 mmol) was added in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 2,4-dimethyl-N-(4-(2-oxo-1-(pyridin-3-ylmethyl)-1,2,3,4-tetrahydroquinolin-6-yl)thiazol-2-yl)thiazole-5-carboxamide (0.039 g, 63%) a white solid. $^1$H NMR (400 MHz, DMSO-d): δ 12.60 (bs, 1H), 8.52 (d, 1H, J=1.6), 8.44 (dd, 1H, J=4.4, 1.6 Hz), 7.80 (d, 2H, J=2.0 Hz), 7.68 (dd, 1H, J=8.4, 2.0 Hz), 7.62 (m, 1H), 7.56 (bs, 1H), 7.33 (dd, 1H, J=7.6, 4.4 Hz), 7.03 (d, 1H, J=8.4 Hz), 5.22 (s, 2H), 3.01 (m, 2H), 2.75 (m, 2H), 2.67 (s, 3H), 2.60 (s, 3H). MS (ESI): Calcd. for $C_{24}H_{21}N_5O_2S_2$: 475, found 476 (M+1)$^+$.

Example 106

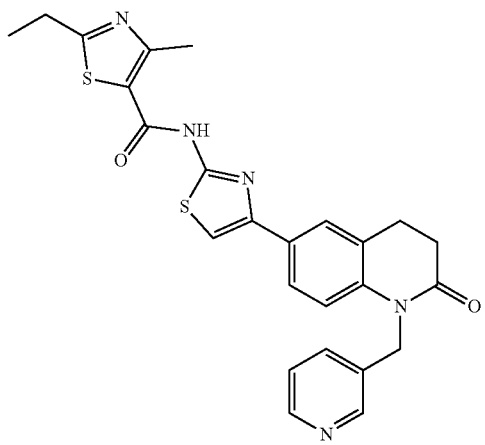 [SMILES: CCc1nc(C)c(C(=O)Nc2nc(-c3ccc4c(c3)CCC(=O)N4Cc3cccnc3)cs2)s1]

To a solution of 2-ethyl-4-methyl-N-(4-(2-oxo-1,2,3,4-tetrahydroquinolin-6-yl)thiazol-2-yl)thiazole-5-carboxamide (0.050 g, 0.126 mmol) in anhydrous dimethylformamide (3 mL) in a flamed dried flask under argon atmosphere at 0° C. was added sodium hydride (60% in mineral oil, 0.018 g, 0.439 mmol) was added in one portion. The reaction was stirred for 10 min at 0° C. then 3-(bromomethyl)pyridine hydrobromide (0.035 g, 0.138 mmol) was added in one portion as a, solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 2-ethyl-4-methyl-N-(4-(2-oxo-1-(pyridin-3-ylmethyl)-1,2,3,4-tetrahydroquinoinolin-6-yl)thiazol-2-yl)thiazole-5-carboxamide (0.051 g, 33%) an off-white solid. $^1$H NMR (400 MHz, DMSO-d): δ 12.60 (bs, 1H), 8.53 (d, 1H, J=1.6), 8.44 (dd, 1H, J=4.8, 2.0 Hz), 7.80 (d, 2H, J=1.6 Hz), 7.68 (dd, 1H, J=8.8, 2.0 Hz), 7.62 (m, 1H), 7.56 (bs, 1H), 7.33 (dd, 1H, J=8.8, 4.8 Hz), 7.03 (d, 1H, J=8.4 Hz), 5.22 (s, 2H), 3.00 (m, 4H), 2.75 (m, 2H), 2.61 (s, 3H), 1.31 (t, 3H, J=7.6 Hz). MS (ESI): Calcd. for $C_{25}H_{23}N_5O_2S_2$: 489, found 490 (M+1)$^+$.

Example 107

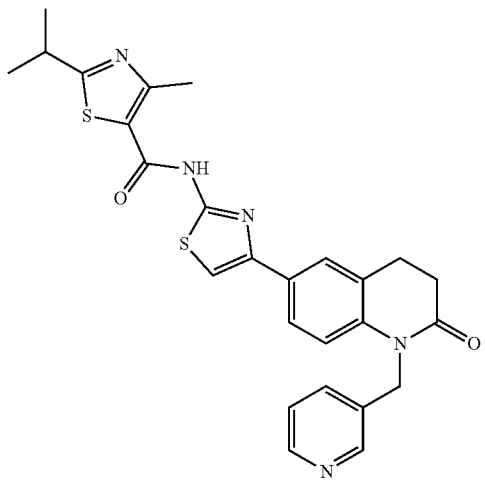 [SMILES: Cc1nc(C(C)C)sc1C(=O)Nc1nc(-c2ccc3c(c2)CCC(=O)N3Cc2cccnc2)cs1]

To a solution of 2-isopropyl-4-methyl-N-(4-(2-oxo-1,2,3,4-tetrahydroquinolin-6-yl)thiazol-2-yl)thiazole-5-carboxamide (0.050 g, 0.125 mmol) in anhydrous dimethylformamide (3 mL) in a flamed dried flask under argon atmosphere at 0° C. was added sodium hydride (60% in mineral oil, 0.018 g, 0.439 mmol) was added in one portion. The reaction was stirred for 10 min at 0° C. then 3-(bromomethyl)pyridine hydrobromide (0.035 g, 0.138 mmol) was added in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 2-isopropyl-4-methyl-N-(4-(2-oxo-1-(pyridin-3-ylmethyl)-1,2,3,4-tetrahydroquinolin-6-yl)thiazol-2-yl)thiazole-5-carboxamide (0.051 g, 33%) an off-white solid. $^1$H NMR (400 MHz, DMSO-d): δ 12.58 (bs, 1H), 8.53 (d, 1H, J=1.6), 8.44 (dd, 1H, J=4.8, 1.6 Hz), 7.80 (d, 2H, J=1.6 Hz), 7.68 (dd, 1H, J=8.8, 2.0 Hz), 7.62 (m, 1H), 7.56 (bs, 1H), 7.33 (dd, 1H, J=6.8, 4.8 Hz), 7.03 (d, 1H, J=8.4 Hz), 5.22 (s, 2H), 3.27 (septet, 1H, J=6.8 Hz), 3.01 (m, 2H), 2.75 (m, 2H), 2.61 (s, 3H), 1.31 (d, 6H, J=6.8 Hz). MS (ESI): Calcd. for $C_{36}H_{25}N_5O_2S_2$: 489, found 490 (M+1)$^+$.

Example 108

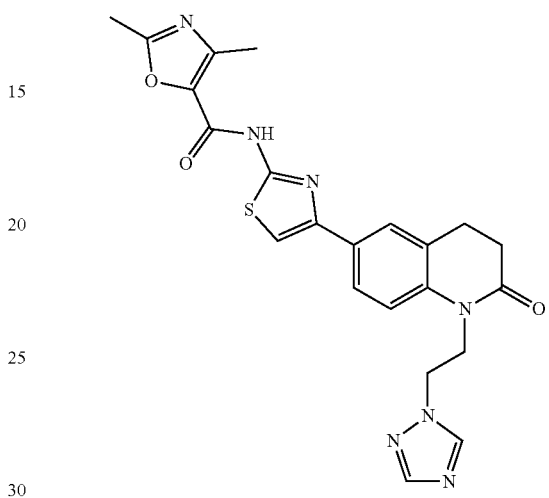

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.019 g, 0.475 mmol) was added in one portion. The reaction was stirred for 10 min at 0° C. then 1-(2-bromomethyl)-1H-1,2-triazole hydrobromide (0.038 g, 0.149 mmol) was in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give N-(4-(1-(2-(1H-1,2,4-triazol-1-yl)ethyl)-2-oxo-1,2,3,4-tetrahydroquinolin-6-yl)thiazol-2-yl)-2,4-dimethyloxazole-5-carboxamide (0.008 g, 1.2%) a white solid. $^1$H NMR (400 MHz, DMSO-d): δ 12.49 (bs, 1H), 8.46 (s, 1H), 7.93 (s, 1H), 7.76 (m, 1H), 7.71 (dd, 1H, J=8.0, 1.6 Hz), 7.58 (bs, 1H), 6.92 (d, 1H, J=8.4 Hz), 4.44 (t, 2H, J=6.0 Hz), 4.30 (t, 2H, J=6.0 Hz), 2.88 (m, 2H), 2.56 (m, 2H), 2.49 (s, 3H), 2.41 (s, 3H). MS (ESI): Calcd. for $C_{22}H_{21}N_7O_3S$: 463, found 464 (M+1)$^+$.

Example 109

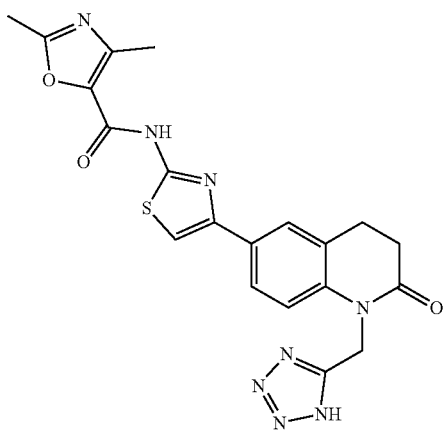 [SMILES: Cc1nc(C)c(C(=O)Nc2nc(-c3ccc4c(c3)CCC(=O)N4Cc3nnn[nH]3)cs2)o1]

To a solution of 2,4-dimethyl-N-(4-(2-oxo-1,2,3,4-tetrahydroquinolin-6-yl)thiazol-2-yl)oxazole-5-carboxamide (0.050 g, 0.136 mmol) in anhydrous dimethylformamide (3 mL) in a flamed dried flask under argon atmosphere at 0° C. was added sodium hydride (60% in mineral oil, 0.014 g, 0.339 mmol) was added in one portion. The reaction was stirred for 10 min at 0° C. then 5-chloromethyl-1H-tetrazole (0.038 g, 0.149 mmol) was in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were adjusted to pH=3 and extracted with 8:2 dichloromethane/isopropanol mixtures (5×15 mL) and washed with brine (2×25 mL). The combined organics were dried over anhydrous sodium sulfate, filtered, and concentrated. The residue was purified by flash chromatography over silica gel using 9:1 dichloromethane/methanol to give N-(4-(1-((1H-tetrazol-5-yl)methyl)-2-oxo-1,2,3,4-tetrahydroquinolin-6-yl)thiazol-2-yl)-2,4-dimethyloxazole-5-carboxamide (0.057 g, 93%) a white solid. $^1$H NMR (400 MHz, DMSO-d): δ 12.54 (bs, 1H), 7.84 (d, 1H, J=2.0 Hz), 7.76 (dd, 1H, J=8.4, 2.0 Hz), 7.61 (s, 1H), 7.01 (d, 1H, J=8.8 Hz), 5.43 (s, 2H), 5.09 (s, 1H), 3.01 (m, 2H), 2.70 (m, 2H), 2.49 (s, 3H), 2.41 (s, 3H). MS (ESI): Calcd. for $C_{20}H_{18}N_8O_3S$: 450, found 451 (M+1)$^+$.

Example 110

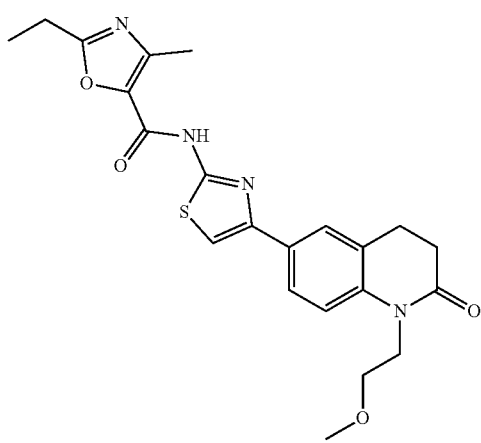 [SMILES: CCc1nc(C)c(C(=O)Nc2nc(-c3ccc4c(c3)CCC(=O)N4CCOC)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.131 mmol) in anhydrous dimethylformamide (3 mL) in a flamed dried flask under argon atmosphere at 0° C. was added sodium hydride (60% in mineral oil, 0.013 g, 0.327 mmol) was added in one portion. The reaction was stirred for 10 min at 0° C. then 2-bromoethyl methyl ether (0.020 g, 0.144 mmol) was added via syringe. The mixture was stirred for 90 minutes, then 20 hours at room temperature. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate and the concentrated residue was purified by flash chromatography over silica gel using 95:5 dichloromethane/methanol to give 2-ethyl-N-(4-(1-(2-methoxyethyl)-2-oxo-1,2,3,4-tetrahydroquinolin-6-yl)thiazol-2-yl)-4-methyloxazole-5-carboxamide (0.050 g, 87%) a white solid. $^1$H NMR (400 MHz, DMSO-d): δ 12.59 (s, 1H), 7.80 (m, 2H), 7.61 (s, 1H), 7.27 (d, 1H, J=8.4 Hz), 4.08 (t, 2H, J=6.0 Hz), 3.52 (t, 2H, J=6.0 Hz), 3.25 (s, 3H), 2.90 (m, 2H), 2.82 (q, 2H, J=7.2 Hz), 2.59 (m, 2H), 2.42 (s, 3H), 1.33 (t, 3H, J=7.2 Hz). MS (ESI): Calcd. for $C_{22}H_{24}N_4O_4S$: 440, found 441 (M+1)$^+$.

Example 111

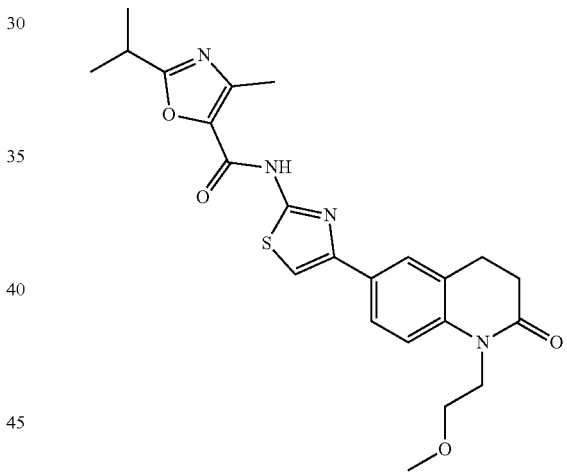

To a solution of 2-isopropyl-4-methyl-N-(4-(2-oxo-1,2,3,4-tetrahydroquinolin-6-yl)thiazol-2-yl)oxazole-5-carboxamide (0.050 g, 0.131 mmol) in anhydrous dimethylformamide (3 mL) in a flamed dried flask under argon atmosphere at 0° C. was added sodium hydride (60% in mineral oil, 0.013 g, 0.327 mmol) was added in one portion. The reaction was stirred for 10 min at 0° C. then 2-bromoethyl methyl ether (0.020 g, 0.144 mmol) was added via syringe. The mixture was stirred for 90 minutes, then 20 hours at room temperature. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate and the concentrated residue was purified by flash chromatography over silica gel using 95:5 dichloromethane/methanol to give 2-isopropyl-NA-(4-(1-(2-methoxyethyl)-2-oxo-1,2,3,4-tetrahydroquinolin-6-yl)thiazol-2-yl)-4-methyloxazole-5-carboxamide (0.053 g, 92%)

a white solid. $^1$H NMR (400 MHz, DMSO-d): δ 12.65 (s, 1H), 7.80 (m, 2H), 7.61 (s, 1H), 7.27 (d, 1H, J=9.2 Hz), 4.08 (t, 2H, J=6.0 Hz), 3.52 (t, 2H, J=5.6 Hz), 3.25 (s, 3H), 3.10 (p, 1H, J=7.2 Hz), 2.90 (m, 2H), 2.58 (m, 2H), 2.42 (s, 3H), 1.35 (d, 6H, J=7.2 Hz). MS (ESI): Calcd. for $C_{23}H_{26}N_4O_4S$: 454, found 455 $(M+1)^+$.

Example 112

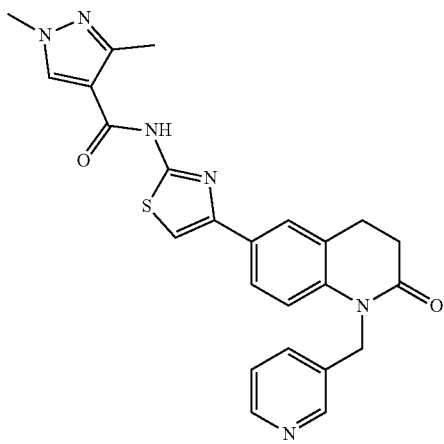 [SMILES: Cc1nn(C)cc1C(=O)Nc1nc(-c2ccc3c(c2)CCC(=O)N3Cc2cccnc2)cs1]

To a solution of 1,3-dimethyl-N-(4-(2-oxo-1,2,3,4-tetrahydroquinolin-6-yl)thiazol-2-yl)-1H-pyrazole-4-carboxamide (0.050 g, 0.136 mmol) in anhydrous dimethylformamide (3 mL) in argon atmosphere at 0° C. was added sodium hydride (60% in mineral oil, 0.014 g, 0.340 mmol) was added in one portion. The reaction was stirred for 10 min at 0° C. then 3-(bromomethyl)pyridine hydrobromide (0.038 g, 0.150 mmol) was added in one portion as a solid. The mixture was stirred for 90 minutes, then 24 hours at room temperature. After consumption of starting material, the reaction mixture was quenched with saturated ammonium chloride (25 mL) and extracted with ethyl acetate (2×25 mL). The combined organics were washed once with saturated sodium bicarbonate (50 mL) and dried over anhydrous sodium sulfate. The concentrated residue was purified by flash chromatography over silica gel using 95:5 dichloromethane/methanol to give 1,3-dimethyl-N-(4-(2-oxo-1-(pyridin-3-ylmethyl)-1,2,3,4-tetrahydroquinolin-6-yl)thiazol-2-yl)-1H-pyrazole-4-carboxamide (0.027 g, 44%) as a off-white solid. $^1$H NMR (400 MHz, DMSO-d): δ 12.16 (s, 1H), 8.53 (m, 2H), 8.44 (dd, 1H, J=4.4, 1.6 Hz), 7.80 (d, 1H, J 4.4 Hz), 7.68 (dd, 1H, J=8.8, 2.4 Hz), 7.61 (dt, 1H, J=7.6, 1.6 Hz), 7.49 (s, 1H), 7.33 (ddd, 1H, J=7.6, 4.4, 0.8 Hz), 7.02 (d, 1H, J=8.4 Hz), 5.22 (s, 2H), 3.82 (s, 3H), 3.01 (m, 2H), 2.75 (m, 2H), 2.38 (s, 3H). MS (ESI): Calcd. for $C_{24}H_{22}N_6O_2S$: 458, found 459 $(M+1)^+$.

Example 113

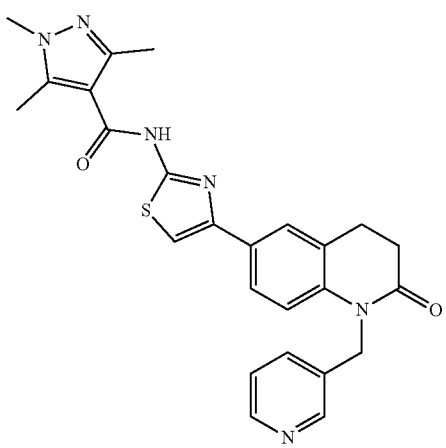 [SMILES: Cc1nn(C)c(C)c1C(=O)Nc1nc(-c2ccc3c(c2)CCC(=O)N3Cc2cccnc2)cs1]

To a solution of 1,3,5-trimethyl-N-(4-(2-oxo-1,2,3,4-tetrahydroquinolin-6-yl)thiazol-2-yl)-1H-pyrazole-4-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.459 mmol) was added in one portion. The reaction was stirred for 10 min at 0° C. then 3-(bromomethyl)pyridine hydrobromide (0.036 g, 0.144 mmol) was added in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1,3,5-trimethyl-N-(4-(2-oxo-1-(pyridin-3-ylmethyl)-1,2,3,4-tetrahydroquinolin-6-yl)thiazol-2-yl)-1H-pyrazole-4-carboxamide (0.014 g, 23%) a white solid. $^1$H NMR (400 MHz, DMSO-d): δ 11.78 (s, 1H), 8.53 (d, 1H, J=1.6 Hz), 8.44 (dd, 1H, J=4.8, 2.0 Hz), 7.80 (d, 2H, J=2.0 Hz), 7.68 (dd, 1H, J=8.8, 2.0 Hz), 7.62 (m, 1H), 7.51 (s, 1H), 7.33 (dd, 1H, J=6.8, 3.6 Hz), 7.02 (d, 1H, J=8.4 Hz), 5.22 (s, 2H), 3.69 (s, 3H), 3.01 (m, 2H), 2.75 (m, 2H), 2.39 (s, 3H), 2.29 (s, 3H). MS (ESI): Calcd. for $C_{25}H_{24}N_6O_2S$: 472, found 473 $(M+1)^+$.

Example 114

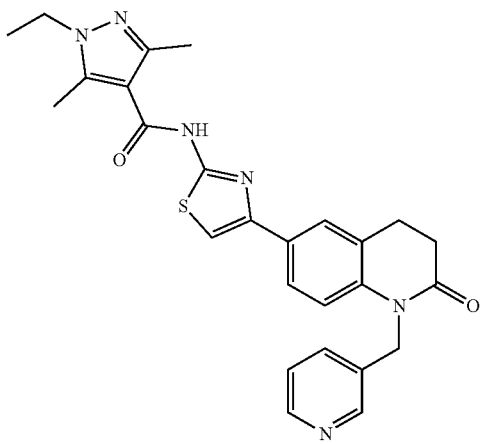 [SMILES: CCn1nc(C)c(C(=O)Nc2nc(-c3ccc4c(c3)CCC(=O)N4Cc3cccnc3)cs2)c1C]

To a solution of 1-ethyl-3,5-dimethyl-N-(4-(2-oxo-1,2,3,4-tetrahydroquinolin-6-yl)thiazol-2-yl)-1H-pyrazole-4-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.459 mmol) was added in one portion. The reaction was stirred for 10 min at 0° C. then 3-(bromomethyl)pyridine hydrobromide (0.036 g, 0.144 mmol) was added in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-ethyl-3,5-dimethyl-N-(4-(2-oxo-1-(pyridin-3-ylmethyl)-1,2,3,4-tetrahydroquinolin-6-yl)thiazol-2-yl)-1H-pyrazole-4-carboxamide (0.021 g, 33%) a white solid. $^1$H NMR (400 MHz, DMSO-d): δ 11.76 (s, 1H), 8.52 (d, 1H, J=1.6), 8.44 (dd, 1H, J=4.8, 2.0 Hz), 7.79 (d, 2H, J=2.0 Hz), 7.67 (dd, 1H, J=8.8, 2.0 Hz), 7.62 (m, 1H), 7.51 (s, 1H), 7.33 (dd, 1H, J=6.8, 3.6 Hz), 7.02 (d, 1H, J=8.4 Hz), 5.22 (s, 2H), 4.02 (q, 2H, J=7.6 Hz), 3.01 (m, 2H), 2.75 (m, 2H), 2.41 (s, 3H), 2.30 (s, 3H), 1.29 (t, 2H, J=7.6 Hz). MS (ESI): Calcd. for $C_{26}H_{26}N_6O_2S$: 486, found 487 (M+1)$^+$.

Example 115

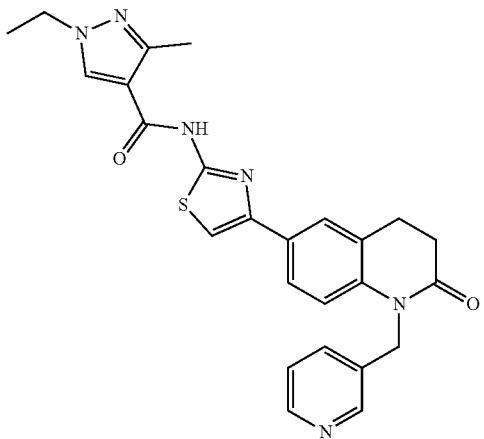 [SMILES: CCn1cc(C(=O)Nc2nc(-c3ccc4c(c3)CCC(=O)N4Cc3cccnc3)cs2)c(C)n1]

To a solution of 1-ethyl-3-methyl-N-(4-(2-oxo-1,2,3,4-tetrahydroquinolin-6-yl)thiazol-2-yl)-1H-pyrazole-4-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.459 mmol) was added in one portion. The reaction was stirred for 10 min at 0° C. then 3-(bromomethyl)pyridine hydrobromide (0.036 g, 0.144 mmol) was added in one portion as solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-ethyl-3-methyl-N-(4-(2-oxo-1-(pyridin-3-ylmethyl)-1,2,3,4-tetrahydroquinolin-6-yl)thiazol-2-yl)-1H-pyrazole-4-carboxamide (0.048 g, 78%) a white solid. $^1$H NMR (400 MHz, DMSO-d): δ 12.13 (s, 1H), 8.62 (s, 1H), 8.53 (d, 1H, J=1.6 Hz), 8.44 (dd, 1H, J=4.8, 2.0 Hz), 7.79 (d, 1H, J=2.0 Hz), 7.68 (dd, 1H, J=8.4, 1.6 Hz), 7.62 (m, 1H), 7.49 (s, 1H), 7.32 (dd, 1H, J=8.4, 4.8 Hz), 7.02 (d, 1H, J=8.4 Hz), 5.22 (s, 2H), 4.10 (q, 2H, J=7.6 Hz), 3.01 (m, 2H), 2.75 (m, 2H), 2.39 (s, 3H), 1.40 (t, 2H, J=7.6 Hz). MS (ESI): Calcd. for $C_{25}H_{24}N_6O_2S$: 472, found 473 (M+1)$^+$.

Example 116

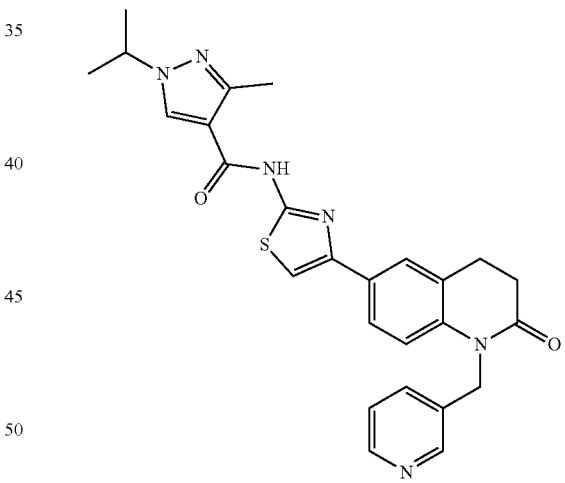

To a solution of 1-ethyl-3-methyl-N-(4-(2-oxo-1,2,3,4-tetrahydroquinolin-6-yl)thiazol-2-yl)-1H-pyrazole-4-carboxamide (0.050 g, 0.126 mmol) in anhydrous dimethylformamide (3 mL) in a flamed dried flask under argon atmosphere at 0° C. was added sodium hydride (60% in mineral oil, 0.018 g, 0.443 mmol) was added in one portion. The reaction was stirred for 10 min at 0° C. then 3-(bromomethyl)pyridine hydrobromide (0.036 g, 0.139 mmol) was added in one portion as solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-isopropyl-3-methyl-N-(4-(2-oxo-1-(pyridin-3-ylmethyl)-1,2,3,4-tetrahydroquinolin-6-yl)thiazol-2-yl)-1-pyrazole-4-carboxamide (0.045 g, 73%) a white solid. $^1$H NMR (400 MHz, DMSO-d): δ 12.10 (s, 1H), 8.70 (s, 1H), 8.53 (d, 1H, J=1.6 Hz), 8.44 (dd, 1H, J=4.8, 2.0 Hz), 7.79 (d, 1H, J=2.0 Hz), 7.68 (dd, 1H, J=8.4, 1.6 Hz), 7.61 (m, 1H), 7.49 (s, 1H), 7.32 (dd, 1H, J=8.4, 4.8 Hz), 7.02 (d, 1H, J=8.4 Hz), 5.22 (s, 2H), 4.43 (p, 1H, J=6.8 Hz), 3.01 (m, 2H), 2.75 (m, 2H), 2.40 (s, 3H), 1.43 (d, 6H, J=6.8 Hz). MS (ESI): Calcd. for $C_{26}H_{26}N_6O_2S$: 486, found 487 (M+1)$^+$.

Example 117

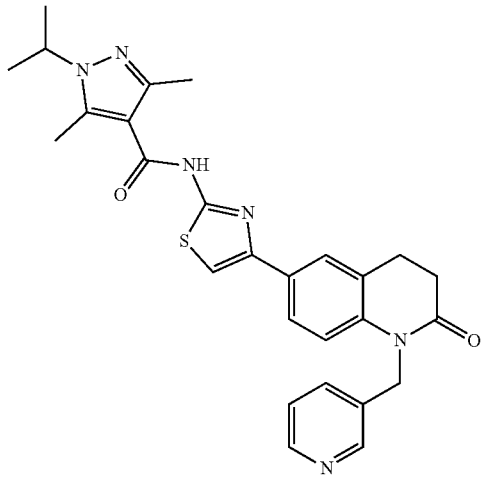 [SMILES: Cc1nn(C(C)C)c(C)c1C(=O)Nc1nc(-c2ccc3c(c2)CCC(=O)N3Cc2cccnc2)cs1]

To a solution of 1-isopropyl-3,5-dimethyl-N-(4-(2-oxo-1,2,3,4-tetrahydroquinolin-6-yl)thiazol-2-yl)-1H-pyrazole-4-carboxamide (0.050 g, 0.122 mmol) in anhydrous dimethylformamide (3 mL) in a flamed dried flask under argon atmosphere at 0° C. was added sodium hydride (60% in mineral oil, 0.018 g, 0.427 mmol) was added in one portion. The reaction was stirred for 10 min at 0° C. then 3-(bromomethyl)pyridine hydrobromide (0.034 g, 0.134 mmol) was added in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-isopropyl-3,5-dimethyl-N-(4-(2-oxo-1-(pyridin-3-ylmethyl)-1,2,3,4-tetrahydroquinolin-6-yl)thiazol-2-yl)-1H-pyrazole-4-carboxamide (0.030 g, 49%) a white solid. $^1$H NMR (400 MHz, DMSO-d): δ 11.75 (s, 1H), 8.53 (d, 1H, J=1.6), 8.44 (dd, 1H, J=4.8, 2.0 Hz), 7.79 (d, 2H, J=2.4 Hz), 7.67 (dd, 1H, J=8.4, 2.0 Hz), 7.62 (m, 1H), 7.51 (s, 1H), 7.33 (dd, 1H, J=8.4, 5.2 Hz), 7.02 (d, 1H, J=8.4 Hz), 5.22 (s, 2H), 4.51 (p, 1H, J=6.8 Hz), 3.01 (m, 2H), 2.75 (m, 2H), 2.41 (s, 3H), 2.32 (s, 3H), 1.35 (d, 6, J=6.8 Hz). MS (ESI): Calcd. for $C_{27}H_{28}N_6O_2S$: 500, found 501 (M+1)$^+$.

Example 118

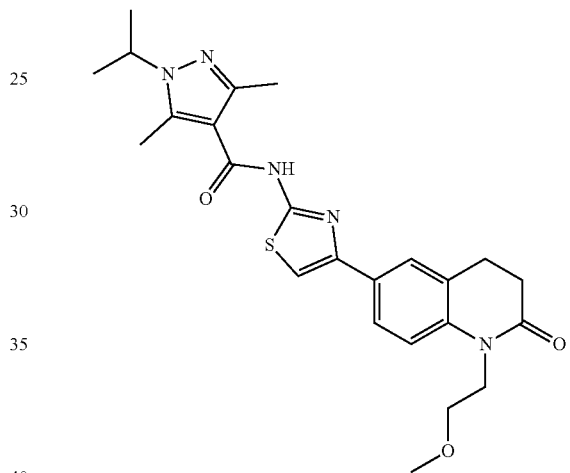

To a solution of 1-isopropyl-3,5-dimethyl-N-(4-(2-oxo-1,2,3,4-tetrahydroquinolin-6-yl)thiazol-2-yl)-1H-pyrazole-4-carboxamide (0.050 g, 0.122 mmol) in anhydrous dimethylformamide (3 mL) in a flamed dried flask under argon atmosphere at 0° C. was added sodium hydride (60% in mineral oil, 0.018 g, 0.305 mmol) was added in one portion. The reaction was stirred for 10 min at 0° C. then 2-bromoethyl methyl ether (0.019 g, 0.122 mmol) was added via syringe. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-isopropyl-N-(4-(1-(2-methoxyethyl)-2-oxo-1,2,3,4-tetrahydroquinolin-6-yl)thiazol-2-yl)-3,5-dimethyl-1H-pyrazole-4-carboxamide (0.050 g, 87%) a white solid. $^1$H NMR (400 MHz, DMSO-d): δ 11.76 (s, 1H), 7.78 (m, 2H), 7.53 (s, 1H), 7.26 (d, 1H, J=8.4 Hz), 4.52 (p, 1H, J=6.8 Hz), 4.07 (t, 2H, J=5.6 Hz), 3.52 (t, 2H, J=5.6 Hz), 3.25 (s, 3H), 2.90 (m, 2H), 2.58 (m, 2H), 2.43 (s, 3H), 2.33 (s, 3H), 1.36 (d, 6H, J=6.8 Hz). MS (ESI): Calcd. for $C_{27}H_{28}N_6O_2S$: 500, found 501 (M+1)$^+$.

Example 119

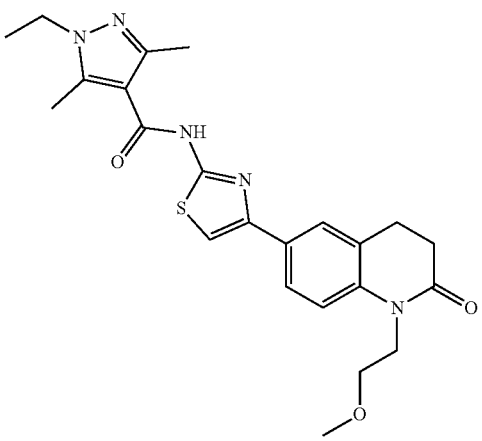 [SMILES: CCn1nc(C)c(C(=O)Nc2nc(-c3ccc4c(c3)CCC(=O)N4CCOC)cs2)c1C]

To a solution of 1-ethyl-3,5-dimethyl-N-(4-(2-oxo-1,2,3,4-tetrahydroquinolin-6-yl)thiazol-2-yl)-1H-pyrazole-4-carboxamide (0.050 g, 0.126 mmol) in anhydrous dimethylformamide (3 mL) in a flamed dried flask under argon atmosphere at 0° C. was added sodium hydride (60% in mineral oil, 0.013 g, 0.316 mmol) was added in one portion. The reaction was stirred for 10 min at 0° C. then 2-bromoethyl methyl ether (0.019 g, 0.139 mmol) was added via syringe. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-ethyl-N-(4-(1-(2-methoxyethyl)-2-oxo-1,2,3,4-tetrahydroquinolin-6-yl)thiazol-2-yl)-3,5-dimethyl-1H-pyrazole-4-carboxamide (0.045 g, 78%) a white solid. $^1$H NMR (400 MHz, DMSO-d): δ 11.76 (s, 1H), 7.78 (m, 2H), 7.53 (s, 1H), 7.26 (d, 1H, J=8.8 Hz), 4.07 (m, 2H), 4.03 (q, 2H, J=7.6 Hz), 3.52 (t, 2H, J=5.6 Hz), 3.25 (s, 3H), 2.90 (m, 2H), 2.58 (m, 2H), 2.42 (s, 3H), 2.32 (s, 3H), 1.30 (t, 3H, J=7.6 Hz). MS (ESI): Calcd. for $C_{23}H_{27}N_5O_3S$: 453, found 454 (M+1)$^+$.

Example 120

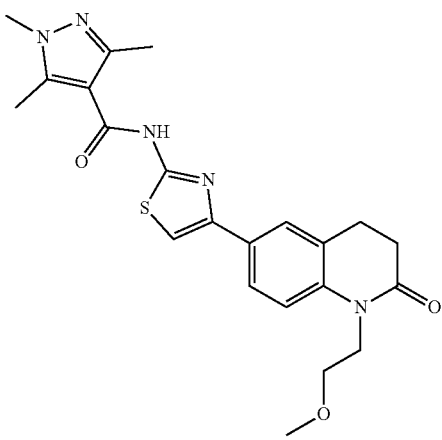 [SMILES: COCCN1C(=O)CCc2cc(-c3csc(NC(=O)c4c(C)nn(C)c4C)n3)ccc21]

To a solution of 1,3,5-trimethyl-N-(4-(2-oxo-1,2,3,4-tetrahydroquinolin-6-yl)thiazol-2-yl)-1H-pyrazole-4-carboxamide (0.050 g, 0.131 mmol) in anhydrous dimethylformamide (3 mL) in a flamed dried flask under argon atmosphere at 0° C. was added sodium hydride (60% in mineral oil, 0.013 g, 0.328 mmol) was added in one portion. The reaction was stirred for 10 min at 0° C. then 2-bromoethyl methyl ether (0.020 g, 0.144 mmol) was added via syringe. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give N-(4-(1-(2-methoxyethyl)-2-oxo-1,2,3,4-tetrahydroquinoinolin-6-yl)thiazol-2-yl)-1,3,5-trimethyl-1H-pyrazole-4-carboxamide (0.052 g, 90%) a white solid. $^1$H NMR (400 MHz, DMSO-d): δ 11.79 (s, 1H), 7.78 (m, 2H), 7.54 (s, 1H), 7.26 (d, 1H, J=8.4 Hz), 4.07 (t, 2H, J=5.6 Hz), 3.70 (s, 3H), 3.52 (t, 2H, J=5.6 Hz), 3.25 (s, 3H), 2.90 (m, 2H), 2.58 (m, 2H), 2.40 (s, 3H), 2.31 (s, 3H). MS (ESI): Calcd, for $C_{22}H_{25}N_5O_3S$: 43.

Example 121

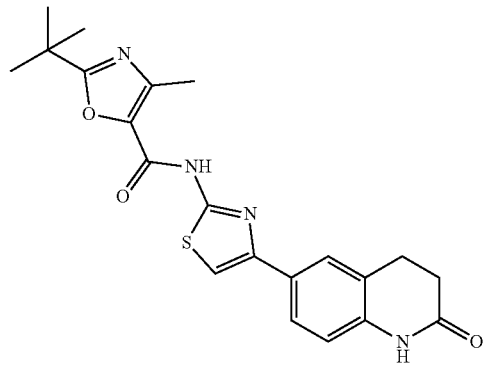 [SMILES: Cc1nc(C(C)(C)C)oc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 2-(tert-butyl)-4-methyloxazole-5-carboxylic acid (0.082 g, 0.45 mmol), and pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 2-(tert-butyl)-4-methyl-N-(4-(2-oxo-1,2,3,4-tetrahydroquinolin-6-yl)thiazol-2-yl)oxazole-5-carboxamide (0.041 g, 24%). $^1$H NMR (400 MHz, DMSO-d): δ 12.67 (bs, 1H), 10.19 (s, 1H), 7.76 (s, 1H), 7.70 (dd, 1H, J=8.4, 2.0 Hz), 7.53 (s, 1H), 6.89 (d, 1H, J=8.0 Hz), 2.93 (t, 2H, J=7.2 Hz), 2.48 (partial masked under d-DMSO, in, 2H), 2.42 (s, 3H), 1.40 (s, 9H); MS (ESI): Calcd. for C21H22N4O3S: 410, found 411 (M+1)$^+$.

Example 122

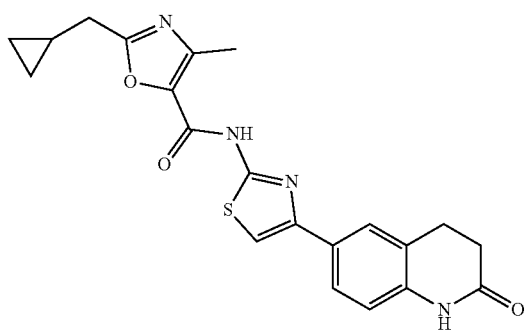 [SMILES: Cc1nc(CC2CC2)oc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 2-(cyclopropylmethyl)-4-methyloxazole-5-carboxylic acid (0.081 g, 0.45 mmol), and pyridine (0.15 m L, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 2-(cyclopropylmethyl)-4-methyl-N-(4-(2-oxo-1,2,3,4-tetrahydroquinolin-6-yl)thiazol-2-yl)oxazole-5-carboxamide (0.116 g, 70%). $^1$H NMR (400 MHz, DMSO-d): δ 12.57 (bs, 1H), 10.18 (s, 1H), 7.76 (s, 1H), 7.70 (dd, 1H, J=8.4, 2.0 Hz), 7.52 (s, 1H), 6.89 (d, 1H, J=8.0 Hz), 2.93 (m, 2H), 2.72 (m, 2H), 1.52 (m, 1H), 0.52 (m, 2H), 0.31 (m, 2H); MS (ESI): Calcd. for C21H20N4O3S: 408, found 409 (M+1)$^+$.

Example 123

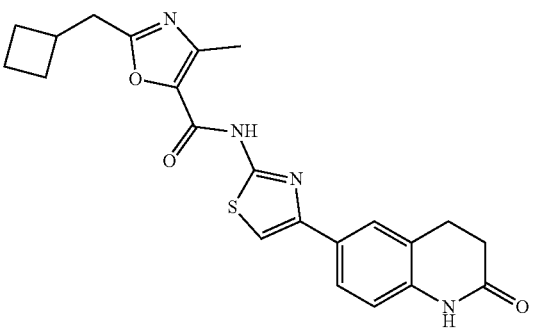 [SMILES: Cc1nc(CC2CCC2)oc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one (0.100 g, 0.41 mmol) and 2-(cyclobutylmethyl)-4-methyloxazole-5-carboxylic acid (0.087 g, 0.45 mmol), and pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h and the precipitation formed. After cooling, the precipitate was collected by filtration and washed with cold 1:1 acetonitrile/water to give 2-(cyclobutylmethyl)-4-methyl-N-(4-(2-oxo-1,2,3,4-tetrahydroquinolin-6-yl)thiazol-2-yl)oxazole-5-carboxamide (0.134 g, 78%). $^1$H NMR (400 MHz, DMSO-d): δ 12.53 (bs, 1H), 10.18 (s, 1H), 7.76 (s, 1H), 7.70 (dd, 1H, J=8.4, 2.0 Hz), 7.52 (s, 1H), 6.89 (d, 1H, J=8.0 Hz), 2.95 (m, 5H), 2.48 (partial masked under d-DMSO, m, 2H), 2.41 (s, 3H), 2.15 (m, 2H), 1.82 (m, 4H); MS (ESI): Calcd. for C22H22N4O3S: 422, found 423 (M+1)$^+$.

Example 124

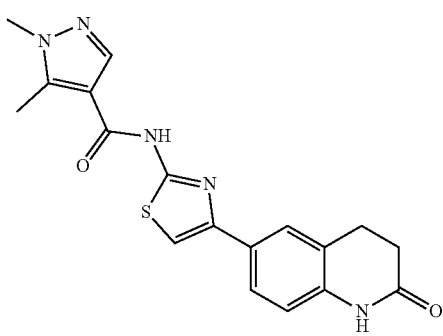 [SMILES: Cc1c(C(=O)Nc2nc(-c3ccc4c(c3)CCC(=O)N4)cs2)cnn1C]

To a suspension of 6-(2-amino-5-chlorothiazol-4-yl)-3,4-dihydroquinolin-2(1H)-one (0.100 g, 0.41 mmol) and 1,5-dimethyl-1H-pyrazole-4-carboxylic acid (0.063 g, 0.22 mmol), and DIPEA (0.16 mL, 0.51 mmol in acetonitrile (5 mL) in a sealed tube was added propylphosphonic anhydride solution (50 wt % in ethyl acetate, 0.61 mL, 0.1.02 mmol). The sealed tube was heated to 100° C. for 16 h. The resulting mixture was cooled to room temperature, and partitioned between EtOAc (50 mL) and 50 mL of water. The organic layer was separated and the aqueous layer was extracted with EtOAc (3×25 mL). The combined organic layers were washed with saturated brine, dried over anhydrous sodium sulfate and then concentrated. The residue was purified by silica gel column chromatography by 0-5% methanol-dichloromethane to give 1,5-dimethyl-N-(4-(2-oxo-1,2,3,4-tetrahydroquinol in-6-yl)thiazol-2-yl)-1H-pyrazole-4-carboxamide (0.044 g, 30%). $^1$H NMR (400 MHz, DMSO-d): δ 12.21 (bs, 1H), 10.18 (s, 1H), 8.30 (s, 1H), 7.74 (m, 1H), 7.69 (dd, 1H, J=8.4, 2.0 Hz), 7.44 (s, 1H), 6.90 (d, 1H, J=8.0 Hz), δ, 3.77 (s, 3H), 2.93 (t, 2H, J=7.2 Hz), 2.91 (s, 3H), 2.50 (partial masked under d-DMSO, m, 2H); MS (ESI): Calcd. For C18H17N5O2S: 367, found 368 (M+1)$^+$.

Example 125

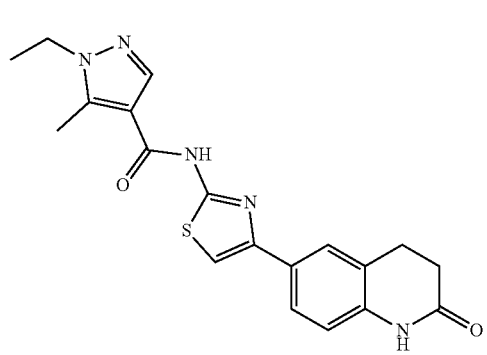 [SMILES: CCn1ncc(C(=O)Nc2nc(-c3ccc4c(c3)CCC(=O)N4)cs2)c1C]

To a suspension of 6-(2-amino-5-chlorothiazol-4-yl)-3,4-dihydroquinolin-2(1H)-one (0.10 g, 0.81 mmol) and 1-ethyl-5-methyl-1H-pyrazole-4-carboxylic acid (0.069 g, 0.89 mmol), and pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 1-ethyl-5-methyl-N-(4-(2-oxo-1,2,3,4-tetrahydroquinolin-6-yl)thiazol-2-yl)-1H-pyrazole-4-carboxamide (0.052 g, 33%). ¹H NMR (400 MHz, DMSO-d): δ 12.22 (bs, 1H), 10.18 (s, 1H), 8.34 (s, 1H), 7.74 (m, 1H), 7.69 (dd, 1H, J=8.4, 2.0 Hz), 7.44 (s, 1H), 6.90 (d, 1H, J=8.0 Hz), δ, 4.15 (m, 2H), 2.93 (t, 2H, J=7.2 Hz), 2.58 (s, 3H0, 2.50 (partial masked under d-DMSO, m, 2H), 1.31 (m, 3H); MS (ESI): Calcd. For C19H19N5O2S3: 381, found 382 (M+1)⁺.

Example 126

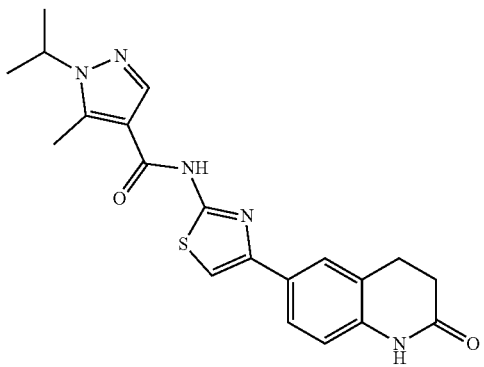 [SMILES: Cc1c(C(=O)Nc2nc(-c3ccc4c(c3)CCC(=O)N4)cs2)cnn1C(C)C]

To a suspension of 6-(2-amino-5-chlorothiazol-4-yl)-3,4-dihydroquinolin-2(1H)-one (0.100 g, 0.41 mmol), 1-isopropyl-5-methyl-1H-pyrazole-4-carboxylic acid (0.075 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 5-1-isopropyl-5-methyl-N-(4-(2-oxo-1,2,3,4-tetrahydroquinolin-6-yl)thiazol-2-yl)-1H-pyrazole-4-carboxamide (0.074 g, 44%) ¹H NMR (400 MHz, DMSO-d): δ 12.21 (bs, 1H), 10.18 (s, 1H), 8.37 (s, 1H), 7.75 (m, 1H), 7.69 (dd, 1H, J=8.4, 2.0 Hz), 7.44 (s, 1H), 6.90 (d, 1H, J=8.0 Hz), 4.63 (m, 1H), 2.94 (t, 2H, J=7.2 Hz), 2.50 (partial masked under d-DMSO, m, 2H), 1.39 (m, 6H); MS (ESI): Calcd. For C20H21N5O2S: 395 found 396 (M)⁺.

Example 127

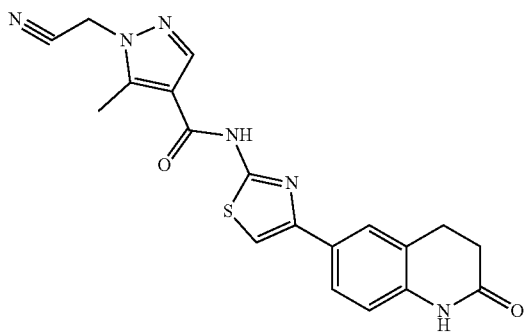 [SMILES: Cc1c(C(=O)Nc2nc(-c3ccc4c(c3)CCC(=O)N4)cs2)cnn1CC#N]

To a suspension of 6-(2-amino-5-chlorothiazol-4-yl)-3,4-dihydroquinolin-2(1H)-one (0.100 g, 0.41 mmol), 1-(cyanomethyl)-5-methyl-1H-pyrazole-4-carboxylic acid (0.074 g, 0.45 mmol), DIPEA (0.32 mL, 1.83 mmol) in acetonitrile (3 mL) in a sealed tube was added propylphosphonic anhydride solution (50 wt % in ethyl acetate, 0.61 mL, 1.02 mmol). The sealed tube was heated to 100° C. for 16 h. After cooling, The resulting mixture was cooled to room temperature, and partitioned between dichloromethane (20 mL) and 20 mL of water. The organic layer was separated and the aqueous layer was extracted with dichloromethane (3×30 mL). The combined organic layers were washed with saturated brine, dried over anhydrous sodium sulfate and then concentrated. The residue was triturated with dichloromethane (5 ml) and the the precipitate was collected by filtration and washed with cold 1:1 acetonitrile/water to give 31-(cyanomethyl)-5-methyl-N-(4-(2-oxo-1,2,3,4-tetrahydroquinolin-6-yl)thiazol-2-yl)-1H-pyrazole-4-carboxamide (0.130 g, 8.01%). ¹H NMR (400 MHz, DMSO-d): δ 12.30 (bs, 1H), 10.18 (s, 1H), 8.42 (s, 1H), 7.75 (m, 1H), 7.69 (dd, 1H, J=8.4, 2.0 Hz), 7.45 (s, 1H), 6.90 (d, 1H, J=8.0 Hz), 4.41 (m, 2H), 3.06 (m, 2H), 2.62 (s, 3H), 2.93 (t, 2H, J=7.2 Hz), 2.62 (s, 3H), 2.50 (partial masked under d-DMSO, m, 2H).

Example 128

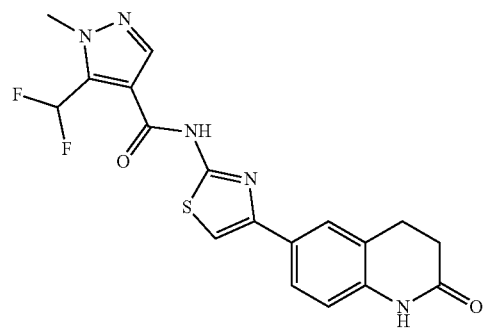 [SMILES: Cn1ncc(C(=O)Nc2nc(-c3ccc4c(c3)CCC(=O)N4)cs2)c1C(F)F]

To a suspension of 6-(2-amino-5-chlorothiazol-4-yl)-3,4-dihydroquinolin-2(1H)-one (0.100 g, 0.41 mmol), 5-(difluoromethyl)-1-methyl-1H-pyrazole-4-carboxylic acid (0.080 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 5-(difluoromethyl)-1-methyl-N-(4-(2-oxo-1,2,3,4-tetrahydroquinolin-6-yl)thiazol-2-yl)-1H-pyrazole-4-carboxamide (0.119 g, 72%). ¹H NMR (400 MHz, DMSO-d): δ 12.74 (bs, 1H), 10.19 (s, 1H), 8.45 (s, 1H), 7.74 (m, 1H), 7.69 (dd, 1H, J=8.4, 2.0 Hz), 7.56 (t, J_{HF}=54 Hz, 1H), 7.53 (s, 1H), 6.90 (d, 1H, J=8.0 Hz), δ, 4.04 (s, 3H), 2.93 (t, 2H, J=7.2 Hz), 2.48 (partial masked under d-DMSO, m, 2H); MS (ESI): Calcd. for C18H15F2N5O2S: 403, found 404 (M+1)⁺.

Example 129

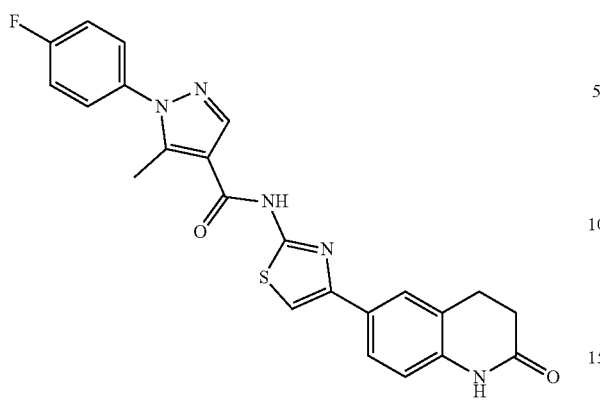

To a suspension of 6-(2-amino-5-chlorothiazol-4-yl)-3,4-dihydroquinolin-2(1-H)-one (0.100 g, 0.41 mmol), 1-(4-fluorophenyl)-5-methyl-1H-pyrazole-4-carboxylic acid (0.0.99 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 1-(4-fluorophenyl)-5-methyl-N-(4-(2-oxo-1,2,3,4-tetrahydroquinolin-6-yl)thiazol-2-yl)-1H-pyrazole-4-carboxamide (0.111 g, 61%). $^1$H NMR (400 MHz, DMSO-d): δ 12.43 (bs, 1H), 10.19 (s, 1H), 8.58 (s, 1H), 7.74 (m, 1H), 7.69 (dd, 1H, J=8.4, 2.0 Hz), 7.63 (m, 2H), 7.48 (s, 1H), 7.44 (m, 2H), 6.90 (d, 1H, J=8.0 Hz), 2.93 (t, 2H, J=7.2 Hz), 2.57 (s, 3H), 2.50 (partial masked under d-DMSO, in, 2H); MS (ESI): Calcd. For C23H18FN5O2S: 447 found 448 (M+1)$^+$.

Example 130

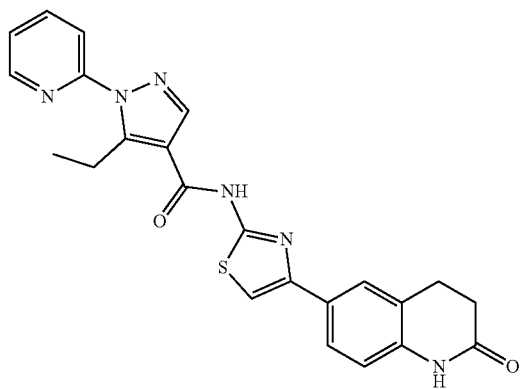 [SMILES: CCc1c(C(=O)Nc2nc(-c3ccc4c(c3)CCC(=O)N4)cs2)cnn1-c1ccccn1]

To a suspension of 6-(2-amino-5-chlorothiazol-4-yl)-3,4-dihydroquinolin-2(1H)-one (0.100 g, 0.41 mmol), 5-ethyl-1-(pyridin-2-yl)-1H-pyrazole-4-carboxylic acid (0.0.97 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 5-ethyl-N-(4-(2-oxo-1,2,3,4-tetrahydroquinolin-6-yl)thiazol-2-yl)-1-(pyridin-2-yl)-1H-pyrazole-4-carboxamide (0.083 g, 46%) $^1$H NMR (400 MHz, DMSO-d): δ 12.47 (bs, 1H), 10.19 (s, 1H), 8.60 (m, 2H), 8.48 (s, 1H), 8.08 (m, 1H), 7.84 (m, 1H), 7.77 (m, 1H), 7.69 (dd, 1H, J=8.4, 2.0 Hz), 7.50 (m, 2H), 6.90 (d, 1H, J=8.0 Hz), 3.40 (m, 2H), 2.94 (t, 2H, J=7.2 Hz), 2.50 (partial masked under d-DMSO, m, 2H), 1.22 (m, 3H); MS (ESI): Calcd. For C23H20N6O2S: 444 found 445 (M)$^+$.

Example 131

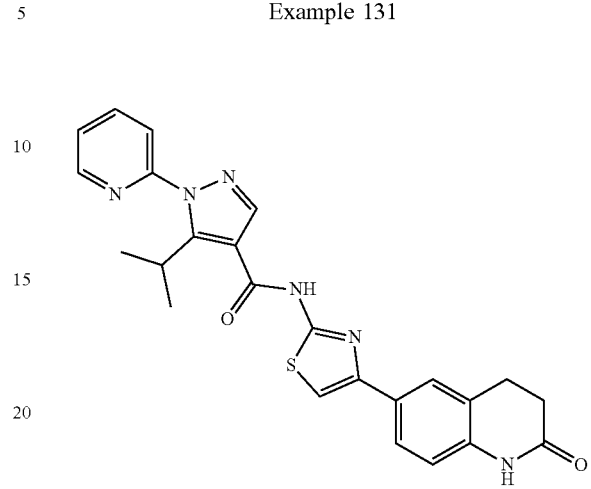

To a suspension of 6-(2-amino-5-chlorothiazol-4-yl)-3,4-dihydroquinolin-2(1H)-one (0.100 g, 0.41 mmol), 5-isopropyl-1-(pyridin-2-yl)-1H-pyrazole-4-carboxylic acid (0.104 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 5-isopropyl-N-(4-(2-oxo-1,2,3,4-tetrahydroquinolin-6-yl)thiazol-2-yl)-1-(pyridin-2-yl)-1H-pyrazole-4-carboxamide (0.082 g, 44%) $^1$H NMR (400 MHz, DMSO-d): δ 12.48 (bs, 1H), 10.19 (s, 1H), 8.62 (m, 1H), 8.48 (s, 1H), 8.09 (m, 1H), 7.77 (m, 1H), 7.69 (dd, 1H, J=8.4, 2.0 Hz), 7.49 (s, 1H), 6.90 (d, 1H, J=8.0 Hz), 3.79 (m, 1H), 2.94 (t, 2H, J=7.2 Hz), 2.50 (partial masked under d-DMSO, m, 2H), 1.34 (m, 6H); MS (ESI): Calcd. For C24H22N6O2S: 458 found 458 (M)$^+$.

Example 132

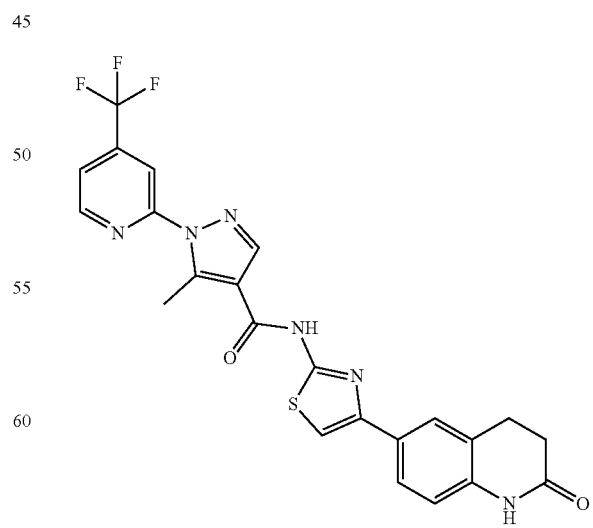

To a suspension of 6-(2-amino-5-chlorothiazol-4-yl)-3,4-dihydroquinolin-2(1H)-one (0.100 g, 0.41 mmol), 5-methyl- 1-(4-(trifluoromethyl)pyridin-2-yl)-1H-pyrazole-4-carboxylic acid (0.122 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 5-methyl-N-(4-(2-oxo-1,2,3,4-tetrahydroquinolin-6-yl)thiazol-2-yl)-1-(4-(trifluoromethyl)pyridin-2-yl)-1H-pyrazole-4-carboxamide (0.0.083 g, 41%) $^1$H NMR (400 MHz, DMSO-d): δ 12.54 (bs, 1H), 10.19 (s, 1H), 9.08 (m, 1H), 8.66 (m, 1H), 8.46 (m, 1H), 8.12 (m, 1H), 7.76 (m, 1H), 7.69 (dd, 1H, J=8.4, 2.0 Hz), 7.50 (s, 1H), 6.90 (d, 1H, J=8.0 Hz), 2.98 (s, 3H), 2.94 (t, 2H, J=7.2 Hz), 2.50 (partial masked under d-DMSO, m, 2H); MS (ESI): Calcd. For C23H17F3N6O2S: 498 found 498 (M)$^+$.

Example 133

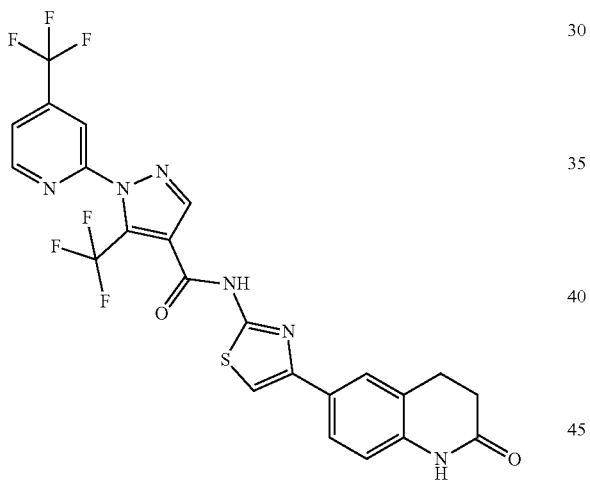

To a suspension of 6-(2-amino-5-chlorothiazol-4-yl)-3,4-dihydroquinolin-2(1H)-one (0.100 g, 0.41 mmol), 5-(trifluoromethyl)-1-(4-(trifluoromethyl)pyridin-2-yl)-1H-pyrazole-4-carboxylic acid (0.146 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give N-(4-(2-oxo-1,2,3,4-tetrahydroquinolin-6-yl)thiazol-2-yl)-5-(trifluoromethyl)-1-(4-(trifluoromethyl)pyridin-2-yl)-1H-pyrazole-4-carboxamide (0.179 g, 79%) $^1$H NMR (400 MHz, DMSO-d): δ 13.09 (bs, 1H), 10.19 (s, 1H), 9.08 (m, 1H), 8.60 (m, 2H), 8.14 (m, 1H), 7.76 (m, 1H), 7.69 (dd, 1H, J=8.4, 2.0 Hz), 7.58 (s, 1H), 6.90 (d, 1H, J=8.0 Hz), 2.94 (t, 2H, J=7.2 Hz), 2.50 (partial masked under d-DMSO, m, 2H); MS (ESI): Calcd. For C23H14F6N6O2S: 552 found 553 (M+1)$^+$.

Example 134

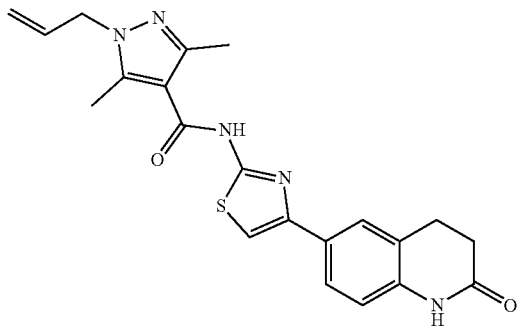 [SMILES: C=CCn1nc(C)c(C(=O)Nc2nc(-c3ccc4c(c3)CCC(=O)N4)cs2)c1C]

To a suspension of 6-(2-amino-5-chlorothiazol-4-yl)-3,4-dihydroquinolin-2(1H)-one (0.100 g, 0.41 mmol), 1-allyl-3,5-dimethyl-1H-pyrazole-4-carboxylic acid (0.81 g, 0.45 mmol), DIPEA (0.32 mL, 1.83 mmol) in acetonitrile (3 mL) in a sealed tube was added propylphosphonic anhydride solution (50 wt % in ethyl acetate, 0.61 mL, 1.02 mmol). The sealed tube was heated to 100° C. for 16 h. After cooling, The resulting mixture was cooled to room temperature, and partitioned between dichloromethane (20 mL) and 20 mL of water. The organic layer was separated and the aqueous layer was extracted with dichloromethane (3×30 mL). The combined organic layers were washed with saturated brine, dried over anhydrous sodium sulfate and then concentrated. The residue was triturated with dichloromethane (5 ml) and the the precipitate was collected by filtration and washed with cold 1:1 acetonitrile/water to give 1-allyl-3,5-dimethyl-N-(4-(2-oxo-1,2,3,4-tetrahydroquinolin-6-yl)thiazol-2-yl)-1H-pyrazole-4-carboxamide (0.105 g, 63%). $^1$H NMR (400 MHz, DMSO-d): δ 11.82 (bs, 1H), 10.17 (s, 1H), 7.74 (m, 1H), 7.69 (dd, 1H, J=8.4, 2.0 Hz, 7.46 (s, 1H), 6.90 (d, 1H, J=8.0 Hz), 5.95 (m, 1H), 5.19 (M, 1H), 5.01 (m, 1H), 4.69 (m, 2H), 2.93 (t, 2H, J=7.2 Hz), 2.50 (partial masked under d-DMSO, in, 2H), 2.39 (s, 3H), 2.31 (s, 3H); MS (ESI): Calcd. For $C_{21}H_{21}N_5O_2S$: 407 found 408 (M+1)$^+$.

Example 135

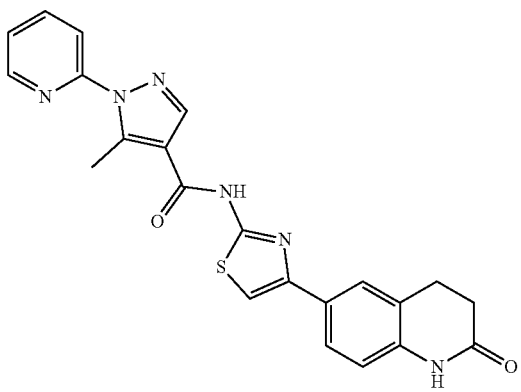 [SMILES: Cc1c(C(=O)Nc2nc(-c3ccc4c(c3)CCC(=O)N4)cs2)cnn1-c1ccccn1]

To a suspension of 6-(2-amino-5-chlorothiazol-4-yl)-3,4-dihydroquinolin-2(1H)-one (0.100 g, 0.41 mmol), 5-methyl-1-(pyridin-2-yl)-1H-pyrazole-4-carboxylic acid (0.0.091 g, 0.45 mmol), pyridine (0.15 mL, 1.83 mmol) in acetonitrile (4 mL) in a sealed tube was added propylphosphonic anhydride solution (50 wt % in ethyl acetate, 0.61 mL, 1.02 mmol). The sealed tube was heated to 100° C. for 16 h. After cooling, the precipitate was collected by filtration and washed with cold 1:1 acetonitrile/water to give 5-methyl-N-(4-(2-oxo-1,2,3,4-tetrahydroquinolin-6-yl)thiazol-2-yl)-1-(pyridin-2-yl)-1H-pyrazole-4-carboxamide (0.104 g, 59%) $^1$H NMR (400 MHz, DMSO-d): δ 12.46 (bs, 1H), 10.19 (s, 1H), 8.59 (m, 2H), 8.08 (m, 1H), 7.85 (m, 1H), 7.74 (m, 1H), 7.69 (dd, 1H, J=8.4, 2.0 Hz), 7.50 (m, 2H), 6.90 (d, 1H, J=8.0 Hz), 2.94 (t, 2H, J=7.2 Hz), 2.88 (s, 3H), 2.50 (partial masked under d-DMSO, m, 2H); MS (ESI): Calcd. For C22H18N6O2S: 430 found 431 (M+1)$^+$.

Example 136

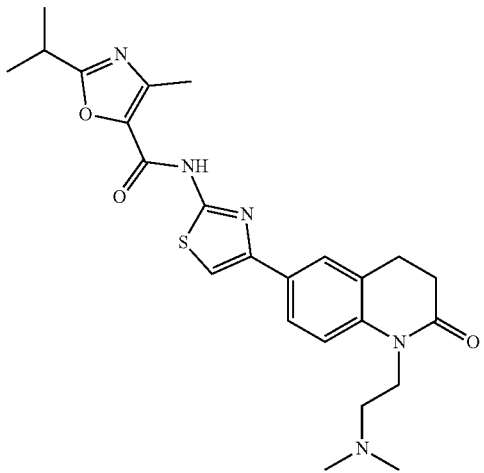 [SMILES: Cc1nc(C(C)C)oc1C(=O)Nc1nc(-c2ccc3c(c2)CCC(=O)N3CCN(C)C)cs1]

To a solution of 2-isopropyl-4-methyl-N-(4-(2-oxo-1,2,3,4-tetrahydroquinolin-6-yl)thiazol-2-yl)oxazole-5-carboxamide (0.050 g, 0.126 mmol) in anhydrous dimethylformamide (3 mL) in a flamed dried flask under argon atmosphere at 0° C. was added sodium hydride (60% in mineral oil, 0.018 g, 0.441 mmol) was added in one portion. The reaction was stirred for 10 min at 0° C. then 2-bromo-N,N-dimethylethylamine hydrobromide (0.032 g, 0.139 mmol) was added as a solid. The mixture was stirred for 90 minutes, then 20 hours at room temperature. After consumption of starting material, the reaction mixture was quenched with water (5 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica, gel using 95:5 dichloromethane/methanol to give N-(4-(1-(2-(dimethylamino)ethyl)-2-oxo-1,2,3,4-tetrahydroquinolin-6-yl)thiazol-2-yl)-2-isopropyl-4-methyloxazole-5-carboxamide (0.049 g, 83%) a beige solid. 1H NMR (400 MHz, DMSO-d): δ 12.59 (bs, 1H), 7.80 (m, 2H), 7.59 (s, 1H), 7.19 (d, 1H, J=8.0 Hz), 4.01 (t, 2H, J=7.2 Hz), 3.11 (p, 1H, J=7.2 Hz), 2.89 (m, 2H), 2.57 (m, 2H), 2.42 (m, 5H), 2.21 (s, 6H), 1.36 (d, 6H, J=7.2 Hz). MS (ESI): Calcd, for $C_{24}H_{29}N_5O_3S$: 467, found 468 (M+1)$^+$.

Example 137

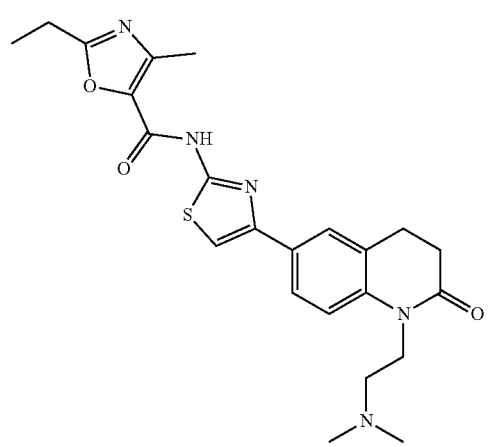 [SMILES: CCc1nc(C)c(C(=O)Nc2nc(-c3ccc4c(c3)CCC(=O)N4CCN(C)C)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.457 mmol) was added in one portion. The reaction was stirred for 10 main at 0° C. then 2-bromo-N,N-dimethylethylamine hydrobromide (0.034 g, 0.144 mmol) was added as a solid. The mixture was stirred for 90 minutes, then 20 hours at room temperature. After consumption of starting material, the reaction mixture was quenched with water (5 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-(2-(dimethylamino)ethyl)-2-oxo-1,2,3,4-tetrahydroquinolin-6-yl)thiazol-2-yl)-2-ethyl-4-methyloxazole-5-carboxamide (0.053 g, 90%) a beige solid. $^1$H NMR (400 MHz, DMSO-d): δ 12.53 (bs, 1H), 7.81 (m, 2H), 7.59 (s, 1H), 7.19 (d, 1H, J=8.0 Hz), 4.01 (t, 2H, J=7.6 Hz), 2.89 (m, 2H), 2.82 (q, 2H, J=7.2 Hz), 2.57 (m, 2H), 2.43 (m, 5H), 2.21 (s, 6H), 1.34 (t, 3H, J=7.2 Hz). MS (ESI): Calcd. for $C_{23}H_{27}N_5O_3S$: 453, found 454 (M+1)$^+$.

Example 138

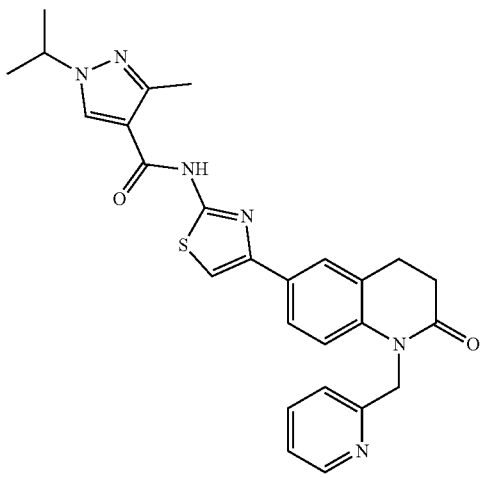 [SMILES: Cc1nn(C(C)C)cc1C(=O)Nc1nc(-c2ccc3c(c2)CCC(=O)N3Cc2ccccn2)cs1]

To a solution of 1-isopropyl-3-methyl-N-(4-(2-oxo-1,2,3,4-tetrahydroquinolin-6-yl)thiazol-2-yl)-1H-pyrazole-4-carboxamide (0.050 g, 0.126 mmol) in anhydrous dimethylformamide (3 mL) in a flamed dried flask under argon atmosphere at 0° C. was added sodium hydride (60% in mineral oil, 0.018 g, 0.443 mmol) was added in one portion. The reaction was stirred for 10 min at 0° C. then 2-(bromomethyl)pyridine hydrobromide (0.036 g, 0.139 mmol) was added in one portion as solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-isopropyl-3-methyl-N-(4-(2-oxo-1-(pyridin-2-ylmethyl)-1,2,3,4-tetrahydroquinolin-6-yl)thiazol-2-yl)-1H-pyrazole-4-carboxamide (0.057 g, 93%) a white solid. $^1$H NMR (400 MHz, DMSO-d): δ 12.10 (s, 1H), 8.70 (s, 1H), 8.53 (m, 1H), 7.80 (d, 1H, J=1.6 Hz), 7.73 (dt, 1H, J=8.0, 2.0 Hz), 7.66 (dd, 1H, J=8.4, 2.4 Hz), 7.47 (s, 1H), 7.26 (m, 1H), 7.21 (d, 1H, J=7.6 Hz), 6.95 (d, 1H, J=8.8 Hz), 5.21 (s, 2H), 4.43 (p, 1H, J=6.8 Hz), 3.02 (m, 2H), 2.73 (m, 2H), 2.40 (s, 3H), 1.43 (d, 6H, J=6.8 Hz). MS (ESI): Calcd. for $C_{26}H_{26}N_6O_2S$: 486, found 487 (M+1)$^+$.

Example 139

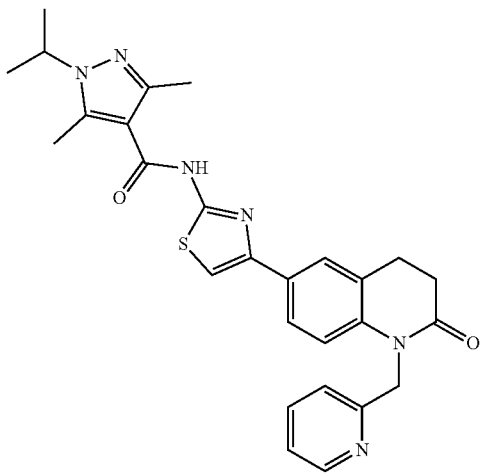 [SMILES: Cc1nn(C(C)C)c(C)c1C(=O)Nc1nc(-c2ccc3c(c2)CCC(=O)N3Cc2ccccn2)cs1]

To a solution of 1-isopropyl-3,5-dimethyl-N-(4-(2-oxo-1,2,3,4-tetrahydroquinolin-6-yl)thiazol-2-yl)-1H-pyrazole-4-carboxamide (0.050 g, 0.122 mmol) in anhydrous dimethylformamide (3 mL) in a flamed dried flask under argon atmosphere at 0° C. was added sodium hydride (60% in mineral oil, 0.018 g, 0.427 mmol) was added in one portion. The reaction was stirred for 10 min at 0° C. then 3-(bromomethyl)pyridine hydrobromide (0.034 g, 0.134 mmol) was added in one portion as a solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-isopropyl-3,5-dimethyl-N-(4-(2-oxo-1-(pyridin-2-ylmethyl)-1,2,3,4-tetrahydroquinolin-6-yl)thiazol-2-yl)-1H-pyrazole-4-carboxamide (0.042 g, 68%) an off-white solid. $^1$H NMR (400 MHz, DMSO-d): δ 11.75 (s, 1H), 8.53 (m, 1H), 7.79 (d, 1H, J=2.0 Hz), 7.73 (dt, 1H, J=8.0, 2.0 Hz), 7.66 (dd, 1H, J=8.0, 2.0 Hz), 7.49 (s, 1H), 7.26 (m, 1H), 7.21 (d, 1H, J=7.6 Hz), 6.94 (d, 1H, J=8.8 Hz), 5.21 (s, 2H), 4.51 (p, 1H, J=6.8 Hz), 3.02 (m, 2H), 2.73 (m, 2H), 2.41 (s, 3H), 2.32 (s, 3H), 1.35 (d, 6H, J=6.8 Hz). MS (ESI): Calcd. for $C_{27}H_{28}N_6O_2S$: 500, found 501 (M+1)$^+$.

Example 140

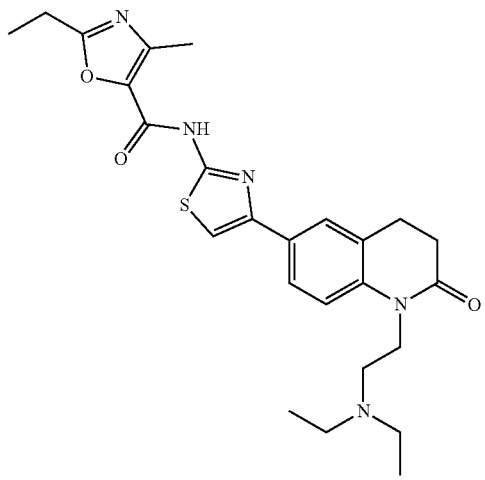 [SMILES: CCc1nc(C)c(C(=O)Nc2nc(-c3ccc4c(c3)CCC(=O)N4CCN(CC)CC)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.457 mmol) was added in one portion. The reaction was stirred for 10 min at 0° C. then 2-diethylaminoethylamine chloride hydrochloride (0.025 g, 0.144 mmol) was added as a solid. The mixture was stirred for 90 minutes, then 20 hours at room temperature. After consumption of starting material, the reaction mixture was quenched with water (5 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give N-(4-(1-(2-(diethylamino)ethyl)-2-oxo-1,2,3,4-tetrahydroquinolin-6-yl)thiazol-2-yl)-2-ethyl-4-methyloxazole-5-carboxamide (0.041 g, 65%) a beige solid. $^1$H NMR (400 MHz, DMSO-d): δ 12.50 (bs, 1H), 7.81 (dd, 1H, J=8.4, 2.0 Hz), 7.78 (d, 1H, J=2.0 Hz), 7.59 (s, 1H), 7.21 (d, 1H, J=8.4 Hz), 3.98 (t, 2H, J=6.8 Hz), 2.89 (t, 2H, J=6.8 Hz), 2.82 (q, 2H, J=7.2 Hz), 2.59-2.48 (m, 6H), 2.42 (s, 3H), 1.32 (t, 3H, J=7.6 Hz), 0.92 (t, 6H, J=7.2 Hz). MS (ESI): Calcd. for $C_{25}H_{31}N_5O_3S$: 481, found 482 (M+1)$^+$.

Example 141

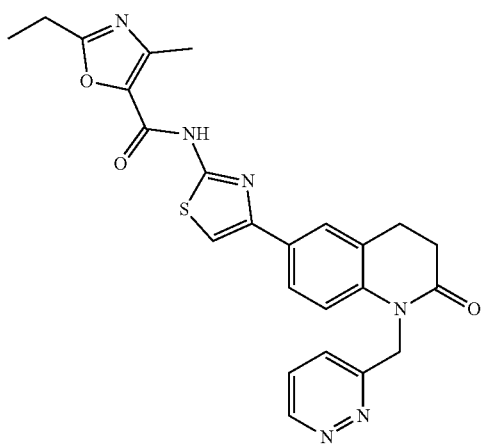 [SMILES: CCc1nc(C)c(C(=O)Nc2nc(-c3ccc4c(c3)CCC(=O)N4Cc3cccnn3)cs2)o1]

To a solution of 2-ethyl-4-methyl-N-(4-(2-oxo-1,2,3,4-tetrahydroquinolin-6-yl)thiazol-2-yl)oxazole-5-carboxamide (0.050 g, 0.131 mmol) in anhydrous dimethylformamide (3 mL) in a flamed dried flask under argon atmosphere at 0° C. was added sodium hydride (60% in mineral oil, 0.018 g, 0.457 mmol) was added in one portion. The reaction was stirred for 10 min at 0° C. then 3-(chloromethyl)pyridazine (0.024 g, 0.144 mmol) was added as a solid. The mixture was stirred for 90 minutes, then 20 hours at room temperature. After consumption of starting material, the reaction mixture was quenched with water (5 mL) and extracted with ethyl acetate (2×25 mL). The combined organics were washed once with saturated sodium bicarbonate (20 mL), brine (20 mL), and dried over anhydrous sodium sulfate. The concentrated residue was purified by flash chromatography over silica gel using 95:5 dichloromethane/methanol to give 2-ethyl-4-methyl-N-(4-(2-oxo-1-(pyridazin-3-ylmethyl)-1,2,3,4-tetrahydroquinolin-6-yl)thiazol-2-yl)oxazole-5-carboxamide (0.051 g, 83%) a beige solid, $^1$H NMR (400 MHz, DMSO-d): δ 12.58 (s, 1H), 9.14 (dd, 1H, J=4.8, 1.6 Hz), 7.83 (d, 1H, J=2.0 Hz), 7.70 (dd, 1H, J 8.0, 1.6 Hz), 7.65 (dd, 1H, J=8.8, 4.8 Hz), 7.58 (s, 1H), 7.55 (dd, 1H, J=8.8, 1.6 Hz), 7.04 (d, 1H, J=8.8 Hz), 5.42 (s, 2H), 3.03 (m, 2H), 2.81 (q, 2H, J=7.6 Hz), 2.74 (m, 2H), 2.41 (s, 3H), 1.32 (t, 3H, J=7.6 Hz). MS (ESI): Calcd. for $C_{24}H_{22}N_6O_3S$: 474, found 475 (M+1)$^+$.

Example 142

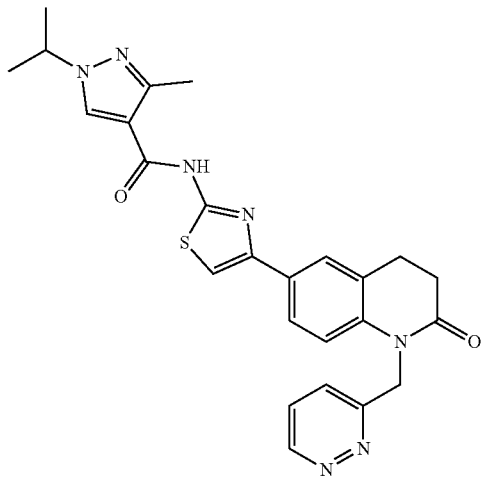 [SMILES: Cc1nn(C(C)C)cc1C(=O)Nc1nc(-c2ccc3c(c2)CCC(=O)N3Cc2cccnn2)cs1]

To a solution of 1-isopropyl-3-methyl-N-(4-(2-oxo-1,2,3,4-tetrahydroquinolin-6-yl)thiazol-2-yl)-1H-pyrazole-4-carboxamide (0.050 g, 0.126 mmol) in anhydrous dimethylformamide (3 mL) in a flamed dried flask under argon atmosphere at 0° C. was added sodium hydride (60% in mineral oil, 0.018 g, 0.443 mmol) was added in one portion. The reaction was stirred for 10 min at 0° C. then 3-(chloromethyl)pyridazine hydrobromide (0.023 g, 0.139 mmol) was added in one portion as solid. The mixture was stirred for 90 minutes and then slowly equilibrated to room temperature for 15 hours. After consumption of starting material, the reaction mixture was quenched with water (1 mL) and sat. sodium bicarbonate (1 mL). The mixtures were extracted with ethyl acetate (2×25 mL) and washed with brine (2×25 mL). The combined organics were dried over anhydrous sodium sulfate, filtered, and concentrated. The residue was purified by flash chromatography over silica gel using 95:5 dichloromethane/methanol to give 1-isopropyl-3-methyl-N-(4-(2-oxo-1-(pyridazin-3-ylmethyl)-1,2,3,4-tetrahydroquinolin-6-yl)thiazol-2-yl)-1H-pyrazole-4-carboxamide (0.049 g, 79%) a beige solid. $^1$H NMR (400 MHz, DMSO-d): δ 12.10 (s, 1H), 9.14 (dd, 1H, J=4.8, 1.6 Hz), 8.70 (s, 1H), 7.81 (d, 1H, J=2.0 Hz), 7.68 (dd, 1H, J=8.8, 2.0 Hz), 7.65 (dd, 1H, J=8.4, 4.8 Hz), 7.65 (dd, 1H, J=8.4, 4.8 Hz), 7.55 (dd, 1H, J=8.4, 1.6 Hz), 7.49 (s, 1H), 7.03 (d, 1H, J=8.4 Hz), 5.42 (s, 2H), 4.43 (p, 1H, J=6.8 Hz), 3.03 (m, 2H), 2.74 (m, 2H), 2.40 (s, 3H), 1.43 (d, 6H, J=6.8 Hz). MS (ESI): Calcd. for $C_{25}H_{25}N_7O_2S$: 487, found 488 (M+1)$^+$.

Example 143

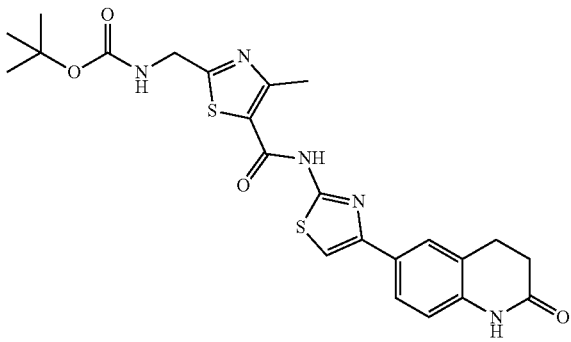 [SMILES: Cc1nc(CNC(=O)OC(C)(C)C)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.200 g, 0.816 mmol) and ({[(tert-butoxyl)carbonyl]amino}-methyl-1,3-thiazole-5-carboxylic acid (0.233 g, 0.856 mmol), and pyridine (0.30 mL, 3.670 mmol) in acetonitrile (8 mL) in a sealed tube was added propylphospsphonic anhydride solution (50 wt % in ethyl acetate, 1.70 mL, 2.851 mmol). The sealed tube was heated to 50° C. for 5 days. The reaction mixture was quenced with sat. NaHCO$_3$ and extracted with 8:2 dichloromethane/isopropanol mixture (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give tert-butyl ((4-methyl-5-((4-(2-oxo-1,2,3,4-tetrahydroquinolin-6-yl)thiazol-2-yl)carbamoyl)thiazol-2-yl)methyl)carbamate (0.291 g, 72%) as a yellow solid. $^1$H NMR (400 MHz, DMSO-d): δ 12.61 (bs, 1H), 10.19 (s, 1H), 7.85 (m, 1H), 7.74 (s, 1H), 7.69 (dd, 1H, J=8.0, 1.6 Hz), 7.51 (bs, 1H), 6.89 (d, 1H, J=8.0 Hz), 4.38 (d, 2H, J=6.0 Hz), 2.93 (m, 2H), 2.62 (s, 3H), 2.49 (partial masked under d-DMSO, m, 2H), 1.43 (s, 9H). MS (ESI): Calcd. for C$_{23}$H$_{25}$N$_5$O$_4$S$_2$: 499, found 500 (M+1)$^+$.

Example 144

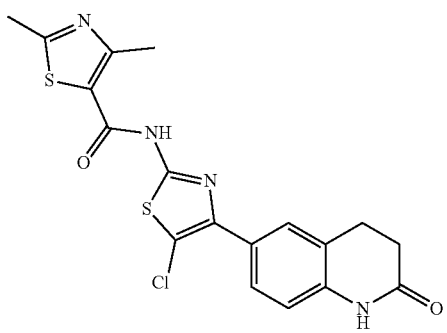 [SMILES: Cc1nc(C)c(C(=O)Nc2nc(-c3ccc4c(c3)CCC(=O)N4)c(Cl)s2)s1]

To a suspension of 6-(2-amino-5-chlorothiazol-4-yl)-3,4-dihydroquinolin-2(1H)-one hydrochloride (0.200 g, 0.633 mmol) and 2,4-dimethyl-1,3-thiazole-5-carboxylic acid (0.109 g, 0.696 mmol), and pyridine (0.28 mL, 3.481 mmol) in acetonitrile (8 mL) in a sealed tube was added propylphosphonic anhydride solution (50 wt % in ethyl acetate, 1.32 mL, 2.211 mmol). The sealed tube was heated to 50° C. for 5 days and the precipitation formed. After cooling, the precipitate was collected by filtration and washed with cold 1:1 acetonitrile/water to give N-(5-chloro-4-(2-oxo-1,2,3,4-tetrahydroquinolin-6-yl)thiazol-2-yl)-2,4-dimethylthiazole-5-carboxamide (0.098 g, 33%) as a reddish pink solid. $^1$H NMR (400 MHz, DMSO-d): δ 12.86 (bs, 1H), 10.26 (s, 1H), 7.72 (s, 1H), 7.69 (dd, 1H, J=8.4, 1.6 Hz), 6.94 (d, 1H, J=8.4 Hz), 2.94 (m, 2H), 2.68 (s, 3H), 2.61 (s, 3H), 2.49 (partial masked under d-DMSO, m, 2H). MS (ESI): Calcd. for C$_{18}$H$_{15}$ClN$_4$O$_2$S$_2$: 418, found 419 (M+1)$_+$.

Example 145

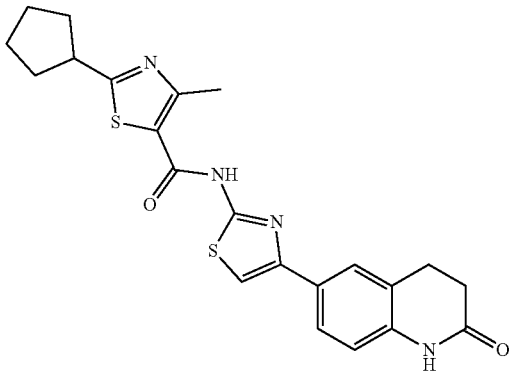 [SMILES: Cc1nc(C2CCCC2)sc1C(=O)Nc1nc(-c2ccc3c(c2)CCC(=O)N3)cs1]

To a suspension of 6-(2-amino-5-chlorothiazol-4-yl)-3,4-dihydroquinolin-2(1H)-one hydrochloride (0.100 g, 0.408 mmol) and 2-cyclopentyl-4-methyl-1,3-thiazole-5-carboxylic acid (0.095 g, 0.448 mmol), and pyridine (0.15 mL, 1.831 mmol) in acetonitrile (4 mL) in a sealed tube was added propylphosphonic anhydride solution (50 wt % in ethyl acetate, 0.85 mL, 1.431 mmol). The sealed tube was heated to 50° C. for 5 days and the precipitation formed. After cooling, the precipitate was collected by filtration and washed with cold 1:1 acetonitrile/water to give 2-cyclopentyl-4-methyl-N-(4-(2-oxo-1,2,3,4-tetrahydroquinolin-6-yl)thiazol-2-yl)thiazole-5-carboxamide (0.143 g, 80%) as a beige solid. $^1$H NMR (400 MHz, DMSO-d): δ 12.53 (bs, 1H), 10.19 (s, 1H), 7.74 (s, 1H), 7.69 (dd, 1H, J=8.4, 1.6 Hz), 7.50 (bs, 1H), 6.89 (d, 1H, J=8.4 Hz), 3.44 (m, 1H), 2.93 (m, 2H), 2.62 (s, 3H), 2.49 (partial masked under d-DMSO, m, 2H), 2.12 (m, 2H), 1.77 (m, 4H), 1.67 (m, 2H). MS (ESI): Calcd. for C$_{22}$H$_{22}$N$_4$O$_2$S$_2$: 438, found 439 (M+1)$^+$.

Example 146

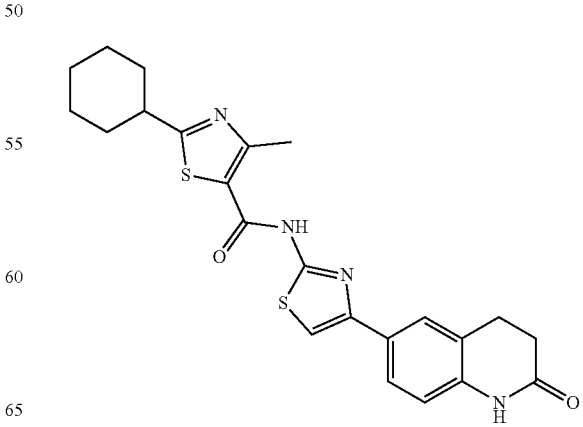

To a suspension of 6-(2-amino-5-chlorothiazol-4-yl)-3,4-dihydroquinolin-2(1H)-one hydrochloride (0.100 g, 0.408 mmol) and 2-cyclohexyl-4-methyl-1,3-thiazole-5-carboxylic acid (0.101 g, 0.448 mmol), and pyridine (0.15 mL, 1.831 mmol) in acetonitrile (4 mL) the sealed tube was added propylphosphonic anhydride solution (50 wt % in ethyl acetate, 0.85 mL, 1.431 mmol). The sealed tube was heated to 50° C. for 5 days and the precipitation formed. After cooling, the precipitate was collected by filtration and washed with cold 1:1 acetonitrile/water to give 2-cyclohexyl-4-methyl-N-(4-(2-oxo-1,2,3,4-tetrahydroquinolin-6-yl)thiazol-2-yl)thiazole-5-carboxamide (0.149 g, 81%) as a beige solid, $^1$H NMR (400 MHz, DMSO-d): δ 12.54 (bs, 1H), 10.19 (s, 1H), 7.74 (s, 1H), 7.69 (dd, 1H, J=8.4, 1.6 Hz), 7.51 (bs, 1H), 6.89 (d, 1H, J=8.4 Hz), 2.99 (m, 1H), 2.93 (m, 2H), 2.62 (s, 3H), 2.49 (partial masked under d-DMSO, m, 2H), 2.06 (m, 2H), 1.78 (m, 4H), 1.55-1.31 (m, 4H), 1.27 (m, 1H). MS (ESI): Calcd. for $C_{23}H_{24}N_4O_2S_2$: 452, found 453 (M+1)$^+$.

Example 147

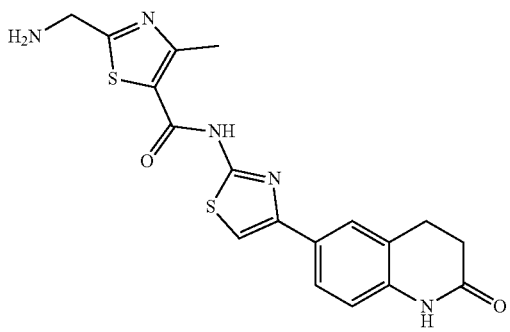 [SMILES: Cc1nc(CN)sc1C(=O)Nc1nc(-c2ccc3c(c2)CCC(=O)N3)cs1]

tert-Butyl ((4-methyl-5-((4-(2-oxo-1,2,3,4-tetrahydroquinolin-6-yl)thiazol-2-yl)carbamoyl)thiazol-2-yl)methyl)carbamate (0.100 g, 0.200 mmol) was suspended 6 mL of 4M hydrogen chloride solution in dioxane in sealed flask. The mixture was stirred for 6 hours at room temperature. The reaction mixture was concentrated in vacuo. The HCl salt was dissolved in minimum amount of methanol and quenched with sat. sodium bicarbonate. The mixture was extracted with 8:2 dichloromethane/isopropanol (6×10 mL). The combined organic layers were washed once with sat. NaHCO$_3$, dried over anhydrous Na$_2$SO$_4$ and concentrated in vacuo. to give 2-(aminomethyl)-4-methyl-N-(4-(2-oxo-1,2,3,4-tetrahydroquinolin-6-yl)thiazol-2-yl)thiazole-5-carboxamide (0.060 g, 75%) as an orange solid. $^1$H NMR (400 MHz, DMSO-d): δ acylic NH (not observed), 10.18 (s, 1H), 7.85 (m, 1H), 7.74 (s, 1H), 7.69 (dd, 1H, J=8.0, 1.6 Hz), 7.45 (s, 1H), 6.89 (d, 1H, J=8.0 Hz), 4.03 (s, 2H), 2.93 (m, 2H), 2.62 (s, 3H), 2.49 (partial masked under d-DMSO, m, 2H), 1.23 (bs, 2H). MS (ESI): Calcd. for $C_{18}H_{17}N_5O_2S_2$: 399, found 400 (M+1)$^+$.

Example 148

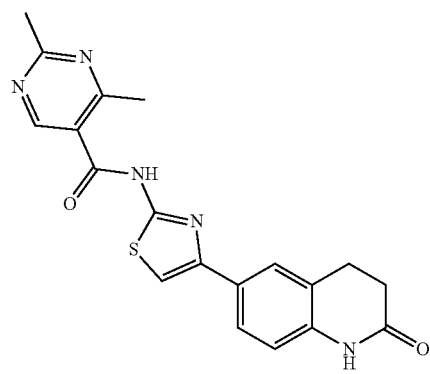 [SMILES: Cc1ncc(C(=O)Nc2nc(-c3ccc4c(c3)CCC(=O)N4)cs2)c(C)n1]

To a suspension of 6-(2-amino-5-chlorothiazol-4-yl)-3,4-dihydroquinolin-2(1H)-one (0.100 g, 0.408 mmol) and 2,4-dimethylpyrimidine-5-carboxylic acid (0.068 g, 0.448 mmol), and pyridine (0.15 mL, 1.831 mmol) in acetonitrile (4 mL) in a sealed tube was added propylphosphonic anhydride solution (50 wt % in ethyl acetate, 0.56 mL, 0.094 mmol). The sealed tube was heated to 100° C. for 16 h and the precipitation formed. After cooling, the precipitate was collected by filtration and washed with cold 1:1 acetonitrile/water to give 2,4-dimethyl-N-(4-(2-oxo-1,2,3,4-tetrahydroquinolin-6-yl)thiazol-2-yl)pyrimidine-5-carboxamide (0.117 g, 83%). $^1$H NMR (400 MHz, DMSO-d): δ 12.94 (bs, 1H), 10.19 (s, 1H), 8.87 (s, 1H), 7.74 (m, 1H), 7.71 (m, 1H), 7.57 (s, 1H), 7.36 (m, 1H), 6.91 (d, 1H, J=8.0 Hz), 2.94 (t, 2H, J=7.2 Hz), 2.65 (s, 3H), 2.58 (s, 3H), 2.48 (partial masked under d-DMSO, m, 2H); MS (ESI): Calcd. for $C_{19}H_{16}N_4O_2S$: 364, found 365 (M+1)$^+$.

Example 149

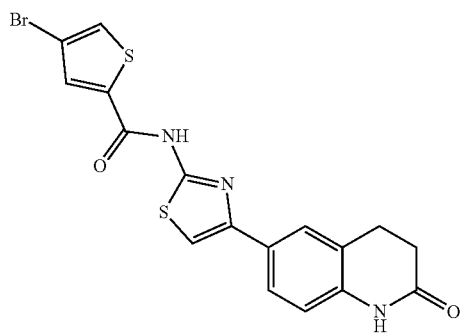 [SMILES: O=C1CCc2cc(-c3csc(NC(=O)c4cc(Br)cs4)n3)ccc2N1]

To a solution of methyl 4-bromothiophene-2-carboxylate (2.0 g, 9.7 mmol) in dry MeOH (8 mL) was added H$_2$SO$_4$ (1-1.2 mL). The reaction mixture was heated to 50° C. for 18 h and was then concentrated under vacuum. The residue was dissolved in DCM and washed several times with saturated NaHCO$_3$ solution. The organic fraction was dried (Na$_2$SO$_4$), concentrated under vacuum to provide 4-bromothiophene-2-carboxylic acid, which was used directly without further purification 1.73 g (81%). $^1$H NMR (400 MHz, DMSO-d): δ 7.69 (d, 1H, J=4.0 Hz), 7.26 (d, 1H, J=4.4 Hz), 3.82 (s, 3H).

To a suspension of 6-(2-aminothiazol-4-yl)-3,4-dihydroquinolin-2(1H)-one (0.100 g, 0.408 mmol) and 4-bromothiophene-2-carboxylic acid (0.093 g, 0.448 mmol), and pyridine (0.15 mL, 1.83 mmol) in acetonitrile (2.5 mL) in a sealed tube was added propylphosphonic anhydride solution (50 wt % in ethyl acetate, 0.56 mL, 0.298 g, 0.938 mmol). The sealed tube was heated overnight in an oil-bath at 100° C. and the precipitation formed. After cooling down to room temperature, the solid was collected by filtration and washed with cold acetonitrile (2 mL×3) to give 4-bromo-N-(4-(2-oxo-1,2,3,4-tetrahydroquinolin-6-yl)thiazol-2-yl)thiophene-2-carboxamide (0.158 g, 89%) as a beige solid. $^1$H NMR (400 MHz, DMSO-d): δ 12.92 (bs, 1H), 10.20 (s, 1H), 8.29 (s, 1H), 8.10 (d, J=1.6 Hz), 7.74 (s, 1H), 7.72 (dd, 1H, J=8.4, 1.6 Hz), 7.54 (bs, 1H), 6.91 (d, 1H, J=8.4 Hz), 2.93 (m, 2H), 2.48 (partial masked under d-DMSO, m, 2H). MS (ESI): Calcd. for C17H12BrN3O2S2: 433, found 434 (M+1)$^+$.

Example 150

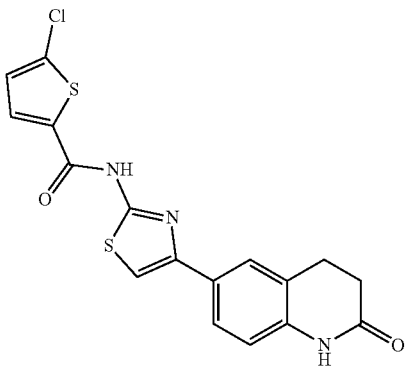 [SMILES: O=C1CCc2cc(-c3csc(NC(=O)c4ccc(Cl)s4)n3)ccc2N1]

To a solution of methyl 5-chlorothiophene-2-carboxylate (10.0 g, 61.5 mmol) in dry MeOH (55 mL) was added H$_2$SO$_4$ (5-7 mL). The reaction mixture was heated to 50° C. for 18 h and was then concentrated under vacuum. The residue was dissolved in DCM and washed several times with saturated NaHCO$_3$ solution. The organic fraction was dried (Na$_2$SO$_4$), concentrated under vacuum provide 4-chlorothiophene-2-carboxylic acid, which was and used directly without further purification 10.85 g (~100%). $^1$H NMR (400 MHz, DMSO-d): δ 7.66 (d, 1H, J=4.0 Hz), 7.23 (d, 1H, J=4.4 Hz), 3.81 (s, 3H).

To a suspension of 6-(2-aminothiazol-4-yl)-3,4-dihydroquinolin-2(1H)-one (0.100 g, 0.408 mmol) and 5-chlorothiophene-2-carboxylic acid (0.073 g, 0.448 mmol), and pyridine (0.15 mL, 1.83 mmol) in acetonitrile (2.5 mL) in a sealed tube was added propylphosphonic anhydride solution (50 wt % in ethyl acetate, 0.56 mL, 0.298 g, 0.938 mmol). The sealed tube was heated overnight in an oil-bath at 100° C. and the precipitation formed. After cooling down to room temperature, the solid was collected by filtration and washed with cold acetonitrile (2 mL×3) to give 5-chloro-N-(4-(2-oxo-1,2,3,4-tetrahydroquinolin-6-yl)thiazol-2-yl)thiophene-2-carboxamide (0,148 g, 93%) as a beige solid. $^1$H NMR (400 MHz, DMSO-d): δ 12.93 (bs, 1H), 10.20 (s, 1H), 8.17 (d, 1H, J=4 Hz), 7.74 (s, 1H), 7.72 (dd, 1H, J=8.4, 1.6 Hz), 7.53 (bs, 1H), 7.32 (d, 1H, J=4 Hz), 6.91 (d, 1H, J=8.4 Hz), 2.93 (m, 2H), 2.48 (partial masked under d-DMSO, m, 2H). MS (ESI): Calcd. for C17H12ClN3O2S2: 389, found 390 (M+1).

Example 151

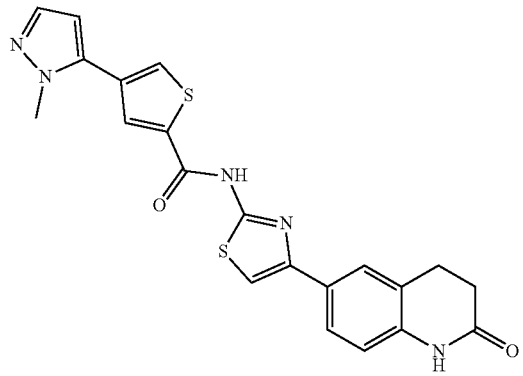 [SMILES: Cn1nccc1-c1csc(C(=O)Nc2nc(-c3ccc4c(c3)CCC(=O)N4)cs2)c1]

To a solution of methyl 4-bromothiophene-2-carboxylate (1.00 g, 4.52 mmol) in dioxane/H$_2$O (30:3 mL) was added K$_2$CO$_3$ (2.69 g, 19.45 mmol), tetrakistriphenylphosphine Pd(O) (0.78 g, 0.678 mmol), and 5-(5,5-dimethyl-1,3,2-dioxaborinan-2-yl)-1-methyl-1H-pyrazole (2.68 g, 12.89 mmol). The reaction mixture was heated to 80° C. in a sealed tube for 18 h. The reaction solution was concentrated under vacuum and purified on silica gel (hexanes/EtOAc, 4:1) to give the title compound methyl 4-(1-methyl-1H-pyrazol-5-yl)thiophene-2-carboxylate (1.01 g, 100%) as yellow solid. $^1$H NMR (400 MHz, DMSO-d): δ 8.16 (d, 1H, J=1.6 Hz), 8.02 (d, 1H, J=1.6 Hz), 7.44 (d, 1H=2.0 Hz), 6.56 (d, 1H, J=2.0 Hz), 3.93 (s, 3H), 3.85 (s, 3H); MS (ESI): Calcd, for C10H10N2O2S: 222.1, found 223.1 (M+1)$^+$.

A solution of methyl 4-(1-methyl-1H-pyrazol-5-yl)thiophene-2-carboxylate (500 mg, 2.25 mmol) in 6N sodium hydroxide (3.75 ml, 22.5 mmol) and Tetrahydrofuran (15 ml) was stirred at 70° C. in a sealed tube for 1 h. The resulting solution was cooled and then partitioned between H$_2$O-DCM. The aqueous phase was adjusted to pH-3 and then washed several times with DCM. The combined organic fractions were dried over Na$_2$SO$_4$ and concentrated affording the desired product 4-(1-methyl-1H-pyrazol-5-yl)thiophene-2-carboxylic acid (240 mg, 51% yield). $^1$H NMR (400 MHz, DMSO-d): δ 7.97 (d, 1H, J=1.6 Hz), 7.81 (d, 1H, J=1.6 Hz), 7.43 (d, 1H, J=2.0 Hz), 6.51 (d, 1H, J=2.0 Hz), 3.92 (s, 3H); MS (ESI): Calcd. for C9H8N2O2S: 208.0, found 209.1 (M+1)$^+$.

To a suspension of 6-(2-aminothiazol-4-yl)-3,4-dihydroquinolin-2(1H)-one (0.100 g, 0.408 mmol) and 4-(1-methyl-1H-pyrazol-5-yl)thiophene-2-carboxylic acid (0.093 g, 0.448 mmol), and pyridine (0.15 mL, 1.83 mmol) in acetonitrile (2.5 mL) in a sealed tube was added propylphosphonic anhydride solution (50 wt % in ethyl acetate, 0.36 mL, 0.194 g, 0.612 mmol). The sealed tube was heated overnight in an oil-bath at 100° C. and the precipitation formed. After cooling down to room temperature, the solid was collected by filtration and washed with cold acetonitrile (2 mL×3) to give 4-(1-methyl-1H-pyrazol-5-yl)-N-(4-(2-oxo-1,2,3,4-tetrahydroquinolin-6-yl)thiazol-2-yl)thiophene-2-carboxamide (0.052 g, 29%) as a beige solid. $^1$H NMR (400 MHz, DMSO-d): δ 12.95 (bs, 1H), 10.20 (s, 1H), 8.56 (s, 1H), 8.21 (s, 1H), 7.76 (s, 1H), 7.71 (dd, 1H, J=8.4, 1.6 Hz), 7.54 (s, 1H), 7.48 (s, 1H), 6.92 (d, 1H, J=8.4 Hz), 6.52 (d, 1H, J=2.0 Hz), 4.0 (s, 3H), 2.95 (m, 2H), 2.48 (partial masked under d-DMSO, nm, 2H). MS (ESI): Calcd. for C21H17N5O2S2: 435.1, found 436.2 (M+1)$^+$.

Example 152

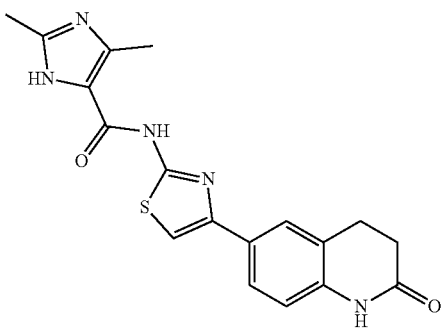 [SMILES: Cc1nc(C)c(C(=O)Nc2nc(-c3ccc4c(c3)CCC(=O)N4)cs2)[nH]1]

To a suspension of 6-(2-aminothiazol-4-yl)-3,4-dihydroquinolin-2(1H)-one (0.100 g, 0.408 mmol) and 2,5-dimethyl-1H-imidazole-4-carboxylic acid (0.063 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 12 days. After cooling, the mixture was quenched with water (3 mL) and extracted with 8:2 dichloromethane/isopropanol (3×50 mL) followed by washing with sat. $NaHCO_3$ (2×50 mL). The crude solid was dried loaded onto silica and purified by flash chromatography using 95:5 dichloromethane/methanol to give 2,4-dimethyl-N-(4-(2-oxo-1,2,3,4-tetrahydroquinolin-6-yl)thiazol-2-yl)-1H-imidazole-5-carboxamide (0.07 g, 47%) as a peach solid. $^1$H NMR (400 MHz, DMSO-d): δ 12.34 (bs, 1H), 10.58 (bs, 1H), 10.16 (s, 1H), 7.74 (s, 1H), 7.69 (dd, 1H, J=8.4, 2.0 Hz), 7.45 (s, 1H), 6.88 (d, 1H, J=8.4 Hz), 2.93 (t, 2H, J=7.2 Hz), 2.49 (partial masked under d-DMSO, m, 5H), 2.31 (s, 3H). MS (ESI): Calcd. for $C_{18}H_{17}N_5O_2S$: 367, found 368 $(M+1)^+$.

Additional Synthetic Protocols

The inventive subject matter includes discovery and development of new or improved protocols for synthesis of desirable intermediates and compounds. FIG. 3A depicts the reaction of reactants SM1 (6-(2-aminothiazol-4-yl)-3,4-dihydroquinolin-2(1H)-one) and SM2 (2,4-dimethylthiazole-5-carboxylic acid) in solution comprising solvent MeCN (acetonitrile), pyridine, and propylphosphonic anhydride (T3P) to form the product useful in the inventive subject matter. FIG. 3B further describes various reaction conditions with variables such as reaction temperature (T), reaction time (Time), amounts of SM1, SM2, T3P, and pyridine (expressed in molar equivalents), amount of solvent (expressed in m L), and recovery, quality, and yield of the product. It should be noted that Test 3 provided the highest yield of product, using 1.0 eq of SM1, 1.1 eq of SM2, 2.3 eq of T3P, and 4.5 eq of Pyridine.

Figure 4:
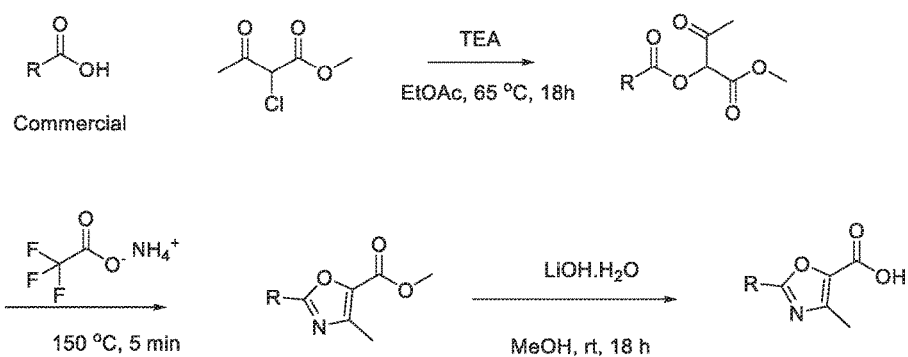
FIG. 4 depicts an exemplary protocol to synthesize selected oxazoles of the inventive subject matter.
Figure 5:
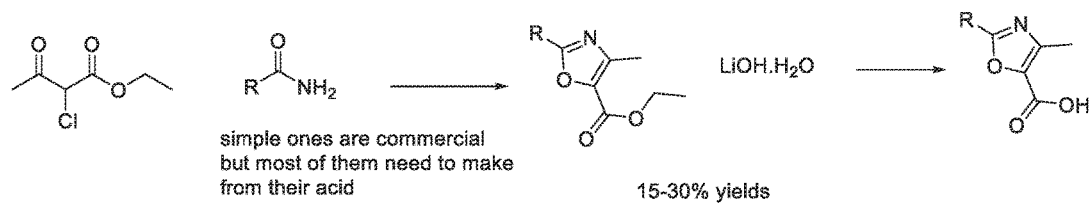
FIG. 5 depicts an alternative protocol to synthesize selected oxazoles of the inventive subject matter.
Figure 6:
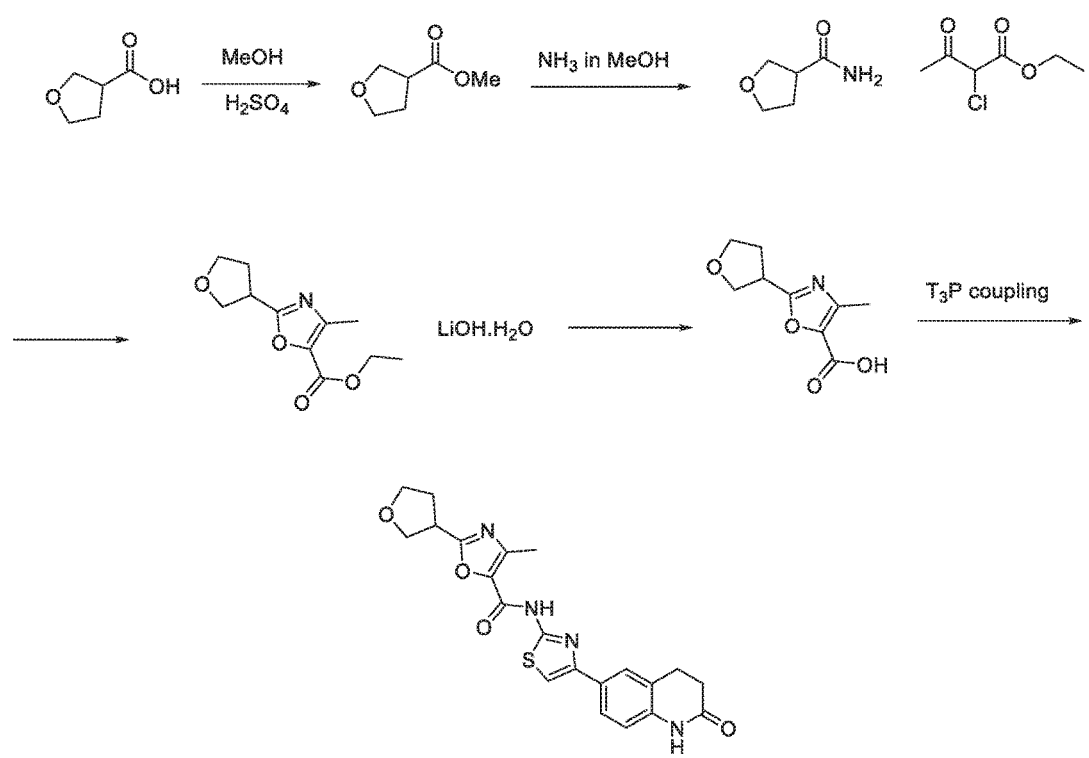
FIG. 6 depicts an exemplary protocol to synthesize a selected compound of the inventive subject matter.

FIGS. 4 and 5 depict protocols for synthesis of oxazole intermediates useful in the inventive subject matter. FIG. 6 depicts a protocol for synthesis of compound of Example 10 (see FIG. 2C) by synthesizing an oxazole intermediate by the protocol of FIG. 5, and reacting the oxazole product with 6-(2-aminothiazol-4-yl)-3,4-dihydroquinolin-2(1H)-one to produce the desired compound.

Figure 7:
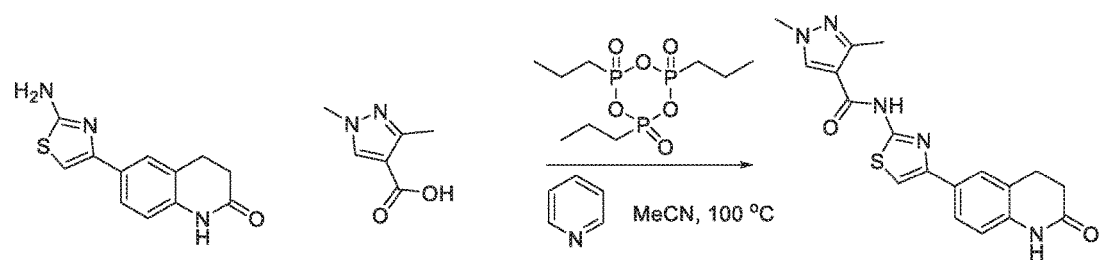
FIG. 7 depicts an exemplary protocol to synthesize selected pyrazoles of the inventive subject matter.
Figure 24:
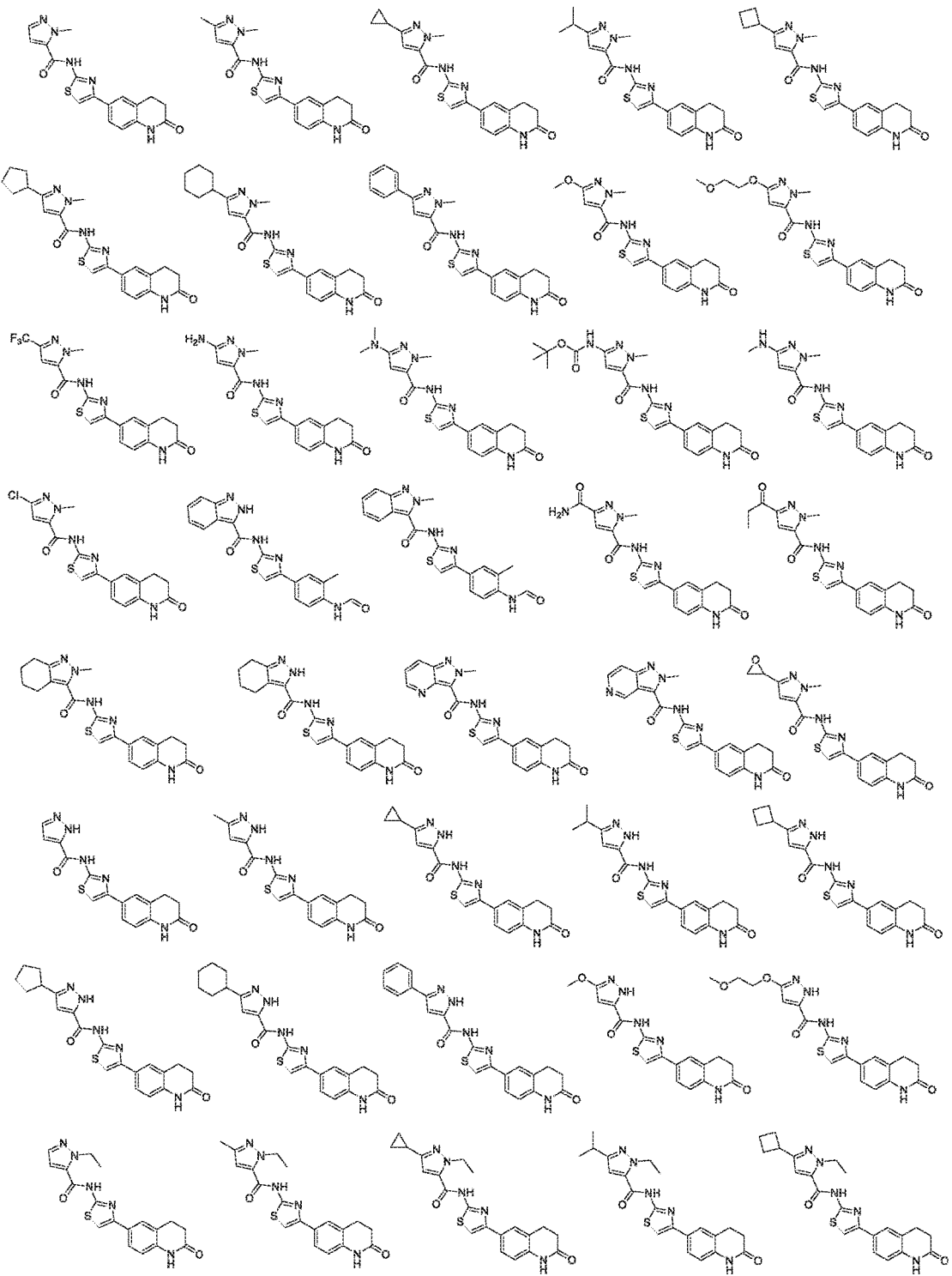
FIGS. 24-54 depict selected compounds of the inventive subject matter.
Figure 25:
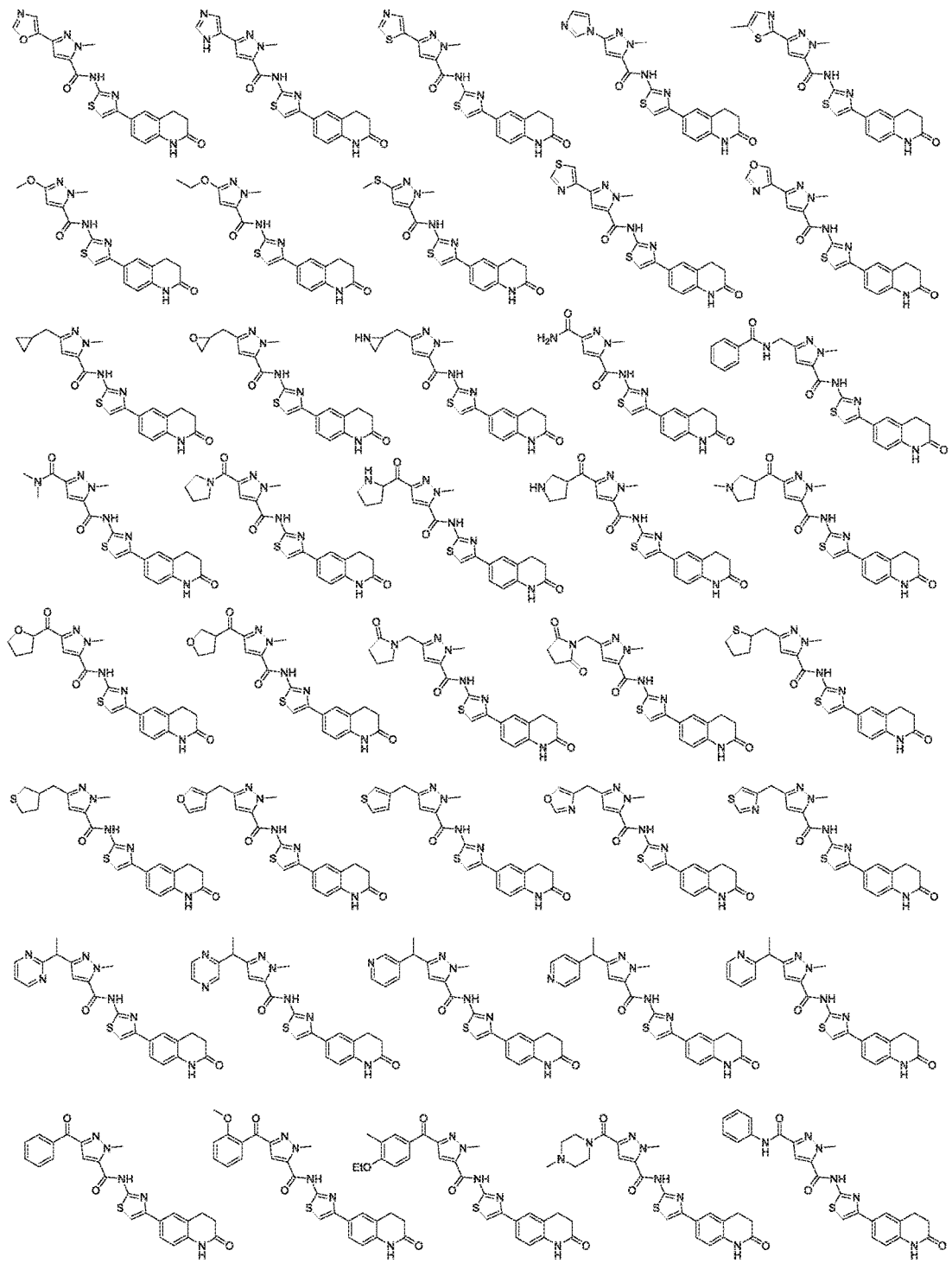
Figure 26:
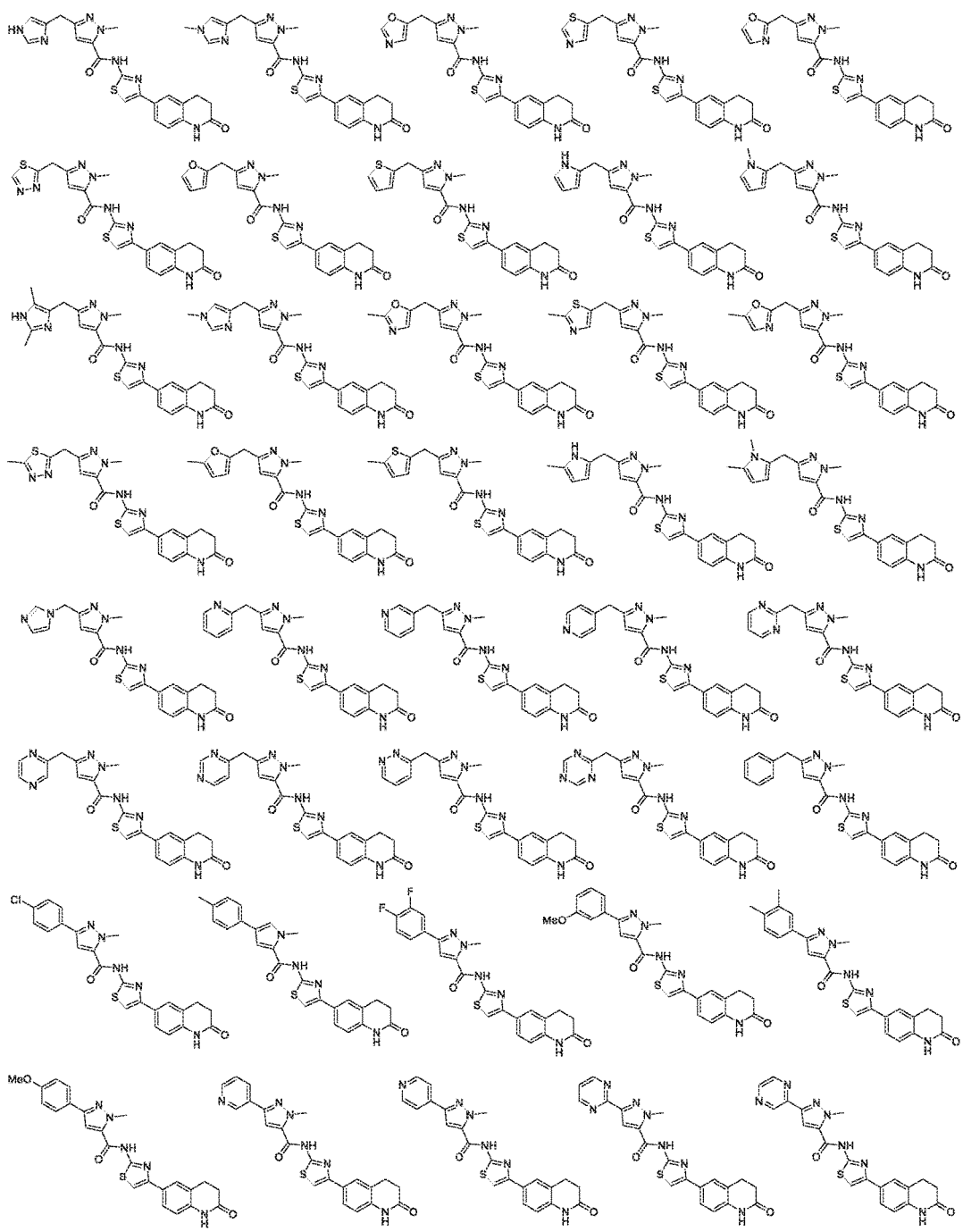
Figure 27:
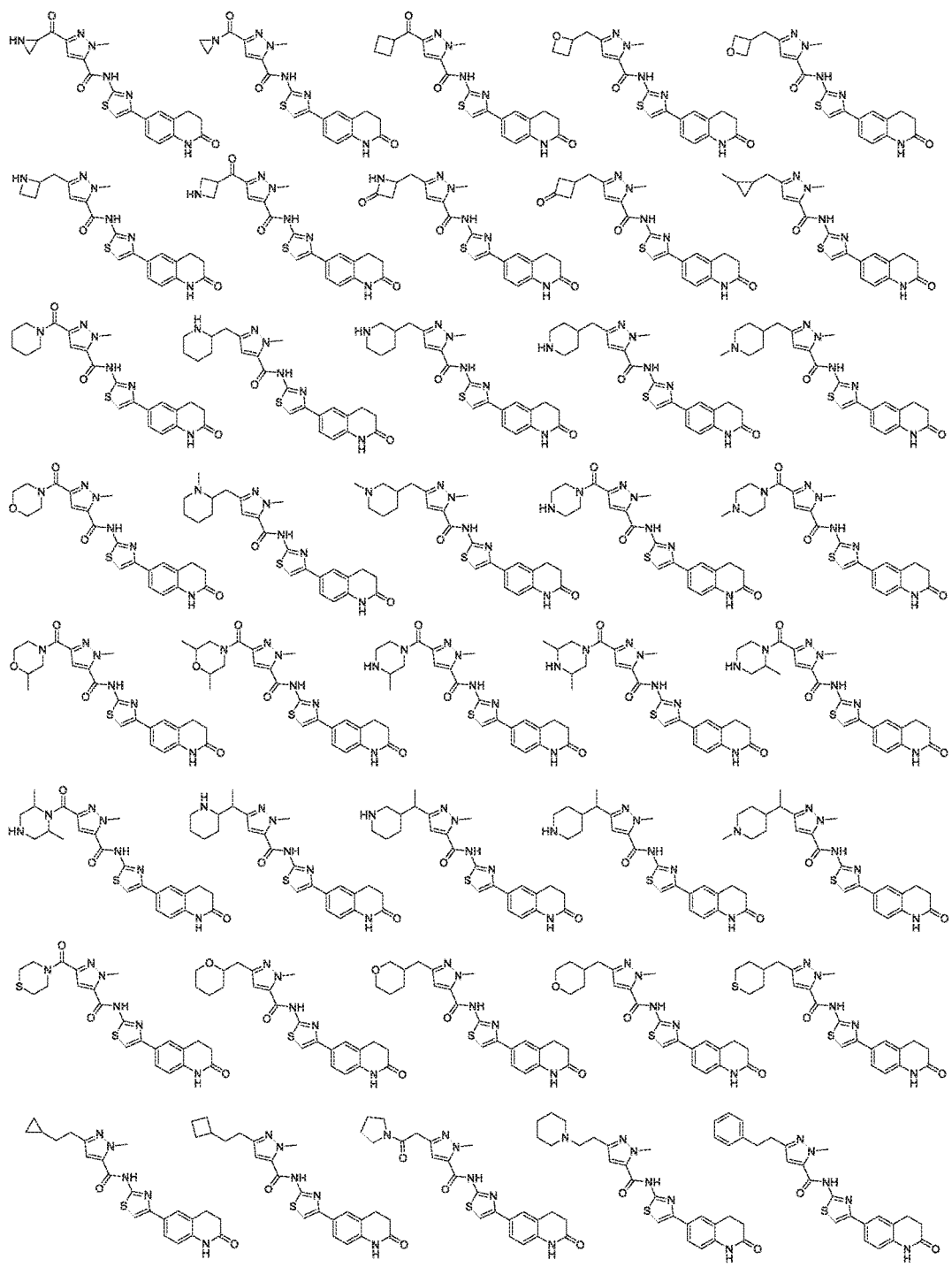
Figure 28:
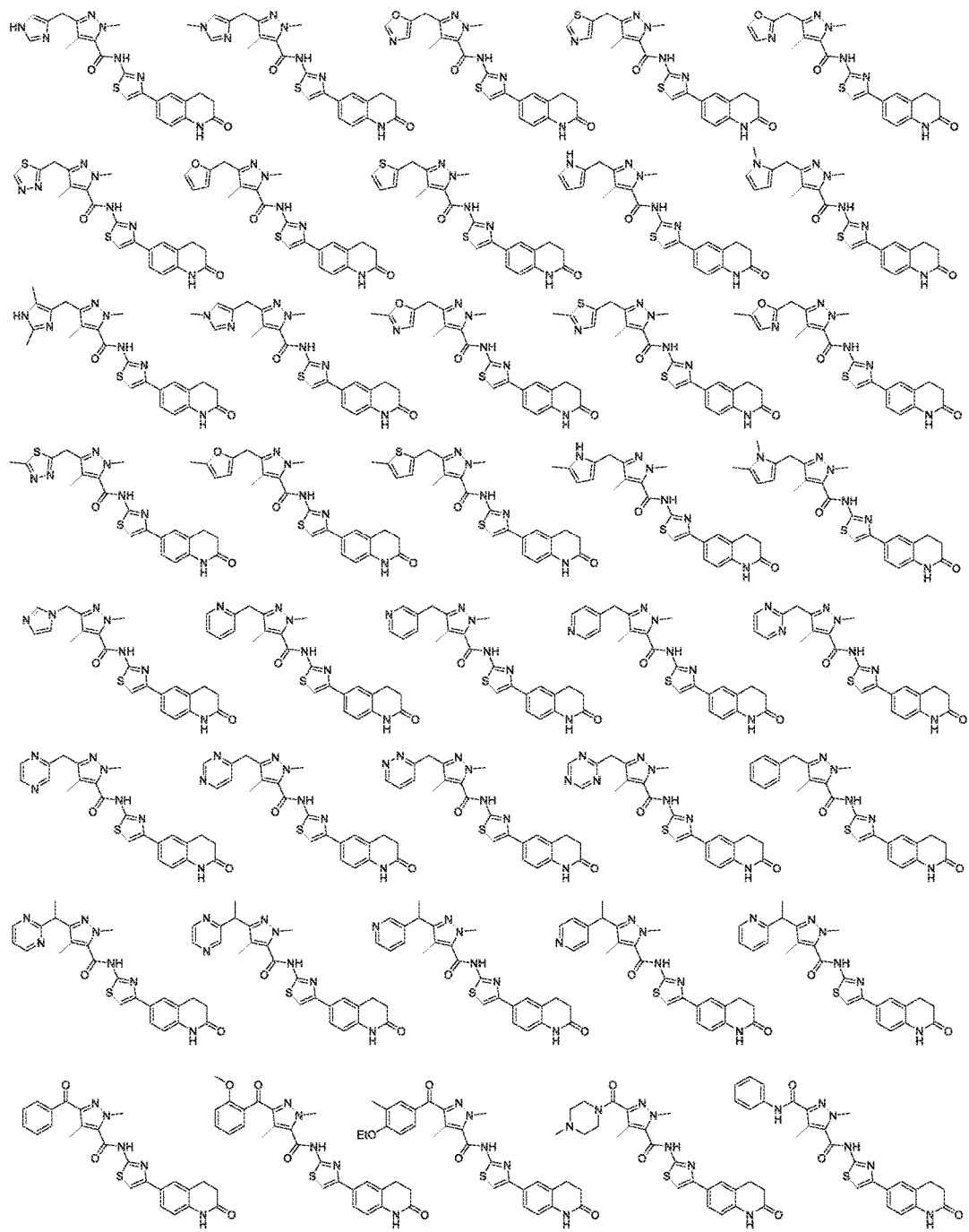
Figure 29:
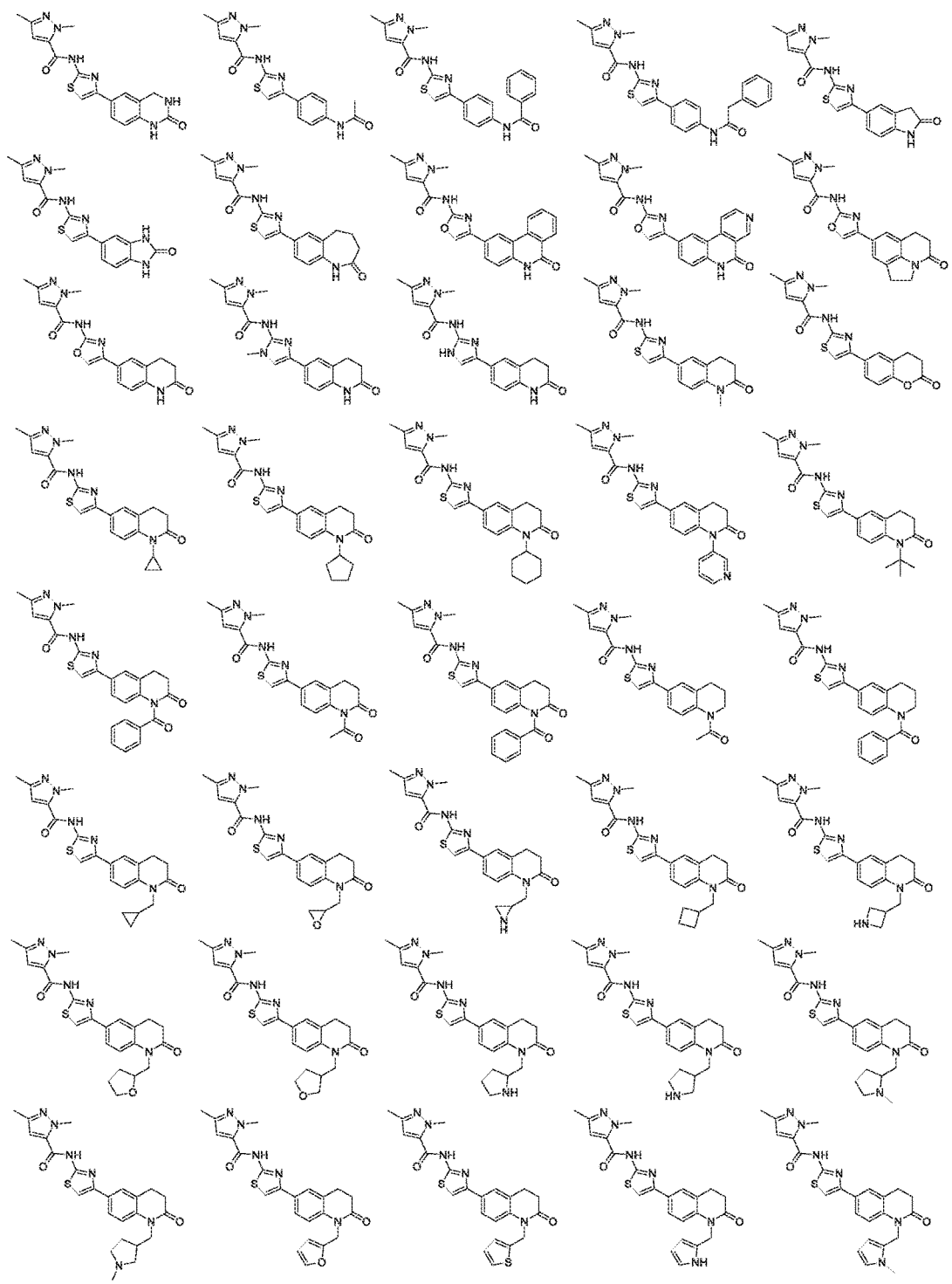
Figure 30:
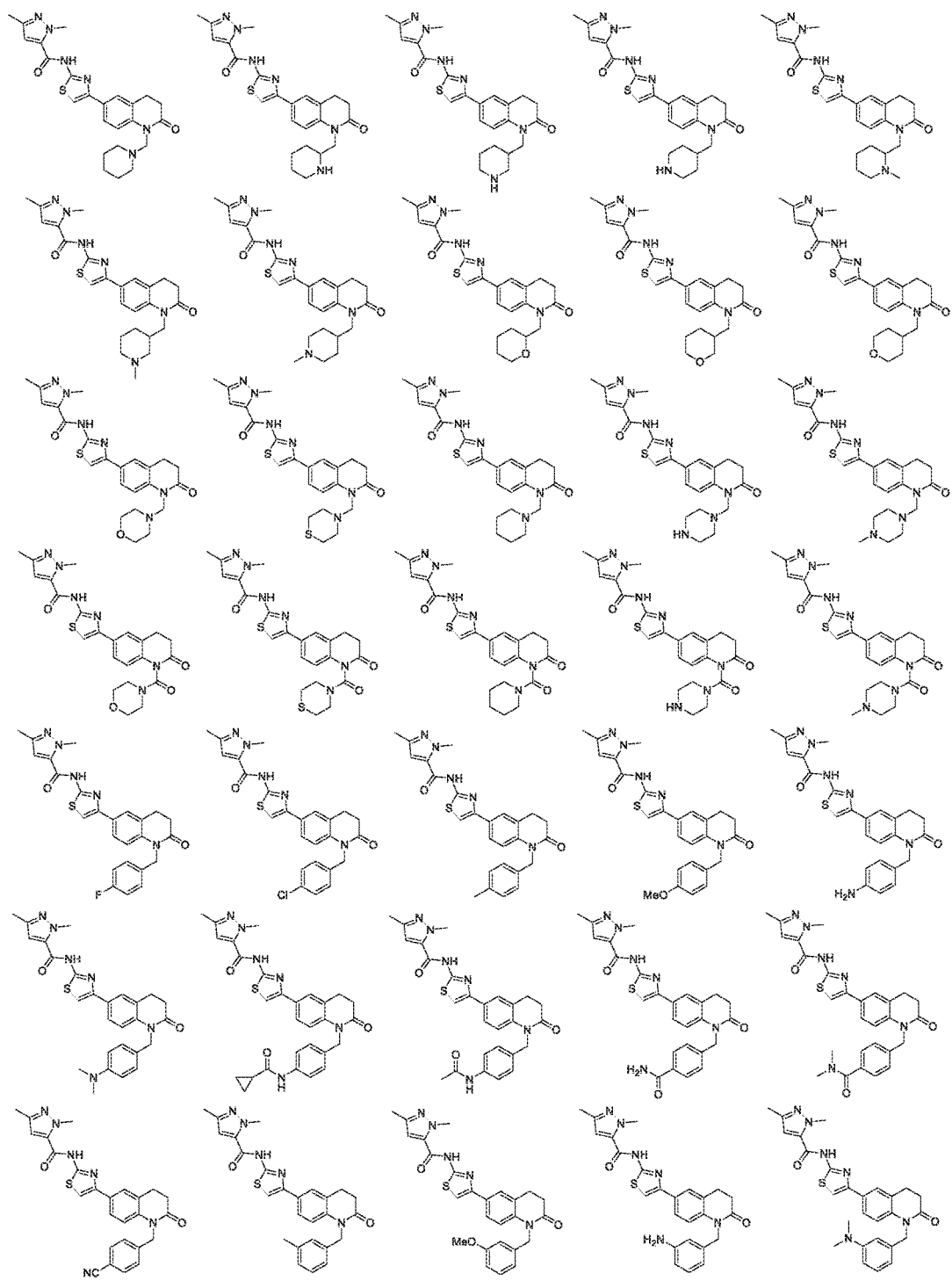
Figure 31:
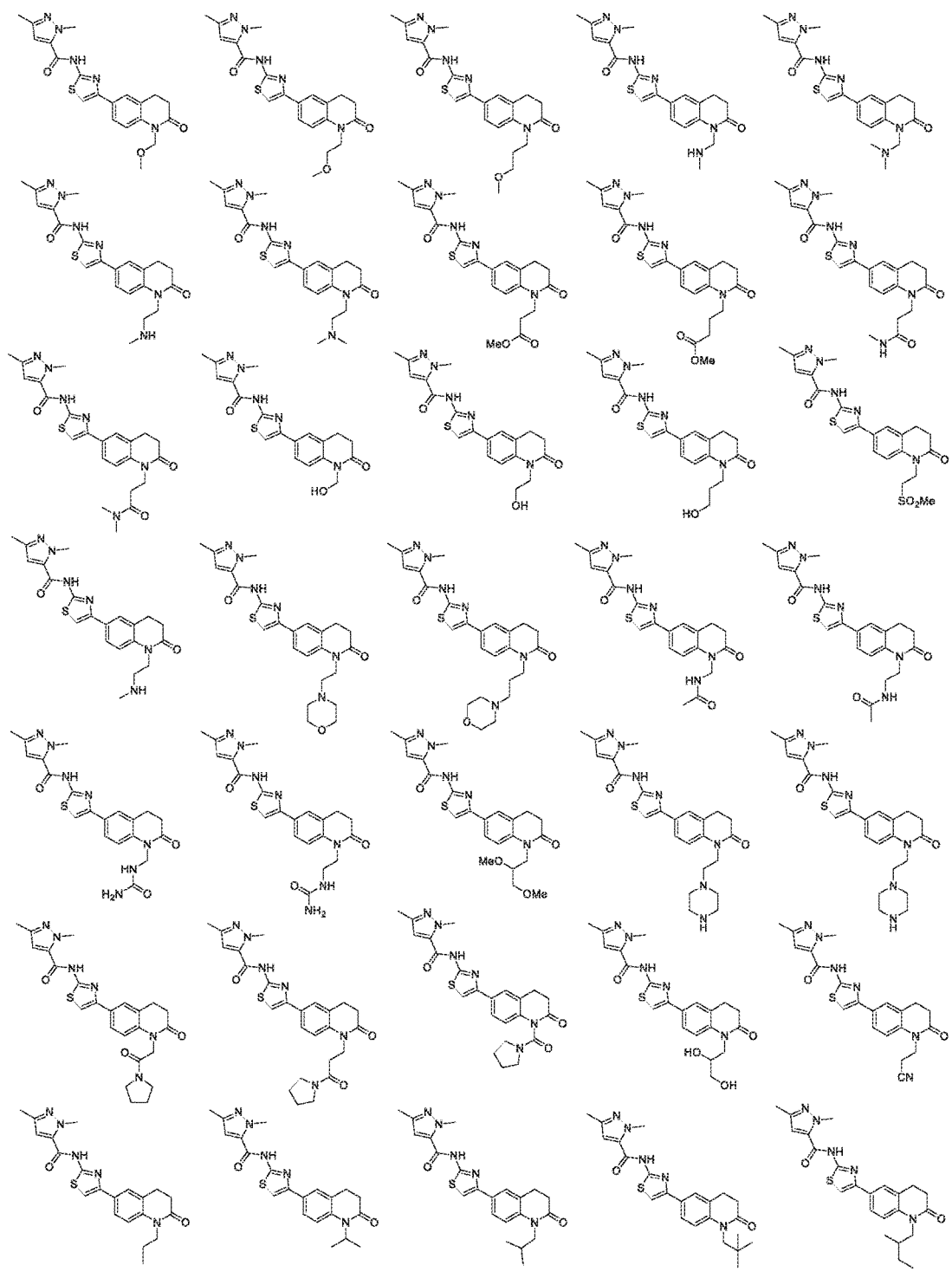
Figure 32:
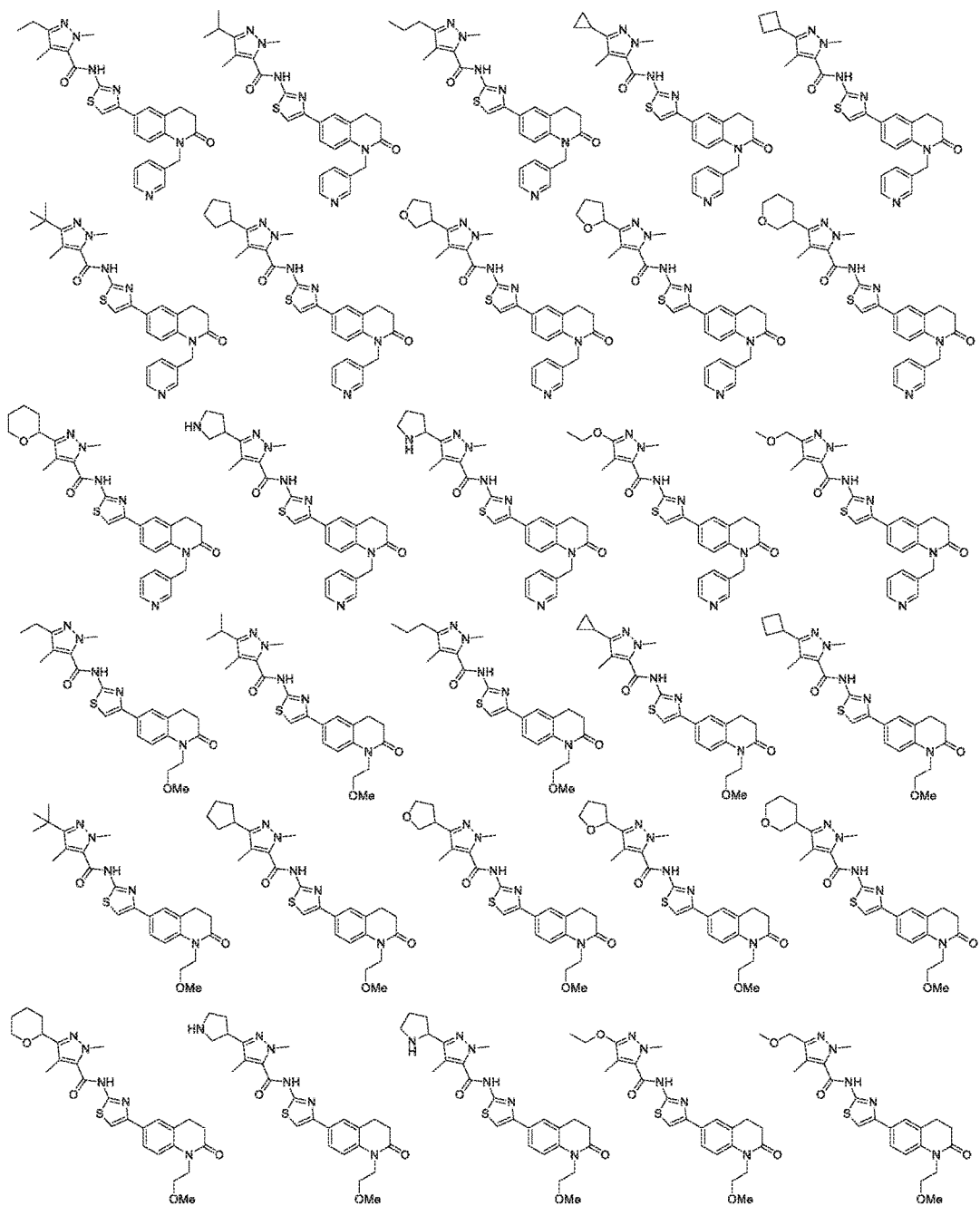
Figure 33:
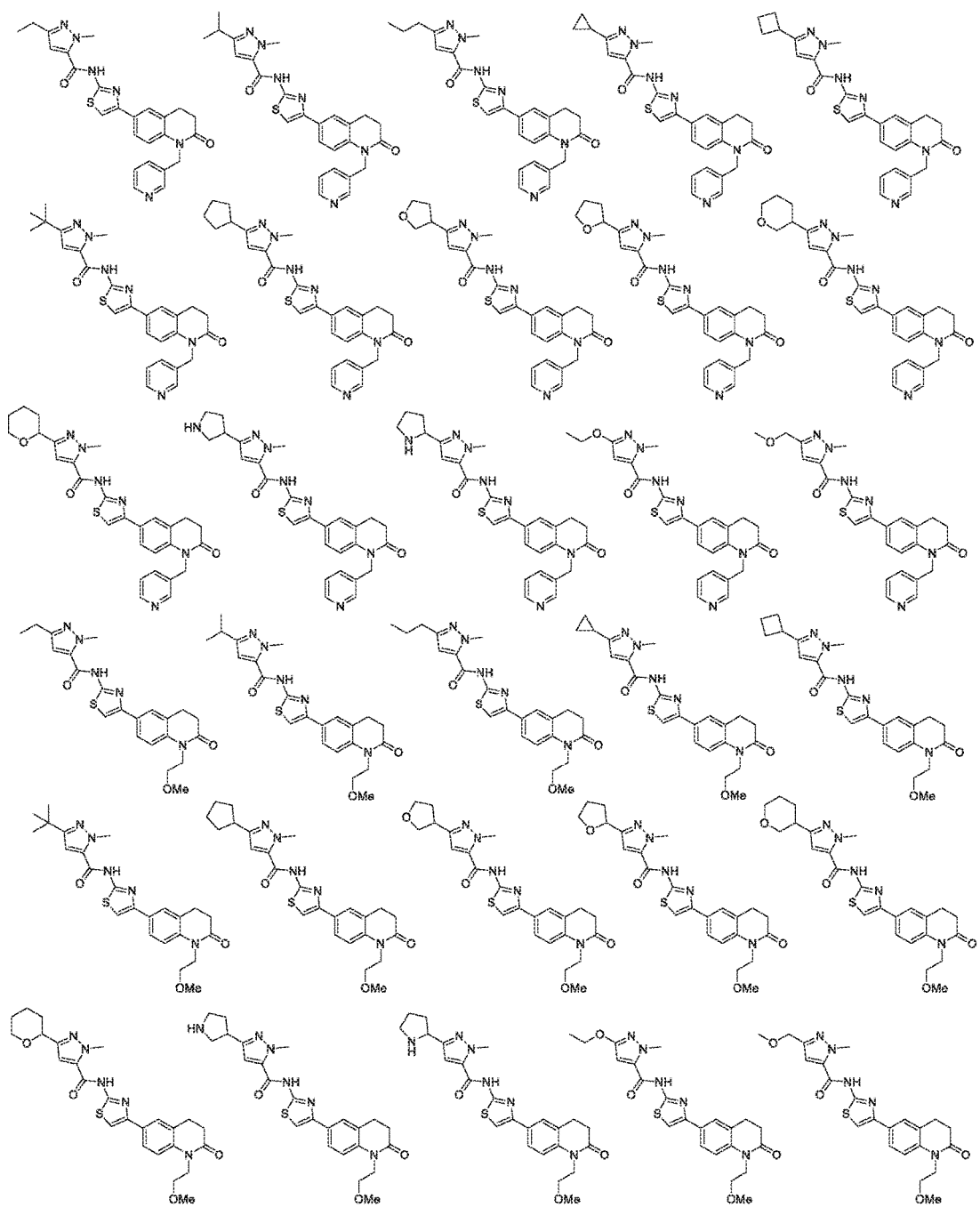
Figure 34:
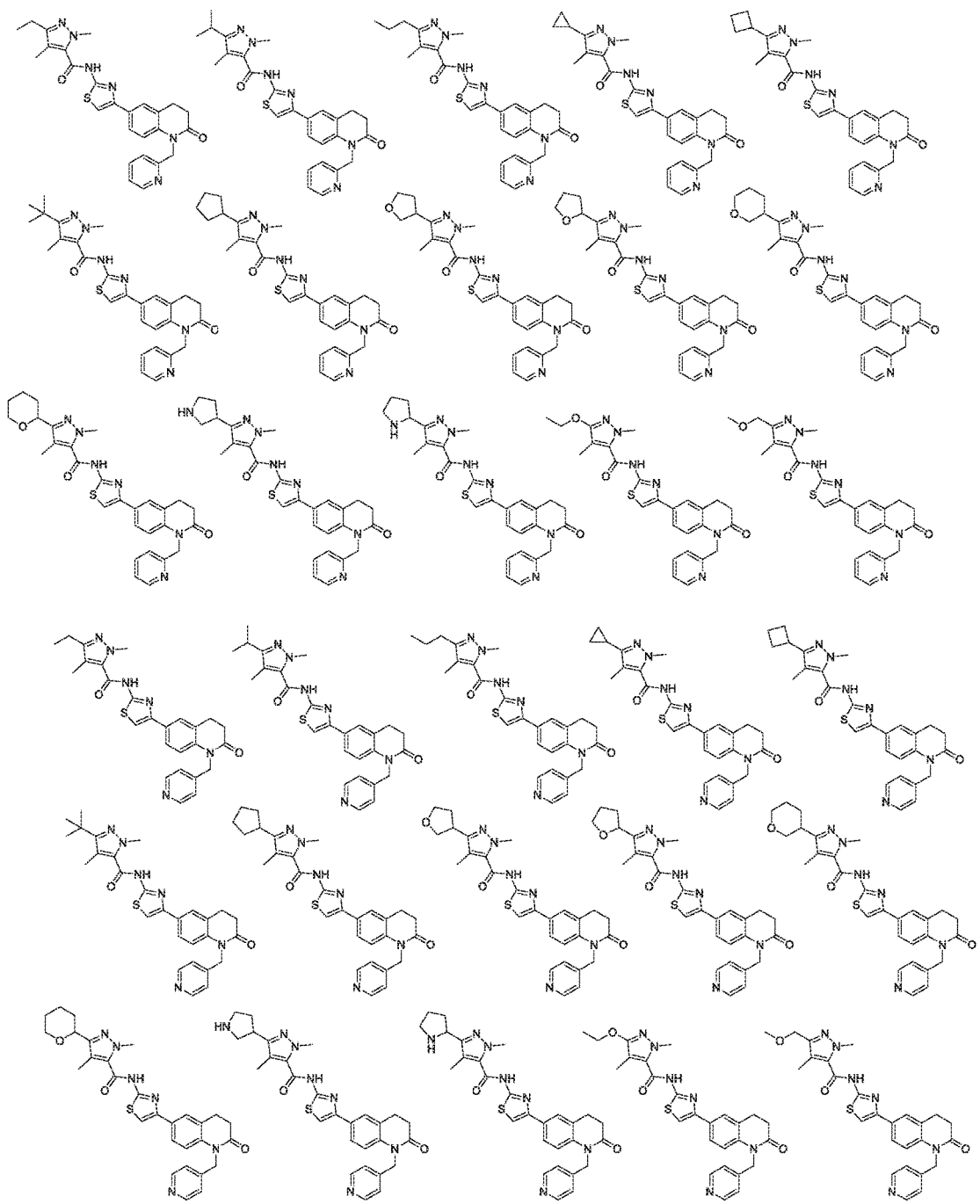
Figure 35:
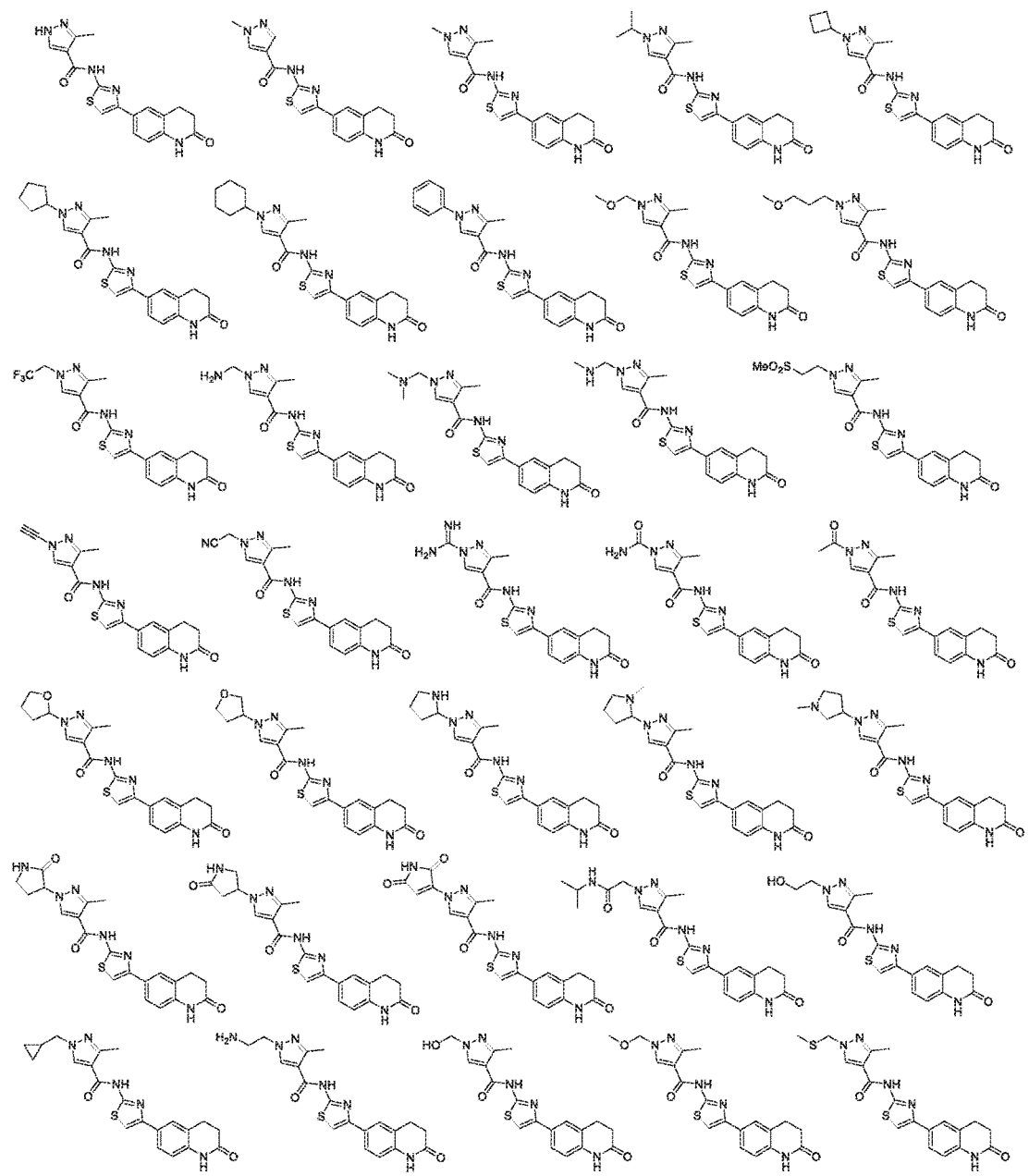
Figure 36:
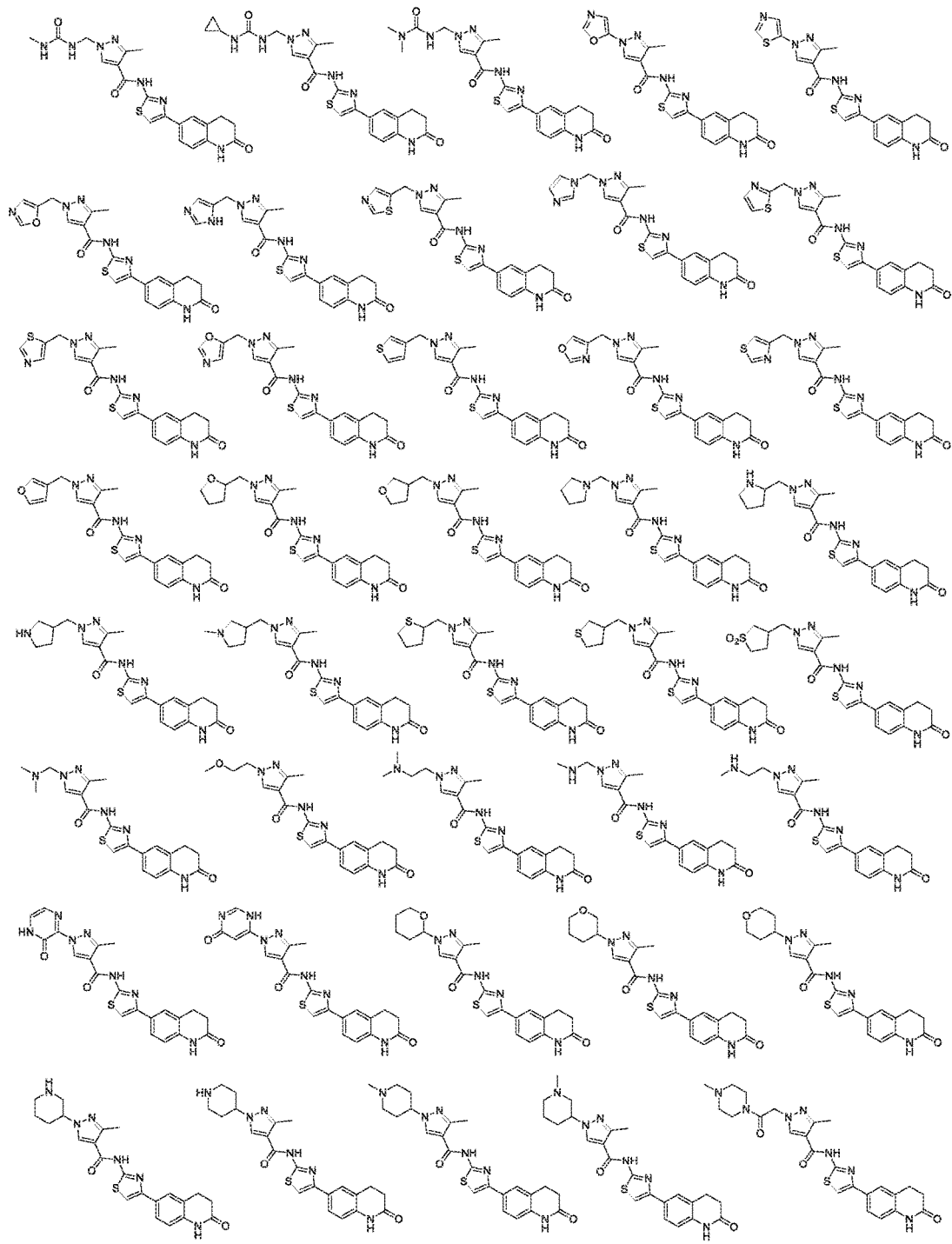
Figure 37:
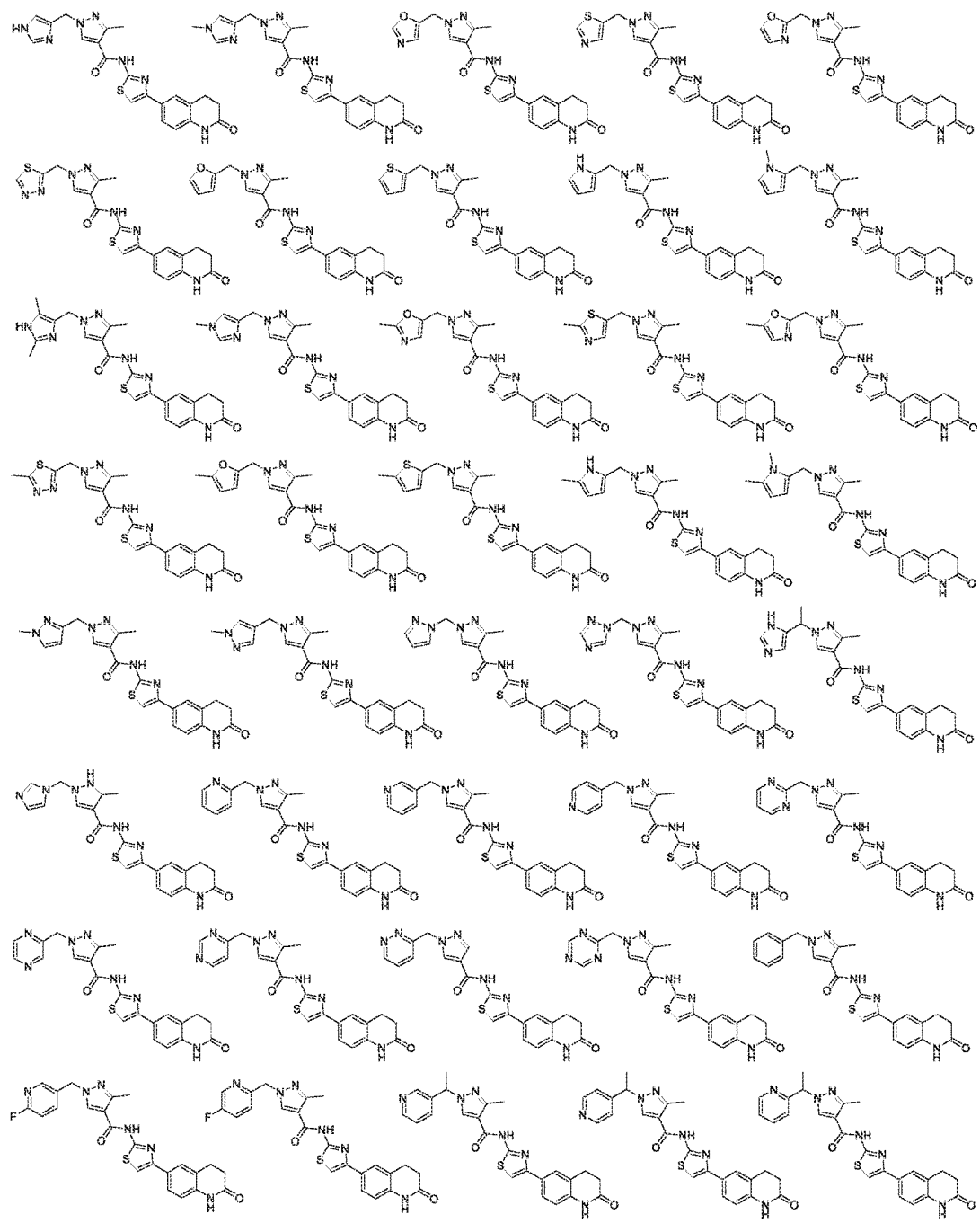
Figure 38:
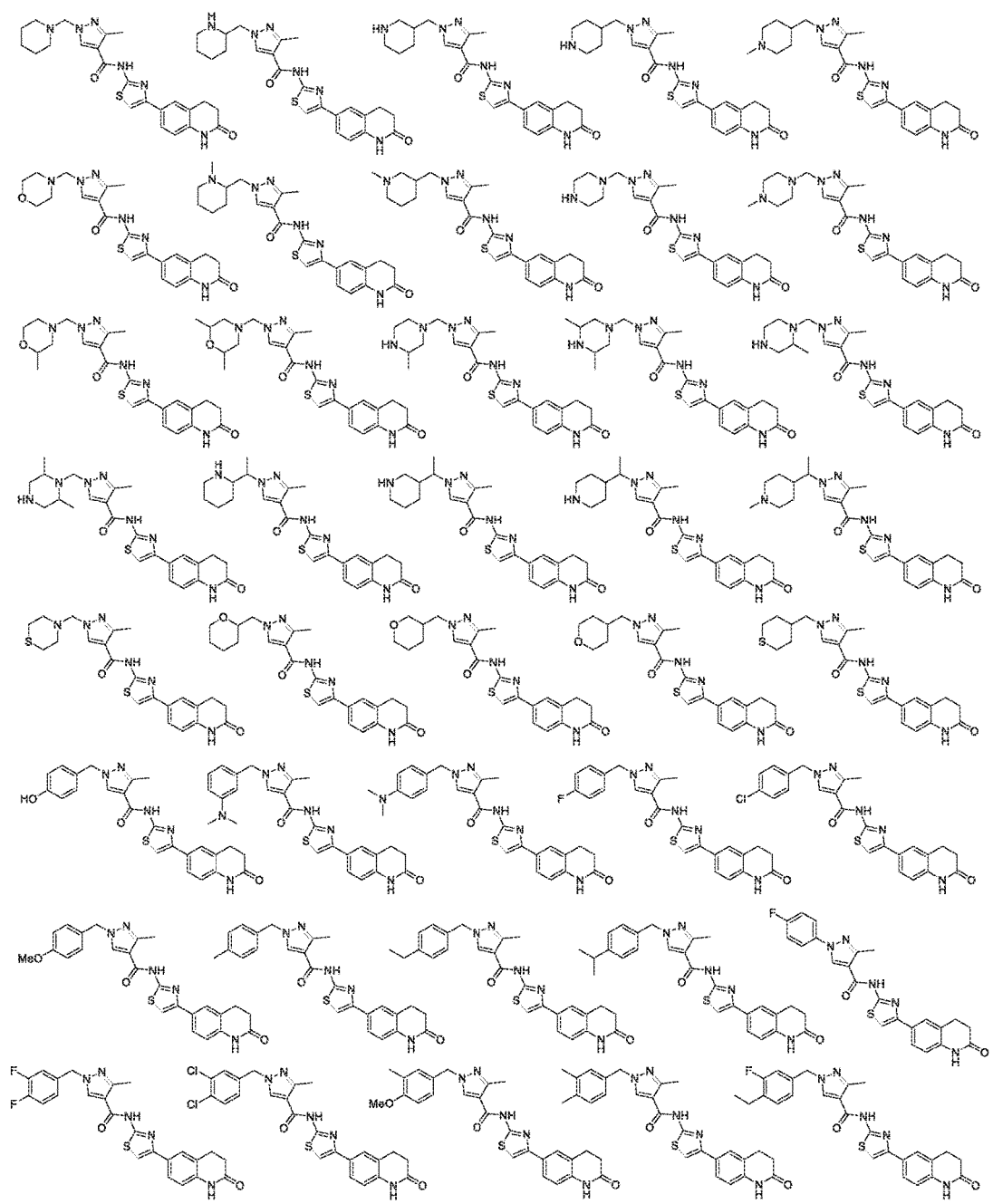
Figure 39:
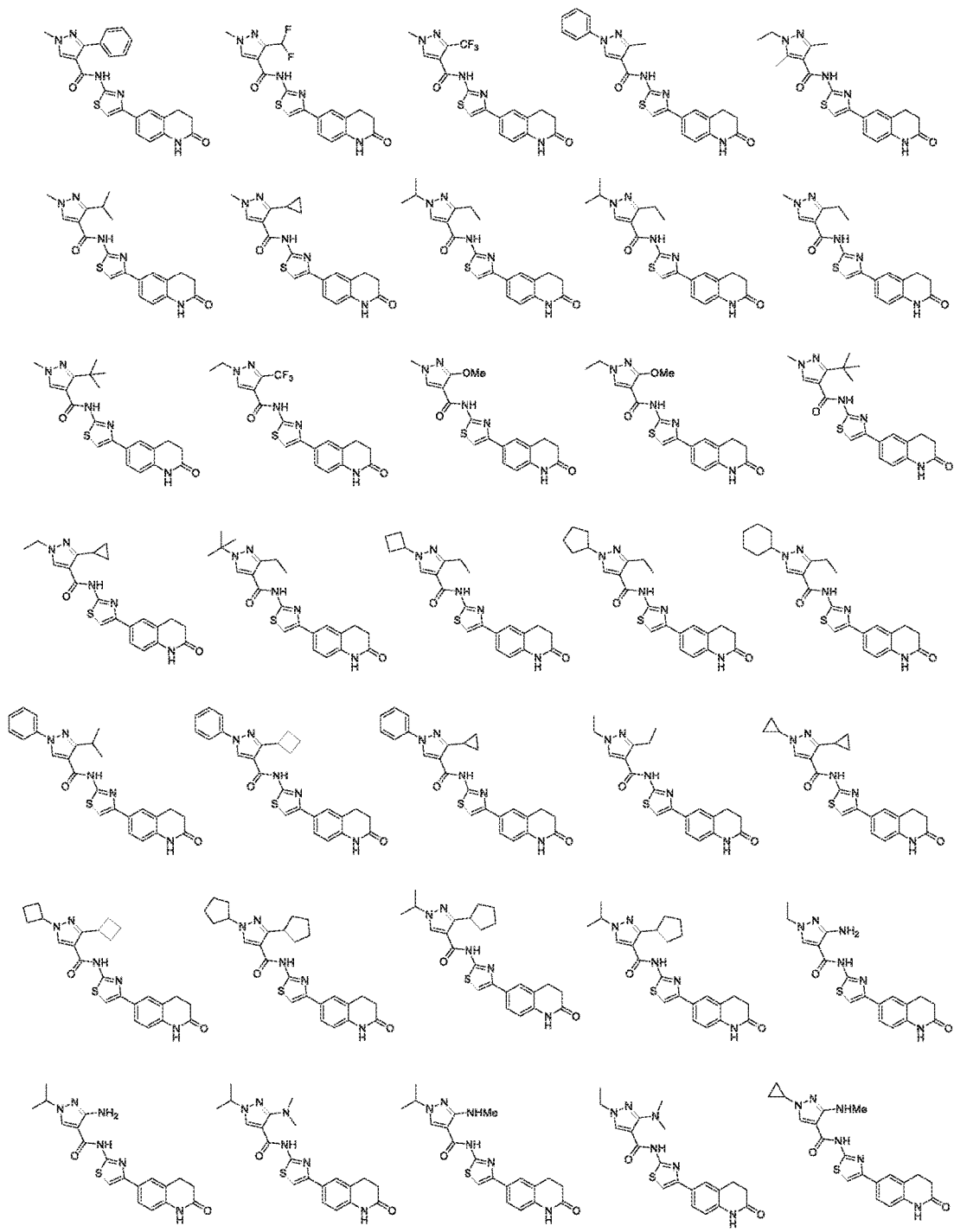
Figure 40:
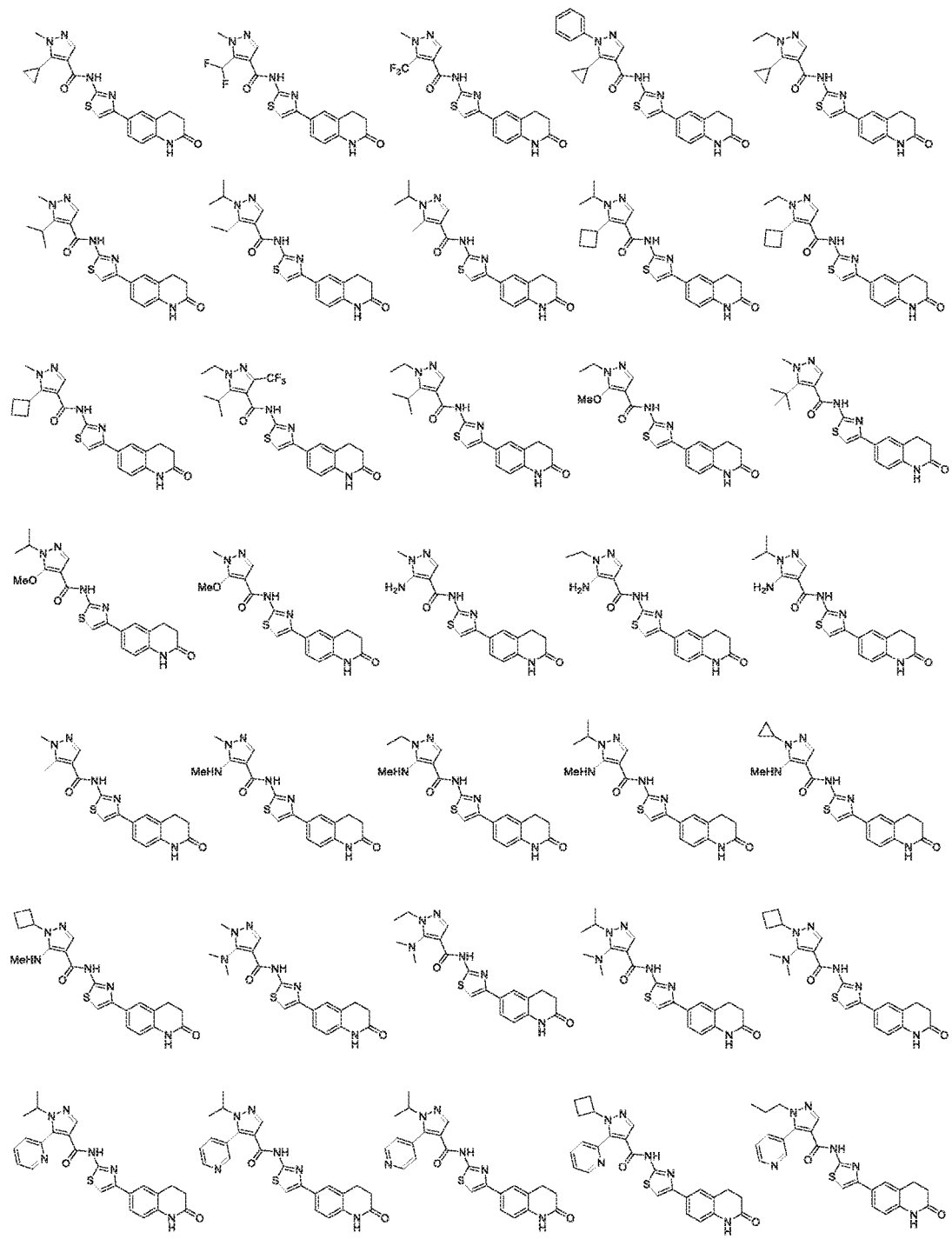
Figure 41:
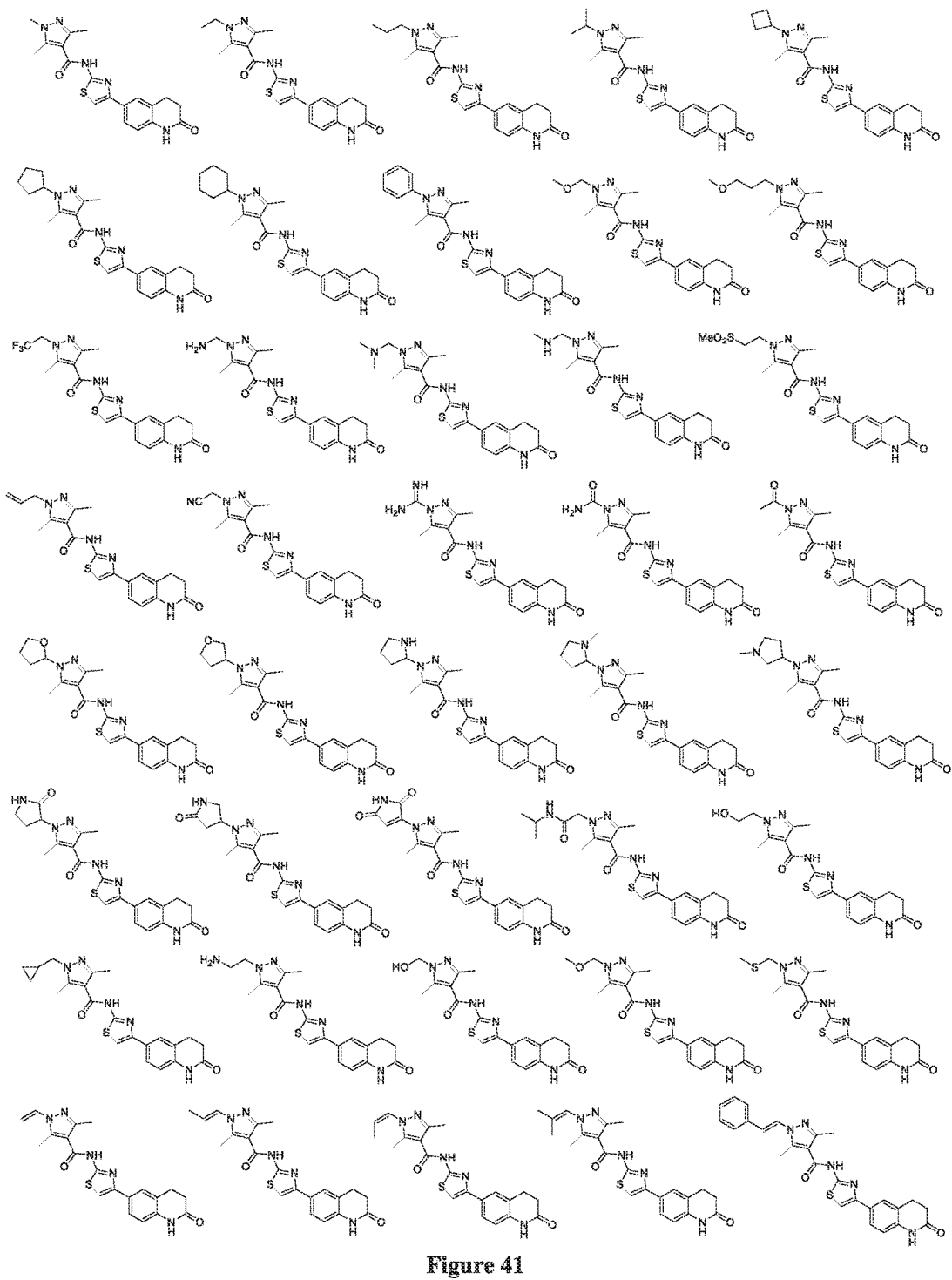
Figure 42:
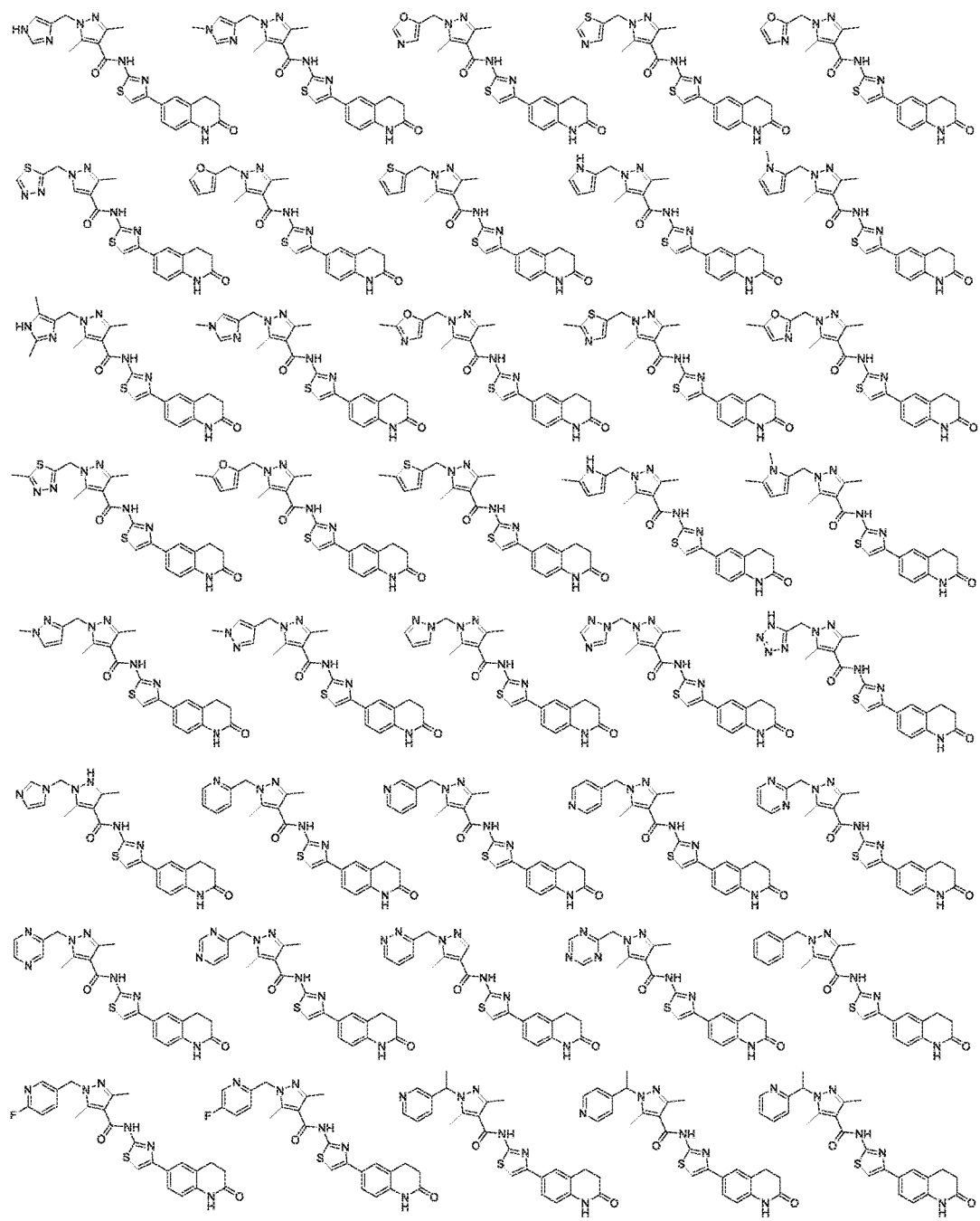
Figure 43:
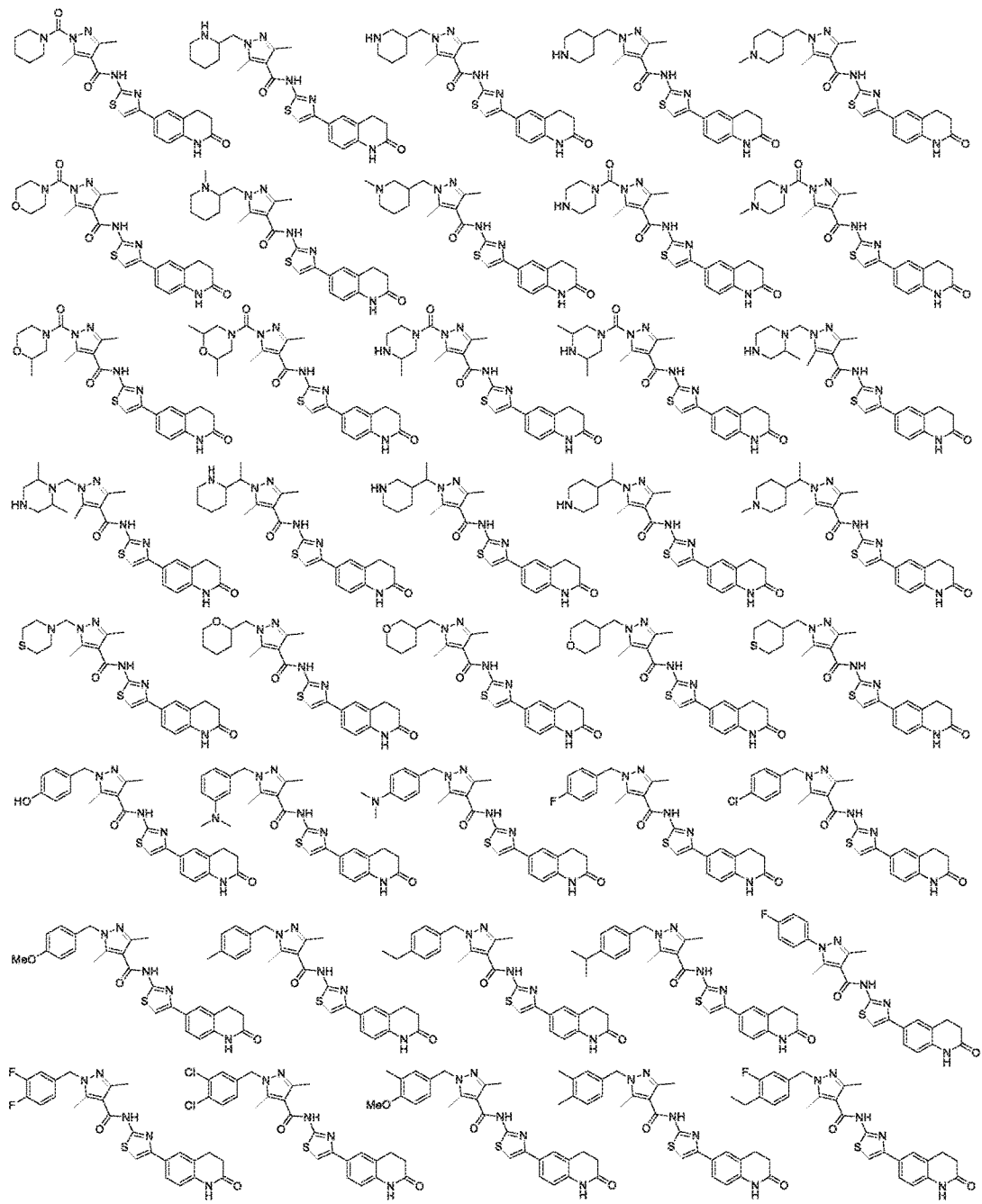
Figure 44:
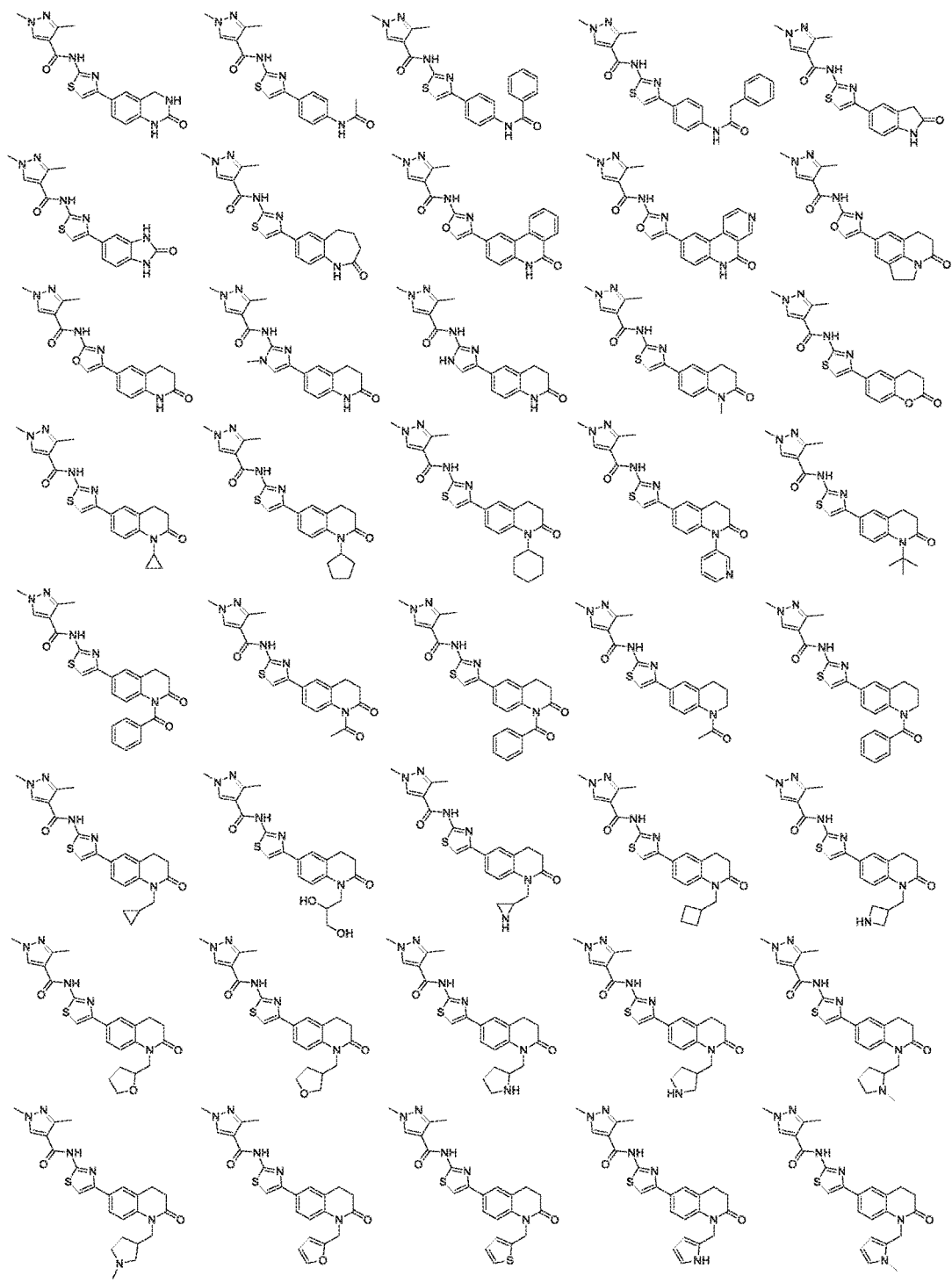
Figure 45:
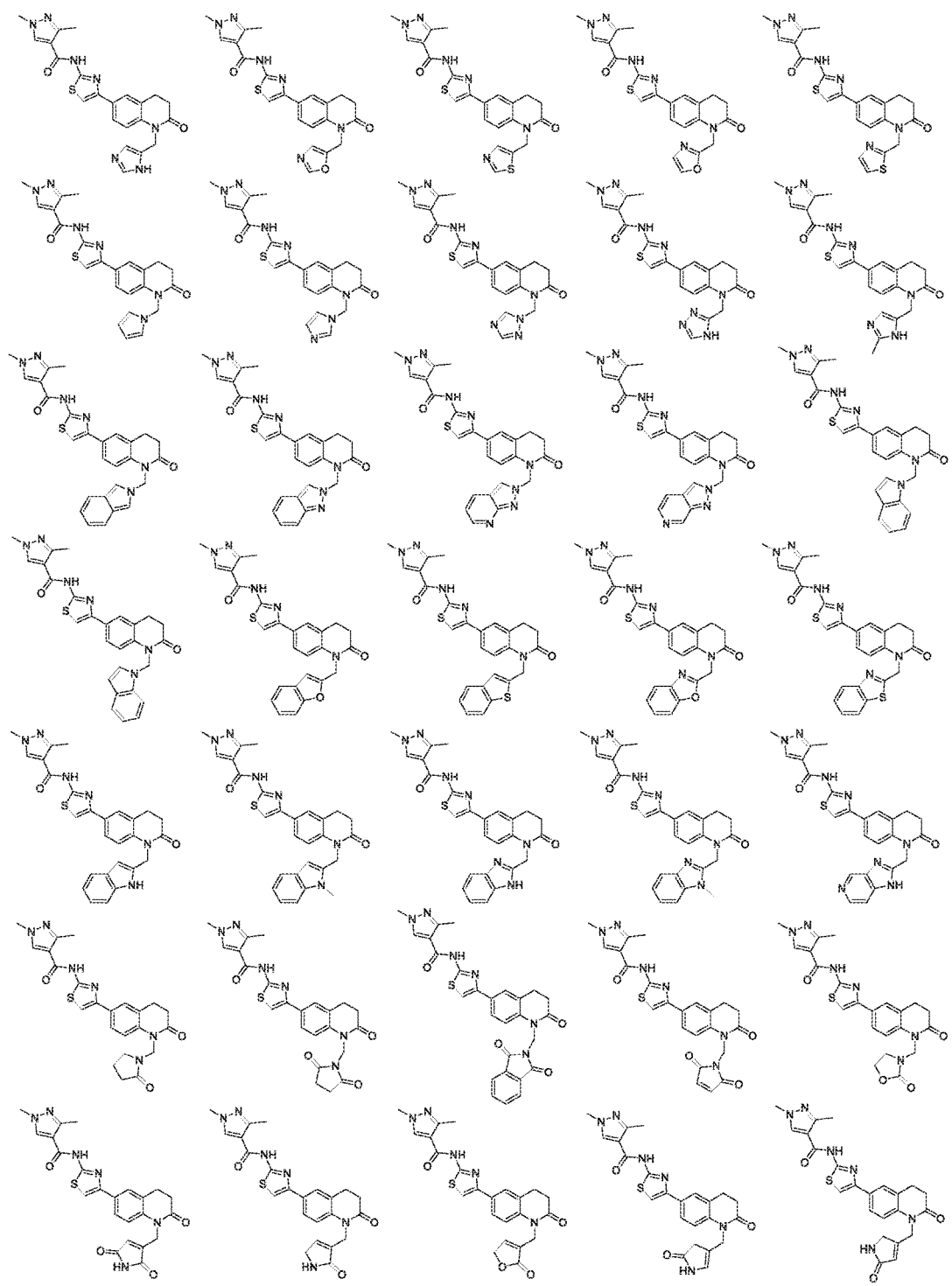
Figure 46:
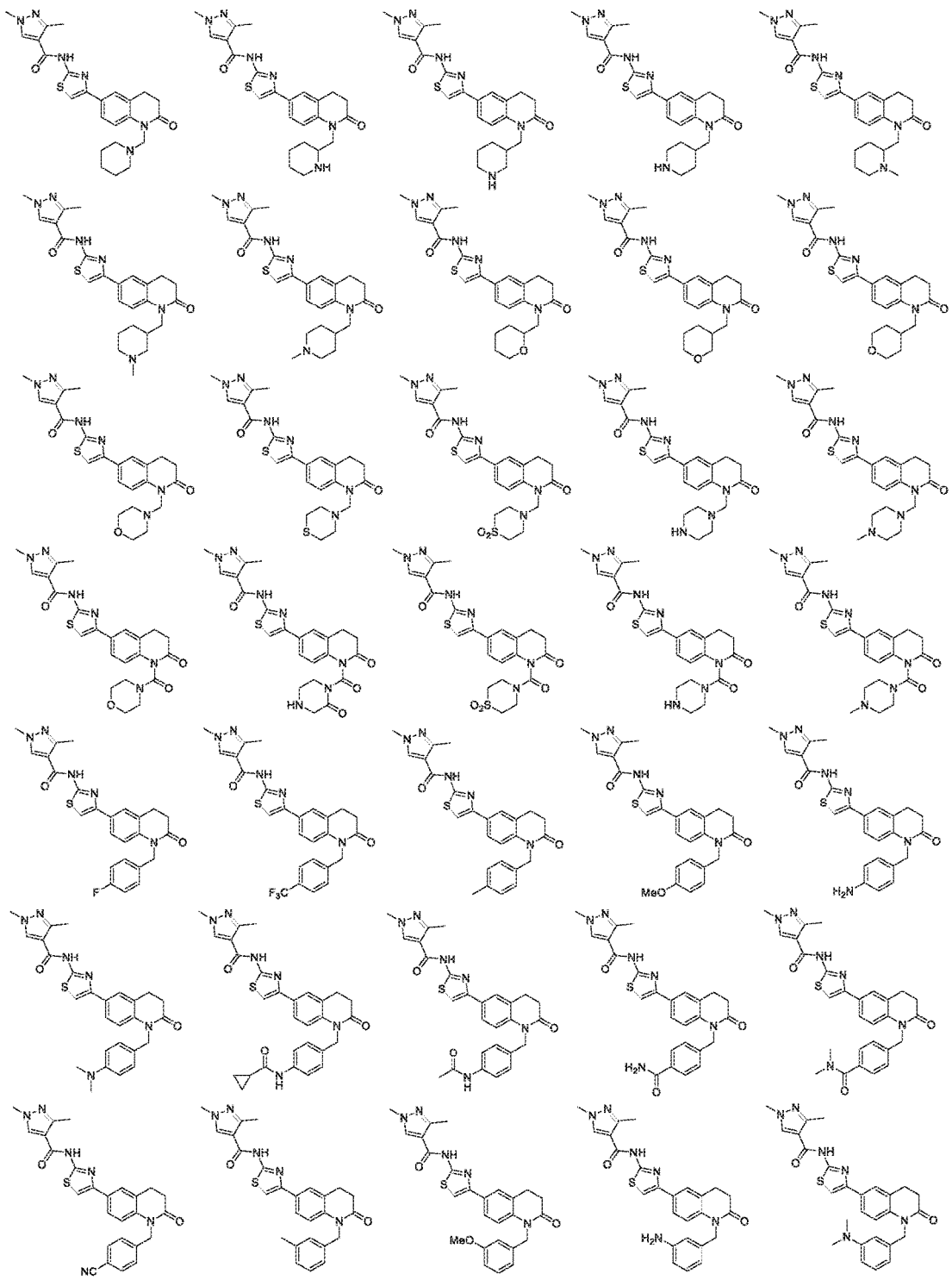
Figure 47:
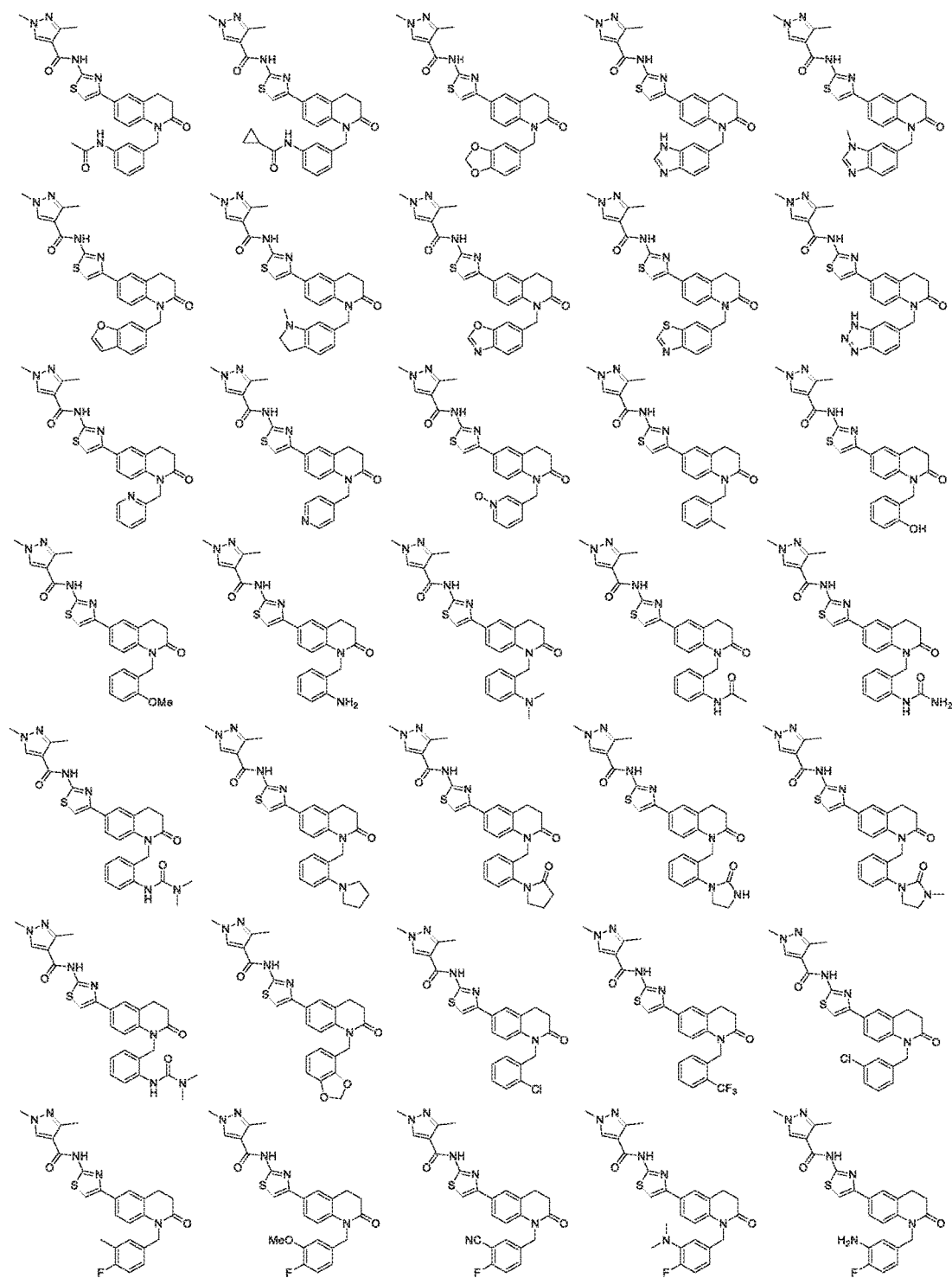
Figure 48:
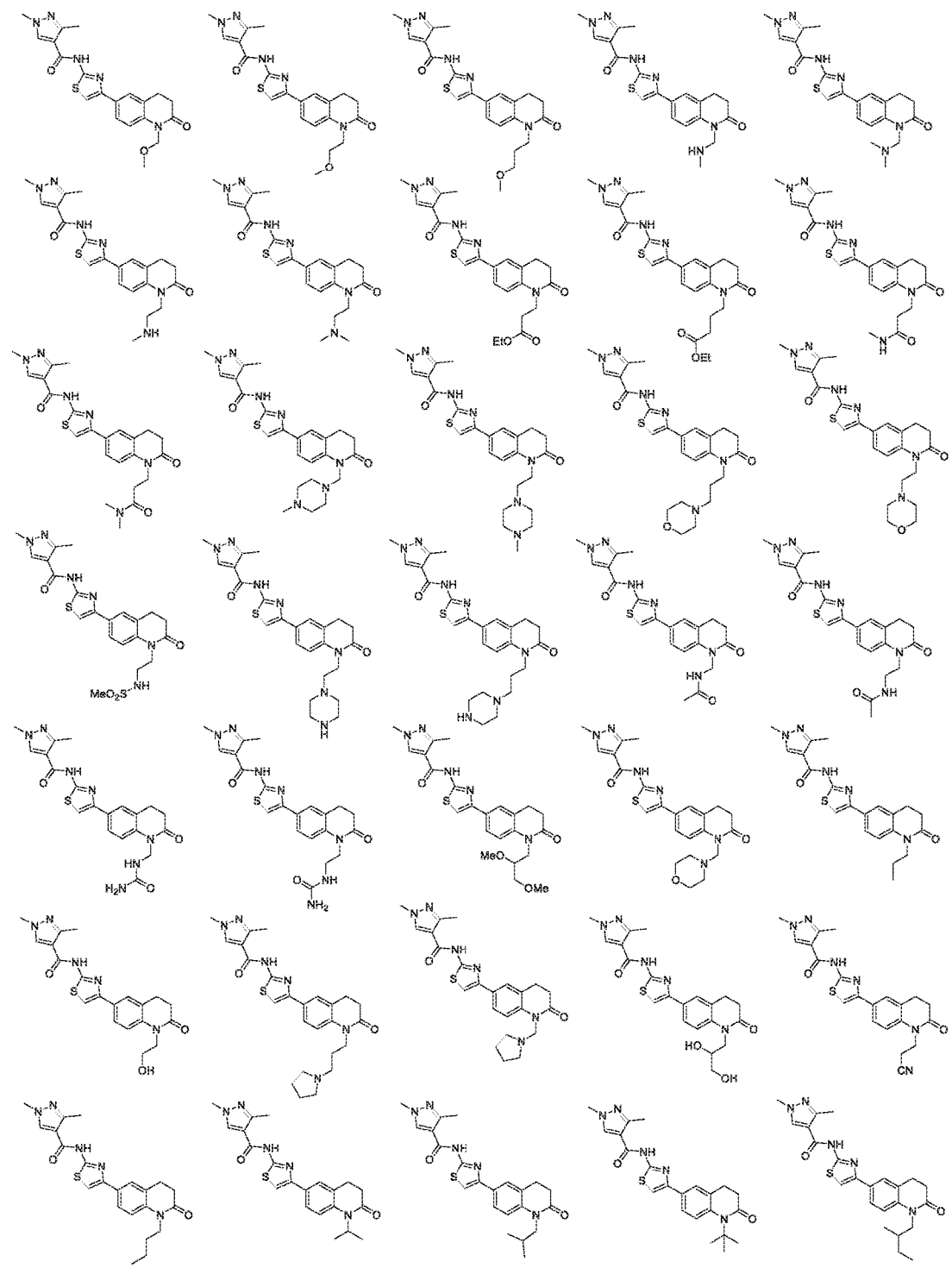
Figure 49:
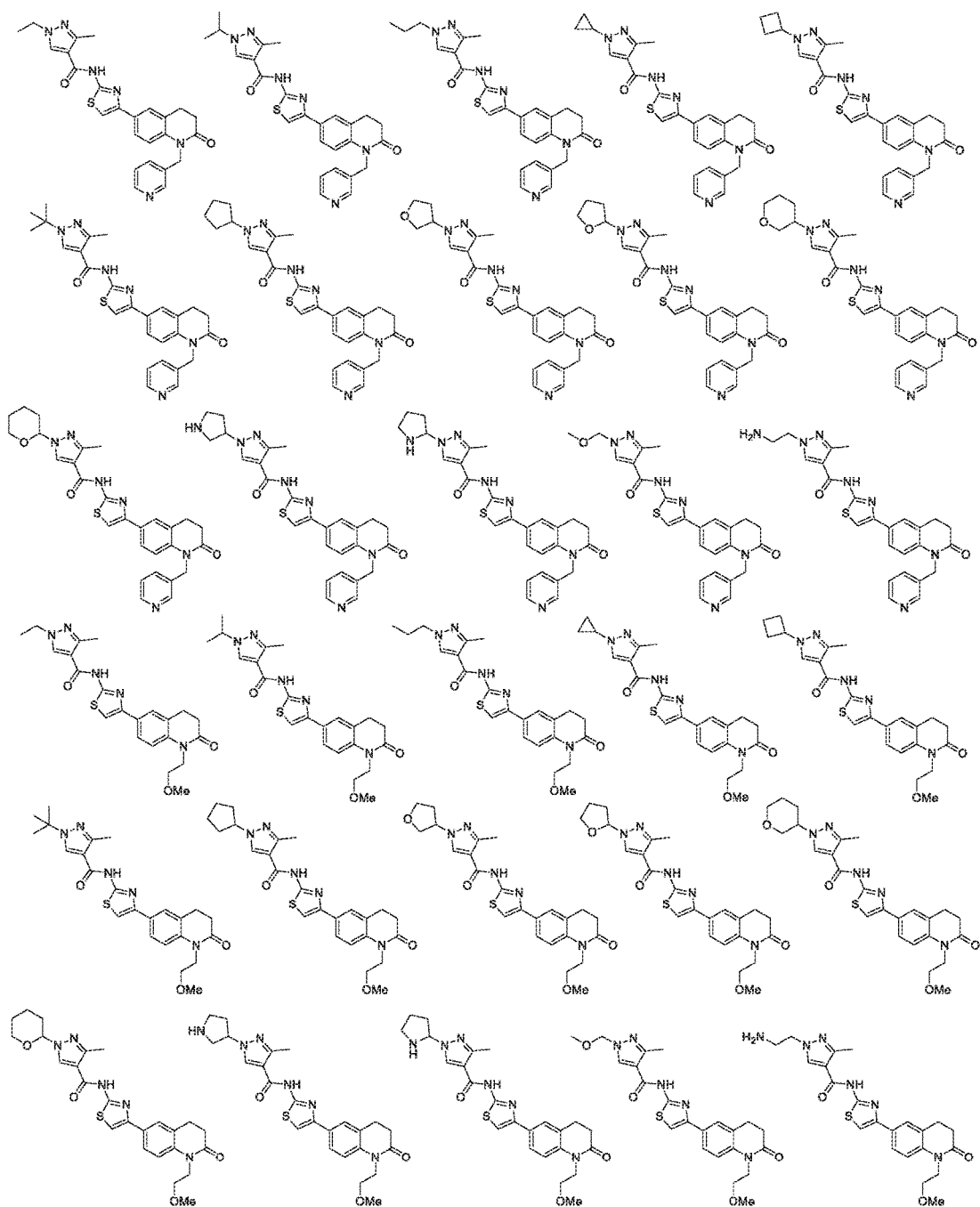
Figure 50:
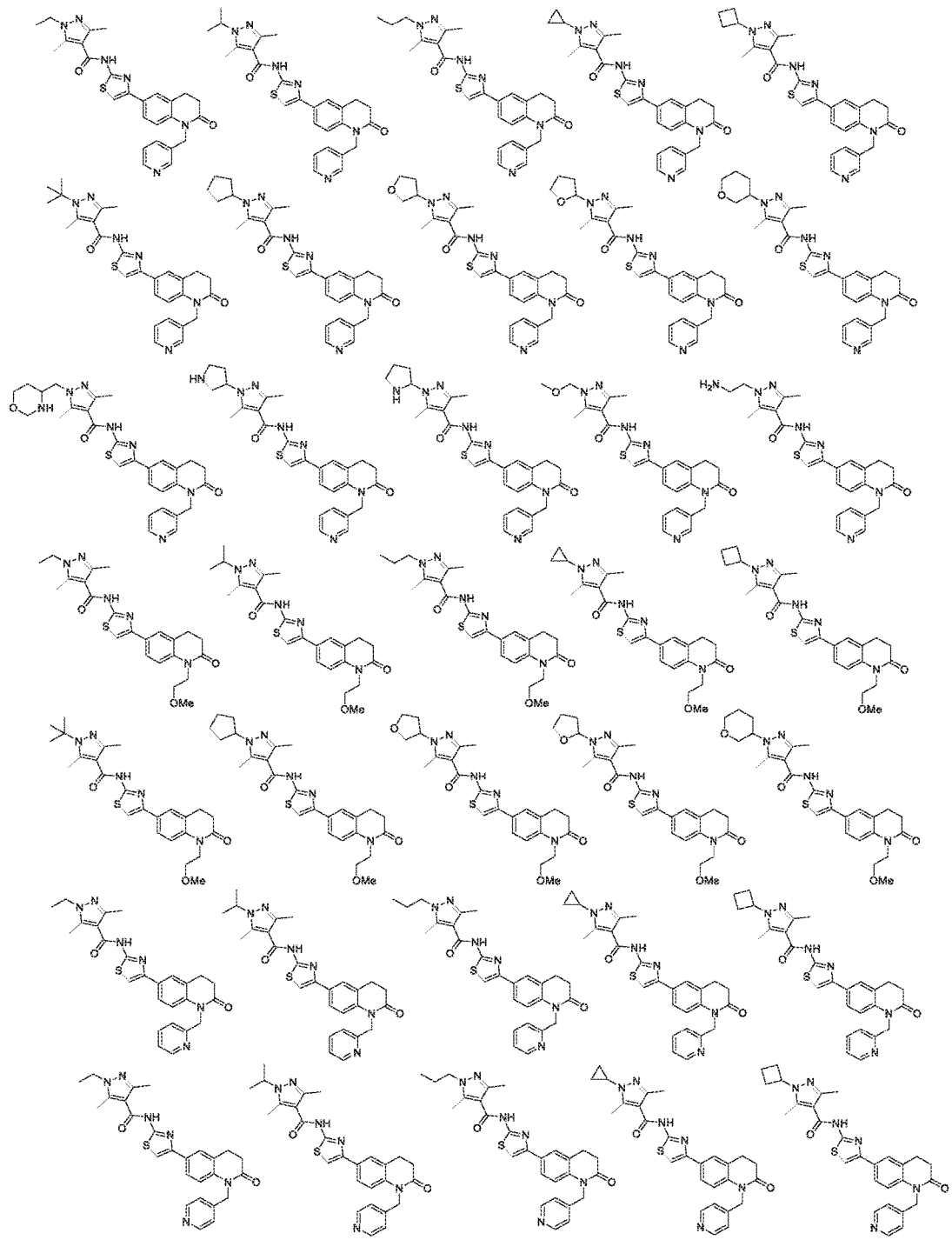
Figure 51:
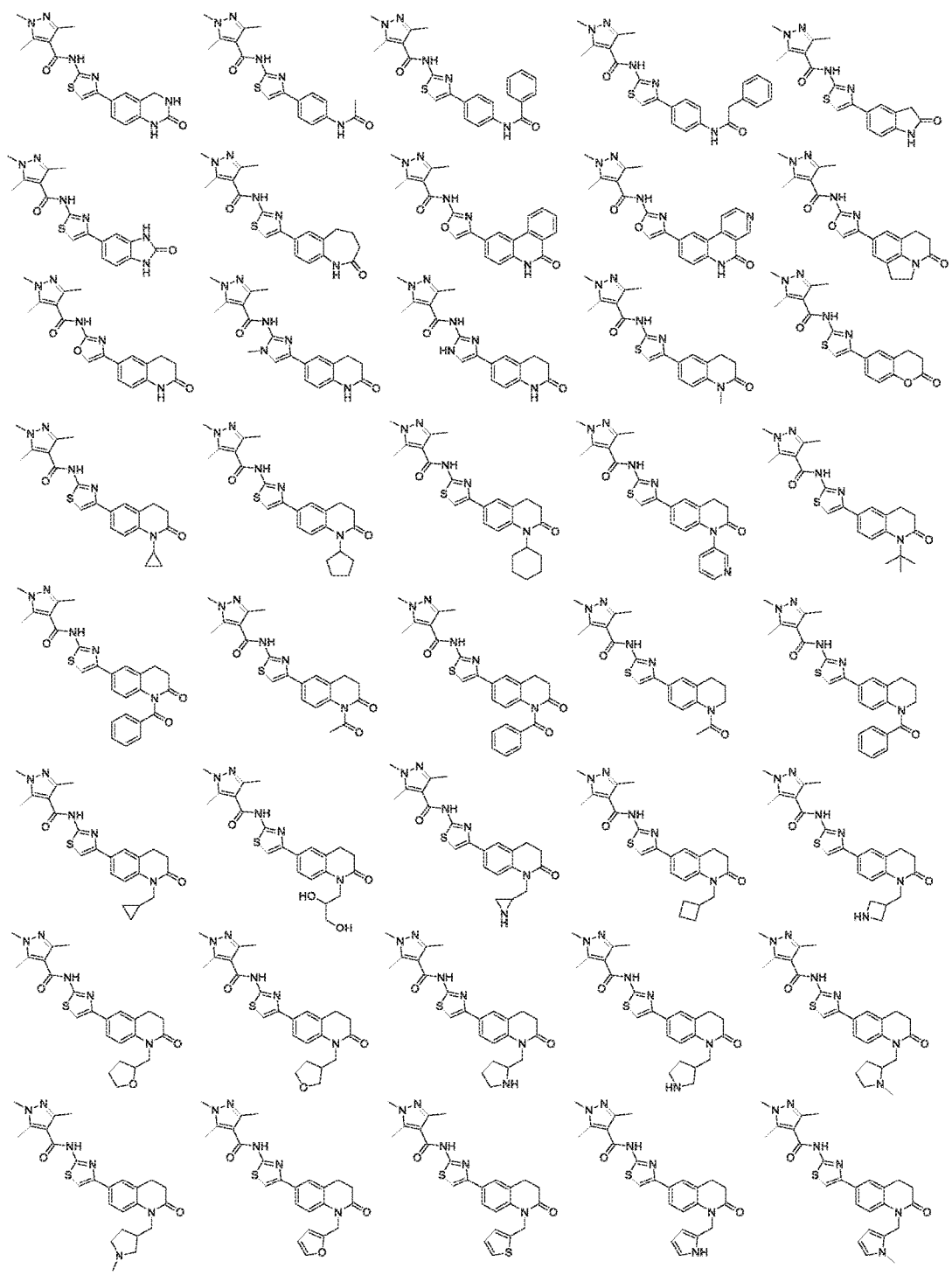
Figure 52:
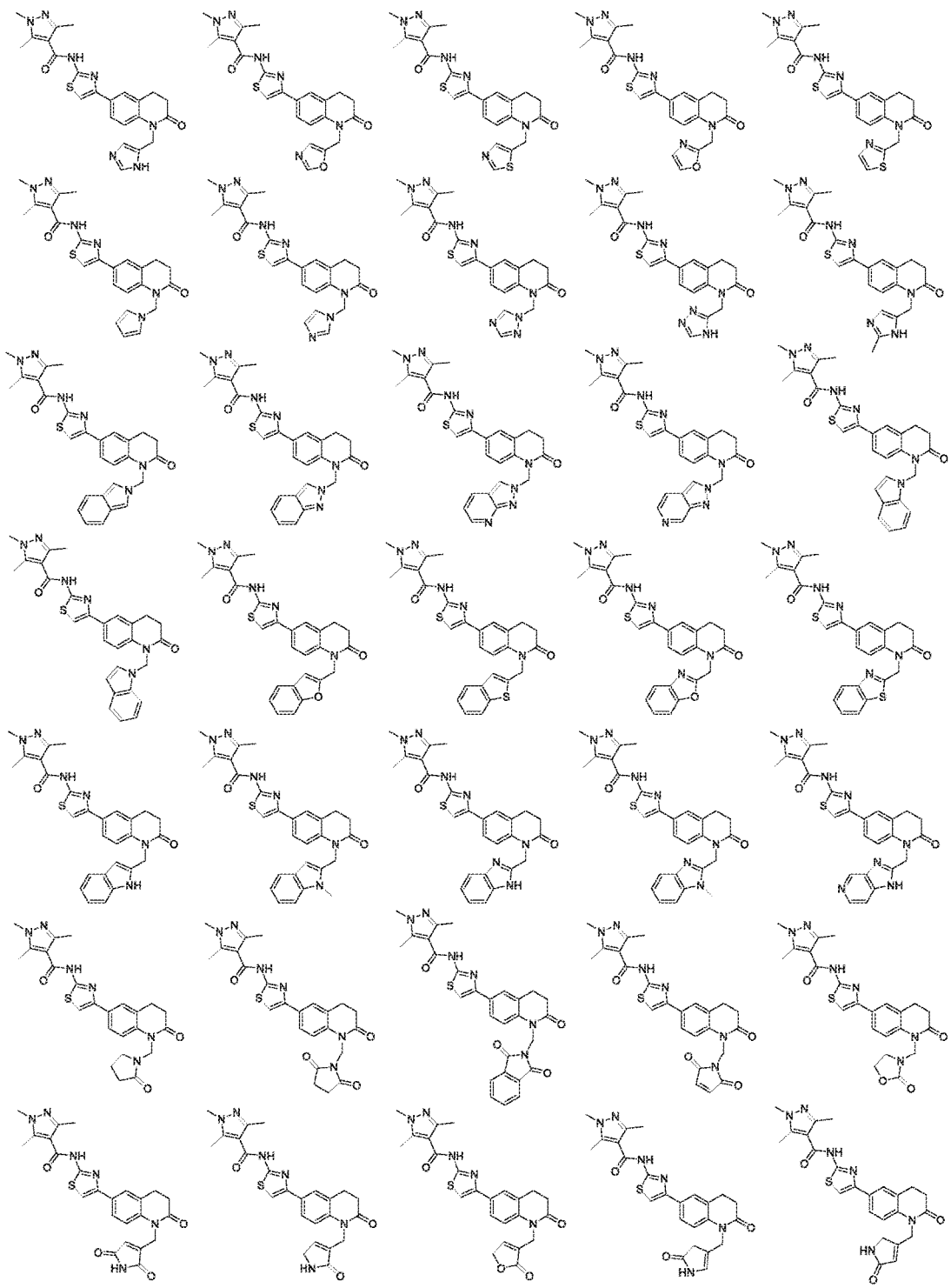
Figure 53:
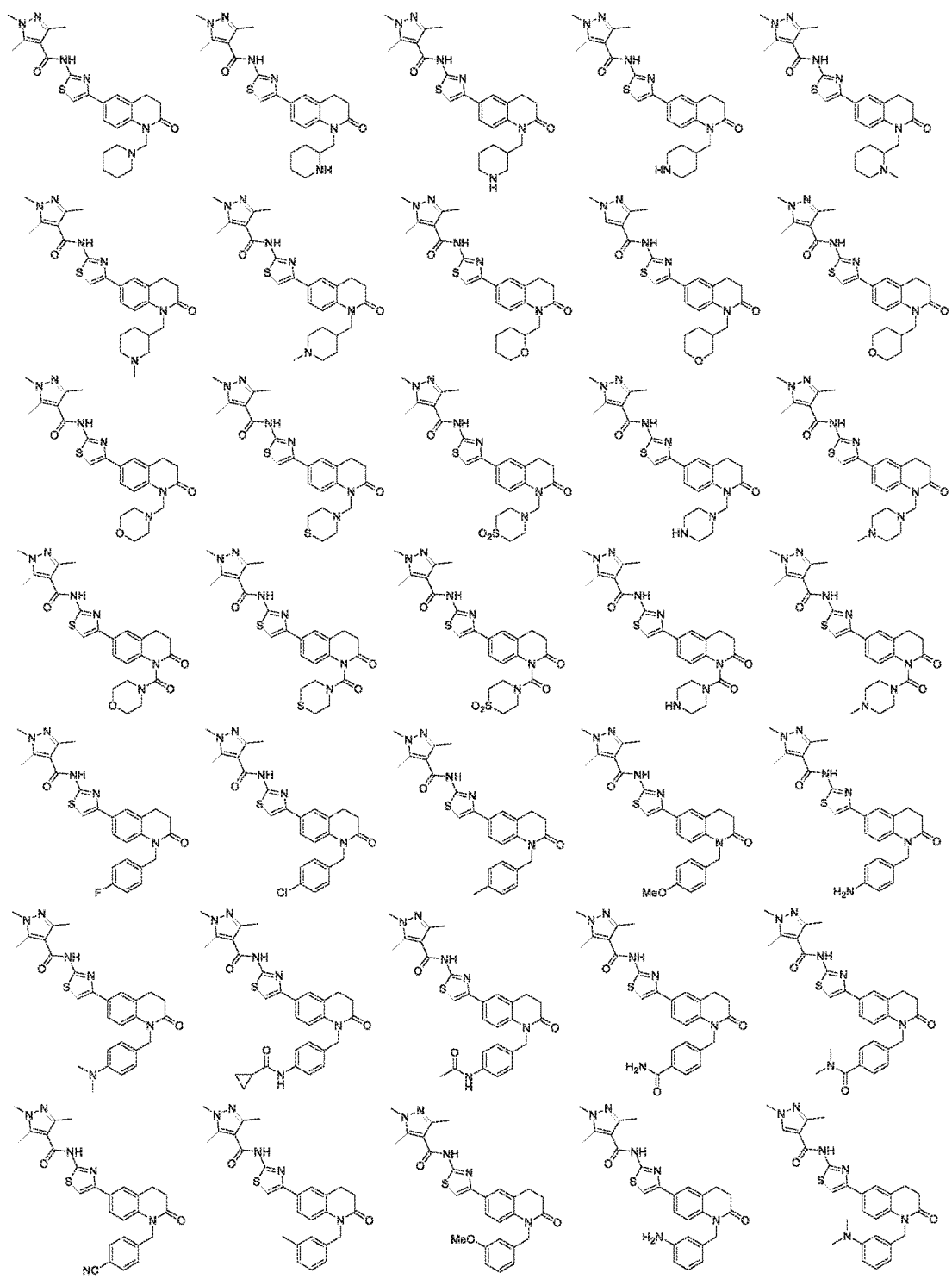
Figure 54:
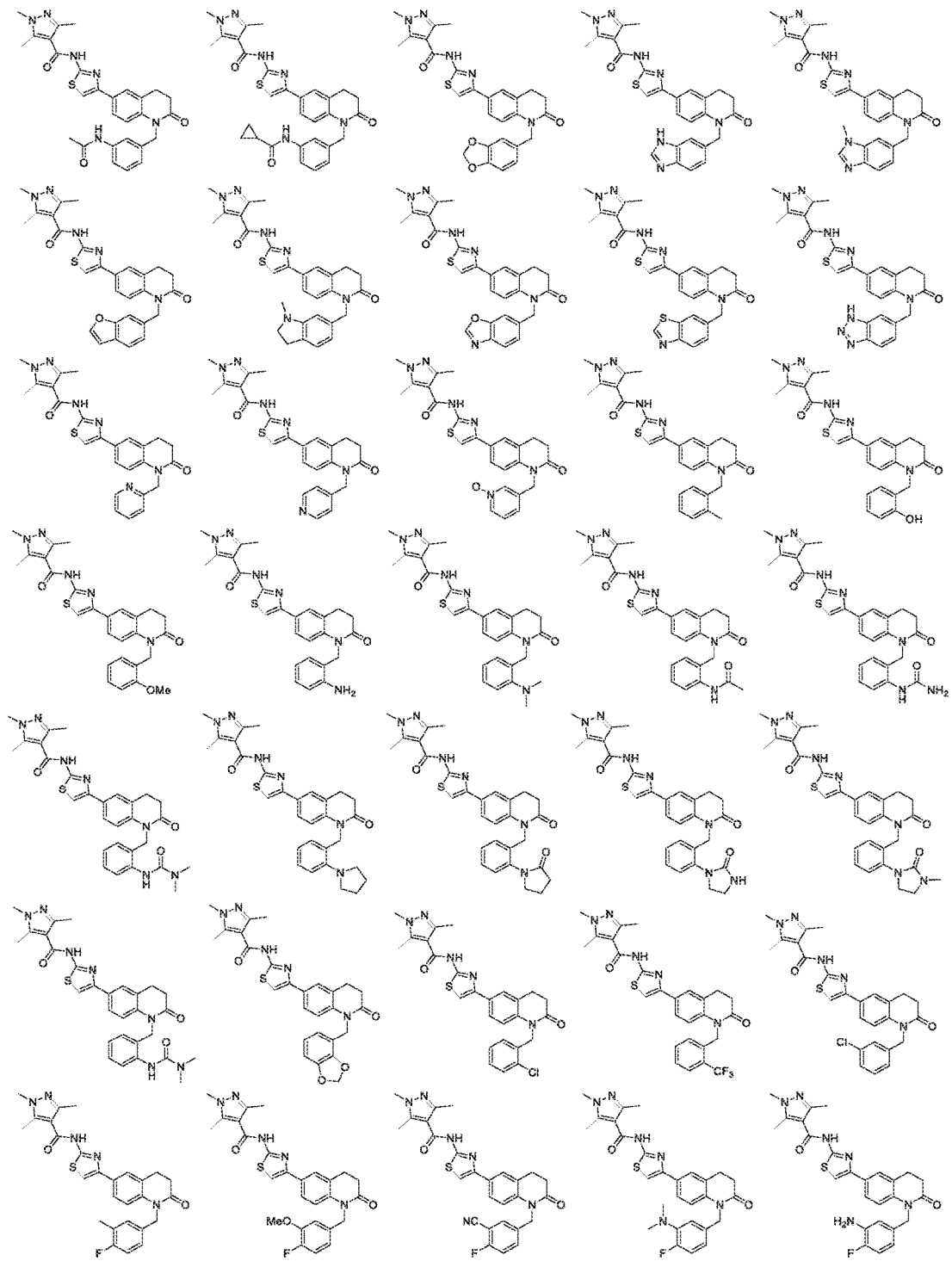

FIG. 7 depicts a protocol for synthesis of compound of Example 21 (see FIG. 2B) by reacting 6-(2-aminothiazol-4-yl)-3,4-dihydroquinolin-2(1H)-one with a pyrazole intermediate in solvent MeCN and pyridine with reagent T3P at 100° C. to produce the desired compound. Additional experiments were performed to optimize reaction variables such as base (e.g., pyridine, DIPEA, TEA, etc) and reaction temperature (e.g., 65° C., 85° C., 100° C., etc). It was discovered that increased yield and purity was achieved using MeCN as solvent, DIPEA as base, 100° C. reaction temperature, and T3P as reagent.

FIGS. 8A-8C depict N-alkylation of 2,4-dimethyl-N-(4-(2-oxo-1,2,3,4-tetrahydroquinolin-6-yl)thiazol-2-yl)-1H-imidazole-5-carboxamide to produce compounds of the inventive subject matter. Reaction conditions of 2.5 eq of NaH, DMF solvent, at 0° C. for 90 minutes provided the a yield of 96% compound 4888 when reacting 2,4-dimethyl-N-(4-(2-oxo-1,2,3,4-tetrahydroquinolin-6-yl)thiazol-2-yl)-1H-imidazole-5-carboxamide with 1 eq benzyl bromide, as depicted in FIG. 8C.

Biological Activities of Selected Compounds

Activity of exemplary compounds according to the inventive subject matter was tested for wild type, K-Ras G12D, and K-Ras G12V following standard G-LISA protocol as further described below, and the IC50 (µM) results are shown in Table 1 while compound formulae are depicted in FIGS. 2A-2G and Examples 1-152, above.

TABLE 1

| Compound | $IC_{50}$ (µM) Wild-type | $IC_{50}$ (µM) G12D | $IC_{50}$ (µM) G12V |
|---|---|---|---|
| 1 | 3.8 µM | 9.3 µM | |
| 2 | | | |
| 3 | 12.0 µM | | |
| 4 | 25.1 µM | 10.9 µM | |
| 5 | 14.1 µM | 10.2 µM | |
| 6 | 10.6 µM | 7.3 µM | 19.4 µM |
| 7 | 11.7 µM | 4.8 µM | >25 µM |
| 8 | 15.5 µM | 5.9 µM | >25 µM |
| 9 | | | |
| 10 | >25 µM | 22.0 µM | |
| 11 | | | |
| 12 | | | |
| 13 | | | |
| 14 | | | |
| 15 | | | |
| 16 | | | |
| 17 | | | |
| 18 | | | |
| 19 | | | |
| 20 | | | |
| 21 | 17.1 µM | 3.8 µM | |
| 22 | 12.6 µM | 4.6 µM | |
| 23 | | | |
| 24 | 7.6 µM | 9.9 µM | |
| 25 | 10.7 µM | 6.6 µM | |
| 26 | >25 µM | 10.6 µM | |
| 27 | | | |
| 28 | | | |
| 29 | | | |
| 30 | | >25 µM | |
| 31 | | | |
| 32 | | | |
| 33 | | >25 µM | |
| 34 | | 15.8 µM | |
| 35 | | >25 µM | |
| 36 | 18.3 µM | 7.0 µM | |
| 37 | | >25 µM | |
| 38 | | | |
| 39 | | | |
| 40 | 23.3 µM | 6.1 µM | |
| 41 | 7.5 µM | 4.3 µM | |
| 42 | | | |
| 43 | >25 µM | >25 µM | |
| 44 | | 4.0 µM | |
| 45 | | 8.8 µM | |
| 46 | | 22.5 µM | |
| 47 | | | |
| 48 | | | |

TABLE 1-continued

| Compound | IC$_{50}$ (μM) Wild-type | IC$_{50}$ (μM) G12D | IC$_{50}$ (μM) G12V |
|---|---|---|---|
| 49 | | 12.3 μM | |
| 50 | | | |
| 51 | | 21.5 μM | |
| 52 | 13.9 μM | 5.2 μM | |
| 53 | 7.7 μM | 6.7 μM | |
| 54 | 10.6 μM | 7.9 μM | |
| 55 | 6.5 μM | 4.0 μM | |
| 56 | 19.2 μM | 6.6 μM | |
| 57 | 30.0 μM | 9.4 μM | |
| 58 | 20.4 μM | 5.2 μM | 21.6 μM |
| 59 | 6.5 μM | 5.8 μM | |
| 60 | 8.6 μM | 7.4 μM | |
| 61 | 8.5 μM | 5.1 μM | |
| 62 | >25 μM | 21.7 μM | |
| 63 | >25 μM | 5.6 μM | 9.8 μM |
| 64 | >25 μM | 3.0 μM | 9.6 μM |
| 65 | | | |
| 66 | 11.1 μM | 4.5 μM | 6.5 μM |
| 67 | >25 μM | 8.0 μM | |
| 68 | 16.7 μM | 10.3 μM | |
| 69 | 18.6 μM | 8.1 μM | |
| 70 | >25 μM | 8.3 μM | |
| 71 | | | |
| 72 | 8.0 μM | 8.0 μM | |
| 73 | 18.8 μM | 19.2 μM | |
| 74 | | 22.4 μM | |
| 75 | | | |
| 76 | 12.6 μM | 13.9 μM | |
| 77 | | | |
| 78 | | | |
| 79 | | | |
| 80 | | | |
| 81 | | | |
| 82 | >25 μM | 24.6 μM | |
| 83 | | >25 μM | |
| 84 | 19.9 μM | 4.9 μM | |
| 85 | 23.4 μM | 7.6 μM | |
| 86 | 16.7 μM | 6.1 μM | |
| 87 | | | |
| 88 | | | |
| 89 | | | |
| 90 | 16.6 μM | 14.2 μM | |
| 91 | 11.7 μM | 8.4 μM | |
| 92 | 15.2 μM | 8.5 μM | |
| 93 | 10.0 μM | 8.6 μM | |
| 94 | | | |
| 95 | 15.4 μM | 5.1 μM | |
| 96 | 12.1 μM | 5.0 μM | |
| 97 | 12.6 μM | 8.1 μM | |
| 98 | | | |
| 99 | 10.2 μM | 6.7 μM | |
| 100 | 9.5 μM | 5.5 μM | |
| 101 | | 9.3 μM | |
| 102 | | 8.2 μM | |
| 103 | | 14.9 μM | |
| 104 | | | |
| 105 | | 10.4 μM | |
| 106 | 9.6 μM | 4.4 μM | |
| 107 | 9.7 μM | 6.6 μM | |
| 108 | | >25 μM | |
| 109 | | | |
| 110 | 6.8 μM | 3.9 μM | |
| 111 | 3.9 μM | 2.5 μM | |
| 112 | 10.7 μM | 10.0 μM | |
| 113 | 9.6 μM | 6.3 μM | |
| 114 | 6.0 μM | 3.0 μM | |
| 115 | 6.3 μM | 3.4 μM | |
| 116 | 6.1 μM | 2.5 μM | |
| 117 | 6.7 μM | 2.6 μM | |
| 118 | | 4.3 μM | |
| 119 | 5.4 μM | 2.6 μM | |
| 120 | 11.9 μM | 3.4 μM | |
| 143 | 19.0 μM | | |
| 144 | | | |
| 145 | >25 μM | 24 μM | |
| 146 | | | |
| 147 | | >25 μM | |
| 148 | | | |
| 149 | | | |
| 150 | | >25 μM | |
| 151 | | 23.5 μM | |

293H cells were seeded in 6-wells at 0.6×10$^6$ cells per well and transfected next day with 5 μg of Ras wild-type, or G12C, G12D or G12V mutant DNA plasmid vector using transfection reagent Lipofectamine 3000. Next day cells were treated with 3.125-25 μM of Ras compounds for 1 hour. Wild-type transfected cells were subsequently treated with 100 ng/ml EGF for 2 minutes. Cells were washed once in ice-cold PBS, lysed in complete lysis buffer on ice, and processed by G-LISA according to Cytoskeleton protocol.

Viability assays were performed on exemplary compounds and Table 2 below lists exemplary results for selected compounds tested on K-Ras wild type cell lines (Ishikawa, U87-MG, HCC827, and A375) and various K-Ras mutant cell lines (Panc1-G12D; Panc10.05-G12D; HCT116-G31D). Results are expressed in μM and corresponding structures are shown in FIGS. 2A-2G and Examples 1-152, above.

TABLE 2

| Compound | 72 hr Cell Viability Ishikawa (wild-type) | 72 hr Cell Viability U87-MG (wild-type) | 72 hr Cell Viability HCC827 (wild-type) | 72 hr Cell Viability A375 (wild-type) | 72 hr Cell Viability Panc1 (G12D) | 72 hr Cell Viability Panc10.05 (G12D) | 72 hr Cell Viability HCT116 (G13D) |
|---|---|---|---|---|---|---|---|
| 1 | | | | | | | |
| 2 | | | | | | | |
| 3 | >25 μM | 12 μM | | | 5.5 μM | 14 μM | 18 μM |
| 4 | | | | | | | |
| 5 | >25 μM | >25 μM | | | 6 μM | 19 μM | 22 μM |
| 6 | 10 μM | 5 μM | | | 2.4 μM | 3.6 μM | >25 μM |
| 7 | >25 μM | >25 μM | >25 μM | >25 μM | 8 μM | 2 μM | >25 μM |
| 8 | >25 μM | | >25 μM | | 17 μM | 1.3 μM | >25 μM |
| 9 | >25 μM | | >25 μM | | >25 μM | >25 μM | >25 μM |
| 10 | 2 μM | 5 μM | 23 μM | | 4 μM | 2 μM | 5 μM |
| 11 | | >25 μM | 21 μM | | >25 μM | 16 μM | 16 μM |
| 12 | | | | | | | |
| 13 | >25 μM | >25 μM | | | >25 μM | >25 μM | 21 μM |
| 14 | >25 μM | >25 μM | | | >25 μM | 6 μM | >25 μM |
| 15 | 15 μM | 15 μM | | | >25 μM | 1.3 μM | >25 μM |
| 16 | >25 μM | >25 μM | | | 3 μM | 11 μM | 9 μM |

TABLE 2-continued

| Compound | 72 hr Cell Viability Ishikawa (wild-type) | 72 hr Cell Viability U87-MG (wild-type) | 72 hr Cell Viability HCC827 (wild-type) | 72 hr Cell Viability A375 (wild-type) | 72 hr Cell Viability Panc1 (G12D) | 72 hr Cell Viability Panc10.05 (G12D) | 72 hr Cell Viability HCT116 (G13D) |
|---|---|---|---|---|---|---|---|
| 17 | >25 μM | | >25 μM | | 7 μM | 4 μM | >25 μM |
| 18 | 2 μM | 11 μM | >25 μM | | 5 μM | 3 μM | 26 μM |
| 19 | 2 μM | 4 μM | 8 μM | | 6 μM | 2 μM | 5 μM |
| 20 | >25 μM | >25 μM | >25 μM | >25 μM | >25 μM | >25 μM | >25 μM |
| 21 | 5 μM | | 6 μM | | 2 μM | 0.797 μM | 10 μM |
| 22 | 4 μM | | 22 μM | | 1.3 μM | 0.734 μM | >25 μM |
| 23 | >25 μM | | >25 μM | | >25 μM | 2 μM | >25 μM |
| 24 | >25 μM | >25 μM | >25 μM | >25 μM | 0.672 μM | 2.76 μM | >25 μM |
| 25 | 1.1 μM | 2 μM | 7 μM | | 2 μM | 0.774 μM | 2 μM |
| 26 | <0.8 μM | 1.4 μM | 6 μM | | 2 μM | 1.1 μM | 1 μM |
| 27 | >25 μM | >25 μM | >25 μM | | >25 μM | 16 μM | >25 μM |
| 28 | >25 μM | >25 μM | >25 μM | | >25 μM | >25 μM | >25 μM |
| 29 | >25 μM | >25 μM | >25 μM | | >25 μM | >25 μM | >25 μM |
| 30 | 18 μM | >25 μM | >25 μM | | >25 μM | 23 μM | >25 μM |
| 31 | >25 μM | >25 μM | >25 μM | | >25 μM | >25 μM | >25 μM |
| 32 | >25 μM | 9 μM | 8 μM | | >25 μM | >25 μM | >25 μM |
| 33 | >25 μM | >25 μM | >25 μM | | >25 μM | >25 μM | >25 μM |
| 34 | 9 μM | >25 μM | >25 μM | | >25 μM | 7 μM | >25 μM |
| 35 | 19 μM | 6 μM | 7 μM | | >25 μM | >25 μM | >25 μM |
| 36 | 7 μM | >25 μM | >25 μM | | 14 μM | 3 μM | >25 μM |
| 37 | >25 μM | 6 μM | 7 μM | | >25 μM | >25 μM | >25 μM |
| 38 | 7 μM | >25 μM | >25 μM | | >25 μM | 7 μM | >25 μM |
| 39 | >25 μM | >25 μM | >25 μM | | >25 μM | >25 μM | >25 μM |
| 40 | >25 μM | 9 μM | 7 μM | | 24 μM | >25 μM | >25 μM |
| 41 | 18 μM | 7 μM | 6 μM | | 12 μM | 19 μM | >25 μM |
| 42 | >25 μM | >25 μM | >25 μM | | >25 μM | >25 μM | >25 μM |
| 43 | >25 μM | >25 μM | >25 μM | >25 μM | >25 μM | >25 μM | >25 μM |
| 44 | >25 μM | >25 μM | >25 μM | >25 μM | >25 μM | 2 μM | >25 μM |
| 45 | >25 μM | >25 μM | >25 μM | >25 μM | >25 μM | 3 μM | >25 μM |
| 46 | >25 μM | >25 μM | >25 μM | >25 μM | >25 μM | 11 μM | >25 μM |
| 47 | >25 μM | >25 μM | >25 μM | >25 μM | >25 μM | >25 μM | >25 μM |
| 48 | >25 μM | >25 μM | >25 μM | >25 μM | >25 μM | >25 μM | >25 μM |
| 49 | >25 μM | >25 μM | >25 μM | >25 μM | >25 μM | >25 μM | >25 μM |
| 50 | >25 μM | >25 μM | >25 μM | >25 μM | >25 μM | >25 μM | >25 μM |
| 51 | >25 μM | >25 μM | >25 μM | >25 μM | >25 μM | >25 μM | >25 μM |
| 52 | 13 μM | 14 μM | 10 μM | 5 μM | 16 μM | 15 μM | 10 μM |
| 53 | 13 μM | 15 μM | 10 μM | 3 μM | 12 μM | 10 μM | 11 μM |
| 54 | >25 μM | 15 μM | 13 μM | 26 μM | 15 μM | 6 μM | 23 μM |
| 55 | >25 μM | >25 μM | >25 μM | >25 μM | >25 μM | >25 μM | >25 μM |
| 56 | 7 μM | 12 μM | 7 μM | 4 μM | 9 μM | 7 μM | 6 μM |
| 57 | >25 μM | >25 μM | >25 μM | 27 μM | >25 μM | 8 μM | >25 μM |
| 58 | 2.3 μM | 4 μM | | | 1.7 μM | 3.4 μM | 4 μM |
| 59 | 4 μM | 10 μM | | | 2 μM | 11 μM | 6 μM |
| 60 | 6 μM | 14 μM | | | 2 μM | 13 μM | 7 μM |
| 61 | 2.1 μM | 1.3 μM | | | 1.6 μM | 0.87 μM | 3 μM |
| 62 | 3 μM | 3 μM | | | 5 μM | 2 μM | 4 μM |
| 63 | 4 μM | 1.5 μM | 5 μM | | 5 μM | 2 μM | 4 μM |
| 64 | 3.5 μM | 2 μM | 10 μM | | 5 μM | 2 μM | 5 μM |
| 65 | >25 μM | >25 μM | | | >25 μM | 15 μM | >25 μM |
| 66 | 2 μM | | 4 μM | | 6 μM | 2 μM | 3 μM |
| 67 | 2 μM | | 3 μM | | 4 μM | 2 μM | 2 μM |
| 68 | 3 μM | | 5 μM | | 8 μM | 3 μM | 5 μM |
| 69 | >25 μM | >25 μM | 2 μM | >25 μM | 7 μM | 3 μM | 2 μM |
| 70 | 24 μM | | >25 μM | | 20 μM | 7 μM | >25 μM |
| 71 | 6 μM | | 7 μM | | 22 μM | 6 μM | 9 μM |
| 72 | 2 μM | | >25 μM | | 13 μM | 2 μM | >25 μM |
| 73 | 4 μM | 3 μM | 12 μM | | 7 μM | 0.733 μM | 3 μM |
| 74 | 16 μM | 6 μM | >25 μM | | 11 μM | 2 μM | >25 μM |
| 75 | >25 μM | >25 μM | >25 μM | | >25 μM | >25 μM | >25 μM |
| 76 | 5 μM | 2 μM | 17 μM | | 5 μM | 0.679 μM | 4 μM |
| 77 | >25 μM | >25 μM | >25 μM | | >25 μM | >25 μM | >25 μM |
| 78 | >25 μM | >25 μM | >25 μM | | >25 μM | >25 μM | >25 μM |
| 79 | >25 μM | >25 μM | >25 μM | | >25 μM | >25 μM | >25 μM |
| 80 | >25 μM | 4 μM | 7 μM | | >25 μM | 9 μM | 9 μM |
| 81 | 10 μM | 2 μM | 7 μM | | 6 μM | 2 μM | 3 μM |
| 82 | 4 μM | 13 μM | >25 μM | | >25 μM | >25 μM | 10 μM |
| 83 | 2 μM | 3 μM | 6 μM | | 12 μM | 4 μM | 4 μM |
| 84 | | 4 μM | 3 μM | | 7 μM | 7 μM | 4 μM |
| 85 | | 5 μM | 5 μM | | 8 μM | 6 μM | 4 μM |
| 86 | | 2 μM | 2 μM | | 5 μM | 5 μM | 2 μM |
| 87 | | >25 μM | >25 μM | | 17 μM | 17 μM | >25 μM |
| 88 | | 19 μM | 15 μM | | >25 μM | 16 μM | 17 μM |
| 89 | | 13 μM | 12 μM | | >25 μM | 12 μM | 11 μM |
| 90 | | 4 μM | 4 μM | | 10 μM | 8 μM | 3 μM |
| 91 | >25 μM | >25 μM | 3 μM | >25 μM | 5 μM | 2 μM | 1.5 μM |

TABLE 2-continued

| Compound | 72 hr Cell Viability Ishikawa (wild-type) | 72 hr Cell Viability U87-MG (wild-type) | 72 hr Cell Viability HCC827 (wild-type) | 72 hr Cell Viability A375 (wild-type) | 72 hr Cell Viability Panc1 (G12D) | 72 hr Cell Viability Panc10.05 (G12D) | 72 hr Cell Viability HCT116 (G13D) |
|---|---|---|---|---|---|---|---|
| 92 | >25 μM | >25 μM | 4 μM | >25 μM | 6 μM | 3 μM | 1.5 μM |
| 93 | >25 μM | >25 μM | >25 μM | >25 μM | 9 μM | 5 μM | 4 μM |
| 94 | >25 μM | >25 μM | >25 μM | >25 μM | >25 μM | >25 μM | >25 μM |
| 95 | >25 μM | >25 μM | 5 μM | >25 μM | 7 μM | 4 μM | 4 μM |
| 96 | >25 μM | >25 μM | 4 μM | >25 μM | 4 μM | 3 μM | 3 μM |
| 97 | >25 μM | >25 μM | 5 μM | >25 μM | 9 μM | 4 μM | 5 μM |
| 98 | 11 μM | >25 μM | 5 μM | 9 μM | 13 μM | >25 μM | >25 μM |
| 99 | 4 μM | >25 μM | >25 μM | 6 μM | 6 μM | 6 μM | >25 μM |
| 100 | 3 μM | >25 μM | >25 μM | 4 μM | 5 μM | 5 μM | >25 μM |
| 101 | 2 μM | >25 μM | >25 μM | 4 μM | 2 μM | 4 μM | 14 μM |
| 102 | >25 μM | >25 μM | >25 μM | >25 μM | >25 μM | 5 μM | 13 μM |
| 103 | >25 μM | >25 μM | >25 μM | >25 μM | >25 μM | 5 μM | 25 μM |
| 104 | >25 μM | >25 μM | >25 μM | 6 μM | 22 μM | 17 μM | 5 μM |
| 105 | >25 μM | >25 μM | >25 μM | 25 μM | 12 μM | 2 μM | 13 μM |
| 106 | >25 μM | >25 μM | >25 μM | 22 μM | 12 μM | 3 μM | 6 μM |
| 107 | >25 μM | >25 μM | >25 μM | 19 μM | >25 μM | 2 μM | 6 μM |
| 108 | >25 μM | >25 μM | >25 μM | >25 μM | >25 μM | >25 μM | >25 μM |
| 109 | >25 μM | >25 μM | >25 μM | >25 μM | >25 μM | >25 μM | >25 μM |
| 110 | 10 μM | 17 μM | 4 μM | >25 μM | 4 μM | 0.778 μM | >25 μM |
| 111 | 4 μM | 7 μM | 2 μM | 7 μM | 2 μM | 0.852 μM | 24 μM |
| 112 | >25 μM | >25 μM | 4 μM | >25 μM | 5 μM | 3 μM | 2 μM |
| 113 | >25 μM | >25 μM | >25 μM | 14 μM | 19 μM | 2 μM | 11 μM |
| 114 | >25 μM | >25 μM | >25 μM | 6 μM | 22 μM | 1.1 μM | 5 μM |
| 115 | 9 μM | 17 μM | 11 μM | 6 μM | 9 μM | 4 μM | 10 μM |
| 116 | 21 μM | >25 μM | 4 μM | 12 μM | 3 μM | 1.2 μM | >25 μM |
| 117 | 5 μM | >25 μM | 4 μM | 14 μM | 3 μM | 1.4 μM | >25 μM |
| 118 | 4 μM | 8 μM | 2 μM | 9 μM | 2 μM | 0.854 μM | 18 μM |
| 119 | 3 μM | 6 μM | 2 μM | 8 μM | 2 μM | 0.710 μM | 16 μM |
| 120 | 10 μM | 13 μM | 4 μM | 20 μM | 4 μM | 0.802 μM | >25 μM |
| 143 | >25 μM | 9 μM | | | 7 μM | 4 μM | >25 μM |
| 144 | >25 μM | 11 μM | | | 8 μM | 10 μM | >25 μM |
| 145 | >25 μM | 16 μM | | | 11 μM | 7 μM | >25 μM |
| 146 | >25 μM | | | | 13 μM | 8 μM | >25 μM |
| 147 | >25 μM | | | | 17 μM | 12 μM | >25 μM |
| 148 | 18 μM | | 11 μM | | 4 μM | 2 μM | >25 μM |
| 149 | 7 μM | 11 μM | 22 μM | | >25 μM | 22 μM | 28 μM |
| 150 | 5 μM | 8 μM | 20 μM | | 27 μM | 20 μM | 27 μM |
| 151 | 1.3 μM | 5 μM | 8 μM | | 4 μM | 1.4 μM | 2 μM |

Cells are counted and seeded at 1000 cells/36 ul medium/well into 384-well microplates. Cells are returned to 37° C. CO2 incubator for 18 hr. Drug is made as 200× in DMSO and diluted into medium to 10×. To each well is added 4 ul 10× drug, and plates are returned to the incubator. Final assay DMSO concentration is 0.5%. After 72 hr, 8 ul CellTiterBlue (Promega) is added to each well. After 3 hr, fluorescence (Ex550/Em590) is determined on the Victor Plate Reader (Perkin Elmer). Assay range is determined by DMSO control (100% viability) and 100 uM tamoxifen (0% viability). GI50 values are calculated using Graphpad Prism.

In-cell phosphorylation assays for Erk and Akt were performed on several of the compounds and exemplary results are shown in Table 3 below using HCC827 and A375 cell lines for wild type K-Ras and Panc1 and Panc10.05 cell lines for G12D K-Ras mutants. Results are expressed in μM and corresponding structures are shown in FIGS. 2A-2G and Examples 1-152, above.

TABLE 3

| Compound | In-Cell Western HCC827 (Wild-type) | | In-Cell Western A375 (Wild-type) | | In-Cell Western Panc1 (G12D) | | In-Cell Western Panc10.05 (G12D) | |
|---|---|---|---|---|---|---|---|---|
| | Erk (P) | Akt (P) | Erk (P) | Akt (P) | Erk (P) | Akt (P) | Erk (P) | Akt (P) |
| 3 | | | | | 2 μM | 9 μM | 3 μM | 8 μM |
| 5 | | | | | | 13 μM | | 8 μM |
| 6 | | | | | 4 μM | 4 μM | 2 μM | 3 μM |
| 7 | >25 μM | | >25 μM | >25 μM | >25 μM | >25 μM | 4 μM | 8 μM |
| 8 | >25 μM | | >25 μM | >25 μM | >25 μM | >25 μM | 2 μM | 6 μM |
| 9 | | | | | >25 μM | >25 μM | >25 μM | >25 μM |
| 13 | | | | | | >25 μM | | >25 μM |
| 14 | | | | | >25 μM | >25 μM | 26 μM | |
| 15 | | | | | 2 μM | | >25 μM | >25 μM |
| 16 | | | | | | >25 μM | | >25 μM |
| 17 | | | | | >25 μM | >25 μM | >25 μM | 23 μM |
| 20 | >25 μM | | >25 μM | >25 μM | >25 μM | >25 μM | >25 μM | >25 μM |
| 21 | | | | | >25 μM | 12 μM | >25 μM | 8 μM |
| 22 | | | | | >25 μM | >25 μM | >25 μM | 27 μM |
| 23 | | | | | >25 μM | >25 μM | >25 μM | >25 μM |

TABLE 3-continued

| | In-Cell Western HCC827 (Wild-type) | | In-Cell Western A375 (Wild-type) | | In-Cell Western Panc1 (G12D) | | In-Cell Western Panc10.05 (G12D) | |
|---|---|---|---|---|---|---|---|---|
| Compound | Erk (P) | Akt (P) | Erk (P) | Akt (P) | Erk (P) | Akt (P) | Erk (P) | Akt (P) |
| 24 | >25 μM | >25 μM | >25 μM | | >25 μM | >25 μM | >25 μM | 13 μM |
| 27 | >25 μM | >25 μM | | | 14 μM | >25 μM | | |
| 28 | 16 μM | >25 μM | | | >25 μM | >25 μM | | |
| 29 | 21 μM | >25 μM | | | 13 μM | >25 μM | | |
| 30 | 16 μM | >25 μM | | | 8 μM | >25 μM | | |
| 31 | >25 μM | >25 μM | | | >25 μM | >25 μM | | |
| 32 | 20 μM | >25 μM | | | >25 μM | 26 μM | | |
| 33 | >25 μM | >25 μM | | | >25 μM | >25 μM | | |
| 34 | >25 μM | >25 μM | | | 15 μM | >25 μM | | |
| 35 | 11 μM | >25 μM | | | >25 μM | >25 μM | | |
| 36 | 20 μM | >25 μM | | | 2 μM | 15 μM | | |
| 37 | >25 μM | >25 μM | | | >25 μM | 26 μM | | |
| 38 | 13 μM | >25 μM | | | >25 μM | 24 μM | | |
| 39 | >25 μM | >25 μM | | | 28 μM | >25 μM | | |
| 40 | >25 μM | 25 μM | | | 8 μM | 7 μM | | |
| 41 | 22 μM | >25 μM | | | 2 μM | 3 μM | | |
| 42 | >25 μM | >25 μM | | | >25 μM | >25 μM | | |
| 43 | 19 μM | | >25 μM | >25 μM | >25 μM | >25 μM | >25 μM | >25 μM |
| 44 | >25 μM | | >25 μM | >25 μM | >25 μM | >25 μM | >25 μM | >25 μM |
| 45 | >25 μM | | >25 μM | >25 μM | >25 μM | >25 μM | 6 μM | 11 μM |
| 46 | >25 μM | | >25 μM | >25 μM | >25 μM | >25 μM | 11 μM | 13 μM |
| 47 | >25 μM | | >25 μM | >25 μM | >25 μM | >25 μM | >25 μM | >25 μM |
| 48 | >25 μM | | >25 μM | >25 μM | >25 μM | >25 μM | >25 μM | >25 μM |
| 49 | >25 μM | | >25 μM | >25 μM | >25 μM | >25 μM | 19 μM | 20 μM |
| 50 | 13 μM | | >25 μM | >25 μM | >25 μM | >25 μM | >25 μM | >25 μM |
| 51 | >25 μM | | >25 μM | >25 μM | >25 μM | >25 μM | 25 μM | 25 μM |
| 52 | 20 μM | >25 μM | 14 μM | 24 μM | 8 μM | >25 μM | 4 μM | 18 μM |
| 53 | 14 μM | >25 μM | 6 μM | 10 μM | 16 μM | >25 μM | 3 μM | 15 μM |
| 54 | >25 μM | >25 μM | >25 μM | >25 μM | >25 μM | >25 μM | 3 μM | >25 μM |
| 55 | >25 μM | >25 μM | >25 μM | >25 μM | >25 μM | >25 μM | 14 μM | >25 μM |
| 56 | 9 μM | >25 μM | 16 μM | >25 μM | 3 μM | 27 μM | 3 μM | 21 μM |
| 57 | >25 μM | >25 μM | >25 μM | >25 μM | 26 μM | >25 μM | 6 μM | >25 μM |
| 58 | | | | | | 6 μM | | 3 μM |
| 59 | | | | | 3 μM | 6 μM | 3 μM | 3 μM |
| 60 | | | | | 4 μM | 6 μM | 3 μM | 3 μM |
| 61 | | | | | 0.528 μM | 2 μM | 2 μM | |
| 62 | | | | | 2 μM | 6 μM | 6 μM | |
| 63 | 6 μM | 10 μM | | | 3 μM | 4 μM | 7 μM | >25 μM |
| 64 | 7 μM | 15 μM | | | 5 μM | 6 μM | 9 μM | >25 μM |
| 65 | | | | | >25 μM | >25 μM | >25 μM | |
| 66 | 4 μM | 15 μM | | | 3 μM | 2 μM | 3 μM | 18 μM |
| 67 | 4 μM | 10 μM | | | 3 μM | 3 μM | 6 μM | 23 μM |
| 68 | 6 μM | 13 μM | | | 5 μM | 4 μM | 7 μM | 23 μM |
| 69 | 5 μM | | 3 μM | 2 μM | 8 μM | 6 μM | 2 μM | 17 μM |
| 70 | 22 μM | 19 μM | | | 10 μM | 22 μM | 25 μM | >25 μM |
| 71 | 16 μM | 27 μM | | | 25 μM | 18 μM | 16 μM | >25 μM |
| 72 | 14 μM | 19 μM | | | 3 μM | 2 μM | 5 μM | 19 μM |
| 91 | 11 μM | | 5 μM | 5 μM | 8 μM | 4 μM | 1.4 μM | 12 μM |
| 92 | 15 μM | | >25 μM | >25 μM | 6 μM | 6 μM | 2 μM | 17 μM |
| 93 | >25 μM | | >25 μM | >25 μM | 8 μM | 6 μM | 1.2 μM | 15 μM |
| 94 | >25 μM | | >25 μM | >25 μM | >25 μM | >25 μM | >25 μM | >25 μM |
| 95 | 10 μM | | >25 μM | >25 μM | 10 μM | 6 μM | 2 μM | 14 μM |
| 96 | 7 μM | | 6 μM | 6 μM | 7 μM | 4 μM | 1.1 μM | 9 μM |
| 97 | >25 μM | | 8 μM | 10 μM | 5 μM | 6 μM | 1.2 μM | 12 μM |
| 98 | >25 μM | | >25 μM | >25 μM | >25 μM | >25 μM | >25 μM | >25 μM |
| 99 | 5 μM | | >25 μM | >25 μM | 14 μM | >25 μM | 5 μM | 10 μM |
| 100 | 3 μM | | 4 μM | 5 μM | 17 μM | 25 μM | 3 μM | 7 μM |
| 101 | 14 μM | | >25 μM | >25 μM | 18 μM | >25 μM | 3 μM | >25 μM |
| 102 | 11 μM | | 26 μM | >25 μM | 8 μM | >25 μM | 19 μM | >25 μM |
| 103 | 14 μM | | 29 μM | >25 μM | >25 μM | >25 μM | >25 μM | >25 μM |
| 104 | >25 μM | | >25 μM | >25 μM | >25 μM | >25 μM | >25 μM | >25 μM |
| 105 | 19 μM | | >25 μM | >25 μM | 5 μM | >25 μM | 11 μM | >25 μM |
| 106 | 7 μM | | 20 μM | >25 μM | 5 μM | 25 μM | 10 μM | >25 μM |
| 107 | 6 μM | | 16 μM | >25 μM | 6 μM | >25 μM | 10 μM | >25 μM |
| 108 | >25 μM | >25 μM | >25 μM | >25 μM | >25 μM | >25 μM | 21 μM | >25 μM |
| 109 | >25 μM | >25 μM | >25 μM | >25 μM | >25 μM | >25 μM | >25 μM | >25 μM |
| 110 | 4 μM | >25 μM | 23 μM | >25 μM | 3 μM | 23 μM | 1.3 μM | 3 μM |
| 111 | 1.6 μM | >25 μM | 12 μM | >25 μM | 1.4 μM | 16 μM | 0.767 μM | 2 μM |
| 112 | 17 μM | | 8 μM | 11 μM | 4 μM | 5 μM | 1 μM | 18 μM |
| 113 | 6 μM | | 13 μM | >25 μM | 2 μM | >25 μM | 7 μM | >25 μM |
| 114 | 4 μM | | 5 μM | >25 μM | 1.1 μM | 17 μM | 1.9 μM | 17 μM |
| 115 | 6 μM | >25 μM | 9 μM | >25 μM | 2 μM | 18 μM | 2 μM | 12 μM |
| 116 | 3 μM | >25 μM | 12 μM | >25 μM | 3 μM | 22 μM | 0.745 μM | 2 μM |
| 117 | 4 μM | >25 μM | 15 μM | >25 μM | 4 μM | 23 μM | 0.914 μM | 3 μM |
| 118 | 1.2 μM | >25 μM | 10 μM | 23 μM | 6 μM | 26 μM | 0.969 μM | 2 μM |

TABLE 3-continued

| | In-Cell Western HCC827 (Wild-type) | | In-Cell Western A375 (Wild-type) | | In-Cell Western Panc1 (G12D) | | In-Cell Western Panc10.05 (G12D) | |
|---|---|---|---|---|---|---|---|---|
| Compound | Erk (P) | Akt (P) | Erk (P) | Akt (P) | Erk (P) | Akt (P) | Erk (P) | Akt (P) |
| 119 | 1.1 µM | >25 µM | 8 µM | 12 µM | 3 µM | 19 µM | 0.759 µM | 1.5 µM |
| 120 | 3 µM | >25 µM | 24 µM | >25 µM | 5 µM | 26 µM | 1.2 µM | 5 µM |
| 143 | | | | | 8 µM | 14 µM | 8 µM | 12 µM |
| 144 | | | | | 6 µM | 16 µM | 10 µM | >25 µM |
| 145 | | | | | 5 µM | 18 µM | 7 µM | 17 µM |
| 146 | | | | | 5 µM | >25 µM | 9 µM | >25 µM |
| 147 | | | | | 12 µM | >25 µM | 14 µM | >25 µM |
| 148 | | | | | >25 µM | >25 µM | >25 µM | >25 µM |

Cells are seeded in complete medium into black sided, clear-bottom 384-well microplates at 3000 cells/27 ul/well. Plates are returned to 37° C. CO2 incubator for 18 hr. Drug is made as 200× in DMSO and diluted into medium to 10×. To each well is added 4 ul 10× test article or controls, and plates are returned to the incubator. Final assay DMSO concentration is 0.5%. After one hour, cells are fixed in formaldehyde, rinsed & permeabilized with triton X-100, and blocked with BSA/Goat serum blocking solution. Primary phospho-Akt and phospho-ERK antibodies are added and plates are incubated overnight at 4° C. Plates are rinsed with Tween-20 wash buffer and secondary antibody (Goat anti-rabbit, Thermofisher) is added. After 2 hours, plates are rinsed in Tween-20 wash buffer, and then PBS. Plates are imaged on the Celigo (Nexcelom) and cellular fluorescence is quantitated. Full inhibition of phospho-Akt is achieved with 1 uM BEZ235 (Sellekchem), while full inhibition of phospho-ERK is achieved with 1 uM MEK Inhibitor II Calbiochem). EC50 values are calculated using Graphpad Prism.

FIGS. 9 and 10 depict experimental results of selected compounds of the inventive subject matter, including the compounds of Examples 1, 4, 9, 17, 21-23, and 152, as above (see also, FIGS. 2B and 2F).

The data indicates that for each series of compounds with pyrazole, oxazole, and thiazole groups, the lone pare electrons of the sp² Nitrogen in the 3 position is a key factor for inhibition activity.

FIG. 11 depicts experimental results of selected thiazole (Example 1, depicted above), oxazole (Example 4, depicted above), and pyrazole (Examples 21-22 and 152, as above and on FIG. 2B) lead compound series of the inventive subject matter.

FIG. 12 depicts experimental results of selected pyrazole compounds (Examples 21, 25, 28, 31, and 36, see above and FIGS. 2B-2D) of Formula V of the inventive subject matter. The data indicates increasing the size of the $R_2$ group in Formula V compounds decreases K-Ras inhibition potency.

FIG. 13 depicts experimental results of selected pyrazole compounds (Examples 21, 27, 29, 30, 32, 35, 37, 38, and 42, see above and FIGS. 2B and 2D-2F) of Formula V of the inventive subject matter. The data indicates electron withdrawing of large $R_{4a}$ or $R_{4b}$ groups in Formula V compounds decreases K-Ras inhibition potency.

FIG. 14 depicts experimental results of selected pyrazole compounds (Examples 40-41, see above and FIG. 2E) of Formula V of the inventive subject matter. The data indicates larger $R_2$ groups in Formula V compounds that are tri-substituted (e.g., substituted at $R_1$, $R_2$, $R_{4a}$ and $R_{4b}$) increases K-Ras inhibition potency.

FIG. 15 depicts experimental results of selected pyrazole compounds (Examples 9, 24, and 26, see above and FIGS. 2B-2C) of Formula VI of the inventive subject matter. The data indicates Formula VI compounds have increased selectivity to Panc1 cells, and Panc1 cells have increased sensitivity to such compounds.

FIG. 16 depicts experimental results of selected oxazole compounds (Examples 5, 59, and 64, see FIGS. 2A-2B) of Formula VIII of the inventive subject matter. The data indicates N-alkylation at $R_8$ provides possible new binding cites for improved potency and selectivity.

FIG. 17 depicts experimental results of selected oxazole compounds (Examples 64, 70, 72, 85, 91, 92, and 101, see above and FIGS. 2B and 2D-F) of Formula VIII of the inventive subject matter. The data indicates that for compounds of Formula VIII with N-alkylation at $R_8$, substituting an ethyl at $R_2$ increases K-Ras inhibition potency.

FIG. 18 depicts experimental results of selected thiazole (Example 105, see FIG. 2F), oxazole (Example 70, see FIG. 2B), and pyrazole (Examples 112 and 113, see FIGS. 2E-2F) compounds of the inventive subject matter. The data indicates compounds a more electron rich sp² Nitrogen at the 3 position have increased K-Ras inhibition potency. It also suggests compounds with tri-substituted pyrazoles are the most potent series of compounds.

FIG. 19 depicts experimental results of selected oxazole compounds (Examples 70, 73, 74, 76-78, and 93, see FIGS. 2B-2C and 2E) of Formula VIII of the inventive subject matter. The data indicates that compounds of Formula VIII with N-alkylation at $R_8$ have increased K-Ras inhibition potency.

FIG. 20 depicts experimental results of selected oxazole compounds (Examples 70, 89, 95-100, and 103, see FIGS. 2B and 2D-2F) of Formula VIII of the inventive subject matter. The data indicates that compounds of Formula VIII with N-alkylation at $R_8$ have increased K-Ras inhibition potency.

FIG. 21 depicts experimental results of preferred thiazole (Examples 1 and 12, depicted above) and oxazoles (Examples 4, 7-8, see above and FIG. 2B) compounds of the inventive subject matter. Compounds of Examples 7-8 and 12 are especially preferred.

FIG. 22 depicts experimental results of preferred pyrazole compounds (Examples 21, 26, and 40-41, see FIGS. 2B-2C and 2E) of the inventive subject matter.

FIG. 23 depicts experimental results of preferred oxazole compounds (Examples 64 and 95, see FIGS. 2B and 2E) of Formula VIII of the inventive subject matter with N-alkylation at $R_8$.

Additional contemplated compounds, intermediates, and synthetic protocols are taught in PCT/US 16/25697, published as WO 2016/161361, which is incorporated by reference in its entirety.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a, non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What we claim is:

1. A compound having a structure according to Formula I

[Formula I: structure showing $R_6$-NH-thiazole with $R_7$, fused to dihydroquinolinone with $R_8$ on N]

wherein $R_6$ has the structure

[Formula III: pyridine/pyrimidine ring with $R_5$, V, X, CH$_3$, and carbonyl]

[Formula V: pyrazole with $R_{4a}$-N, $R_2$, $R_1$, and carbonyl]

[Formula VIII: oxazole with $R_3$, CH$_3$, and carbonyl]

[Formula XI: pyrazole with $R_2$-N, $R_{4b}$, $R_1$, and carbonyl]

or

[Formula XIII: oxazole with $R_2$, CH$_3$, and carbonyl]

wherein:

V represents C($R_5$) or N;

X represents C($R_2$) or N;

Wherein $R_1$ is selected from the group consisting of H, alkyl and cycloalkyl;

wherein $R_2$ is selected from the group consisting of H, halo, alkyl, substituted alkyl, fluoroalkyl, cycloalkyl, heterocycloalkyl, substituted heterocycloalkyl, aryl, substituted aryl, aralkyl, polycycloalkyl, hetero-polycycloalkyl, polycycloaryl, hetero-polycycloaryl, acyloxy, alkyloxycarbonyl, amino, amido, sulfonamido, pyrazolyl, and substituted pyrazolyl;

wherein $R_3$ and $R_7$ are independently H or halo;

wherein $R_{4a}$ is independently selected from the group consisting of H, alkyl, substituted alkyl, fluoroalkyl, and aryl;

wherein $R_{4b}$ are independently selected from the group consisting of H, alkyl, substituted alkyl, fluoroalkyl, aryl, and alkyloxy;

wherein $R_5$ is alkyl; and wherein $R_8$ is selected from the group consisting of H, substituted alkyl, aminoalkyl, alkyl amido, cycloalkyl, aralkyl, substituted aralkyl, heteroaralkyl, substituted heteroaralkyl, alkyl cycloalkyl, alkyl heterocycloalkyl, polycycloaryl, alkyloxy, acyloxy, alkyloxycarbonyl, and amino.

2. The compound of claim 1, wherein $R_6$ has the structure according to Formula V or Formula XI.

3. The compound of claim 2, wherein $R_{4a}$ of Formula V is H, CF$_3$, CHF$_2$, CH$_2$F, CH$_3$, and $R_{4b}$ of Formula XI is H, CF$_3$, CHF$_2$, CH$_2$F, CH$_3$, or alkyloxy.

4. The compound of claim 2, wherein $R_{4a}$ of Formula V and $R_{4b}$ of Formula XI are methyl, and $R_1$ is methyl.

5. The compound of claim 4, wherein $R_2$ is alkyl, aryl, or aralkyl.

6. The compound of claim 2, wherein one of $R_2$ or $R_{4a}$ of Formula V or $R_{4b}$ of Formula XI is H and $R_1$ is cycloalkyl.

7. The compound of claim 1, wherein $R_6$ is Formula XI, $R_2$ is alkyl, and $R_{4b}$ is H or methyl; or $R_6$ is Formula V, $R_2$ is alkyl, and $R_{4a}$ is methyl.

8. The compound of claim 1, wherein $R_6$ has the structure according to Formula XI.

9. The compound of claim 8, wherein $R_{4b}$ is methyl and $R_2$ is alkyl.

10. The compound of claim 1, wherein $R_6$ has the structure according to Formula VIII or Formula XIII and $R_2$ of Formula XIII is alkyl or cycloalkyl.

11. The compound of claim 1, wherein $R_8$ is H, optionally substituted benzyl, heterobenzyl, aminoalkyl, alkyl amido, alkyloxy, acyloxy, or alkyloxycarbonyl.

12. The compound of claim 1, wherein $R_8$ has a structure selected from the group consisting of

[structures: 3-pyridylmethyl, 2-pyridylmethyl, 4-pyridylmethyl]

[structures: benzodioxolylmethyl, 3-methoxybenzyl, 2,3-dimethoxybenzyl]

[structures: methoxyalkyl chain, aminoalkyl chain], and

[structures: ester alkyl chain, amide alkyl chain]

and n is 1-3.

13. A pharmaceutical composition comprising a pharmaceutically acceptable carrier and a compound of claim 1.

14. A method of inhibiting mutant K-Ras, comprising contacting a mutant K-Ras with a compound of claim 1, at a concentration effective to inhibit the mutant K-Ras, wherein the mutant K-Ras is in a GTP-bound, or active state before the contacting step.

15. A method of treating a neoplastic disease in a mammal in need thereof, comprising a step of administering to the mammal an effective amount of a compound of claim 1, wherein the neoplastic disease comprises a mutant K-Ras with a mutation at glycine-12 (Gly12), Gly13, and/or glutamine-61 (Gln61).

* * * * *

SEQUENCE LISTING

<160> NUMBER OF SEQ ID NOS: 4

<210> SEQ ID NO 1
<211> LENGTH: 570
<212> TYPE: DNA
<213> ORGANISM: Homo sapiens
<220> FEATURE:
<221> NAME/KEY: misc_feature
<223> OTHER INFORMATION: Wild Type KRAS CDS

<400> SEQUENCE: 1

```
atgactgaat ataaacttgt ggtagttgga gctggtggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
caagaggagt acagtgcaat gagggaccag tacatgagga ctggggaggg ctttctttgt     240
gtatttgcca taaataatac taaatcattt gaagatattc accattatag agaacaaatt     300
aaaagagtta aggactctga agatgtacct atggtcctag taggaaataa atgtgatttg     360
ccttctagaa cagtagacac aaaacaggct caggacttag caagaagtta tggaattcct     420
tttattgaaa catcagcaaa gacaagacag agagtggagg atgcttttta tacattggtg     480
agagagatcc gacaatacag attgaaaaaa atcagcaaag aagaaaagac tcctggctgt     540
gtgaaaatta aaaaatgcat tataatgtaa                                      570
```

<210> SEQ ID NO 2
<211> LENGTH: 570
<212> TYPE: DNA
<213> ORGANISM: Homo sapiens
<220> FEATURE:
<221> NAME/KEY: misc_feature
<223> OTHER INFORMATION: KRAS G12C

<400> SEQUENCE: 2

```
atgactgaat ataaacttgt ggtagttgga gcttgtggcg taggcaagag tgccttgacg      60
atacagctaa ttcagaatca ttttgtggac gaatatgatc caacaataga ggattcctac     120
```

```
aggaagcaag tagtaattga tggagaaacc tgtctcttgg atattctcga cacagcaggt      180
caagaggagt acagtgcaat gagggaccag tacatgagga ctggggaggg ctttctttgt      240
gtatttgcca taaataatac taaatcattt gaagatattc accattatag agaacaaatt      300
aaaagagtta aggactctga agatgtacct atggtcctag taggaaataa atgtgatttg      360
ccttctagaa cagtagacac aaaacaggct caggacttag caagaagtta tggaattcct      420
tttattgaaa catcagcaaa gacaagacag agagtggagg atgcttttta tacattggtg      480
agagagatcc gacaatacag attgaaaaaa atcagcaaag aagaaaagac tcctggctgt      540
gtgaaaatta aaaaatgcat tataatgtaa                                      570

<210> SEQ ID NO 3
<211> LENGTH: 570
<212> TYPE: DNA
<213> ORGANISM: Homo sapiens
<220> FEATURE:
<221> NAME/KEY: misc_feature
<223> OTHER INFORMATION: KRAS G12D

<400> SEQUENCE: 3
atgactgaat ataaacttgt ggtagttgga gctgatggcg taggcaagag tgccttgacg       60
atacagctaa ttcagaatca ttttgtggac gaatatgatc caacaataga ggattcctac      120
aggaagcaag tagtaattga tggagaaacc tgtctcttgg atattctcga cacagcaggt      180
caagaggagt acagtgcaat gagggaccag tacatgagga ctggggaggg ctttctttgt      240
gtatttgcca taaataatac taaatcattt gaagatattc accattatag agaacaaatt      300
aaaagagtta aggactctga agatgtacct atggtcctag taggaaataa atgtgatttg      360
ccttctagaa cagtagacac aaaacaggct caggacttag caagaagtta tggaattcct      420
tttattgaaa catcagcaaa gacaagacag agagtggagg atgcttttta tacattggtg      480
agagagatcc gacaatacag attgaaaaaa atcagcaaag aagaaaagac tcctggctgt      540
gtgaaaatta aaaaatgcat tataatgtaa                                      570

<210> SEQ ID NO 4
<211> LENGTH: 570
<212> TYPE: DNA
<213> ORGANISM: Homo sapiens
<220> FEATURE:
<221> NAME/KEY: misc_feature
<223> OTHER INFORMATION: KRAS G12V

<400> SEQUENCE: 4
atgactgaat ataaacttgt ggtagttgga gctgttggcg taggcaagag tgccttgacg       60
atacagctaa ttcagaatca ttttgtggac gaatatgatc caacaataga ggattcctac      120
aggaagcaag tagtaattga tggagaaacc tgtctcttgg atattctcga cacagcaggt      180
caagaggagt acagtgcaat gagggaccag tacatgagga ctggggaggg ctttctttgt      240
gtatttgcca taaataatac taaatcattt gaagatattc accattatag agaacaaatt      300
aaaagagtta aggactctga agatgtacct atggtcctag taggaaataa atgtgatttg      360
ccttctagaa cagtagacac aaaacaggct caggacttag caagaagtta tggaattcct      420
tttattgaaa catcagcaaa gacaagacag agagtggagg atgcttttta tacattggtg      480
agagagatcc gacaatacag attgaaaaaa atcagcaaag aagaaaagac tcctggctgt      540
gtgaaaatta aaaaatgcat tataatgtaa                                      570
```